US009006178B2

(12) United States Patent
Kofoed et al.

(10) Patent No.: US 9,006,178 B2
(45) Date of Patent: Apr. 14, 2015

(54) DOUBLE-ACYLATED GLP-1 DERIVATIVES WITH A LINKER

(75) Inventors: Jacob Kofoed, Vaerloese (DK); Jesper Lau, Farum (DK); Lars Linderoth, Alleroed (DK); Patrick William Garibay, Holte (DK); Thomas Kruse, Herlev (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/883,946

(22) PCT Filed: Nov. 9, 2011

(86) PCT No.: PCT/EP2011/069743
§ 371 (c)(1),
(2), (4) Date: Jul. 17, 2013

(87) PCT Pub. No.: WO2012/062804
PCT Pub. Date: May 18, 2012

(65) Prior Publication Data
US 2013/0338068 A1    Dec. 19, 2013

Related U.S. Application Data

(60) Provisional application No. 61/414,221, filed on Nov. 16, 2010, provisional application No. 61/497,123, filed on Jun. 15, 2011.

(30) Foreign Application Priority Data

Nov. 9, 2010   (EP) ..................................... 10190515
Jun. 9, 2011   (EP) ..................................... 11169276

(51) Int. Cl.
| | | |
|---|---|---|
| A61K 38/26 | (2006.01) | |
| A61P 3/10 | (2006.01) | |
| A61P 7/12 | (2006.01) | |
| C07K 14/605 | (2006.01) | |
| A61K 38/28 | (2006.01) | |
| C07K 5/00 | (2006.01) | |
| C07K 7/00 | (2006.01) | |
| C07K 16/00 | (2006.01) | |
| C07K 17/00 | (2006.01) | |
| A61K 47/48 | (2006.01) | |

(52) U.S. Cl.
CPC ......... *C07K 14/605* (2013.01); *A61K 47/48038* (2013.01)

(58) Field of Classification Search
CPC .................. C07K 14/605; A61K 47/48038
See application file for complete search history.

(56) References Cited

U.S. PATENT DOCUMENTS

2011/0166321 A1*   7/2011   Garibay et al. ............... 530/323
2013/0288960 A1*   10/2013  Madsen et al. ................ 514/7.2

FOREIGN PATENT DOCUMENTS

| WO | 99/43706 A1 | 9/1999 |
|---|---|---|
| WO | WO 9943706 A1 * | 9/1999 |
| WO | 2006/097537 A2 | 9/2006 |
| WO | 2009/030771 A1 | 3/2009 |
| WO | 2009/042922 A2 | 4/2009 |
| WO | 2009/083549 A1 | 7/2009 |
| WO | 2010/029159 A1 | 3/2010 |
| WO | 2011/080103 A1 | 7/2011 |

OTHER PUBLICATIONS

Christoph E. Dumelin et al., Angewandte Chemie (International Ed. in English), A Portable Albumin Binder From a DNA-Encoded Chemical Library, 2008, vol. 47, No. 17, pp. 3196-3201.
Lotte B. Knudsen et al., Journal of Medicinal Chemistry, Potent Derivatives of Glucagon-Like Peptide-1 With Pharmacokinetic Properties Suitable for Once Daily Administration, 2000, vol. 43, No. 9, pp. 1664-1669.

* cited by examiner

*Primary Examiner* — James H Alstrum Acevedo
*Assistant Examiner* — Zachary J Miknis
(74) *Attorney, Agent, or Firm* — Richard W. Bork

(57) ABSTRACT

The invention relates to a derivative of a GLP-1 analog, which analog comprises a first K residue at a position corresponding to position 18 of GLP-1(7-37) (SEQ ID NO: 1), a second K residue at another position, and a maximum of twelve amino acid changes as compared to GLP-1(7-37); which derivative comprises two protracting moieties attached to said first and second K residue, respectively, via a linker, wherein the protracting moiety is selected from Chem. 1: HOOC—$(CH_2)_x$—CO—*, and Chem. 2: HOOC—$C_6H_4$-0-$(CH_2)_y$—CO—*, in which x is an integer in the range of 6-18, and y is an integer in the range of 3-17; and the linker comprises Chem. 3:   *—NH—$(CH_2)_q$—CH[$(CH_2)_w$—$NH_2$]—CO—*, wherein q is an integer in the range of 0-5, and w is an integer in the range of 0-5; or a pharmaceutically acceptable salt, amide, or ester thereof. The invention also relates to the pharmaceutical use thereof, for example in the treatment and/or prevention of all forms of diabetes and related diseases, as well as to corresponding novel peptides and side chain intermediates. The derivatives are potent, protracted, and suitable for oral administration.

26 Claims, No Drawings

DOUBLE-ACYLATED GLP-1 DERIVATIVES WITH A LINKER

REFERENCE TO RELATED APPLICATIONS

This application is a 35 U.S.C. §371 National Stage application of International Application PCT/EP2011/069743 (WO 2012/062804 A1), filed Nov. 9, 2011, which claims priority from EP10190515.6 filed 9 Nov. 2010 and EP 11169276.0 filed 9 Jun. 2011. It also claims priority under 35 U.S.C. §119 of U.S. Provisional Patent Application Ser. No. 61/414,221 filed on 16 Nov. 2010, and U.S. Provisional Patent Application Ser. No. 61/497,123 filed on 15 Jun. 2011 under 35 U.S.C. Each of these is incorporated herein by reference in its entirety.

TECHNICAL FIELD

The present invention relates to derivatives of analogues of Glucagon-Like Peptide 1 (GLP-1), more in particular to GLP-1 derivatives that are double-acylated at $K^{18}$ and at another K residue of the peptide, via a novel linker, and their pharmaceutical use.

INCORPORATION-BY-REFERENCE OF THE SEQUENCE LISTING

The Sequence Listing, entitled "SEQUENCE LISTING", is 10,605 bytes, was created on Sep. 23, 2014 and is incorporated herein by reference.

BACKGROUND

WO 99/43706 discloses a number of mono- and double-acylated GLP-1 derivatives including some $K^{18,26}$ and $K^{18,34}$ derivatives.

WO 2011/080103 which published after the priority dates of the present application discloses a number of GLP-1 derivatives that are double-acylated at $K^{26,37}$.

WO 06/097537 discloses a number of GLP-1 derivatives including semaglutide (Example 4), a mono-acylated GLP-1 derivative for once weekly administration which is under development by Novo Nordisk A/S.

Angewandte Chemie International Edition 2008, vol. 47, p. 3196-3201 reports the discovery and characterisation of a class of 4-(p-iodophenyl)butyric acid derivatives which purportedly display a stable noncovalent binding interaction with both mouse serum albumin (MSA) and human serum albumin (HSA).

SUMMARY

The invention relates to derivatives of GLP-1 peptides.

The derivatives are acylated at a lysine substituted for the native serine at position 18, as well as at another lysine residue. The other lysine residue may be a native lysine, or a lysine substituted for another amino acid residue. The side chains are albumin binding moieties. They comprise a protracting moiety, preferably selected from fatty diacids, and fatty acids with a terminal, or distal, phenyl or phenoxy group, both optionally substituted. A carboxy group of the fatty acid or fatty diacid, optionally via a linker, is acylated to a lysine residue of the GLP-1 peptide, preferably at the epsilon-amino group thereof. The GLP-1 peptide may be an analogue of GLP-1(7-37) (SEQ ID NO: 1) having a total of up to twelve amino acid differences as compared to GLP-1(7-37), for example one or more additions, one or more deletions, and/or one or more substitutions. The protracting moiety is attached to the peptide via a linker. The linker comprises a free amino group (—$NH_2$ substituent), and is a diradical with a *—NH end and a CO—* end.

More in particular, the invention relates to a derivative of a GLP-1 analogue, which analogue comprises a first K residue at a position corresponding to position 18 of GLP-1(7-37) (SEQ ID NO: 1), a second K residue at another position, and a maximum of twelve amino acid changes as compared to GLP-1(7-37), which derivative comprises two protracting moieties attached to said first and second K residue, respectively, each via a linker, wherein the protracting moiety is selected from Chem. 1, and Chem. 2:

Chem. 1: HOOC—$(CH_2)_x$—CO—*; and Chem. 2: HOOC—$C_6H_4$—O—$(CH_2)_y$—CO—*, in which x is an integer in the range of 6-18, and y is an integer in the range of 3-17; and the linker comprises Chem. 3: *—NH—$(CH_2)_q$—CH[$(CH_2)_w$—$NH_2$]—CO—*, wherein q is an integer in the range of 0-5, and w is an integer in the range of 0-5; or a pharmaceutically acceptable salt, amide, or ester thereof.

The invention also relates to such derivative for use as a medicament, in particular for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

The invention furthermore relates to intermediate products in the form of the GLP-1 peptides of the GLP-1 derivatives of the invention.

The derivatives of the invention are biologically active. Also, or alternatively, they have a protracted pharmacokinetic profile. Also, or alternatively, they have a high oral bioavailability. These properties are of importance in the development of next generation GLP-1 compounds for subcutaneous, intravenous, and/or in particular oral administration.

DESCRIPTION

In what follows, Greek letters may be represented by their symbol or the corresponding written name, for example: α=alpha; β=beta; γ=gamma; δ=delta; ε=epsilon; ζ=zeta; ω=omega; etc. Also, the Greek letter of μ may be represented by "u", e.g. in μl=ul, or in μM=uM.

An asterisk (*) in a chemical formula designates i) a point of attachment, ii) a radical, and/or iii) an unshared electron.

The invention relates to a derivative of a GLP-1 analogue, which analogue comprises a first K residue at a position corresponding to position 18 of GLP-1(7-37) (SEQ ID NO: 1), a second K residue at another position, and a maximum of twelve amino acid changes as compared to GLP-1(7-37), which derivative comprises two protracting moieties attached to said first and second K residue, respectively, via a linker, wherein the protracting moiety is selected from Chem. 1: HOOC—$(CH_2)_x$—CO—*, and Chem. 2: HOOC—$C_6H_4$—O—$(CH_2)_y$—CO—*, in which x is an integer in the range of 6-18, and y is an integer in the range of 3-17; and the linker comprises Chem. 3: *—NH—$(CH_2)_q$—CH[$(CH_2)_w$—$NH_2$]—CO—*, wherein q is an integer in the range of 0-5, and w is an integer in the range of 0-5; or a pharmaceutically acceptable salt, amide, or ester thereof.

GLP-1 Analogues

The term "GLP-1 analogue" or "analogue of GLP-1" as used herein refers to a peptide, or a compound, which is a variant of the human Glucagon-Like Peptide-1 (GLP-1(7-37)), the sequence of which is included in the sequence listing as SEQ ID NO: 1. The peptide having the sequence of SEQ ID NO: 1 may also be designated native GLP-1.

In the sequence listing, the first amino acid residue of SEQ ID NO: 1 (histidine) is assigned no. 1. However, in what follows—according to established practice in the art—this histidine residue is referred to as no. 7, and subsequent amino acid residues are numbered accordingly, ending with glycine no. 37. Therefore, generally, any reference herein to an amino acid residue number or a position number of the GLP-1(7-37) sequence is to the sequence starting with His at position 7 and ending with Gly at position 37.

GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change.

The GLP-1 analogue of the derivative of the invention comprises a first lysine residue at a position corresponding to position 18 of GLP-1(7-37). If the amino acid sequence of this analogue is otherwise identical to that of native GLP-1, such analogue may be designated $K^{18}$-GLP-1(7-37). This designation accordingly represents the amino acid sequence of native GLP-1 where serine at position 18 has been substituted with lysine. As an added remark, this analogue comprises a second Lys residue at position 26, and a third Lys residue at position 34 (viz. the native lysines of GLP-1(7-37)).

The GLP-1 analogue of the derivative of the invention furthermore comprises a second lysine residue at another position, which position may be designated "T". T accordingly represents any other position than position 18.

For example, T may represent 26, in which case the analogue, in addition to the lysine at position 18, comprises a lysine at a position corresponding to position 26 in native GLP-1. Such analogue would still be designated $K^{18}$-GLP-1 (7-37), provided that, except for the $K^{18}$-substitution, its amino acid sequence would be identical to that of native GLP-1.

As another example, T may represent 34, in which case the analogue, in addition to the lysine at position 18, comprises a lysine at a position corresponding to position 34 in native GLP-1. Such analogue would also still be designated $K^{18}$-GLP-1(7-37), provided that, except for the $K^{18}$-substitution, its amino acid sequence would be identical to that of native GLP-1.

But T may also represent a number in the range of 7-37 other than 18, 26, or 34. Such analogue would be designated $K^{18},K^{T}$-GLP-1(7-37), provided that, except for the $K^{18}$- and the $K^{T}$-substitutions, its amino acid sequence is identical to that of native GLP-1.

The GLP-1 analogue forming part of the derivative of the invention comprises, preferably has, a maximum of twelve amino acid changes when compared with native GLP-1 (SEQ ID NO: 1)—in other words, it is a GLP-1 peptide in which a number of amino acid residues have been changed when compared to native GLP-1(7-37) (SEQ ID NO: 1). These changes may represent, independently, one or more amino acid substitutions, additions, and/or deletions.

The following are non-limiting examples of appropriate analogue nomenclature.

For example, the analogue [Aib8,Lys18,Glu22,Val25,Arg26,Lys31,Arg34]-GLP-1-(7-37)(SEQ ID NO:3) designates a GLP-1(7-37) peptide which, when compared to native GLP-1, is changed by the following substitutions: Substitution of alanine at position 8 with Aib (α-aminoisobutyric acid), of serine at position 18 with lysine, of glycine at position 22 with glutamic acid, of alanine at position 25 with valine, of lysine at position 26 with arginine, of tryptophan at position 31 with lysine, and of lysine at position 34 with arginine. This analogue may also be briefly designated (8Aib, 18K, 22E, 25V, 26R, 31K, 34R)(SEQ ID NO:3).

As another example, the analogue [Lys18,Glu22,Arg26,Lys27,His31,Gly34]-GLP-1-(7-34)(SEQ ID NO:2) designates a GLP-1(7-37) peptide, which, when compared to native GLP-1, is changed by substitution of serine at position 18 with lysine, substitution of glycine at position 22 with glutamic acid, substitution of lysine at position 26 with arginine, substitution of glutamic acid at position 27 with lysine, substitution of tryptophan at position 31 with histidine, substitution of lysine at position 34 with glycine, and by deletion of the C-terminus of glycine-arginine-glycine at position 35-36-37. This analogue may also be briefly designated (18K, 22E, 26R, 27K, 31H, 34G, des35-37)(SEQ ID NO:2), where reference to GLP-1(7-37) is implied, and "des" represents a deletion.

As a still further example, an analogue comprising $Imp^7$, and/or ($Aib^8$ or $S^8$) refers to a GLP-1(7-37) peptide, which, when compared to native GLP-1, comprises a substitution of histidine at position 7 with imidazopropionic acid (Imp); and/or a substitution of alanine at position 8 with α-aminoisobutyric acid (Aib), or with serine. This analogue may comprise further changes as compared to SEQ ID NO: 1.

As is apparent from the above examples, amino acid residues may be identified by their full name, their one-letter code, and/or their three-letter code. These three ways are fully equivalent.

The expressions "a position equivalent to" or "corresponding position" may be used to characterise the site of change in a GLP-1 sequence by reference to native GLP-1(7-37) (SEQ ID NO: 1). Equivalent or corresponding positions are easily deduced, e.g. by simple handwriting and eyeballing; and/or a standard protein or peptide alignment program may be used, such as "align" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −10 (minus 10) and the penalties for additional residues in a gap at −0.5 (minus 0.5).

An example of such alignment is inserted hereinbelow, in which sequence no. 1 is SEQ ID NO: 1, and sequence no. 2 is SEQ ID NO:2; the analogue (18K, 22E, 26R, 27K, 31H, 34G, des35-37) thereof:

```
# 1: GLP-1(7-37)
# 2: GLP-1(7-37)_ANALOGUE
# Matrix: EBLOSUM62
# Gap_penalty: 10.0
# Extend_penalty: 0.5
# Length: 31
# Identity: 22/31 (71.0%)
# Similarity: 24/31 (77.4%)
# Gaps: 3/31 (9.7%)
# Score: 105.0
1  1 HAEGTFTSDVSSYLEGQAAKEFIAWLVKGRG 31
     ||||||||||| .||| .|||::|||.||.
2  1 HAEGTFTSDVSKYLEEQAARKFIAHLVG--- 28
```

In case of non-natural amino acids such as Imp and/or Aib being included in the sequence, they may, for alignment purposes, be replaced with X. If desired, X can later be manually corrected.

The term "peptide", as e.g. used in the context of the GLP-1 analogues of the derivatives of the invention, refers to a compound which comprises a series of amino acids interconnected by amide (or peptide) bonds.

The peptides of the invention comprise at least five constituent amino acids connected by peptide bonds. In particular embodiments the peptide comprises at least 10, preferably at least 15, more preferably at least 20, even more preferably at least 25, or most preferably at least 27 amino acids.

In particular embodiments, the peptide is composed of at least five constituent amino acids, preferably composed of at least 10, at least 15, at least 20, at least 25, or most preferably composed of at least 27 amino acids. In still further particular embodiments the peptide is composed of at least 28, at least 29, at least 30, at least 31, or at least 32 amino acids.

In a still further particular embodiment the peptide consists of amino acids interconnected by peptide bonds.

Amino acids are molecules containing an amine group and a carboxylic acid group, and, optionally, one or more additional groups, often referred to as the amino acid side chain.

The term "amino acid" includes proteogenic amino acids (encoded by the genetic code, including natural amino acids, and standard amino acids), as well as non-proteogenic (not found in proteins, and/or not coded for in the standard genetic code), and synthetic amino acids. Thus, the amino acids may be selected from the group of proteinogenic amino acids, non-proteinogenic amino acids, and/or synthetic amino acids.

Non-limiting examples of amino acids which are not encoded by the genetic code are gamma-carboxyglutamate, ornithine, and phosphoserine. Non-limiting examples of synthetic amino acids are the D-isomers of the amino acids such as D-alanine and D-leucine, Aib (α-aminoisobutyric acid), β-alanine, and des-amino-histidine (desH, alternative name imidazopropionic acid, abbreviated Imp).

In what follows, all amino acids for which the optical isomer is not stated is to be understood to mean the L-isomer (unless otherwise specified).

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention may suitably be tested for GLP-1 activity using the in vitro potency assay described in Example 59 herein.

GLP-1 Derivatives

The term "derivative" as used herein in the context of a GLP-1 peptide or analogue means a chemically modified GLP-1 peptide or analogue, in which one or more substituents have been covalently attached to the peptide. The substituent may also be referred to as a side chain.

In a particular embodiment, the side chain is capable of forming non-covalent aggregates with albumin, thereby promoting the circulation of the derivative with the blood stream, and also having the effect of protracting the time of action of the derivative, due to the fact that the aggregate of the GLP-1-derivative and albumin is only slowly disintegrated to release the active pharmaceutical ingredient. Thus, the substituent, or side chain, as a whole may be referred to as an albumin binding moiety.

In another particular embodiment the albumin binding moiety comprises a portion which is particularly relevant for the albumin binding and thereby the protraction, which portion may accordingly be referred to as a protracting moiety. The protracting moiety may be at, or near, the opposite end of the albumin binding moiety, relative to its point of attachment to the peptide.

In a still further particular embodiment the albumin binding moiety comprises a portion inbetween the protracting moiety and the point of attachment to the peptide, which portion may be referred to as a linker, a linker moiety, a spacer, or the like.

In particular embodiments, the protracting moiety is lipophilic, and/or negatively charged at physiological pH (7.4).

The albumin binding moiety, the protracting moiety, or the linker may be covalently attached to a lysine residue of the GLP-1 peptide by acylation.

In a preferred embodiment, an active ester of the albumin binding moiety, preferably comprising a protracting moiety and a linker, is covalently linked to an amino group of a lysine residue, preferably the epsilon amino group thereof, under formation of an amide bond (this process being referred to as acylation).

Unless otherwise stated, when reference is made to an acylation of a lysine residue, it is understood to be to the epsilon-amino group thereof.

A derivative comprising two protracting moieties attached to a first and a second K residue (e.g., to $K^{18}$ and $K^T$) via a linker may be referred to as a derivative which has been acylated twice, double-acylated, or dual acylated at the epsilon-amino groups of the first and second lysine residues, e.g. at position 18 and T, respectively, of the GLP-1 peptide.

For the present purposes, the terms "albumin binding moiety", "protracting moiety", and "linker" include the molecule itself as well as radicals thereof. Whether or not one or the other form is meant is clear from the context in which the term is used. In a preferred embodiment, these terms refer to radicals. The radicals are preferably suitable for forming one or more amide bonds, i.e. with one or two unshared electrons (*) in connection with a carbonyl group and/or an amino group. Examples of such radicals are Chem. 1, Chem. 2, and Chem. 3, the structures of which are shown in the following.

In one aspect, each protracting moiety comprises, or consists of, a protracting moiety, independently selected from Chem. 1: HOOC—$(CH_2)_x$—CO—*, and Chem. 2: HOOC—$C_6H_4$—O—$(CH_2)_y$—CO—*, in which x is an integer in the range of 6-18, and y is an integer in the range of 3-17.

In one embodiment, *—$(CH_2)_x$—* refers to straight or branched, preferably straight, alkylene in which x is an integer in the range of 6-18.

In another embodiment, *—$(CH_2)_y$—* refers to straight or branched, preferably straight, alkylene in which y is an integer in the range of 3-17.

The nomenclature is as is usual in the art, for example in the above formulas *—COOH refers to carboxy, *—$C_6H_4$—* to phenylene, and *—CO—* to carbonyl (O=C<**). In particular embodiments, the phenylene radical is ortho, meta, or para, respectively.

In a particular embodiment, the derivative of the invention has a first protracting moiety attached to a first K residue at a position corresponding to position 18 of GLP-1(7-37) (SEQ ID NO: 1), and a second protracting moiety attached to a second K residue at another position.

In other particular embodiments, the two albumin binding moieties (i.e. the entire side chains) are similar, preferably substantially identical, or, most preferably, identical.

In still further particular embodiments, the two protracting moieties (or the first and the second protracting moiety), are similar, preferably substantially identical, or, most preferably, identical.

In still further particular embodiments, the two linkers are similar, preferably substantially identical, or, most preferably identical.

The term "substantially identical" includes differences from identity which are due to formation of one or more salts, esters, and/or amides; preferably formation of one or more salts, methyl esters, and simple amides; more preferably formation of no more than two salts, methyl esters, and/or simple amides; even more preferably formation of no more than one salt, methyl ester, and/or simple amide; or most preferably formation of no more than one salt.

In the context of chemical compounds such as albumin binding moieties, protracting moieties, and linkers, similarity and/or identity may be determined using any suitable computer program and/or algorithm known in the art.

For example, the similarity of two protracting moieties, two linkers, and/or two entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protracting moieties, the two linkers, and/or the two entire side chains are represented as a) ECFP_6 fingerprints; b) UNITY fingerprints; and/or c) MDL fingerprints.

The Tanimoto coefficient is preferably used for calculating the similarity of the two fingerprints, whether a), b), or c) is used.

In particular embodiments, whether a), b) or c) is used, the two protracting moieties, the two linkers, and/or the two entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA). For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008—both from Accelrys Software Inc., San Diego, US, and the guides http://www.tripos.com/tripos_resources/fileroot/pdfs/Unity_111408.pdf, and http://www.tripos.com/data/SYBYL/SYBYL_072505.pdf.

An example of a similarity calculation is inserted hereinbelow, in which a known entire side chain of a known GLP-1 derivative was compared with a methyl ester thereof, the two side chains being shown hereinbelow:

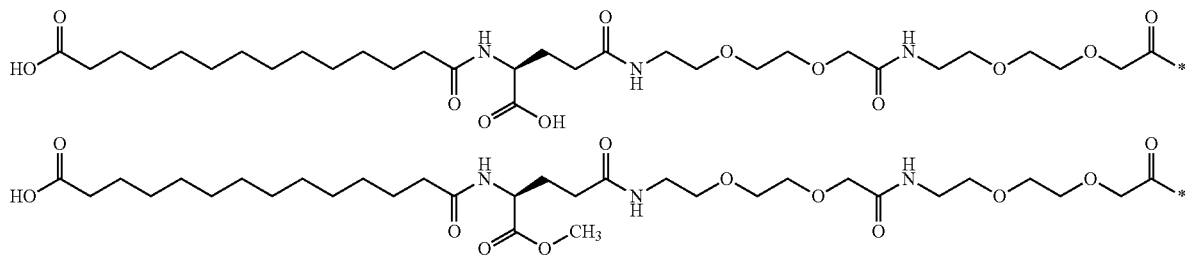

Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

Each of the two linkers of the derivative of the invention comprises the following first linker element (A): Chem. 3:   *—NH—$(CH_2)_q$—CH[$(CH_2)_w$—$NH_2$]—CO—*, wherein q is an integer in the range of 0-5, and w is an integer in the range of 0-5.

In a particular embodiment, the first protracting moiety is attached to the first K residue at a position corresponding to position 18 of GLP-1(7-37) (SEQ ID NO: 1) via a first linker comprising the above first linker element, and the second protracting moiety is attached to the second K residue at another position, via a second linker comprising the above first linker element.

Non-limiting examples of linkers comprising this first linker element of Chem. 3 include diradicals of ornithine, lysine, and homolysine; each in an alpha-version or in an omega-version. Ornithine refers to 2,5-diaminopentanoic acid, lysine refers to 2,6-diaminohexanoic acid, and homolysine refers to 2,7-diaminoheptanoic acid.

For the alpha-versions, q=0. In other words, the alpha refers to the fact that it is the amino group in the alpha position (to the —CO—* radical) that is radicalised (to *—NH). When w=3, 4, and 5, the formula Chem. 3 refers to alpha-ornithine (alpha-Orn; Chem. 9), alpha-lysine (alpha-Lys; Chem. 7), and alpha-homolysine (alpha-Homolys; Chem. 11), respectively.

For the omega versions, w=0. In other words, the omega refers to the fact that it is the amino group at the distal C-atom of the alkyl substituent chain that is radicalised (to *—NH). When q=3, 4, and 5, the formula Chem. 3 refers to delta-ornithine (delta-Orn; Chem. 8), epsilon-lysine (eps-Lys; Chem. 6), and zeta-homolysine (zeta-Homolys; Chem. 10), respectively.

In a preferred embodiment, these linkers are in their L-form. The linker may comprise 1 or 2 times Chem. 3. When z is 2 the Chem. 3 elements are preferably interconnected via an amide bond. For example, the linker may comprise two times epsilon-Lys (2×eps-Lys; 2×Chem. 6).

The linker (each of the first and second linker) may further (i.e., in addition to one or two times the first linker element (A)) comprise one or more additional linker elements, independently selected from the second (B), third (C), and/or fourth (D) linker elements, as defined in the following:

A second linker element (B):

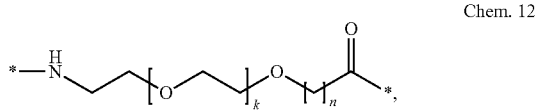

Chem. 12 wherein k is an integer in the range of 1-5, and n is an integer in the range of 1-5.

In a particular embodiment, when k=1 and n=1, this linker element may be designated OEG, or 8-amino-3,6-dioxaoctanic acid, and/or it may be represented by the following formula:

$$*-NH-(CH_2)_2-O-(CH_2)_2-O-CH_2-CO-*. \quad \text{Chem. 12a}$$

A third linker element (C), glutamic acid (Glu), in either of the following two versions:

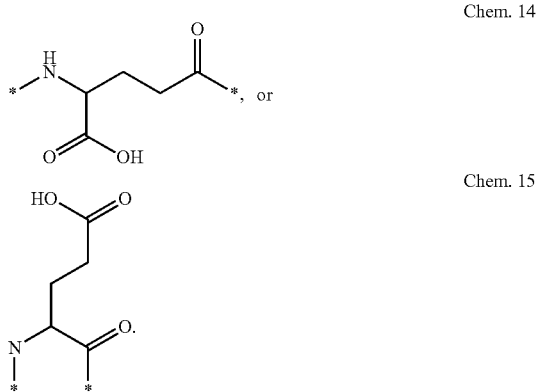

Chem. 14

Chem. 15

In the Chem. 14 version, the third linker element may also be referred to as gamma-Glu, or briefly gGlu, due to the fact that it is the gamma carboxy group of the amino acid glutamic acid which is here used for connection to another linker element, or to the epsilon-amino group of lysine. In the Chem. 15 version, it may also be referred to as alpha-Glu, or briefly aGlu, due to the fact that it is the alpha carboxy group which is used for the connection.

In particular embodiments, Chem. 14 is a) in the L-form, or b) in the D-form.

A fourth linker element (D):

$$*-NH-(CH_2)_s-CO-*, \quad \text{Chem. 16}$$

in which s is an integer in the range of 3-13.

In Chem. 16, the group $*-(CH_2)_s-*$ may represent straight or branched, preferably straight, alkylene.

In still further particular embodiments the linker has a) from 6 to 41 C-atoms; and/or b) from 4 to 28 hetero atoms. Particular and non-limiting examples of hetero atoms are N-, and O-atoms. H-atoms are not hetero atoms.

In a particular embodiment, each linker consists of Chem. 14 and two times Chem. 6, interconnected via amide bonds and in the sequence indicated, connected at its *—NH end to the *—CO end of the protracting moiety, and at its *—CO end to the epsilon amino group of the first or the second K residue of the GLP-1 analogue.

For example, the first linker consists of Chem. 14 and two times Chem. 6, interconnected via amide bonds and in the sequence indicated, connected at its *—NH end to the *—CO end of the first protracting moiety, and at its *—CO end to the epsilon amino group of the first K residue of the GLP-1 analogue; and the second linker consists of Chem. 14 and two times Chem. 6, interconnected via amide bonds and in the sequence indicated, connected at its *—NH end to the *—CO end of the second protracting moiety, and at its *—CO end to the epsilon amino group of the second K residue of the GLP-1 analogue.

Needless to say, just for the sake of good order: Here and in the following the phrase "in the sequence indicated" means, that the *—NH end of the first-mentioned linker element (here Chem. 14) is connected to the *—CO end of the protractor, and the *—CO end of the last-mentioned linker element (here the last one of the two times Chem. 6) is connected to the epsilon amino group of the K residue in question of the GLP-1 analogue.

In another particular embodiment, each linker (the first and the second linker) consists of Chem. 14, two times Chem. 13, and Chem. 6, interconnected via amide bonds and in the sequence indicated, connected at its *—NH end to the *—CO end of the protracting moiety, and at its *—CO end to the epsilon amino group of the first or the second K residue of the GLP-1 analogue.

For example, the first linker consists of Chem. 14, two times Chem. 13, and Chem. 6, interconnected via amide bonds and in the sequence indicated, connected at its *—NH end to the *—CO end of the first protracting moiety, and at its *—CO end to the epsilon amino group of the first K residue of the GLP-1 analogue; and the second linker consists of Chem. 14, two times Chem. 13, and Chem. 6, interconnected via amide bonds and in the sequence indicated, connected at its *—NH end to the *—CO end of the second protracting moiety, and at its *—CO end to the epsilon amino group of the second K residue of the GLP-1 analogue.

Additional PARTICULAR EMBODIMENTS (numbered 58-66) are listed further below, and additional embodiments in which these PARTICULAR EMBODIMENTS have been reformulated in a corresponding way as explained above for the linkers (Chem. 14, 2×Chem. 6) and (Chem. 14, 2×Chem. 13, and Chem.6), in the sentences starting "For example, —", are specifically herein incorporated by reference.

In still further particular embodiments, the invention relates to:

(a) A derivative of a GLP-1 analogue, which analogue comprises a first K residue at a position corresponding to position 18 of GLP-1(7-37) (SEQ ID NO: 1), a second K residue at position 26 of GLP-1(7-37) (SEQ ID NO: 1), and a maximum of four amino acid changes as compared to GLP-1(7-37), which derivative comprises two protracting moieties attached to said first and second K residue, respectively, via a linker, wherein the protracting moiety is Chem. 1: HOOC—$(CH_2)_x$—CO—*, or Chem. 2: HOOC—$C_6H_4$—O—$(CH_2)_y$—CO—*, in which x is 12, and y is 9 or 11; and the linker comprises Chem. 3: *—NH—$(CH_2)_q$—CH[$(CH_2)_w$—NH_2$]—CO—*, wherein q is 4, and w is 0; or a pharmaceutically acceptable salt, amide, or ester thereof.

(b) The derivative of (a), wherein the linker consists of Chem. 14 and two times Chem. 6, interconnected via amide bonds and in the sequence indicated, connected at its *—NH end to the *—CO end of the protracting moiety, and at its *—CO end to the epsilon amino group of the first or the second K residue of the GLP-1 analogue.

(c) The derivative of (a), wherein the linker consists of Chem. 14, two times Chem. 13, and Chem. 6, interconnected via amide bonds and in the sequence indicated, connected at its *—NH end to the *—CO end of the protracting moiety, and at its *—CO end to the epsilon amino group of the first or the second K residue of the GLP-1 analogue.

(d) The derivative of any of (a), (b), or (c), wherein the analogue, in addition to the change $K^{18}$, further comprises $Q^{34}$.

(e) The derivative of any of (a), (b), (c), or (d), wherein the analogue comprises $Aib^8$.

(f) The derivative of any of (a), (b), (c), (d), or (e), wherein the analogue comprises $E^{22}$.

(g) The derivative of any of (a), (b), (c), (d), (e), or (f), wherein the analogue comprises, preferably has, Formula I:

Xaa$_7$-Xaa$_8$-Glu-Gly-Thr-Xaa$_{12}$-Thr-Ser-Asp-Xaa$_{16}$-Ser-Lys-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$(SEQ ID NO: 4), wherein Xaa$_7$ is His or desamino-histidine (imidazopropionyl); Xaa$_8$ is Aib; Xaa$_{12}$ is Phe; Xaa$_{16}$ is Val; Xaa$_{19}$ is Tyr; Xaa$_{20}$ is Leu; Xaa$_{22}$ is Gly or Glu; Xaa$_{23}$ is Gln; Xaa$_{25}$ is Ala or Val; Xaa$_{26}$ is Lys; Xaa$_{27}$ is Glu; Xaa$_{30}$ is Ala; Xaa$_{31}$ is Trp; Xaa$_{33}$ is Val; Xaa$_{34}$ is Gln; Xaa$_{35}$ is Gly; Xaa$_{36}$ is Arg; Xaa$_{37}$ is Gly; and Xaa$_{38}$ is absent.

(h) A compound selected from Chem. 24, Chem. 25, Chem. 30, Chem. 38, Chem. 37, and Chem. 39; or a pharmaceutically acceptable salt, amide, or ester thereof.

(i) The derivative of any of embodiments (a), (b), (c), (d), (e), (f), (g), or (h), which has a potency corresponding to an $EC_{50}$ below 500 pM, preferably below 400 pM, more preferably below 300 pM, even more preferably below 200 pM, or most preferably below 100 pM; wherein the potency is determined as $EC_{50}$ for stimulation of the formation of cAMP in a medium containing the human GLP-1 receptor, using a stable transfected cell-line such as BHK467-12A (tk-ts13); and wherein cAMP is determined using a functional receptor assay, e.g. based on competition between endogenously formed cAMP and exogenously added biotin-labelled cAMP, and e.g. capturing cAMP using a specific antibody, such as the AlphaScreen cAMP Assay, e.g. as described in Example 59.

(j) The derivative of any of embodiments (a), (b), (c), (d), (e), (f), (g), (h), or (i), for which the GLP-1 receptor binding affinity ($IC_{50}$) in the presence of 0.005% HSA (low albumin) is below 10 nM, preferably below 8.0 nM, still more preferably below 6.0 nM, even more preferably below 4.0 nM, or most preferably below 2.00 nM; wherein the binding affinity to the GLP-1 receptor is measured by way of displacement of $^{125}$I-GLP-1 from the receptor, for example using a SPA binding assay; and wherein the GLP-1 receptor is prepared using a stable, transfected baby hamster kidney cell line, such as BHK tk-ts13; and wherein the $IC_{50}$ value is determined as the concentration which displaces 50% of $^{125}$I-GLP-1 from the receptor.

(k) The derivative of any of embodiments (a), (b), (c), (d), (e), (f), (g), (h), (i), or (j), wherein the terminal half-life ($T_{1/2}$) after i.v. administration in rat is at least three times the terminal half-life of semaglutide; wherein the half-life is determined in in vivo pharmacokinetic studies in rat, for example as described in Example 65.

(l) The derivative of any of embodiments (a), (b), (c), (d), (e), (f), (g), (h), (i), (j), or (k), wherein in an oral gavage experiment in rats in vivo the AUC of the dose-corrected plasma exposure from time 30 to 180 min (in the unit of (min×pM/pmol), is at least 20, preferably at least 40, more preferably at least 60, or most preferably at least 75; wherein the AUC may be determined as described in Example 62.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO09/030738 on p. 116-118. A preferred assay is the LOCI assay described in 150 herein.

Intermediate Products

The invention also relates to an intermediate product in the form of a GLP-1 analogue which comprises the following changes as compared to GLP-1(7-37) (SEQ ID NO: 1): (a) 7Imp, 8Aib, 18K, 22E, 34Q (SEQ ID NO: 5); (b) 7Imp, 18K, 22E 25V, 26R, 31K, 34R(SEQ ID NO: 6); or (c) 8Aib, 18K, 19Q, 22E, 34Q (SEQ ID NO: 7); or a pharmaceutically acceptable salt, amide, or ester thereof.

Pharmaceutically Acceptable Salt, Amide, or Ester

The analogues and derivatives of the invention may be in the form of a pharmaceutically acceptable salt, amide, or ester.

Salts are e.g. formed by a chemical reaction between a base and an acid, e.g.: $2 NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions that react with anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivatives of the invention may, e.g., be formed by the reaction of an activated form of a free carboxylic acid group with an amine or a substituted amine, or by reaction of a free or substituted amino group with an activated form of a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Functional Properties

In a first aspect, the derivatives of the invention have a good potency. Also, or alternatively, in a second aspect, they have a protracted pharmacokinetic profile. Also, or alternatively, in a third aspect, they have a high oral bioavailability. Also, or alternatively, in a fourth aspect, they have good biophysical properties.

Biological Activity (Potency)

According to the first aspect, the derivatives of the invention, as well as the constituent GLP-1 peptides as such (such as $K^{18}$-GLP-1(7-37) or analogues thereof), are biologically active, or potent. In fact, the derivatives of the invention have a surprisingly good potency. This may appear to be so in particular when the second acylation position is at a position corresponding to around position 26 of GLP-1(7-37) (SEQ ID NO: 1). Without wishing to be bound by this theory it is contemplated that this may have to do with the free amino group of the specific linker.

In a particular embodiment, potency and/or activity refers to in vitro potency, i.e. performance in a functional GLP-1 receptor assay, more in particular to the capability of stimulating cAMP formation in a cell line expressing the cloned human GLP-1 receptor.

The stimulation of the formation of cAMP in a medium containing the human GLP-1 receptor may preferably be determined using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 59.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$, the better the potency.

In a particular embodiment, the medium has the following composition (final in-assay concentrations): 50 mM TRIS-HCl; 5 mM HEPES; 10 mM $MgCl_2$, $6H_2O$; 150 mM NaCl; 0.01% Tween; 0.1% BSA; 0.5 mM IBMX; 1 mM ATP; 1 uM GTP. A first alternative medium is: 50 mM TRIS-HCl; 5 mM HEPES; 10 mM $MgCl_2$, $6H_2O$; 150 mM NaCl; 0.01% Tween. A second alternative medium is: 50 mM Tris-HCl, 1 mM EGTA, 1.5 mM $MgSO_4$, 1.7 mM ATP, 20 mM GTP, 2 mM 3-isobutyl-1-methylxanthine (IBMX), 0.01% Tween-20, pH 7.4.

In a further particular embodiment, the derivative of the invention has an in vitro potency corresponding to an $EC_{50}$ at or below 10000 pM, more preferably below 5000 pM, even more preferably below 1000 pM, or most preferably below 500 pM.

The ability of the derivatives of the invention to bind to the GLP-1 receptor may also be used as a measure of the GLP-1 activity (receptor affinity). This ability may be determined as described in Example 60. Generally, the binding to the GLP-1 receptor at low albumin concentration should be as good as possible, corresponding to a low $IC_{50}$ value. In particular embodiments, the $IC_{50}$ value of a derivative of the invention, in the presence of 0.005% HSA (low albumin), is below the corresponding $IC_{50}$ value for semaglutide, preferably below 90% thereof, more preferably below 80% thereof, even more preferably below 70% thereof, or most preferably below 50% thereof.

In another particular embodiment the derivatives of the invention are potent in vivo, which may be determined as is known in the art in any suitable animal model, as well as in clinical trials.

The diabetic db/db mouse is one example of a suitable animal model, and the blood glucose lowering effect, and/or the body weight lowering effect may be determined in such mice in vivo, e.g. as described in Example 63.

The LYD pig is another example of a suitable animal model, and the reduction in food intake may be determined in such pigs in vivo, e.g. as described in Example 64.

Protraction—Receptor Binding/Low and High Albumin

According to the second aspect, the derivatives of the invention are protracted.

The ability of the derivatives of the invention to bind to the GLP-1 receptor in the presence of a low and a high concentration of albumin, respectively, may be determined as described in Example 60.

Generally, the binding to the GLP-1 receptor at low albumin concentration should be as good as possible, corresponding to a low $IC_{50}$ value.

The $IC_{50}$ value at high albumin concentration is a measure of the influence of albumin on the binding of the derivative to the GLP-1 receptor. As is known, the GLP-1 derivatives also bind to albumin. This is a generally desirable effect, which extends their lifetime in plasma. Therefore, the $IC_{50}$ value at high albumin will generally be higher than the $IC_{50}$ value at low albumin, corresponding to a reduced binding to the GLP-1 receptor, caused by albumin binding competing with the binding to the GLP-1 receptor.

A high ratio ($IC_{50}$ value (high albumin)/$IC_{50}$ value (low albumin)) may therefore be taken as an indication that the derivative in question binds well to albumin (may have a long half-life), and also per se binds well to the GLP-1 receptor (the $IC_{50}$ value (high albumin) is high, and the $IC_{50}$ value (low albumin) is low). On the other hand, albumin binding may not always be desirable, or the binding to albumin may become too strong. Therefore, the desirable ranges for $IC_{50}$ (low albumin), $IC_{50}$ (high albumin)/, and the ratio high/low may vary from compound to compound, depending on the intended use and the circumstances surrounding such use, and on other compound properties of potential interest.

As an example, in one particular embodiment, the ratio (hi/lo), vis. [GLP-1 receptor binding affinity ($IC_{50}$) in the presence of 2.0% human serum albumin (HSA), divided by GLP-1 receptor binding affinity ($IC_{50}$) in the presence of 0.005% HSA], is at least 1, preferably at least 10, more preferably at least 20, even more preferably at least 30, or most preferably at least 50.

Protraction—Half Life In Vivo

According to the second aspect, the derivatives of the invention are protracted.

Protraction may be determined as terminal half-life ($T_{1/2}$) in vivo in rats after i.v. administration, as described in Example 65. In particular embodiments, the half-life in rat is at least 7 hours, preferably at least 10 hours, even more preferably at least 20 hours, or most preferably at least 30 hours.

Or, protraction may be determined in another animal species, for example as terminal half-life ($T_{1/2}$) in vivo in minipigs after i.v. administration, as described in Example 66. In particular embodiments, the terminal half-life in minipigs is at least 8 hours, preferably at least 24 hours, even more preferably at least 40 hours, or most preferably at least 60 hours.

Surprisingly, the present inventors identified a novel class of GLP-1 derivatives, object of the present invention, which have a high potency, and at the same time preferably a good half-life.

Oral Bioavailability

According to the third aspect, the derivatives of the invention have a high oral bioavailability.

The oral bioavailability of commercial GLP-1 derivatives is very low. The oral bioavailability of GLP-1 derivatives under development for i.v. or s.c. administration is also low.

Accordingly, there is a need in the art for GLP-1 derivatives of an improved oral bioavailability. Such derivatives could be suitable candidates for oral administration, as long as mainly their potency is generally satisfactory, and/or as long as their half-life is also generally satisfactory.

Generally, the term bioavailability refers to the fraction of an administered dose of an active pharmaceutical ingredient (API), such as a derivative of the invention that reaches the systemic circulation unchanged. By definition, when an API is administered intravenously, its bioavailability is 100%. However, when it is administered via other routes (such as orally), its bioavailability decreases (due to incomplete absorption and first-pass metabolism). Knowledge about bioavailability is important when calculating dosages for non-intravenous routes of administration.

Absolute oral bioavailability compares the bioavailability (estimated as the area under the curve, or AUC) of the API in systemic circulation following oral administration, with the bioavailability of the same API following intravenous administration. It is the fraction of the API absorbed through non-intravenous administration compared with the corresponding intravenous administration of the same API. The comparison must be dose normalised if different doses are used; consequently, each AUC is corrected by dividing by the corresponding dose administered.

A plasma API concentration vs time plot is made after both oral and intravenous administration. The absolute bioavailability (F) is the dose-corrected AUC-oral divided by AUC-intravenous.

In a particular embodiment, the derivative of the invention has an absolute oral bioavailability which is higher than that of semaglutide, preferably at least 10% higher, more preferably at least 20% higher, even more preferably at least 30% higher, or most preferably at least 40% higher. In additional particular embodiments, it has an absolute oral bioavailability which is at least 1.5 times that of semaglutide, preferably at least 2.0 times, more preferably at least 3.0 times, even more preferably at least 4.0 times, or most preferably at least 5.0 times that of semaglutide.

Before testing oral bioavailability the derivatives of the invention may suitably be formulated as is known in the art of oral formulations of insulinotropic compounds, e.g. using any one or more of the formulations described in WO 2008/145728.

A couple of tests have been developed, described in Examples 61 and 62, which were found to give an acceptable prediction of oral bioavailability. According to these tests, after direct injection of the GLP-1 derivative into the intestinal lumen of rats, or after oral gavage of rats, the concentration (exposure) thereof in plasma is determined, and the ratio of plasma concentration (pmol/l) divided by the concentration of the dosing solution (umol/l) is calculated for t=30 min; or the AUC of the dose-corrected plasma exposure from time 30 to 180 min is calculated (min×pM/pmol). These figures are measures of oral/intestinal bioavailability, and they are expected to correlate with actual oral bioavailability data.

Biophysical Properties

According to the fourth aspect, the peptides/derivatives of the invention have good biophysical properties. These properties include but are not limited to physical stability and/or solubility. These and other biophysical properties may be measured using standard methods known in the art of protein chemistry. In a particular embodiment, these properties are improved as compared to native GLP-1 (SEQ ID NO: 1). Changed oligomeric properties of the peptides/derivatives may be at least partly responsible for the improved biophysical properties.

Additional particular embodiments of the derivatives of the invention are described in the sections headed "PARTICULAR EMBODIMENTS", "Additional particular embodiments", and "Still further additional particular embodiments", before the experimental section.

Production Processes

The production of peptides like GLP-1(7-37) and GLP-1 analogues is well known in the art.

The GLP-1 moiety of the derivatives of the invention, viz. $K^{18}$-GLP-1(7-37) or an analogue thereof, may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli*, *Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of the derivatives of the invention are included in the experimental part.

Pharmaceutical Compositions

Pharmaceutical composition comprising a derivative of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. 19$^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations, i.e. formulations comprising water. A liquid formulation may be a solution, or a suspension. An aqueous formulation typically comprises at least 50% w/w water, or at least 60%, 70%, 80%, or even at least 90% w/w of water.

Alternatively a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

A pharmaceutical composition may comprise a buffer. The buffer may e.g. be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorhexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml.

A pharmaceutical composition may comprise an isotonic agent. The isotonic agent may e.g. be selected from the group consisting of a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol)polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the peptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present. Methionine (or other sulphuric amino acids or amino acid analogous) may be added to inhibit oxidation of methionine residues to methionine sulfoxide when the peptide is a polypeptide comprising at least one methionine residue susceptible to such oxidation. Any stereoisomer of methionine (L or D) or combinations thereof can be used.

A pharmaceutical composition may comprise a stabiliser selected from the group of high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride).

A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants, for example a surfactant, at least one surfactant, or two different surfactants. The term "surfactant" refers to any molecules or ions that are comprised of a water-soluble (hydrophilic) part, and a fat-soluble (lipophilic) part. The surfactant may e.g. be selected from the group consisting of anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl. Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

An administered dose may contain from 0.01 mg-100 mg of the derivative, or from 0.01-50 mg, or from 0.01-20 mg, or from 0.01 mg-10 mg of the derivative.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral; epidermal; dermal; transdermal; conjunctival; uretal; vaginal; rectal; and/or ocular. In a particular embodiment the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant. A composition may further be compounded in a drug carrier or drug delivery system, e.g. in order to improve stability, bioavailability, and/or solubility. A composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with a derivative according to this invention may also be combined with a surgery that influences the glucose levels, and/or lipid homeostasis such as gastric banding or gastric bypass.

Pharmaceutical Indications

The present invention also relates to a derivative of the invention for use as a medicament.

In particular embodiments, the derivative of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;
(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;
(iii) improving β-cell function, such as decreasing β-cell apoptosis, increasing β-cell function and/or β-cell mass, and/or for restoring glucose sensitivity to β-cells;
(iv) prevention and/or treatment of cognitive disorders;
(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;
(vi) prevention and/or treatment of diabetic complications, such as neuropathy, including peripheral neuropathy; nephropathy; or retinopathy;
(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;
(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis oblitterens); diastolic dysfunction; and/or systolic dysfunction;
(ix) prevention and/or treatment of gastrointestinal diseases, such as inflammatory bowel syndrome; small bowel syndrome, or Crohn's disease; dyspepsia; and/or gastric ulcers;
(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or
(xi) prevention and/or treatment of polycystic ovary syndrome (PCOS).
In a particular embodiment, the indication is selected from the group consisting of (i)-(iii) and (v)-(iix), such as indications (i), (ii), and/or (iii); or indication (v), indication (vi), indication (vii), and/or indication (iix).

In another particular embodiment, the indication is (i). In a further particular embodiment the indication is (v). In a still further particular embodiment the indication is (iix).

The following indications are particularly preferred: Type 2 diabetes, and/or obesity.

PARTICULAR EMBODIMENTS

The following are particular embodiments of the invention:
1. A derivative of a GLP-1 analogue,
which analogue comprises a first K residue at a position corresponding to position 18 of GLP-1(7-37) (SEQ ID NO: 1), a second K residue at another position, and a maximum of twelve amino acid changes as compared to GLP-1(7-37),
which derivative comprises two protracting moieties attached to said first and second K residue, respectively, via a linker, wherein
the protracting moiety is selected from Chem. 1, and Chem. 2:

$$HOOC-(CH_2)_x-CO-*\qquad\qquad\text{Chem. 1}$$

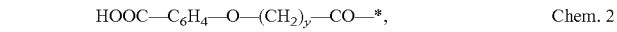

$$HOOC-C_6H_4-O-(CH_2)_y-CO-*,\qquad\qquad\text{Chem. 2}$$

in which x is an integer in the range of 6-18, and y is an integer in the range of 3-17; and
the linker comprises

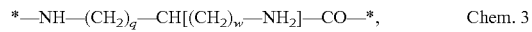

$$*-NH-(CH_2)_q-CH[(CH_2)_w-NH_2]-CO-*,\qquad\qquad\text{Chem. 3}$$

wherein q is an integer in the range of 0-5, and w is an integer in the range of 0-5;
or a pharmaceutically acceptable salt, amide, or ester thereof.
2. The derivative of embodiment 1, wherein the linker comprises z times Chem. 3, wherein z is an integer in the range of 1-2.
3. The derivative of embodiment 2, wherein z is 1.
4. The derivative of embodiment 2, wherein z is 2.
5. The derivative of any of embodiments 2 and 4, wherein when z is 2 the Chem. 3 elements are interconnected via an amide bond.
6. The derivative of any of embodiments 1-5, wherein w is 0.
7. The derivative of any of embodiments 1-6, wherein q is an integer in the range of 3-5.
8. The derivative of any of embodiments 1-7, wherein the linker comprises

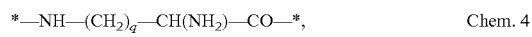

$$*-NH-(CH_2)_q-CH(NH_2)-CO-*,\qquad\qquad\text{Chem. 4}$$

wherein q is an integer in the range of 3-5.
9. The derivative of any of embodiments 1-8, wherein q is 3.
10. The derivative of any of embodiments 1-8, wherein q is 4.
11. The derivative of any of embodiments 1-8, wherein q is 5.
12. The derivative of any of embodiments 1-5, wherein q is 0.
13. The derivative of any of embodiments 1-5, and 12, wherein w is an integer in the range of 3-5.
14. The derivative of any of embodiments 1-5, and 12-13, wherein the linker comprises

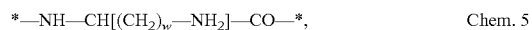

$$*-NH-CH[(CH_2)_w-NH_2]-CO-*,\qquad\qquad\text{Chem. 5}$$

wherein w is an integer in the range of 3-5.
15. The derivative of any of embodiments 1-5, and 12-14, wherein w is 3.
16. The derivative of any of embodiments 1-5, and 12-14, wherein w is 4.
17. The derivative of any of embodiments 1-5, and 12-14, wherein w is 5.
18. The derivative of any of embodiments 1-8, 10, 12-14, and 16, wherein Chem. 3, Chem. 4, or Chem. 5, respectively, is a di-radical of lysine.
19. The derivative of any of embodiments 1-8, 10, and 18, wherein the linker comprises Chem. 6: $*-NH-(CH_2)_4-CH(NH_2)-CO-*$.

20. The derivative of any of embodiments 1-2, 4-8, 10, and 18, wherein the linker comprises

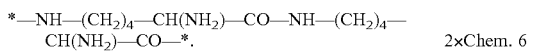  2×Chem. 6

21. The derivative of any of embodiments 1-5, 12-14, 16, and 18, wherein the linker comprises

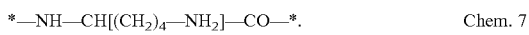  Chem. 7

22. The derivative of any of embodiments 18-21, wherein lysine is L-lysine.
23. The derivative of any of embodiments 1-9, and 12-15, wherein Chem. 3, Chem. 4, or Chem. 5, respectively, is a di-radical of ornithine.
24. The derivative of any of embodiments 1-9, and 23, wherein the linker comprises

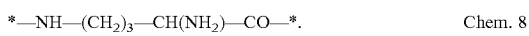  Chem. 8

25. The derivative of any of embodiments 1-5, 12-15, and 23, wherein the linker comprises

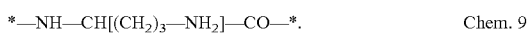  Chem. 9

26. The derivative of any of embodiments 23-25, wherein the linker is L-ornithine.
27. The derivative of any of embodiments 1-8, 11-14, and 17, wherein Chem. 3, Chem. 4, or Chem. 5, respectively, is a di-radical of homolysine.
28. The derivative of any of embodiments 1-8, 11, and 27, wherein the linker comprises

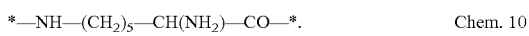  Chem. 10

29. The derivative of any of embodiments 1-5, 12-14, 17, and 27, wherein the linker comprises

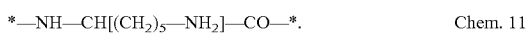  Chem. 11

30. The derivative of any of embodiments 27-29, wherein the linker comprises L-homolysine.
31. The derivative of any of embodiments 1-30, wherein Chem. 3, Chem. 4, Chem. 5, Chem. 6, 2×Chem. 6, Chem. 7, Chem. 8, Chem. 9, Chem. 10, or Chem. 11, respectively, is a first linker element.
32. The derivative of any of embodiments 1-31, wherein the linker comprises a second linker element, Chem. 12:

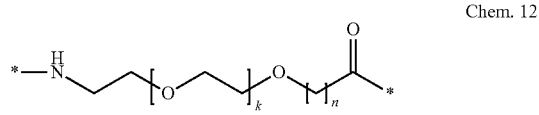  Chem. 12 wherein k is an integer in the range of 1-5, and n is an integer in the range of 1-5.
33. The derivative of embodiment 32, wherein k is 1.
34. The derivative of any of embodiments 32-33, wherein n is 1.
35. The derivative of any of embodiments 32-34, wherein the second linker element is

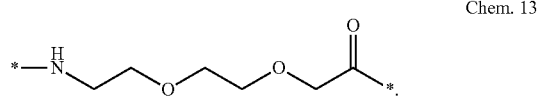  Chem. 13

36. The derivative of any of embodiments 32-35, wherein Chem. 13 is included m times, wherein m is 0, or an integer in the range of 1-10.

37. The derivative of embodiment 36, wherein m is 0, 1, or 2.
38. The derivative of any of embodiments 36-37, wherein m is 0.
39. The derivative of any of embodiments 36-37, wherein m is 1.
40. The derivative of any of embodiments 36-37, wherein m is 2.
41. The derivative of any of embodiments 36-37, and 40, wherein, when m is different from 1, the Chem. 13 elements are interconnected via amide bond(s).
42. The derivative of any of embodiments 1-41, wherein the linker comprises a third linker element selected from Chem. 14 and Chem. 15:

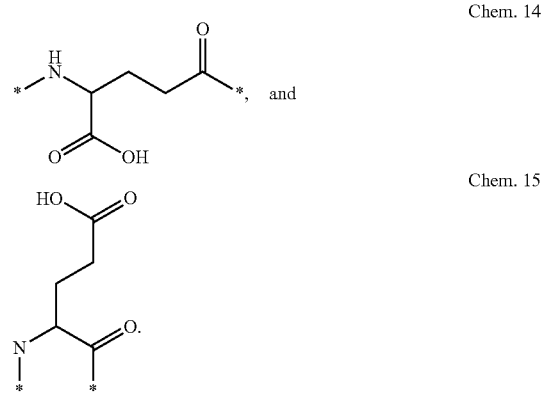

43. The derivative of embodiment 42, wherein the third linker element is Chem. 14.
44. The derivative of embodiment 43, wherein Chem. 14 is included p times, wherein p is 0, or an integer in the range of 1-3.
45. The derivative of embodiment 44, wherein p is 0.
46. The derivative of embodiment 44, wherein p is 1.
47. The derivative of embodiment 44, wherein p is 2.
48. The derivative of embodiment 44, wherein p is 3.
49. The derivative any of embodiments 42-48, wherein Chem. 14 is a di-radical of L-Glu.
50. The derivative of any of embodiments 42-44, and 47-49, wherein, when p is different from 0 and different from 1, the Chem. 14 elements are interconnected via amide bond(s).
51. The derivative of any of embodiments 1-50, wherein the linker comprises a fourth linker element:

  Chem. 16 in which s is an integer in the range of 3-13.
52. The derivative of embodiment 51, wherein s is 5, 7, or 11; preferably 7.
53. The derivative of embodiment 52, wherein the fourth linker element is

  Chem. 17

54. The derivative of any of embodiments 51-53, wherein Chem. 16 is a di-radical of amino octanoic acid.
55. The derivative of any of embodiments 1-54, wherein the linker and the protracting moiety are interconnected via an amide bond.
56. The derivative of any of embodiments 1-55, wherein the linker and the GLP-1 analogue are interconnected via an amide bond.
57. The derivative of any of embodiments 1-55, wherein the linker is attached to the epsilon-amino group of the first or the second K residue.

58. The derivative of any of embodiments 1-3, 6-8, 10, 18-19, 22, 32-38, 42-44, 46, and 49, wherein the linker consists of Chem. 14 and Chem. 6, interconnected via an amide bond and in the sequence indicated, connected at its *—NH end to the *—CO end of the protracting moiety, and at its *—CO end to the epsilon amino group of the first or the second K residue of the GLP-1 analogue.

59. The derivative of any of embodiments 1-2, 4-5, 6-8, 10, 18-20, 22, 32-38, 42-44, 46, and 49, wherein the linker consists of Chem. 14 and two times Chem. 6, interconnected via amide bonds and in the sequence indicated, connected at its *—NH end to the *—CO end of the protracting moiety, and at its *—CO end to the epsilon amino group of the first or the second K residue of the GLP-1 analogue.

60. The derivative of any of embodiments 1-3, 6-8, 10, 18-19, 22, 32-38, 42-44, 47, and 49, wherein the linker consists of two times Chem. 14 and Chem. 6, interconnected via amide bonds and in the sequence indicated, connected at its *—NH end to the *—CO end of the protracting moiety, and at its *—CO end to the epsilon amino group of the first or the second K residue of the GLP-1 analogue.

61. The derivative of any of embodiments 1-3, 6-8, 10, 18-19, 22, 32-38, 42-44, 48, and 49, wherein the linker consists of three times Chem. 14 and Chem. 6, interconnected via amide bonds and in the sequence indicated, connected at its *—NH end to the *—CO end of the protracting moiety, and at its *—CO end to the epsilon amino group of the first or the second K residue of the GLP-1 analogue.

62. The derivative of any of embodiments 1-3, 6-8, 10, 18-19, 22, 32-37, 39, and 42-45, wherein the linker consists of Chem. 13 and Chem. 6, interconnected via amide bonds and in the sequence indicated, connected at its *—NH end to the *—CO end of the protracting moiety, and at its *—CO end to the epsilon amino group of the first or the second K residue of the GLP-1 analogue.

63. The derivative of any of embodiments 1-3, 6-8, 10, 18-19, 22, 32-37, 39, 42-44, 46, and 49, wherein the linker consists of Chem. 14, Chem. 13, and Chem. 6, interconnected via amide bonds and in the sequence indicated, connected at its *—NH end to the *—CO end of the protracting moiety, and at its *—CO end to the epsilon amino group of the first or the second K residue of the GLP-1 analogue.

64. The derivative of any of embodiments 1-3, 6-8, 10, 18-19, 22, 32-37, 40-44, 46, and 49, wherein the linker consists of Chem. 14, two times Chem. 13, and Chem. 6, interconnected via amide bonds and in the sequence indicated, connected at its *—NH end to the *—CO end of the protracting moiety, and at its *—CO end to the epsilon amino group of the first or the second K residue of the GLP-1 analogue.

65. The derivative of any of embodiments 1-3, 6-8, 10, 18-19, 22, 32-37, 40, 42-44, 46, and 49, wherein the linker consists of Chem. 13, Chem. 14, Chem. 13, and Chem. 6, interconnected via amide bonds and in the sequence indicated, connected at its *—NH end to the *—CO end of the protracting moiety, and at its *—CO end to the epsilon amino group of the first or the second K residue of the GLP-1 analogue.

66. The derivative of any of embodiments 1-2, 4, 6-8, 10, 18-20, 22, 32-38, 42-44, 46, and 49, wherein the linker consists of Chem. 17, Chem. 14, and two times Chem. 6, interconnected via amide bonds and in the sequence indicated, connected at its *—NH end to the *—CO end of the protracting moiety, and at its *—CO end to the epsilon amino group of the first or the second K residue of the GLP-1 analogue.

67. The derivative of any of embodiments 1-66, wherein the protracting moiety is Chem. 1.

68. The derivative of embodiment 67, wherein x is an even number.

69. The derivative of any of embodiments 67-68, wherein x is an integer in the range of 10-18.

70. The derivative of any of embodiments 67-69, wherein x is 12.

71. The derivative of any of embodiments 67-69, wherein x is 14.

72. The derivative of any of embodiments 67-69, wherein x is 16.

73. The derivative of any of embodiments 67-69, wherein x is 18.

74. The derivative of any of embodiments 1-66, wherein the protracting moiety is Chem. 2.

75. The derivative of embodiment 74, wherein y is an odd number.

76. The derivative of any of embodiments 74-75, wherein y is an integer in the range of 7-11.

77. The derivative of any of embodiments 74-76, wherein y is 9.

78. The derivative of any of embodiments 74-76, wherein y is 11.

79. The derivative of any of embodiments 1-73, wherein Chem. 1 is represented by

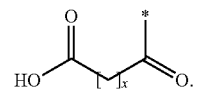

Chem. 1a

80. The derivative of any of embodiments 1-66 and 74-78, wherein Chem. 2 is represented by

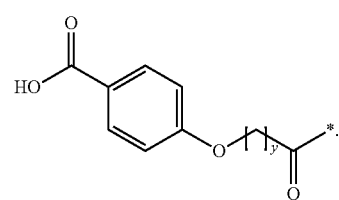

Chem. 2a

81. The derivative of any of embodiments 1-80, wherein the two protracting moieties are substantially identical.

82. The derivative of any of embodiments 1-81, wherein the two protracting moieties have a similarity of at least 0.5; preferably at least 0.6; more preferably at least 0.7, or at least 0.8; even more preferably at least 0.9; or most preferably at least 0.99, such as a similarity of 1.0.

83. The derivative of any of embodiments 1-82, wherein the two linkers are substantially identical.

84. The derivative of any of embodiments 1-83, wherein the two linkers have a similarity of at least 0.5; preferably at least 0.6; more preferably at least 0.7, or at least 0.8; even more preferably at least 0.9; or most preferably at least 0.99, such as a similarity of 1.0.

85. The derivative of any of embodiments 1-84, wherein the two side chains consisting of protracting moiety and linker are substantially identical.

86. The derivative of any of embodiments 1-85, wherein the two side chains consisting of protracting moiety and linker have a similarity of at least 0.5; preferably at least 0.6; more preferably at least 0.7, or at least 0.8; even more preferably at least 0.9; or most preferably at least 0.99, such as a similarity of 1.0.

87. The derivative of any of embodiments 81-86, wherein the two chemical structures to be compared are represented as fingerprints, such as a) ECFP_6 fingerprints; b) UNITY fingerprints; and/or c) MDL fingerprints; and wherein for each of a), b) and c) the Tanimoto coefficient is preferably used for calculating the similarity of the two fingerprints.

88. The derivative of any of embodiments 1-87, wherein the first K residue is designated $K^{18}$.

89. The derivative of any of embodiments 1-88, wherein the second K residue is at a position corresponding to position T of GLP-1(7-37) (SEQ ID NO: 1).

90. The derivative of any of embodiments 1-89, wherein the second K residue is designated $K^T$.

91. The derivative of any of embodiments 89-90, wherein T is an integer selected from the range of 7-17 or from the range of 19-37.

92. The derivative of any of embodiments 89-91, wherein T is an integer selected from the range of 12-17.

93. The derivative of any of embodiments 89-92, wherein T is selected from the range of 19-37.

94. The derivative of any of 89-93, wherein T is selected from the group consisting of 22, 26, 27, 30, 31, 34, and 37

95. The derivative of any of embodiments 89-93, wherein T=22.

96. The derivative of any of embodiments 89-93, wherein T=26.

97. The derivative of any of embodiments 89-93, wherein T=27.

98. The derivative of any of embodiments 89-93, wherein T=30.

99. The derivative of any of embodiments 89-93, wherein T=31.

100. The derivative of any of embodiments 89-93, wherein T=34.

101. The derivative of any of embodiments 89-93, wherein T=37.

102. The derivative of any of embodiments 89-93, wherein T is 26 or 31.

103. The derivative of any of embodiments 1-102, wherein the position corresponding to position 18 of GLP-1(7-37) (SEQ ID NO: 1) is identified by handwriting and eyeballing.

104. The derivative of any of embodiments 89-103, wherein the position corresponding to position T of GLP-1(7-37) (SEQ ID NO: 1) is identified by handwriting and eyeballing.

105. The derivative of any of embodiments 1-104, wherein the number of amino acid changes as compared to GLP-1(7-37) (SEQ ID NO: 1) are identified by handwriting and eyeballing.

106. The derivative of any of embodiments 1-105, wherein the position corresponding to position 18 of GLP-1(7-37) (SEQ ID NO: 1) is identified by use of a standard protein or peptide alignment program.

107. The derivative of any of embodiments 89-106, wherein the position corresponding to position T of GLP-1(7-37) (SEQ ID NO: 1) is identified by use of a standard protein or peptide alignment program.

108. The derivative of any of embodiments 1-107, wherein the number of amino acid changes as compared to GLP-1(7-37) (SEQ ID NO: 1) are identified by use of a standard protein or peptide alignment program.

109. The derivative of any of embodiments 107-108, wherein the alignment program is a Needleman-Wunsch alignment.

110. The derivative of any of embodiments 107-109, wherein the default scoring matrix and the default identity matrix is used.

111. The derivative of any of embodiments 107-110, wherein the scoring matrix is BLOSUM62.

112. The derivative of any of embodiments 107-111, wherein the penalty for the first residue in a gap is −10 (minus ten).

113. The derivative of any of embodiments 107-112, wherein the penalties for additional residues in a gap is −0.5 (minus point five).

114. The derivative of any of embodiments 1-113, wherein the analogue comprises no K residues other than the first and the second K residue.

115. The derivative of any of embodiments 1-114, wherein the maximum twelve amino acid change(s) is (are) at one or more positions corresponding to the following positions in GLP-1(7-37) (SEQ ID NO: 1): 7, 8, 12, 18, 19, 22, 23, 25, 26, 27, 30, 31, 34, 35, 36, and 37.

116. The derivative of any of embodiments 1-115, wherein the maximum twelve amino acid change(s) is (are) at one or more positions corresponding to the following positions in GLP-1(7-37) (SEQ ID NO: 1): 7, 8, 18, 19, 22, 23, 25, 26, 27, 30, 31, 34, 35, 36, and 37.

117. The derivative of any of embodiments 1-116, wherein the analogue comprises $K^{18}$.

118. The derivative of any of embodiments 1-117, wherein the analogue comprises at least one of the following changes: $Imp^7$, $Aib^8$ or $S^8$, $L^{12}$, $Q^{19}$, $K^{22}$ or $E^{22}$, $R^{23}$ or $E^{23}$, $V^{25}$, $R^{26}$ or $H^{26}$ or $V^{26}$, $K^{27}$ or $L^{27}$ or $H^{27}$, $K^{30}$ or $E^{30}$, $K^{31}$ or $H^{31}$, $G^{34}$ or $R^{34}$ or $Q^{34}$ or $Des^{34}$ or $H^{34}$, $Des^{35}$, $Des^{36}$, $K^{37}$ or $Des^{37}$.

119. The derivative of any of embodiments 1-118, wherein the second K residue is $K^{22}$, and wherein the analogue, in addition to the change $K^{18}$, further comprises i) a change selected from $Des^{34}$, $G^{34}$, $R^{34}$, and $Q^{34}$, and ii) a change selected from $R^{26}$, $H^{26}$, and $V^{26}$.

120. The derivative of any of embodiments 1-119, wherein the second K residue is $K^{22}$, and wherein the analogue, in addition to the change $K^{18}$, further comprises $Q^{34}$, and $R^{26}$.

121. The derivative of any of embodiments 1-118, wherein the second K residue is $K^{26}$, and wherein the analogue, in addition to the change $K^{18}$, further comprises a change selected from $G^{34}$, $R^{34}$, $H^{34}$, and $Q^{34}$; preferably selected from $R^{34}$, and $Q^{34}$.

122. The derivative of any of embodiments 1-118, and 121, wherein the second K residue is $K^{26}$, and wherein the analogue, in addition to the change $K^{18}$, further comprises $R^{34}$.

123. The derivative of any of embodiments 1-118, and 121, wherein the second K residue is $K^{26}$, and wherein the analogue, in addition to the change $K^{18}$, further comprises $Q^{34}$.

124. The derivative of any of embodiments 1-118, and 121, wherein the second K residue is $K^{26}$, and wherein the analogue, in addition to the change $K^{18}$, further comprises $H^{34}$.

125. The derivative of any of embodiments 1-118, wherein the second K residue is $K^{27}$, and wherein the analogue, in addition to the change $K^{18}$, further comprises i) a change selected from $Des^{34}$, $G^{34}$, $R^{34}$, and $Q^{34}$, and ii) a change selected from $R^{26}$, $H^{26}$, and $V^{26}$.

126. The derivative of any of embodiments 1-118, and 125, wherein the second K residue is $K^{27}$, and wherein the analogue, in addition to the change $K^{18}$, further comprises $Q^{34}$ and $R^{26}$.

127. The derivative of any of embodiments 1-118, and 125, wherein the second K residue is $K^{27}$, and wherein the analogue, in addition to the change $K^{18}$, further comprises $R^{34}$ and $R^{26}$.

128. The derivative of any of embodiments 1-118, and 125, wherein the second K residue is $K^{27}$, and wherein the analogue, in addition to the change $K^{18}$, further comprises $G^{34}$ and $R^{26}$.

129. The derivative of any of embodiments 1-118, and 125, wherein the second K residue is $K^{27}$, and wherein the analogue, in addition to the change $K^{18}$, further comprises $Q^{34}$ and $H^{26}$.

130. The derivative of any of embodiments 1-118, and 125, wherein the second K residue is $K^{27}$, and wherein the analogue, in addition to the change $K^{18}$, further comprises $R^{34}$ and $H^{26}$.

131. The derivative of any of embodiments 1-118, and 125, wherein the second K residue is $K^{27}$, and wherein the analogue, in addition to the change $K^{18}$, further comprises $R^{34}$ and $V^{26}$.

132. The derivative of any of embodiments 1-118, wherein the second K residue is $K^{30}$ and wherein the analogue, in addition to the change $K^{18}$, further comprises i) a change selected from $Des^{34}$, $G^{34}$, $R^{34}$, and $Q^{34}$, and ii) a change selected from $R^{26}$, $H^{26}$, and $V^{26}$.

133. The derivative of any of embodiments 1-118, and 132, wherein the second K residue is $K^{30}$, and wherein the analogue, in addition to the change $K^{18}$, further comprises $R^{34}$ and $R^{26}$.

134. The derivative of any of embodiments 1-118, and 132, wherein the second K residue is $K^{30}$, and wherein the analogue, in addition to the change $K^{18}$, further comprises $G^{34}$ and $R^{26}$.

135. The derivative of any of embodiments 1-118, and 132, wherein the second K residue is $K^{30}$, and wherein the analogue, in addition to the change $K^{18}$, further comprises $R^{34}$ and $H^{26}$.

136. The derivative of any of embodiments 1-118, and 132, wherein the second K residue is $K^{31}$, and wherein the analogue, in addition to the change $K^{18}$, further comprises i) a change selected from $Des^{34}$, $G^{34}$, $R^{34}$, and $Q^{34}$, and ii) a change selected from $R^{26}$, $H^{26}$, and $V^{26}$.

137. The derivative of any of embodiments 1-118, wherein the second K residue is $K^{31}$ and wherein the analogue, in addition to the change $K^{18}$, further comprises $Des^{34}$ and $R^{26}$.

138. The derivative of any of embodiments 1-118, and 137, wherein the second K residue is $K^{31}$, and wherein the analogue, in addition to the change $K^{18}$, further comprises $Q^{34}$ and $R^{26}$.

139. The derivative of any of embodiments 1-118, and 137, wherein the second K residue is $K^{31}$, and wherein the analogue, in addition to the change $K^{18}$, further comprises $R^{34}$ and $R^{26}$.

140. The derivative of any of embodiments 1-118, and 137, wherein the second K residue is $K^{31}$, and wherein the analogue, in addition to the change $K^{18}$, further comprises $G^{34}$ and $R^{26}$.

141. The derivative of any of embodiments 1-118, and 137, wherein the second K residue is $K^{31}$, and wherein the analogue, in addition to the change $K^{18}$, further comprises $R^{34}$ and $H^{26}$.

142. The derivative of any of embodiments 1-118, and 137, wherein the second K residue is $K^{31}$, and wherein the analogue, in addition to the change $K^{18}$, further comprises $G^{34}$ and $H^{26}$.

143. The derivative of any of embodiments 1-118, wherein the second K residue is $K^{34}$ and wherein the analogue, in addition to the change $K^{18}$, further comprises a change selected from $R^{26}$, $H^{26}$, and $V^{26}$.

144. The derivative of any of embodiments 1-118, and 143, wherein the second K residue is $K^{34}$, and wherein the analogue, in addition to the change $K^{18}$, further comprises $R^{26}$.

145. The derivative of any of embodiments 1-118, wherein the second K residue is $K^{37}$, and wherein the analogue, in addition to the change $K^{18}$, further comprises i) a change selected from $Des^{34}$, $G^{34}$, $R^{34}$, and $Q^{34}$, and ii) a change selected from $R^{26}$, $H^{26}$, and $V^{26}$.

146. The derivative of any of embodiments 1-118, and 145, wherein the second K residue is $K^{37}$, and wherein the analogue, in addition to the change $K^{18}$, further comprises $R^{34}$ and $R^{26}$.

147. The derivative of any of embodiments 1-146, wherein the analogue comprises at least one of the following changes: $Imp^7$, $Aib^8$ or $S^8$, $L^{12}$, $Q^{19}$, $E^{22}$, $R^{23}$ or $E^{23}$, $V^{25}$, $L^{27}$ or $H^{27}$, $E^{30}$, $H^{31}$, $Des^{34}$, $Des^{35}$, $Des^{36}$, or $Des^{37}$.

148. The derivative of any of embodiments 1-147, wherein the analogue comprises at least one of the following changes: $Imp^7$, $Aib^8$, $Q^{19}$, $E^{22}$, $R^{23}$ or $E^{23}$, $V^{25}$, $L^{27}$ or $H^{27}$, $E^{30}$, $H^{31}$, $Des^{34}$, $Des^{35}$, $Des^{36}$, or $Des^{37}$; preferably at least one of the following changes: $Imp^7$, $Aib^8$, $Q^{19}$, $E^{22}$, Or $V^{25}$.

149. The derivative of any of embodiments 115-148, wherein if the amino acid residue at the position corresponding to position 34 is deleted ($Des^{34}$), then the amino acid residues at the positions corresponding to positions 35-37 are also deleted ($Des^{35}$, $Des^{36}$, and $Des^{37}$).

150. The derivative of any of embodiments 115-148, wherein if the amino acid residue at the position corresponding to position 35 is deleted ($Des^{35}$), then the amino acid residues at the positions corresponding to positions 36-37 are also deleted ($Des^{36}$ and $Des^{37}$).

151. The derivative of any of embodiments 115-148, wherein if the amino acid residue at the position corresponding to position 36 is deleted ($Des^{36}$), then the amino acid residue at the position corresponding to position 37 is also deleted ($Des^{37}$).

152. The derivative of any of embodiments 1-151, wherein the analogue comprises $Imp^7$.

153. The derivative of any of embodiments 1-152, wherein the analogue comprises $Aib^8$.

154. The derivative of any of embodiments 1-152, wherein the analogue comprises $S^8$.

155. The derivative of any of embodiments 1-154, wherein the analogue comprises $L^{12}$.

156. The derivative of any of embodiments 1-155, wherein the analogue comprises $Q^{19}$.

157. The derivative of any of embodiments 1-156, wherein the analogue comprises $E^{22}$.

158. The derivative of any of embodiments 1-157, wherein the analogue comprises $R^{23}$.

159. The derivative of any of embodiments 1-156, wherein the analogue comprises $E^{23}$.

160. The derivative of any of embodiments 1-159, wherein the analogue comprises $V^{25}$.

161. The derivative of any of embodiments 1-160, wherein the analogue comprises $L^{27}$.

162. The derivative of any of embodiments 1-161, wherein the analogue comprises $H^{27}$.

163. The derivative of any of embodiments 1-162, wherein the analogue comprises $E^{30}$.

164. The derivative of any of embodiments 1-163, wherein the analogue comprises $H^{31}$.

165. The derivative of any of embodiments 1-164, wherein, for determination of the changes in the analogue, the amino acid sequence of the analogue is compared to the amino acid sequence of native GLP-1(7-37) (SEQ ID NO: 1).

166. The derivative of any of embodiments 1-165, wherein, for determination of a position in an analogue which corresponds to a specified position in native GLP-1(7-37) (SEQ ID NO: 1), the amino acid sequence of the analogue is compared to the amino acid sequence of native GLP-1(7-37) (SEQ ID NO: 1).

167. The derivative of any of embodiments 1-166, wherein the comparison of the amino acid sequence of the analogue with that of GLP-1(7-37) (SEQ ID NO: 1) is done by handwriting and eyeballing.
168. The derivative of any of embodiments 1-167, wherein the comparison of the amino acid sequence of the analogue with that of GLP-1(7-37) (SEQ ID NO: 1) is done by use of a standard protein or peptide alignment program.
169. The derivative of embodiment 168, wherein the alignment program is a Needleman-Wunsch alignment.
170. The derivative of any of embodiments 168-169, wherein the default scoring matrix and the default identity matrix is used.
171. The derivative of any of embodiments 168-170, wherein the scoring matrix is BLOSUM62.
172. The derivative of any of embodiments 168-171, wherein the penalty for the first residue in a gap is −10 (minus ten).
173. The derivative of any of embodiments 168-172, wherein the penalties for additional residues in a gap is −0.5 (minus point five).
174. The derivative of any of embodiments 168-173, wherein the position corresponding to any of the indicated positions of GLP-1(7-37) (SEQ ID NO: 1) is identified by handwriting and eyeballing.
175. The derivative of any of embodiments 168-173, wherein the position corresponding to any of the indicated positions of GLP-1(7-37) (SEQ ID NO: 1) is identified as described for position 18 and position T in any of embodiments 103-113.
176. The derivative of any of embodiments 1-175, which is a derivative of GLP-1(7-33) (amino acids 1-27 of SEQ ID NO: 1).
177. The derivative of any of embodiments 1-175, which is a derivative of GLP-1(7-34) (amino acids 1-28 of SEQ ID NO: 1).
178. The derivative of any of embodiments 1-175, which is a derivative of GLP-1(7-35) (amino acids 1-29 of SEQ ID NO: 1).
179. The derivative of any of embodiments 1-178, wherein the analogue has a maximum of eleven amino acid changes.
180. The derivative of any of embodiments 1-178, wherein the analogue has a maximum of ten amino acid changes.
181. The derivative of any of embodiments 1-178, wherein the analogue has a maximum of nine amino acid changes.
182. The derivative of any of embodiments 1-178, wherein the analogue has a maximum of eight amino acid changes.
183. The derivative of any of embodiments 1-178, wherein the analogue has a maximum of seven amino acid changes.
184. The derivative of any of embodiments 1-178, wherein the analogue has a maximum of six amino acid changes.
185. The derivative of any of embodiments 1-178, wherein the analogue has a maximum of five amino acid changes.
186. The derivative of any of embodiments 1-178, wherein the analogue has a maximum of four amino acid changes.
187. The derivative of any of embodiments 1-178, wherein the analogue has a maximum of three amino acid changes.
188. The derivative of any of embodiments 1-178, wherein the analogue has a maximum of two amino acid changes.
189. The derivative of any of embodiments 1-178, wherein the analogue has a minimum of one amino acid modification.
190. The derivative of any of embodiments 1-178, wherein the analogue has a minimum of two amino acid changes.
191. The derivative of any of embodiments 1-178, wherein the analogue has a minimum of three amino acid changes.
192. The derivative of any of embodiments 1-178, wherein the analogue has a minimum of four amino acid changes.
193. The derivative of any of embodiments 1-178, wherein the analogue has a minimum of five amino acid changes.
194. The derivative of any of embodiments 1-178, wherein the analogue has a minimum of six amino acid changes.
195. The derivative of any of embodiments 1-178, wherein the analogue has a minimum of seven amino acid changes.
196. The derivative of any of embodiments 1-178, wherein the analogue has a minimum of eight amino acid changes.
197. The derivative of any of embodiments 1-178, wherein the analogue has a minimum of nine amino acid changes.
198. The derivative of any of embodiments 1-178, wherein the analogue has a minimum of ten amino acid changes.
199. The derivative of any of embodiments 1-178, wherein the analogue has a minimum of eleven amino acid changes.
200. The derivative of any of embodiments 1-178, wherein the analogue has one amino acid changes.
201. The derivative of any of embodiments 1-178, wherein the analogue has two amino acid changes.
202. The derivative of any of embodiments 1-178, wherein the analogue has three amino acid changes.
203. The derivative of any of embodiments 1-178, wherein the analogue has four amino acid changes.
204. The derivative of any of embodiments 1-178, wherein the analogue has five amino acid changes.
205. The derivative of any of embodiments 1-178, wherein the analogue has six amino acid changes.
206. The derivative of any of embodiments 1-178, wherein the analogue has seven amino acid changes.
207. The derivative of any of embodiments 1-178, wherein the analogue has eight amino acid changes.
208. The derivative of any of embodiments 1-178, wherein the analogue has nine amino acid changes.
209. The derivative of any of embodiments 1-178, wherein the analogue has ten amino acid changes.
210. The derivative of any of embodiments 1-178, wherein the analogue has eleven amino acid changes.
211. The derivative of any of embodiments 1-210, wherein the changes are, independently, substitutions, additions, and/or deletions.
212. The derivative of any of embodiments 1-210, wherein the changes are, independently, substitutions, and/or deletions.
213. The derivative of any of embodiments 1-212, wherein the changes are substitutions.
214. The derivative of any of embodiments 1-212, wherein the changes are deletions.
215. The derivative of any of embodiments 1-214, wherein the analogue a) comprises a GLP-1 analogue of Formula I; and/or b) is a GLP-1 analogue of Formula I:

Formula I: $Xaa_7$-$Xaa_8$-Glu-Gly-Thr-$Xaa_{12}$-Thr-Ser-Asp-$Xaa_6$-Ser-Lys-$Xaa_9$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$(SEQ ID NO: 8), wherein $Xaa_7$ is L-histidine, imidazopropionyl, α-hydroxy-histidine, D-histidine, desamino-histidine, 2-amino-histidine, -hydroxy-histidine, homohistidine, $N^\alpha$-acetyl-histidine, $N^\alpha$-formyl-histidine, α-fluoromethyl-histidine, α-methyl-histidine, 3-pyridylalanine, 2-pyridylalanine, or 4-pyridylalanine;

$Xaa_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{12}$ is Phe or Leu;
$Xaa_{16}$ is Val or Leu;
$Xaa_{19}$ is Tyr or Gln;
$Xaa_{20}$ is Leu or Met;
$Xaa_{22}$ is Gly, Glu, Lys, or Aib;
$Xaa_{23}$ is Gln, Glu, or Arg;

Xaa$_{25}$ is Ala or Val;
Xaa$_{26}$ is Val, His, Lys, or Arg;
Xaa$_{27}$ is Glu, Leu, or Lys;
Xaa$_{30}$ is Ala, Glu, Lys, or Arg;
Xaa$_{31}$ is Trp, Lys, or His
Xaa$_{33}$ is Val or Lys;
Xaa$_{34}$ is Lys, Glu, Asn, Gly, Gln, Arg, His, or absent;
Xaa$_{35}$ is Gly, Aib, or absent;
Xaa$_{36}$ is Arg, Gly, Lys, or absent;
Xaa$_{37}$ is Gly, Ala, Glu, Pro, Lys, Arg, or absent; and
Xaa$_{38}$ is Ser, Gly, Ala, Glu, Pro, Lys, Arg, or absent.

216. The derivative of embodiment 215, wherein the peptide of Formula I is an analogue of GLP-1 (7-37) (SEQ ID NO: 1).

217. The derivative of any of embodiments 215-216, wherein if Xaa$_{37}$ is absent, then Xaa$_{38}$ is also absent.

218. The derivative of any of embodiments 215-217, wherein if Xaa$_{36}$ is absent, then Xaa$_{37}$, and Xaa$_{38}$ are also absent.

219. The derivative of any of embodiments 215-218, wherein if Xaa$_{35}$ is absent, then Xaa$_{36}$, Xaa$_{37}$, and Xaa$_{38}$ are also absent.

220. The derivative of any of embodiments 215-219, wherein if Xaa$_{34}$ is absent, then Xaa$_{35}$, Xaa$_{36}$, Xaa$_{37}$, and Xaa$_{38}$ are also absent.

221. The derivative of any of embodiments 215-220, wherein Xaa$_7$ is His or desamino-histidine (imidazopropionyl); Xaa$_8$ is Ala, Ser, or Aib; Xaa$_{12}$ is Phe or Leu; Xaa$_{16}$ is Val; Xaa$_{19}$ is Tyr; Xaa$_{20}$ is Leu; Xaa$_{22}$ is Gly, Glu, or Lys; Xaa$_{23}$ is Gln, Glu, or Arg; Xaa$_{25}$ is Ala or Val; Xaa$_{26}$ is Val, His, Lys, or Arg; Xaa$_{27}$ is Glu, Leu, or Lys; Xaa$_{30}$ is Ala, Glu, or Lys; Xaa$_{31}$ is Trp, Lys, or His; Xaa$_{33}$ is Val; Xaa$_{34}$ is Lys, Gly, Gln, Arg, His, or absent; Xaa$_{35}$ is Gly or absent; Xaa$_{36}$ is Arg or absent; Xaa$_{37}$ is Gly, Lys, or absent; and Xaa$_{38}$ is absent.

222. The derivative of any of embodiments 215-221, wherein Xaa$_7$ is His or desamino-histidine; Xaa$_8$ is Ala or Aib; Xaa$_{12}$ is Phe; Xaa$_{16}$ is Val; Xaa$_{19}$ is Tyr; Xaa$_{20}$ is Leu; Xaa$_{22}$ is Gly, Glu, or Lys; Xaa$_{23}$ is Gln, Glu, or Arg; Xaa$_{25}$ is Ala or Val; Xaa$_{26}$ is Val, His, Lys, or Arg; Xaa$_{27}$ is Glu, Leu, or Lys; Xaa$_{30}$ is Ala, Glu, or Lys; Xaa$_{31}$ is Trp, Lys, or His; Xaa$_{33}$ is Val; Xaa$_{34}$ is Lys, Gly, Gln, Arg, His, or absent; Xaa$_{35}$ is Gly or absent; Xaa$_{36}$ is Arg or absent;
Xaa$_{37}$ is Gly, Lys, or absent; and Xaa$_{38}$ is absent.

223. The derivative of any of embodiments 215-222, wherein Xaa$_7$ is His or desamino-histidine; Xaa$_8$ is Ala or Aib; Xaa$_{12}$ is Phe; Xaa$_{16}$ is Val; Xaa$_{19}$ is Tyr or Gln; Xaa$_{20}$ is Leu; Xaa$_{22}$ is Gly or Glu; Xaa$_{23}$ is Gln; Xaa$_{25}$ is Ala or Val; Xaa$_{26}$ is Lys or Arg; Xaa$_{27}$ is Glu; Xaa$_{30}$ is Ala; Xaa$_{31}$ is Trp or Lys; Xaa$_{33}$ is Val; Xaa$_{34}$ is Lys, Gln, or Arg; Xaa$_{35}$ is Gly; Xaa$_{36}$ is Arg; Xaa$_{37}$ is Gly; and Xaa$_{38}$ is absent.

224. The derivative of any of embodiments 215-223, wherein Xaa$_7$ is His.

225. The derivative of any of embodiments 215-223, wherein Xaa$_7$ is desamino-histidine (imidazopropionyl).

226. The derivative of any of embodiments 215-225, wherein Xaa$_8$ is Ala.

227. The derivative of any of embodiments 215-225, wherein Xaa$_8$ is Ser.

228. The derivative of any of embodiments 215-225, wherein Xaa$_8$ is Aib.

229. The derivative of any of embodiments 215-228, wherein Xaa$_{12}$ is Phe.

230. The derivative of any of embodiments 215-228, wherein Xaa$_{12}$ is Leu.

231. The derivative of any of embodiments 215-230, wherein Xaa$_{16}$ is Val.

232. The derivative of any of embodiments 215-231, wherein Xaa$_{19}$ is Tyr.

233. The derivative of any of embodiments 215-232, wherein Xaa$_{20}$ is Leu.

234. The derivative of any of embodiments 215-233, wherein Xaa$_{22}$ is Gly.

235. The derivative of any of embodiments 215-233, wherein Xaa$_{22}$ is Glu.

236. The derivative of any of embodiments 215-233, wherein Xaa$_{22}$ is Lys.

237. The derivative of any of embodiments 215-236, wherein Xaa$_{23}$ is Gln.

238. The derivative of any of embodiments 215-236, wherein Xaa$_{23}$ is Glu.

239. The derivative of any of embodiments 215-236, wherein Xaa$_{23}$ is Arg.

240. The derivative of any of embodiments 215-239, wherein Xaa$_{25}$ is Ala.

241. The derivative of any of embodiments 215-239, wherein Xaa$_{25}$ is Val.

242. The derivative of any of embodiments 215-241, wherein Xaa$_{26}$ is His.

243. The derivative of any of embodiments 215-241, wherein Xaa$_{26}$ is Lys.

244. The derivative of any of embodiments 215-241, wherein Xaa$_{26}$ is Arg.

245. The derivative of any of embodiments 215-244, wherein Xaa$_{27}$ is Glu.

246. The derivative of any of embodiments 215-244, wherein Xaa$_{27}$ is Leu.

247. The derivative of any of embodiments 215-244, wherein Xaa$_{27}$ is Lys.

248. The derivative of any of embodiments 215-247, wherein Xaa$_{30}$ is Ala.

249. The derivative of any of embodiments 215-247, wherein Xaa$_{30}$ is Glu.

250. The derivative of any of embodiments 215-247, wherein Xaa$_{30}$ is Lys.

251. The derivative of any of embodiments 215-250, wherein Xaa$_{31}$ is Trp.

252. The derivative of any of embodiments 215-250, wherein Xaa$_{31}$ is Lys.

253. The derivative of any of embodiments 215-250, wherein Xaa$_{31}$ is His.

254. The derivative of any of embodiments 215-253, wherein Xaa$_{33}$ is Val.

255. The derivative of any of embodiments 215-254, wherein Xaa$_{34}$ is Lys.

256. The derivative of any of embodiments 215-254, wherein Xaa$_{34}$ is Gly.

257. The derivative of any of embodiments 215-254, wherein Xaa$_{34}$ is Gln.

258. The derivative of any of embodiments 215-254, wherein Xaa$_{34}$ is Arg.

259. The derivative of any of embodiments 215-254, wherein Xaa$_{34}$ is His.

260. The derivative of any of embodiments 215-254, wherein Xaa$_{34}$ absent.

261. The derivative of any of embodiments 215-260, wherein Xaa$_{35}$ is Gly.

262. The derivative of any of embodiments 215-260, wherein Xaa$_{35}$ is absent.

263. The derivative of any of embodiments 215-262, wherein Xaa$_{36}$ is Arg.

264. The derivative of any of embodiments 215-262, wherein Xaa$_{36}$ is absent.

265. The derivative of any of embodiments 215-264, wherein Xaa$_{37}$ is Gly.

266. The derivative of any of embodiments 215-265, wherein Xaa₃₇ is Lys.
267. The derivative of any of embodiments 215-266, wherein Xaa₃₇ is absent.
268. The derivative of any of embodiments 215-267, wherein Xaa₃₈ is absent.
269. The derivative of any of embodiments 1-268, wherein the analogue comprises the following amino acid changes, as compared to GLP-1(7-37) (SEQ ID NO: 1):
(i) 8Aib, 18K, 34R; (ii) 8Aib, 18K, 34Q; (iii) 8Aib, 18K, 22E, 34R; (iv) 8Aib, 18K, 22E, 34Q; (v) 8Aib, 12L, 18K, 34Q; (vi) 7Imp, 18K, 22E, 34Q; (vii) 18K, 34R; (iix) 18K, 34Q; (ix) 18K, 22E, 34R; (x) 18K, 22E, 34Q; (xi) 18K, 26R, 31K, 34R; (xii) 18K, 26H, 31K, 34R; (xiii) 18K, 26H, 27K, 34Q; (xiv) 18K, 22K, 26R, 34Q; (xv) 18K, 25V, 26R, 31K, 34R; (xvi) 18K, 22E, 26R, 31K, 34R; (xvii) 18K, 22E, 26H, 27K, 34R; (iixx) 18K, 22E, 26H, 27K, 34Q; (ixx) 18K, 22E, 26H, 27K, 31H, 34R; (xx) 18K, 22E, 26H, 27K, 31H, 34Q; (xxi) 18K, 22E, 25V, 26R, 31K, 34R; (xxii) 18K, 22E, 25V, 26R, 31K, 34Q; (xxiii) 18K, 22E, 25V, 26R, 31K, 34G; (xxiv) 18K, 22E, 25V, 26R, 27K, 34R; (xxv) 18K, 22E, 25V, 26R, 27K, 34Q; (xxvi) 18K, 22E, 25V, 26R, 27K, 31H, 34R; (xxvii) 18K, 22E, 25V, 26R, 27K, 31H, 34Q; (iixxx) 18K, 22E, 23E, 25V, 26R, 27K, 34R; (ixxx) 18K, 22E, 23E, 25V, 26R, 27K, 34Q; (xxx) 18K, 22E, 25V, 26R, 31K, 34G, des35-37; (xxxi) 18K, 22E, 25V, 26R, 31H, des35-37; (xxxii) 18K, 22E, 25V, 26R, 30K, 34G, des35-37; (xxxiii) 18K, 22E, 25V, 26R, 30K, 31H, 34G, des35-37; (xxxiv) 18K, 22E, 25V, 26R, 27L, 30K, 34G, des35-37); (xxxv) 18K, 22E, 26R, 31K, 34G, des35-37; (xxxvi) 18K, 22E, 26R, 27K, 31H, 34G, des35-37; (xxxvii) 7Imp, 18K, 22E, 26R, 34R, 37K; (iixxxx) 7Imp, 18K, 22E, 26R, 27K, 31H, 34G, des35-37; (ixxxx) 7Imp, 18K, 22E, 25V, 26R, 31K, 34G, des35-37; (xxxx) 7Imp, 8Aib, 18K, 22E, 25V, 26R, 31K, 34G, des35-37; (xxxxi) 8S, 18K, 22E, 25V, 26R, 31K, 34G, des35-37; (xxxxii) 8Aib, 18K, 26V, 27K, 34R; (xxxxiii) 8Aib, 18K, 26H, 30K, 34R, des36-37; (xxxxiv) 8Aib, 18K, 25V, 26R, 31K, 34R; (xxxxv) 8Aib, 18K, 22E, 34R, des36-37; (xxxxvi) 8Aib, 18K, 22E, 26R, 34R, 37K; (xxxxvii) 8Aib, 18K, 22E, 26R, 31K, 34R; (iixxxxx) 8Aib, 18K, 22E, 26R, 31K, 34G, des35-37; (ixxxxx) 8Aib, 18K, 22E, 26R, 30K, 34R, des36-37; (xxxxx) 8Aib, 18K, 22E, 26R, 30K, 34R; (xxxxxi) 8Aib, 18K, 22E, 26R, 27K, 31H, 34R, des36-37; (xxxxxii) 8Aib, 18K, 22E, 25V, 26R, 31K, des34-37; (xxxxxiii) 8Aib, 18K, 22E, 25V, 26R, 31K, 34R; (xxxxxiv) 8Aib, 18K, 22E, 25V, 26R, 31K, 34G, des35-37; (xxxxxv) 8Aib, 18K, 22E, 25V, 26R, 30E, 31K, 34G, des35-37; (xxxxxvi) 8Aib, 18K, 22E, 25V, 26R, 27L, des35-37; (xxxxxvii) 8Aib, 18K, 22E, 25V, 26R, 27K, 34Q; (iixxxxxx) 8Aib, 18K, 22E, 25V, 26R, 27K, 31H, 34G, des35-37; (ixxxxxx) 8Aib, 18K, 22E, 25V, 26H, 31K, 34G, des35-37; (xxxxxx) 8Aib, 18K, 22E, 23R, 25V, 26R, 31K, 34G, des35-37; (xxxxxxi) 18K, 22E, 25V, 26R, 27L, 30K, 34G, des35-37; (xxxxxxii) 7Imp, 18K, 22E, 26R, 27K, 34Q; (xxxxxxiii) 8Aib, 18K, 34H; (xxxxxxiv) 7Imp, 8Aib, 18K, 22E, 34Q; (xxxxxxv) 7Imp, 18K, 22E 25V, 26R, 31K, 34R; or (xxxxxxvi) 8Aib, 18K, 19Q, 22E, 34Q.
270. The derivative of any of embodiments 1-269, wherein the analogue has the following amino acid changes, as compared to GLP-1(7-37) (SEQ ID NO: 1):
(i) 8Aib, 18K, 34R; (ii) 8Aib, 18K, 34Q; (iii) 8Aib, 18K, 22E, 34R; (iv) 8Aib, 18K, 22E, 34Q; (v) 8Aib, 12L, 18K, 34Q; (vi) 7Imp, 18K, 22E, 34Q; (vii) 18K, 34R; (iix) 18K, 34Q; (ix) 18K, 22E, 34R; (x) 18K, 22E, 34Q; (xi) 18K, 26R, 31K, 34R; (xii) 18K, 26H, 31K, 34R; (xiii) 18K, 26H, 27K, 34Q; (xiv) 18K, 22K, 26R, 34Q; (xv) 18K, 25V, 26R, 31K, 34R; (xvi) 18K, 22E, 26R, 31K, 34R; (xvii) 18K, 22E, 26H, 27K, 34R; (iixx) 18K, 22E, 26H, 27K, 34Q; (ixx) 18K, 22E, 26H, 27K, 31H, 34R; (xx) 18K, 22E, 26H, 27K, 31H, 34Q; (xxi) 18K, 22E, 25V, 26R, 31K, 34R; (xxii) 18K, 22E, 25V, 26R, 31K, 34Q; (xxiii) 18K, 22E, 25V, 26R, 31K, 34G; (xxiv) 18K, 22E, 25V, 26R, 27K, 34R; (xxv) 18K, 22E, 25V, 26R, 27K, 34Q; (xxvi) 18K, 22E, 25V, 26R, 27K, 31H, 34R; (xxvii) 18K, 22E, 25V, 26R, 27K, 31H, 34Q; (iixxx) 18K, 22E, 23E, 25V, 26R, 27K, 34R; (ixxx) 18K, 22E, 23E, 25V, 26R, 27K, 34Q; (xxx) 18K, 22E, 25V, 26R, 31K, 34G, des35-37; (xxxi) 18K, 22E, 25V, 26R, 31H, des35-37; (xxxii) 18K, 22E, 25V, 26R, 30K, 34G, des35-37; (xxxiii) 18K, 22E, 25V, 26R, 30K, 31H, 34G, des35-37; (xxxiv) 18K, 22E, 25V, 26R, 27L, 30K, 34G, des35-37); (xxxv) 18K, 22E, 26R, 31K, 34G, des35-37; (xxxvi) 18K, 22E, 26R, 27K, 31H, 34G, des35-37; (xxxvii) 7Imp, 18K, 22E, 26R, 34R, 37K; (iixxxx) 7Imp, 18K, 22E, 26R, 27K, 31H, 34G, des35-37; (ixxxx) 7Imp, 18K, 22E, 25V, 26R, 31K, 34G, des35-37; (xxxx) 7Imp, 8Aib, 18K, 22E, 25V, 26R, 31K, 34G, des35-37; (xxxxi) 8S, 18K, 22E, 25V, 26R, 31K, 34G, des35-37; (xxxxii) 8Aib, 18K, 26V, 27K, 34R; (xxxxiii) 8Aib, 18K, 26H, 30K, 34R, des36-37; (xxxxiv) 8Aib, 18K, 25V, 26R, 31K, 34R; (xxxxv) 8Aib, 18K, 22E, 34R, des36-37; (xxxxvi) 8Aib, 18K, 22E, 26R, 34R, 37K; (xxxxvii) 8Aib, 18K, 22E, 26R, 31K, 34R; (iixxxxx) 8Aib, 18K, 22E, 26R, 31K, 34G, des35-37; (ixxxxx) 8Aib, 18K, 22E, 26R, 30K, 34R, des36-37; (xxxxx) 8Aib, 18K, 22E, 26R, 30K, 34R; (xxxxxi) 8Aib, 18K, 22E, 26R, 27K, 31H, 34R, des36-37; (xxxxxii) 8Aib, 18K, 22E, 25V, 26R, 31K, des34-37; (xxxxxiii) 8Aib, 18K, 22E, 25V, 26R, 31K, 34R; (xxxxxiv) 8Aib, 18K, 22E, 25V, 26R, 31K, 34G, des35-37; (xxxxxv) 8Aib, 18K, 22E, 25V, 26R, 30E, 31K, 34G, des35-37; (xxxxxvi) 8Aib, 18K, 22E, 25V, 26R, 27L, des35-37; (xxxxxvii) 8Aib, 18K, 22E, 25V, 26R, 27K, 34Q; (iixxxxxx) 8Aib, 18K, 22E, 25V, 26R, 27K, 31H, 34G, des35-37; (ixxxxxx) 8Aib, 18K, 22E, 25V, 26H, 31K, 34G, des35-37; (xxxxxx) 8Aib, 18K, 22E, 23R, 25V, 26R, 31K, 34G, des35-37; (xxxxxxi) 18K, 22E, 25V, 26R, 27L, 30K, 34G, des35-37; (xxxxxxii) 7Imp, 18K, 22E, 26R, 27K, 34Q; (xxxxxxiii) 8Aib, 18K, 34H; (xxxxxxiv) 7Imp, 8Aib, 18K, 22E, 34Q; (xxxxxxv) 7Imp, 18K, 22E 25V, 26R, 31K, 34R; or (xxxxxxvi) 8Aib, 18K, 19Q, 22E, 34Q.
271. The derivative of any of embodiments 1-270, wherein the analogue is modified so as to comprise a C-terminal amide.
272. The derivative of any of embodiments 1-271, wherein a carboxylic acid group of the C-terminal amino acid of the analogue is converted into carboxylic acid amide.
273. The derivative of embodiment 272, wherein the carboxylic acid group which is converted into carboxylic acid amide is not in the side chain of the C-terminal amino acid.
274. The derivative of any of embodiments 1-270, wherein the analogue has a C-terminal carboxylic acid.
275. A compound, preferably according to any of embodiments 1-275, selected from the following: Chem. 20, Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, Chem. 42, Chem. 43, Chem. 44, Chem. 45, Chem. 46, Chem. 47, Chem. 48, Chem. 49, Chem. 50, Chem. 51, Chem. 52, Chem. 53, Chem. 54, Chem. 55, Chem. 56, Chem. 57, Chem. 58, Chem. 59, Chem. 60, Chem. 61, Chem. 62, Chem. 63, Chem. 64, Chem. 65, Chem. 66, Chem. 67, Chem. 68, Chem. 69, Chem. 70, Chem. 71, Chem. 72, Chem. 73, Chem. 74, Chem. 75, Chem. 76, or Chem. 77; or a pharmaceutically acceptable salt, amide, or ester thereof.
276. A compound, preferably according to any of embodiments 1-275, selected from the following: Chem. 20, Chem. 21, Chem. 22, Chem. 23, Chem. 24, Chem. 25, Chem. 26, Chem. 27, Chem. 29, Chem. 30, Chem. 31, Chem. 32, Chem. 33, Chem. 34, Chem. 38, or Chem. 39; or a pharmaceutically acceptable salt, amide, or ester thereof.

277. A compound characterised by its name, and selected from a listing of each of the names of the compounds of Examples 1-58 herein; or a pharmaceutically acceptable salt, amide, or ester thereof.

278. A compound characterised by its name, and selected from a listing of each of the names of the compounds of Examples 1-8, 10-15, and 19-20 herein; or a pharmaceutically acceptable salt, amide, or ester thereof.

279. The compound of embodiment 277, which is a compound of embodiment 275.

280. The compound of embodiment 278, which is a compound of embodiment 276.

281. The derivative of any of embodiments 1-280, which has GLP-1 activity.

282. The derivative of embodiment 281, wherein GLP-1 activity refers to the capability of activating the human GLP-1 receptor.

283. The derivative of embodiment 282, wherein activation of the human GLP-1 receptor is measured in an in vitro assay, as the potency of cAMP production.

284. The derivative of any of embodiments 1-283, which has a potency corresponding to an $EC_{50}$
a) below 18000 pM, preferably below 10000 pM, more preferably below 5000 pM, even more preferably below 4000 pM, or most preferably below 3000 pM;
b) below 2000 pM, preferably below 1200 pM, more preferably below 1000 pM, even more preferably below 800 pM, or most preferably below 600 pM;
c) below 400 pM, preferably below 300 pM, more preferably below 200 pM, even more preferably below 150 pM, or most preferably below 100 pM; or
d) below 80 pM, preferably below 60 pM, more preferably below 50 pM, even more preferably below 40 pM, or most preferably below 30 pM.

285. The derivative of embodiment 284, wherein the potency is determined as $EC_{50}$ for stimulation of the formation of cAMP in a medium containing the human GLP-1 receptor, preferably using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 59.

286. The derivative of any of embodiments 1-285, for which the ratio [GLP-1 receptor binding affinity ($IC_{50}$ in nM) in the presence of 2.0% HSA (high albumin), divided by GLP-1 receptor binding affinity ($IC_{50}$ in nM) in the presence of 0.005% HSA (low albumin)] is:
a) at least 1, preferably at least 10, more preferably at least 20, even more preferably at least 30, or most preferably at least 40;
b) at least 50, preferably at least 60, more preferably at least 70, even more preferably at least 80, or most preferably at least 90;
c) at least 100, preferably at least 200, more preferably at least 300, still more preferably at least 400, even more preferably at least 500, or most preferably at least 600;
d) at least 700, preferably at least 800, more preferably at least 900, still more preferably at least 1000, even more preferably at least 1200, or most preferably at least 1400; or
e) at least 1500, preferably at least 1800, more preferably at least 2000, still more preferably at least 2300, even more preferably at least 2500, or most preferably at least 2800.

287. The derivative of any of embodiments 1-286, for which the GLP-1 receptor binding affinity ($IC_{50}$) in the presence of 0.005% HSA (low albumin) is
a) below 1000 nM, preferably below 500 nM, more preferably below 100 nM, or most preferably below 50 nM;
b) below 10 nM, preferably below 8.0 nM, still more preferably below 6.0 nM, even more preferably below 5.0 nM, or most preferably below 2.00 nM; or
c) below 1.00 nM, preferably below 0.50 nM, even more preferably below 0.25 nM, or most preferably below 0.15 nM.

288. The derivative of any of embodiments 1-287, for which the GLP-1 receptor binding affinity ($IC_{50}$) in the presence of 2.0% HSA (high albumin) is
a) below 1000 nM, preferably below 800 nM;
b) below 700 nM, preferably below 500 nM, more preferably below 300 nM; or
c) below 200 nM, preferably below 100 nM, or more preferably below 50 nM.

289. The derivative of any of embodiments 286-288, wherein the binding affinity to the GLP-1 receptor is measured by way of displacement of $^{125}$I-GLP-1 from the receptor, preferably using a SPA binding assay.

290. The derivative of embodiment 289, wherein the GLP-1 receptor is prepared using a stable, transfected cell line, preferably a hamster cell line, more preferably a baby hamster kidney cell line, such as BHK tk-ts13.

291. The derivative of any of embodiments 286-290, wherein the $IC_{50}$ value is determined as the concentration which displaces 50% of $^{125}$I-GLP-1 from the receptor.

292. The derivative of any of embodiments 1-291, which has an oral bioavailability, preferably an absolute oral bioavailability, which is higher than that of semaglutide.

293. The derivative of any of embodiments 1-292, which has an oral bioavailability, preferably an absolute oral bioavailability, which is higher than that of liraglutide.

294. The derivative of any of embodiments 292-293, wherein oral bioavailability is measured in vivo in rats, as exposure in plasma after direct injection into the intestinal lumen.

295. The derivative of any of embodiments 1-294, for which the plasma concentration (pM) of the derivative, determined 30 minutes after injection of a solution of the derivative in the jejunum of rat, divided by the concentration (μM) of the injected solution (dose-corrected exposure at 30 min) is
a) at least 20, preferably at least 40, more preferably at least 45, even more preferably at least 50, or most preferably at least 60; or
b) at least 70, preferably at least 80, or most preferably at least 100.

296. The derivative of any of embodiments 1-295, for which the plasma concentration (pM) of the derivative, determined 30 minutes after injection of a solution of the derivative in the jejunum of rat, divided by the concentration (μM) of the injected solution (dose-corrected exposure at 30 min) is at least 110, preferably at least 120, more preferably at least 130, still more preferably at least 140, even more preferably at least 150, or most preferably at least 160.

297. The derivative of any of embodiments 1-296, for which the plasma concentration (pM) of the derivative, determined 30 minutes after injection of a solution of the derivative in the jejunum of rat, divided by the concentration (μM) of the injected solution (dose-corrected exposure at 30 min) is at least 180, preferably at least 190, more preferably at least 200, still more preferably at least 210, even more preferably at least 220, or most preferably at least 230.

298. The derivative of any of embodiments 1-297, for which the plasma concentration (pM) of the derivative, determined 30 minutes after injection of a solution of the derivative in the jejunum of rat, divided by the concentration (μM) of the injected solution (dose-corrected exposure at 30 min) is at least 240, preferably at least 250, more preferably at least 260, or most preferably at least 270.

299. The derivative of any of embodiments 292-298, wherein the GLP-1 derivative is tested in a concentration of 1000 uM in a solution of 55 mg/ml sodium caprate.

300. The derivative of any of embodiments 1-294, for which the AUC of the dose-corrected (i.e., divided by the dose in pmol of injected derivative) plasma exposure curve (i.e., concentration in plasma in pM vs time) from time 30 to 180 min is determined (i.e., the result is indicated in (min×pM/pmol) or simply in min/L).

301. The derivative of embodiment 300, wherein the AUC of the dose-corrected plasma exposure curve is
a) at least 50, preferably at least 100, or more preferably at least 150 min/L;
b) at least 200, preferably at least 250, more preferably at least 300, or most preferably at least 320 min/L; or
c) at least 1.5 times, preferably at least 2 times, more preferably at least 3 times, or most preferably at least 4 times the corresponding AUC value for semaglutide.

302. The derivative of any of embodiments 1-293, wherein oral bioavailability is measured in vivo in rats, as exposure in plasma after oral gavage.

303. The derivative of embodiment 302, for which the AUC of the dose-corrected (i.e., divided by the dose in pmol of administered derivative) plasma exposure curve (i.e., concentration in plasma in pM vs time) from time 30 to 180 min is determined (i.e., the result may be indicated in (min×pM/pmol) or simply in min/L).

304. The derivative of embodiment 303, wherein the AUC of the dose-corrected plasma exposure curve is
a) at least 10, preferably at least 20, or more preferably at least 30 min/L;
b) at least 40, preferably at least 50, more preferably at least 60, or most preferably at least 70 min/L; or
c) at least 1.5 times, preferably at least 2 times, more preferably at least 3 times, or most preferably at least 4 times the corresponding AUC value for semaglutide.

305. The derivative of any of embodiments 300-304, wherein the GLP-1 derivative is tested in a concentration of about 1000 uM in a solution of 250 mg/ml of sodium N-[8-(2-hydroxybenzoyl)amino]caprylate (SNAC).

306. The derivative of any of embodiments 292-305, wherein male Sprague Dawley rats are used, preferably with a body weight upon arrival of approximately 240 g.

307. The derivative of any of embodiments 292-306, wherein the rats are fasted for approximately 18 hours before the experiment.

308. The derivative of any of embodiments 292-307, wherein the rats are and taken into general anaesthesia after having fasted and before the injection of the derivative in the jejunum, or the oral gavage, respectively.

309. The derivative of any of embodiments 292-308, wherein for injection in the intestinal lumen the derivative is administered in the proximal part of the jejunum (10 cm distal for the duodenum) or in the mid-intestine (50 cm proximal for the cecum), preferably in the proximal part of the jejunum.

310. The derivative of any of embodiments 292-309, wherein 100 μl of the derivative is injected into the jejunal lumen through a catheter with a 1 ml syringe, and subsequently 200 μl of air is pushed into the jejunal lumen with another syringe, which is then left connected to the catheter to prevent flow back into the catheter.

311. The derivative of any of embodiments 292-310, wherein blood samples (200 ul) are collected into EDTA tubes from the tail vein at desired intervals, such as at times 0, 10, 30, 60, 120 and 240 min, and centrifuged 5 minutes, 10000G, at 4° C. within 20 minutes.

312. The derivative of any of embodiments 292-311, wherein plasma (e.g. 75 ul) is separated, immediately frozen, and kept at −20° C. until analyzed for plasma concentration of the derivative.

313. The derivative of any of embodiments 292-312, wherein LOCI (Luminescent Oxygen Channeling Immunoassay) is used for analyzing the plasma concentration of the derivative.

314. The derivative of any of embodiments 1-313, wherein the derivative is effective at lowering blood glucose in vivo in db/db mice.

315. The derivative of any of embodiments 1-314, wherein the derivative is effective at lowering body weight in vivo in db/db mice.

316. The derivative of any of embodiments 314-316, wherein db/db mice are treated, s.c., with a suitable range of doses of the GLP-1 derivative, and blood glucose and/or bodyweight is/are determined at appropriate intervals.

317. The derivative of any of embodiments 313-316, wherein the dose of the GLP-1 derivative is 0.3 nmol/kg, 1.0 nmol/kg, 3.0 nmol/kg, 10 nmol/kg, 30 nmol/kg, and 100 nmol/kg, wherein kg refers to the body weight of the mouse.

318. The derivative of any of embodiments 313-317, wherein a control group is treated with vehicle, s.c., preferably the medium in which the GLP-1 derivative is dissolved, e.g. with the following composition: 50 mM sodium phosphate, 145 mM sodium chloride, 0.05% tween 80, pH 7.4.

319. The derivative of any of embodiments 313-318, wherein blood glucose is determined, and/or the mice are weighed, at time−½ h (half an hour prior to dosing (t=0)), and at times 1, 2, 4, and 8 h.

320. The derivative of any of embodiments 313-319, wherein the glucose concentration is measured using the glucose oxidase method.

321. The derivative of any of embodiments 313-320, wherein
(i) $ED_{50}$ (body weight (BW)) is calculated as the dose giving rise to half-maximum effect on delta (e.g., decrease) BW 8 hours following the subcutaneous administration of the derivative; and/or
(ii) $ED_{50}$ (blood glucose (BG)) is calculated as the dose giving rise to half-maximum effect on AUC (Area Under the Curve) delta (e.g., decrease) BG 8 hours and/or 24 hours following the subcutaneous administration of the analogue.

322. The derivative of any of embodiments 313-321, wherein a sigmoidal dose-response relationship exists, preferably with a clear definition of the maximum response.

323. The derivative of any of embodiments 313-322, wherein $ED_{50}$ (BG) 8 hours is below 5.0 nmol/kg, preferably below 4.0 nmol/kg, more preferably below 3.0 nmol/kg, even more preferably below 2.0 nmol/kg, or most preferably below 1.0 nmol/kg.

324. The derivative of any of embodiments 313-323, wherein $ED_{50}$ (BW) 8 hours is
a) below 10, nmol/kg, preferably below 8 nmol/kg, even more preferably below 6.0 nmol/kg, or most preferably below 5.0 nmol/kg; or
b) below 4.0 nmol/kg, preferably below 3.0 nmol/kg, even more preferably below 2.0 nmol/kg, or most preferably below 1.0 nmol/kg.

325. The derivative of any of embodiments 1-324 which, in a PD study in pigs, reduces food intake on day 1, 2, 3, and/or 4 after s.c. administration of a single dose of the derivative, as compared to a vehicle-treated control group.

326. The derivative of embodiment 325, wherein the study is conducted and the data compiled and analysed as described in Example 64.

327. The derivative of any of embodiments 1-326, which has a more protracted profile of action than liraglutide.

328. The derivative of embodiment 327, wherein protraction means half-life in vivo in a relevant animal species, such as db/db mice, rat, pig, and/or, preferably, minipig; wherein the derivative is administered i) s.c., and/or, ii) i.v.; preferably ii) i.v.

329. The derivative of any of embodiments 1-328, wherein the terminal half-life ($T_{1/2}$) after i.v. administration in rat is higher than that of semaglutide.

330. The derivative of any of embodiments 1-329, wherein the terminal half-life ($T_{1/2}$) after i.v. administration in rat is at least twice the terminal half-life of semaglutide.

331. The derivative of any of embodiments 1-330, wherein the terminal half-life ($T_{1/2}$) after i.v. administration in rat is at least three times the terminal half-life of semaglutide.

332. The derivative of any of embodiments 1-331, wherein the terminal half-life ($T_{1/2}$) after i.v. administration in rat is at least four times the terminal half-life of semaglutide.

333. The derivative of any of embodiments 1-332, wherein the terminal half-life ($T_{1/2}$) after i.v. administration in rat is at least five times the terminal half-life of semaglutide.

334. The derivative of any of embodiments 1-333, wherein the half-life is determined in in vivo pharmacokinetic studies in rat, for example as described in Example 65.

335. The derivative of any of embodiments 1-334, wherein the terminal half-life ($T_{1/2}$) after i.v. administration in minipigs is
a) at least 8 hours, preferably at least 16 hours, more preferably at least 24 hours, even more preferably at least 32 hours, or most preferably at least 40 hours; or
b) at least 50 hours, preferably at least 58 hours, more preferably at least 70 hours, even more preferably at least 80 hours, or most preferably at least 84 hours.

336. The derivative of embodiment 335, wherein the minipigs are male Göttingen minipigs.

337. The derivative of any of embodiments 335-336, wherein the minipigs are 7-14 months of age, and preferably weighing from 16-35 kg.

338. The derivative of any of embodiments 335-337, wherein the minipigs are housed individually, and fed once or twice daily, preferably with SDS minipig diet.

339. The derivative of any of embodiments 335-338, wherein the derivative is dosed, i.v., after at least 2 weeks of acclimatization.

340. The derivative of any of embodiments 335-339, wherein the animals are fasted for approximately 18 h before dosing and for at least 4 h after dosing, and have ad libitum access to water during the whole period.

341. The derivative of any of embodiments 335-340, wherein the GLP-1 derivative is dissolved in 50 mM sodium phosphate, 145 mM sodium chloride, 0.05% tween 80, pH 7.4 to a suitable concentration, preferably from 20-60 nmol/ml.

342. The derivative of any of embodiments 335-341, wherein intravenous injections of the derivative are given in a volume corresponding to 1-2 nmol/kg.

343. An intermediate product in the form of a GLP-1 analogue which comprises the following changes as compared to GLP-1(7-37) (SEQ ID NO: 1): (a) 7Imp, 8Aib, 18K, 22E, 34Q (SEQ ID NO: 5); (b) 7Imp, 18K, 22E 25V, 26R, 31K, 34R(SEQ ID NO: 6); or (c) 8Aib, 18K, 19Q, 22E, 34Q (SEQ ID NO: 7); or a pharmaceutically acceptable salt, amide, or ester of any of the analogues of (a)-(c).

344. An intermediate product in the form of a GLP-1 analogue selected from the following analogues of GLP-1(7-37) (SEQ ID NO: 1): (a) 7Imp, 8Aib, 18K, 22E, 34Q (SEQ ID NO: 5); (b) 7Imp, 18K, 22E 25V, 26R, 31K, 34R(SEQ ID NO: 6); or (c) 8Aib, 18K, 19Q, 22E, 34Q (SEQ ID NO: 7); or a pharmaceutically acceptable salt, amide, or ester of any of the analogues of (a)-(c).

345. The analogue of any of embodiments 343-344, which comprises a C-terminal amide.

346. The analogue of any of embodiments 343-345, wherein a carboxylic acid group of the C-terminal amino acid of the analogue is converted into carboxylic acid amide.

347. The analogue of embodiment 346, wherein the carboxylic acid group which is converted into carboxylic acid amide is not in the side chain of the C-terminal amino acid.

348. The analogue of any of embodiments 343-344, which comprises a C-terminal carboxylic acid.

349. The analogue of any of embodiments 343-348, wherein the comparison with GLP-1(7-37) (SEQ ID NO: 1) is made by handwriting and eyeballing.

350. The analogue of any of embodiments 343-349, wherein the comparison with GLP-1(7-37) (SEQ ID NO: 1) is made by use of a standard protein or peptide alignment program.

351. The analogue of embodiment 350, wherein the alignment program is a Needleman-Wunsch alignment.

352. The analogue of any of embodiments 350-351, wherein the default scoring matrix and the default identity matrix is used.

353. The analogue of any of embodiments 350-352, wherein the scoring matrix is BLOSUM62.

354. The analogue of any of embodiments 350-353, wherein the penalty for the first residue in a gap is −10 (minus ten).

355. The analogue of any of embodiments 350-354, wherein the penalties for additional residues in a gap is −0.5 (minus point five).

356. A derivative according to any of embodiments 1-342, for use as a medicament.

357. A derivative according to any of embodiments 1-342, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving 1-cell function, and/or for delaying or preventing diabetic disease progression.

358. Use of a derivative according to any of embodiments 1-342 in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

359. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a derivative according to any of embodiments 1-342.

Additional Particular Embodiments

The following (A) are additional particular embodiments of the invention:

A

1. A derivative of a GLP-1 analogue, which analogue comprises a first K residue at a position corresponding to position 18 of GLP-1(7-37) (SEQ ID NO: 1), a second K residue at another position, and a maximum of twelve amino acid modifications as compared to GLP-1(7-37), which derivative comprises two protracting moieties attached to said first and second K residue, respectively, via a linker, wherein the protracting moiety is selected from Chem. A, Chem. B, and Chem. C:

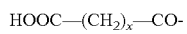  Chem. A

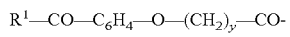  Chem. B

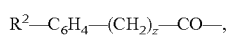  Chem. C in which x is an integer in the range of 6-18, y is an integer in the range of 3-11, z is an integer in the range of 1-5, $R^1$— is —OH, and $R^2$ is a group having a molar mass not higher than 150 Da; and the linker comprises

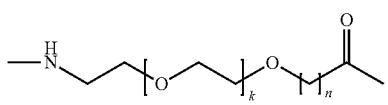  Chem. D wherein k is an integer in the range of 1-5, and n is an integer in the range of 1-5; or a pharmaceutically acceptable salt, amide, or ester thereof.

2. The derivative of embodiment 1, wherein Chem. D is a first linker element.

3. The derivative of any one of embodiments 1-2, wherein k is 1.

4. The derivative of any one of embodiments 1-3, wherein n is 1.

5. The derivative of any one of embodiments 1-4, wherein Chem. D is included m times, wherein m is an integer in the range of 1-10.

6. The derivative of embodiment 5, wherein m is an integer in the range of 1-6; preferably m is 1, 2, 4, or 6; more preferably m is 1, 2, or 4; even more preferably m is 1 or 4; or most preferably m is 2.

7. The derivative of any one of embodiments 5-6, wherein, when m is different from 1, the Chem. 4 elements are interconnected via amide bond(s).

8. The derivative of any one of embodiments 1-7, wherein the linker further comprises a second linker element.

9. The derivative of embodiment 8, wherein the second linker element is

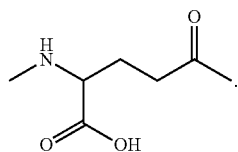  Chem. E

10. The derivative of embodiment 9, wherein Chem. E is included p times, wherein p is an integer in the range of 1-3.
11. The derivative of embodiment 10, wherein p is 1, 2, or 3; preferably 2 or 3, or most preferably 1.
12. The derivative of any one of embodiments 9-11, wherein Chem. E is a radical of L-Glu or D-Glu, preferably of L-Glu.
13. The derivative of any one of embodiments 10-12, wherein, when p is different from 1, the Chem. E elements are interconnected via amide bond(s).
14. The derivative of any one of embodiments 1-13, wherein the linker further comprises a third linker element.
15. The derivative of embodiment 14, wherein the third linker element is

  Chem. F in which q is an integer in the range of 2-12, and $R^3$ is amino ($NH_2$).
16. The derivative of embodiment 15, wherein q is 4, 6, or 10.
17. The derivative of any one of embodiments 15-16, wherein Chem. F is a radical of lysine.
18. The derivative of embodiment 17, wherein the radicalised amino group is at the epsilon position.

Still Further Additional Particular Embodiments

The following (B) are still further additional particular embodiments of the invention:

B

8. A derivative of a GLP-1 analogue, which analogue comprises a first K residue at a position corresponding to position 18 of GLP-1(7-37) (SEQ ID NO: 1), a second K residue at another position, and a maximum of twelve amino acid changes as compared to GLP-1(7-37), which derivative comprises two protracting moieties attached to said first and second K residue, respectively, via a linker, wherein the protracting moiety is selected from Chem. A, Chem. B, and Chem. C:

  Chem. A

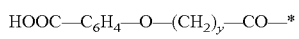  Chem. B

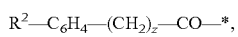  Chem. C in which x is an integer in the range of 6-18, y is an integer in the range of 3-17, z is an integer in the range of 1-5, and $R^2$ is a group having a molar mass not higher than 150 Da; and the linker comprises

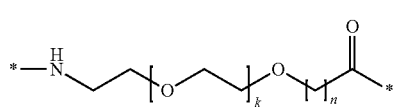  Chem. D wherein k is an integer in the range of 1-5, and n is an integer in the range of 1-5; or a pharmaceutically acceptable salt, amide, or ester thereof.

9. The derivative of any of embodiments 1, and 4-8, wherein Chem. D is a first linker element.
10. The derivative of embodiment 9, wherein k is 1.
11. The derivative of any of embodiments 9-10, wherein n is 1.
12. The derivative of any of embodiments 9-11, wherein Chem. D is included m times, wherein m is an integer in the range of 1-10.
13. The derivative of embodiment 12, wherein m is an integer in the range of 1-6.
14. The derivative of any of embodiments 12-13, wherein m is 1, 2, 4, or 6.
15. The derivative of any of embodiments 12-14, wherein m is 1.
16. The derivative of any of embodiments 12-14, wherein m is 2.
17. The derivative of any of embodiments 12-14, wherein m is 4.
18. The derivative of any of embodiments 12-14, wherein m is 6.
19. The derivative of any of embodiments 12-14, and 16-18, wherein, when m is different from 1, the Chem. D elements are interconnected via amide bond(s).
20. The derivative of any of embodiments 8-19, wherein the linker comprises a second, optional, linker element.
21. The derivative of embodiment 20, wherein the second linker element is selected from Chem. E1 and Chem. E2:

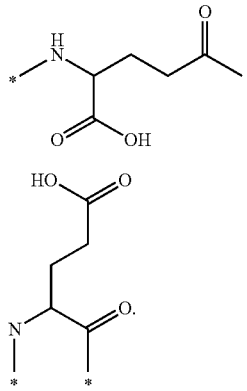

Chem. E1

Chem. E2

22. The derivative of any of embodiments 20-21, wherein the second linker element is Chem. E1.
23. The derivative of embodiment 22, wherein Chem. E1 is included p times, wherein p is 0, or an integer in the range of 1-3.
24. The derivative of embodiment 23, wherein p is 0.
25. The derivative of embodiment 23, wherein p is 1.
26. The derivative of embodiment 23, wherein p is 2.
27. The derivative of embodiment 23, wherein p is 3.
28. The derivative any of embodiments 21-27, wherein Chem. E1 is a di-radical of L-Glu or D-Glu.
29. The derivative of embodiment 28, wherein Chem. E1 is a di-radical of L-Glu.
30. The derivative of any of embodiments 23-29, wherein, when p is different from 0 and different from 1, the Chem. E1 elements are interconnected via amide bond(s).
31. The derivative of any of embodiments 23-30, wherein the linker comprises a third, optional, linker element.

32. The derivative of embodiment 31, wherein the third linker element is $$*-NH-(CH_2)_q-CHR^3-CO-*, \qquad \text{Chem. F}$$

in which q is an integer in the range of 2-12, and $R^3$ is amino ($NH_2$).
33. The derivative of embodiment 32, wherein q is 4.
34. The derivative of embodiment 32, wherein q is 6.
35. The derivative of embodiment 32, wherein q is 10.
37. The derivative of any of embodiments 32-35, wherein $R^3$ is amino ($NH_2$).
38. The derivative of any of embodiments 32-37, wherein Chem. F is a di-radical of lysine.

The combination of any of the above A or B embodiments with any of the PARTICULAR EMBODIMENTS 1-359 listed hereinabove is hereby specifically incorporated by reference.

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods).

The examples serve to illustrate the invention.

LIST OF ABBREVIATIONS

Aib: α-aminoisobutyric acid
API: Active Pharmaceutical Ingredient
AUC: Area Under the Curve
BG: Blood Glucose
BHK Baby Hamster Kidney
BW: Body Weight
Boc: t-butyloxycarbonyl
Bom: benzyloxymethyl
BSA: Bovine serum albumin
Bzl: benzyl
CAS: Chemical Abstracts Service
Clt: 2-chlorotrityl
collidine: 2,4,6-trimethylpyridine
DCM: dichloromethane
Dde: 1-(4,4-dimethyl-2,6-dioxocyclohexylidene)ethyl
DesH: des-amino histidine (may also be referred to as imidazopropionic acid, Imp)
DIC: diisopropylcarbodiimide
DIPEA: diisopropylethylamine
DMEM: Dulbecco's Modified Eagle's Medium (DMEM)
EDTA: ethylenediaminetetraacetic acid
EGTA: ethylene glycol tetraacetic acid
FCS: Fetal Calf Serum
Fmoc: 9-fluorenylmethyloxycarbonyl
HATU: (O-(7-azabenzotriazol-1-yl)-1,1,3,3-tetramethyluronium hexafluorophosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
HPLC: High Performance Liquid Chromatography HSA: Human Serum Albumin
IBMX: 3-isobutyl-1-methylxanthine
Imp: Imidazopropionic acid (also referred to as des-amino histidine, DesH)
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: methanol
Mmt: 4-methoxytrityl
Mtt: 4-methyltrityl
NMP: N-methyl pyrrolidone
OBz: benzoyl ester
OEG: 8-amino-3,6-dioxaoctanic acid
OPfp: pentafluorophenoxy
OPnp: para-nitrophenoxy
OSu: O-succinimidyl esters (hydroxysuccinimide esters)
OtBu: tert butyl ester
Pbf: 2,2,4,6,7-pentamethyldihydrobenzofuran-5-sulfonyl
PBS: Phosphate Buffered Saline
PD: Pharmacodynamic
Pen/Strep: Penicillin/Streptomycin
PK: Pharmacokinetic
RP: Reverse Phase
RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquid Chromatography
SEM: Standard Error of Mean
SPA: Scintillation Proximity Assay
SPPS: Solid Phase Peptide Synthesis
tBu: tert. butyl
TFA: trifluoroacetic acid
TIS: triisopropylsilane
TLC: Thin Layer Chromatography
Tos: tosylate (or pare-toluenesulfonyl)
Tris: tris(hydroxymethyl)aminomethane or 2-amino-2-hydroxymethyl-propane-1,3-diol
Trt: triphenylmethyl (trityl)
Trx: tranexamic acid
UPLC: Ultra Performance Liquid Chromatography
Materials and Methods
Materials
N-α,N-β-Di-Fmoc-L-2,3-Diaminopropionic Acid (CAS 201473-90-7)
3,5-Di-tert-butyl-4-hydroxybenzoic acid (CAS 1421-49-4)
3,5-Di-tert-butylbenzoic Acid (CAS 16225-26-6)
Fmoc-8-amino-3,6-dioxaoctanoic acid (CAS 166108-71-0)
17-(9-Fluorenylmethyloxycarbonyl-amino)-9-aza-3,6,12,15-tetraoxa-10-on-heptadecanoic acid (IRIS Biotech GmbH)
Fmoc-L-Glutamic acid 1-tert-butyl ester (CAS 84793-07-7)
2-(2-Methoxyethoxy)acetic acid (CAS 16024-56-9)
N-α,N-ε-Bis(9-fluorenylmethyloxycarbonyl)-L-lysine (CAS 78081-87-5)
1-[(9H-fluoren-9-ylmethoxy)carbonyl]piperidine-4-carboxylic acid (CAS 148928-15-8)
FMOC-8-Aminocapryl acid (CAS 126631-93-4)
4-Phenylbutyric acid (CAS 1716-12-7)
4-(4-Nitrophenyl)butyric acid (CAS 5600-62-4)
4-(4-Chlorophenyl)butyric acid (CAS 4619-18-5)
FMOC-6-Aminohexanoic acid (CAS 88574-06-5)
FMOC-12-Aminododecanoic acid (CAS 128917-74-8)
4-(9-carboxy-nonyloxy)-benzoic acid tert-butyl ester (prepared as described in Example 25, step 1 and 2 of WO 2006/082204)
4-(8-Carboxy-octyloxy)-benzoic acid tert-butyl ester (M.p.: 71-72° C.
$^1$H NMR (300 MHz, CDCl$_3$, δ$_H$): 7.93 (d, J=8.9 Hz, 2H); 6.88 (d, J=8.9 Hz, 2H); 4.00 (t, J=6.4 Hz, 2H); 2.36 (t, J=7.4 Hz, 2H); 1.80 (m, 2H); 1.65 (m, 2H); 1.59 (s, 9H); 1.53-1.30 (m, 8H) (prepared as described in Example 25, step 1 and 2 of WO 2006/082204, replacing methyl 10-bromodecanoate with ethyl 9-Bromononanoate (CAS 28598-81-4))
4-(7-Carboxy-heptyloxy)-benzoic acid tert-butyl ester ($^1$H NMR spectrum (300 MHz, CDCl$_3$, δ$_H$): 7.93 (d, J=9.0 Hz, 2H); 6.88 (d, J=9.0 Hz, 2H); 4.00 (t, J=6.5 Hz, 2H); 2.37 (t, J=7.4 Hz, 2H); 1.80 (m, 2H); 1.64 (m, 2H); 1.59 (s, 9H); 1.53-1.33 (m, 6H)) (prepared as described in Example 25, step 1 and 2 of WO 2006/082204, replacing methyl 10-bromodecanoate with ethyl 7-bromoheptanoate (CAS 29823-18-5))
Chemical Methods
This section is divided in two: Section A relating to general methods (of preparation (A1); and of detection and characterisation (A2)), and section B, in which the preparation and characterisation of a number of specific example compounds is described.

A. General Methods

A1. Methods of Preparation

This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci. 5, 403). The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g. Anaspec, Bachem, Iris Biotech, or Novabiochem. Were nothing else is specified the natural L-form of the amino acids are used. The N-terminal amino acid was Boc protected at the alpha amino group (e.g. Boc-His(Boc)-OH, or Boc-His(Trt)-OH for peptides with His at the N-terminus). In case of modular albumin binding moiety attachment using SPPS the following suitably protected building blocks such as but not limited to Fmoc-8-amino-3,6-dioxaoctanoic acid, Fmoc-tranexamic acid, Fmoc-Glu-OtBu, octadecanedioic acid mono-tert-butyl ester, nonadecanedioic acid mono-tert-butyl ester, tetradecanedioic acid mono-tert-butyl ester, or 4-(9-carboxynonyloxy)benzoic acid tert-butyl ester were used. All operations stated below were performed at 250-pmol synthesis scale.

1. Synthesis of Resin Bound Protected Peptide Backbone

Method: SPPS_P

SPPS_P was performed on a Prelude Solid Phase Peptide Synthesizer from Protein Technologies (Tucson, Ariz. 85714 U.S.A.) at 250-μmol scale using six fold excess of Fmoc-amino acids (300 mM in NMP with 300 mM HOAt) relative to resin loading, e.g. low load Fmoc-Gly-Wang (0.35 mmol/g). Fmoc-deprotection was performed using 20% piperidine in NMP. Coupling was performed using 3:3:3:4 amino acid/HOAt/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH were "double coupled", meaning that after the first coupling (e.g. 60 min), the resin is drained and more reagents are added (amino acid, HOAt, DIC, and collidine), and the mixture allowed to react again (e.g. 60 min).

Method: SPPS_L

SPPS_L was performed on a microwave-based Liberty peptide synthesiser from CEM Corp. (Matthews, N.C. 28106, U.S.A.) at 250-μmol or 100-μmol scale using six fold excess of Fmoc-amino acids (300 mM in NMP with 300 mM HOAt) relative to resin loading, e.g. low load Fmoc-Gly-Wang (0.35 mmol/g). Fmoc-deprotection was performed using 5% piperidine in NMP at up to 75° C. for 30 seconds where after the resin was drained and washed with NMP and the Fmoc-deprotection was repeated this time for 2 minutes at 75° C. Coupling was performed using 1:1:1 amino acid/HOAt/DIC in NMP. Coupling times and temperatures were generally 5 minutes at up to 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 minutes and then heated to 75° C. for 5 min. Some amino acids such as but not limited to Aib, were "double coupled", meaning that after the first coupling (e.g. 5 min at 75° C.), the resin is drained and more reagents are added (amino acid, HOAt and DIC), and the mixture is heated again (e.g. 5 min at 75° C.). NMP washes (5×10 ml) were performed between deprotection and coupling steps.

Method: SPPS_A

The protected peptidyl resin was synthesised according to the Fmoc strategy on an Applied Biosystems 433 peptide synthesiser in a 250-μmol or 1000 μmol scale with three or four fold excess of Fmoc-amino acids, using the manufacturer supplied FastMoc UV protocols which employ HBTU (2-(1H-Benzotriazol-1-yl-)-1,1,3,3 tetramethyluronium hexafluorophosphate) or HATU (O-(7-azabenzotriazol-1-yl)-1,1,3,3-tetramethyluronium hexafluorophosphate) mediated couplings in NMP and UV monitoring of the deprotection of the Fmoc protection group, in some cases double couplings were used, meaning that after the first coupling, the resin is drained and more Fmoc-amino acids and reagents are added. The starting resin used for the synthesis of the peptide amides was Rink-Amide resin and either preloaded Wang (e.g. low load Fmoc-Gly-Wang or Fmoc-Lys(Mtt)-wang) or chlorotrityl resin for peptides with a carboxy C-terminal. The protected amino acid derivatives used were standard Fmoc-amino acids (supplied from e.g. Anaspec, or Novabiochem) supplied in preweighed cartridges suitable for the ABI433A synthesiser with the exception of unnatural aminoacids such as Fmoc-Aib-OH (Fmoc-aminoisobutyric acid). The N terminal amino acid was Boc protected at the alpha amino group (e.g. Boc-His(Boc)-OH or Boc-His(Trt)-OH was used for peptides with His at the N-terminal). The epsilon amino group of lysines in the sequence were either protected with Mtt, Mmt, Dde, ivDde, or Boc, depending on the route for attachment of the albumin binding moiety and spacer. The synthesis of the peptides may in some cases be improved by the use of dipeptides protected on the dipeptide amide bond with a group that can be cleaved under acidic conditions such but not limited to 2-Fmoc-oxy-4-methoxybenzyl or 2,4,6-trimethoxybenzyl. In cases where a serine or a threonine is present in the peptide, the use of pseudoproline dipeptides may be used (see e.g. catalogue from Novobiochem 2009/2010 or newer version, or W. R. Sampson (1999), J. Pep. Sci. 5, 403).

Method: SPPS_M

SPPS_M refers to synthesis of the protected peptidyl resin using manual Fmoc chemistry. The coupling chemistry was DIC/HOAt/collidine in NMP at a 4-10 fold molar excess. Coupling conditions were 1-6 h at room temperature. Fmoc-deprotection was performed with 20-25% piperidine in NMP (3×20 ml, each 10 min) followed by NMP washings (4×20 mL).

2. Synthesis of Side Chains

Mono Esters of Fatty Diacids

Overnight reflux of the C8, C10, C12, C14, C16 and C18 diacids with Boc-anhydride DMAP t-butanol in toluene gives predominately the t-butyl mono ester. Obtained is after work-up a mixture of mono acid, diacid and diester. Purification is carried out by washing, short plug silica filtration and crystallisation.

3. Attachment of Side Chains to Resin Bound Protected Peptide Backbone

When an acylation is present on a lysine side chain, the epsilon amino group of lysine to be acylated was protected with either Mtt, Mmt, Dde, ivDde, or Boc, depending on the route for attachment of the protracting moiety and linker. Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with hexafluoroisopropanol/DCM (75:25, 5×20 ml, each 10 min) followed by washings as above. In some cases the Mtt group was removed by automated steps on the Liberty peptide synthesiser. Mtt deprotection was performed with hexafluoroisopropanol or hexafluoroisopropanol/DCM (75:25) at room temperature for 30 min followed by washing with DCM (7 ml×5), followed by NMP washings (7 ml×5). The protracting moiety and/or linker can be attached to the peptide either by acylation of the resin bound peptide or by acylation in solution of the unprotected peptide. In case of attachment of the protracting moiety and/or linker to the protected peptidyl resin the attachment can be modular using SPPS and suitably protected building blocks.

Method: SC_P

The N-ε-lysine protection group was removed as described above and the chemical modification of the lysine was performed by one or more automated steps on the Prelude peptide synthesiser using suitably protected building blocks as described above. Double couplings were performed as described in SPPS_P with 3 hours per coupling.

Method: SC_L

The N-ε-lysine protection group was removed as described above and the chemical modification of the lysine was performed by one or more automated steps on the Liberty peptide synthesiser using suitably protected building blocks as described above. Double couplings were performed as described in SPPS_L.

Method: SC_A

The N-ε-lysine protection group was removed as described above and the chemical modification of the lysine was performed by one or more automated steps on the ABI peptide synthesiser using suitably protected building blocks as described in SPPS_A.

Method: SC_M1

The N-ε-lysine protection group was removed as described above. Activated (active ester or symmetric anhydride) protracting moiety or linker such as octadecanedioic acid mono-(2,5-dioxo-pyrrolidin-1-yl) ester (Ebashi et al. EP511600, 4 molar equivalents relative to resin bound peptide) was dissolved in NMP (25 mL), added to the resin and shaken overnight at room temperature. The reaction mixture was filtered and the resin was washed extensively with NMP, DCM, 2-propanol, methanol and diethyl ether.

Method: SC_M2

The N-ε-lysine protection group was removed as described above. The protracting moiety was dissolved in NMP/DCM (1:1, 10 ml). The activating reagent such as HOBt (4 molar equivalents relative to resin) and DIC (4 molar equivalents relative to resin) was added and the solution was stirred for 15 min. The solution was added to the resin and DIPEA (4 molar equivalents relative to resin) was added. The resin was shaken 2 to 24 hours at room temperature. The resin was washed with NMP (2×20 ml), NMP/DCM (1:1, 2×20 ml) and DCM (2×20 ml).

Method: SC_M3

Activated (active ester or symmetric anhydride) protracting moiety or linker such as octadecanedioic acid mono-(2,5-dioxo-pyrrolidin-1-yl) ester (Ebashi et al. EP511600) 1-1.5 molar equivalents relative to the peptide was dissolved in an organic solvent such as acetonitrile, THF, DMF, DMSO or in a mixture of water/organic solvent (1-2 ml) and added to a solution of the peptide in water (10-20 ml) together with 10 molar equivalents of DIPEA. In case of protecting groups on the protracting moiety such as tert-butyl, the reaction mixture was lyophilised overnight and the isolated crude peptide deprotected afterwards. In case of tert-butyl protection groups the deprotection was performed by dissolving the peptide in a mixture of trifluoroacetic acid, water and triisopropylsilane (90:5:5). After 30 min the mixture was evaporated in vacuo and the crude peptide purified by preparative HPLC as described later.

4. Cleavage of Resin Bound Peptide with or without Attached Side Chains and Purification Method: CP_M1

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 µM column, using acetonitrile/water/TFA. The fractions were analysed by a combination of UPLC, MALDI and LCMS methods, and the appropriate fractions were pooled and lyophilised.

Method: CP_L1

After synthesis the resin was washed with DCM, and the peptide was cleaved from the resin by the use of a CEM Accent Microwave Cleavage System (CEM Corp., North Carolina). Cleavage from the resin was performed at 38° C. for 30 minutes by the treatment with TFA/TIS/water (95/2.5/2.5) followed by precipitation with diethylether. The peptide was dissolved in a suitable solvent (such as, e.g., 30% acetic acid) and purified by standard RP-HPLC on a C18, 5 µM column, using acetonitrile/water/TFA. The fractions were analysed by a combination of UPLC, MALDI and LCMS methods, and the appropriate fractions were pooled and lyophilized.

A2. General Methods for Detection and Characterisation

1. LC-MS Methods

Method: LCMS_1

An Agilent Technologies LC/MSD TOF (G1969A) mass spectrometer was used to identify the mass of the sample after elution from an Agilent 1200 series HPLC system. The deconvolution of the protein spectra was calculated with Agilent's protein confirmation software. Eluents: A: 0.1% Trifluoro acetic acid in water; B: 0.1% Trifluoro acetic acid in acetonitrile. Column: Zorbax 5u, 300SB-C3, 4.8×50 mm. Gradient: 25%-95% B over 15 min.

Method: LCMS_2

A Perkin Elmer Sciex API 3000 mass spectrometer was used to identify the mass of the sample after elution from a Perkin Elmer Series 200 HPLC system. Eluents: A: 0.05% Trifluoro acetic acid in water; B: 0.05% Trifluoro acetic acid in acetonitrile. Column: Waters Xterra MS C-18×3 mm id 5 µm. Gradient: 5%-90% B over 7.5 min at 1.5 ml/min.

Method: LCMS_3

A Waters Micromass ZQ mass spectrometer was used to identify the mass of the sample after elution from a Waters Alliance HT HPLC system. Eluents: A: 0.1% Trifluoro acetic acid in water; B: 0.1% Trifluoro acetic acid in acetonitrile. Column: Phenomenex, Jupiter C4 50×4.60 mm id 5 µm. Gradient: 10%-90% B over 7.5 min at 1.0 ml/min.

Method: LCMS_4

LCMS_4 was performed on a setup consisting of Waters Acquity UPLC system and LCT Premier XE mass spectrometer from Micromass. Eluents: A: 0.1% Formic acid in water B: 0.1% Formic acid in acetonitrile The analysis was performed at RT by injecting an appropriate volume of the sample (preferably 2-10 µl) onto the column which was eluted with a gradient of A and B. The UPLC conditions, detector settings and mass spectrometer settings were: Column: Waters Acquity UPLC BEH, C-18, 1.7 µm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES Scan: 100-2000 amu (alternatively 500-2000 amu), step 0.1 amu.

Method: LCMS_AP

A Micromass Quatro micro API mass spectrometer was used to identify the mass of the sample after elution from a HPLC system composed of Waters 2525 binary gradient module, Waters 2767 sample manager, Waters 2996 Photodiode Array Detector and Waters 2420 ELS Detector. Eluents: A: 0.1% Trifluoro acetic acid in water; B: 0.1% Trifluoro acetic acid in acetonitrile. Column: Phenomenex Synergi MAXRP, 4 um, 75×4.6 mm. Gradient: 5%-95% B over 7 min at 1.0 ml/min.

2. UPLC Methods

Method: B5_1

The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 60% A, 40% B to 30% A, 70% B over 8 minutes at a flow-rate of 0.40 ml/min.

Method: B7_1

The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 80% A, 20% B 15 to 40% A, 60% B over 8 minutes at a flow-rate of 0.40 ml/min.

Method: B9_1

The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 70% A, 30% B to 20% A, 80% B over 8 minutes at a flow-rate of 0.40 ml/min.

Method: A2_1

The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 90% $H_2O$, 10% $CH_3CN$, 0.25 M ammonium bicarbonate; B: 70% $CH_3CN$, 30% $H_2O$. The following linear gradient was used: 90% A, 10% B to 60% A, 40% B over 16 minutes at a flow-rate of 0.40 ml/min.

Method: A3_1

The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 90% $H_2O$, 10% $CH_3CN$, 0.25 M ammonium bicarbonate; B: 70% $CH_3CN$, 30% $H_2O$. The following linear gradient was used: 75% A, 25% B to 45% A, 55% B over 16 minutes at a flow-rate of 0.40 ml/min.

Method: A4_1

The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 90% $H_2O$, 10% $CH_3CN$, 0.25 M ammonium bicarbonate; B: 70% $CH_3CN$, 30% $H_2O$. The following linear gradient was used: 65% A, 35% B to 25% A, 65% B over 16 minutes at a flow-rate of 0.40 ml/min.

Method: A6_1

The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 10 mM TRIS, 15 mM ammonium sulphate, 80% $H_2O$, 20% $CH_3CN$, pH 7.3; B: 80% $CH_3CN$, 20% $H_2O$. The following linear gradient was used: 95% A, 5% B to 10% A, 90% B over 16 minutes at a flow-rate of 0.35 ml/min.

Method: A7_1

The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 10 mM TRIS, 15 mM ammonium sulphate, 80% $H_2O$, 20% $CH_3CN$, pH 7.3; B: 80% $CH_3CN$, 20% $H_2O$. The following linear gradient was used: 95% A, 5% B to 40% A, 60% B over 16 minutes at a flow-rate of 0.40 ml/min.

Method: B2_1

The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 40% A, 60% B over 16 minutes at a flow-rate of 0.40 ml/min.

Method: B4_1

The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 95% A, 5% B over 16 minutes at a flow-rate of 0.40 ml/min.

Method: B10_1

The RP-analyses was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 40% A, 60% B to 20% A, 80% B over 8 minutes at a flow-rate of 0.40 ml/min.

Method: B14_1

The RP-analyses was performed using a Waters UPLC system fitted with a dual band detector. UV detections at 214 nm and 254 nm were collected using an ACQUITY UPLC BEH ShieldRP 18, 1.7 um, 2.1 mm×150 mm column, 50° C. The UPLC system was connected to two eluent reservoirs containing: A: 99.95% $H_2O$, 0.05% TFA; B: 99.95% $CH_3CN$, 0.05% TFA. The following linear gradient was used: 70% A, 30% B to 40% A, 60% B over 12 minutes at a flow-rate of 0.40 ml/min.

Method: B8_1

The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 50% A, 50% B to 20% A, 80% B over 8 minutes at a flow-rate of 0.40 ml/min.

Method: B29_1

The RP-analysis was performed using a Waters UPLC system fitted with a dual band detector. UV detections at 215 nm and 254 nm were collected using an kinetex 1.7u C18, 100A 2.1×150 mm column, 60° C. The UPLC system was connected to two eluent reservoirs containing: A: 90% water and 10% $CH_3CN$ with 0.045M $(NH_4)_2HPO_4$, pH 3.6, B: 20% isopropanol, 20% water and 60% $CH_3CN$. The following step gradient was used: 35% B and 65% A over 2 minutes, then 35% B, 65% A to 65% B, 35% A over 15 minutes, then 65% B, 35% A to 80% B, 20% A over 3 minutes at a flowrate of 0.5 ml/min.

Method: B31_1

The RP-analysis was performed using a Waters UPLC system fitted with a dual band detector. UV detections at 215 nm and 254 nm were collected using an kinetex 1.7u C18, 100A 2.1×150 mm column, 60° C. The UPLC system was connected to two eluent reservoirs containing: A: 90% water and 10% MeCN with 0.045M $(NH_4)_2HPO_4$, pH 3.6, B: 20% isopropanol, 20% water and 60% $CH_3CN$. The following step gradient was used: 25% B and 75% A over 2 minutes, then 25% B, 75% A to 55% B, 45% A over 15 minutes, then 55% B, 45% A to 80% B, 20% A over 3 minutes at a flowrate of 0.5 ml/min.

Method: AP_B4_1

The RP-analysis was performed using a Waters UPLC system fitted with a dual band detector. UV detections at 214 nm and 254 nm were collected using an ACQUITY UPLC BEH130, C18, 130A, 1.7 um, 2.1 mm×150 mm column, 30° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 5% A, 95% B over 16 minutes at a flow-rate of 0.30 ml/min.

Method: A9_1

The RP-analysis was performed using a Waters UPLC system fitted with a dual band detector. UV detections at 214 nm and 254 nm were collected using an ACQUITY UPLC BEH Shield RP18, C18, 1.7 um, 2.1 mm×150 mm column, 60° C. The UPLC system was connected to two eluent reservoirs containing: A: 200 mM $Na_2SO_4$+20 mM $Na_2HPO_4$+20 mM $NaH_2PO_4$ in 90% $H_2O$/10% $CH_3CN$, pH 7.2; B: 70% $CH_3CN$, 30% $H_2O$. The following step gradient was used: 90% A, 10% B to 80% A, 20% B over 3 minutes, 80% A, 20% B to 50% A, 50% B over 17 minutes at a flow-rate of 0.40 ml/min.

Method: B30_1

The RP-analysis was performed using a Waters UPLC system fitted with a dual band detector. UV detections at 215 nm and 254 nm were collected using a kinetex 1.7u C18, 100A 2.1×150 mm column, 60° C. The UPLC system was connected to two eluent reservoirs containing: A: 0.09M $(NH_4)_2HPO_4$ and 10% MeCN, pH 3.6, B: 20% isopropanol, 20% water and 60% $CH_3CN$. The following step gradient was used: 45% B and 55% A over 2 minutes, then 45% B, 55% A to 75% B, 25% A over 15 minutes, then 75% B, 25% A to 90% B, 10% A over 3 minutes at a flowrate of 0.5 ml/min.

Method: B39_2

The RP-analyses was performed using a Waters UPLC system fitted with a dual band detector. UV detections at 214 nm and 254 nm were collected using an ACQUITY UPLC BEH C18, 1.7 um, 2.1 mm×50 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 70% A, 30% B to 50% A, 50% B over 3.5 minutes at a flow-rate of 0.450 ml/min.

3. MALDI-MS Method

Method: MALDI_MS

Molecular weights were determined using matrix-assisted laser desorption and ionisation time-of-flight mass spectroscopy, recorded on a Microflex or Autoflex (Bruker). A matrix of alpha-cyano-4-hydroxy cinnamic acid was used.

B. Specific Example Compounds

Example 1

$N^{\epsilon 18}$-[(2S)-2-amino-6-[[2-[2-[2-[[(4S)-4-carboxy-4-(13-carboxytridecanoylamino)butanoyl]amino]ethoxy]ethoxy]acetyl]amino]hexanoyl], $N^{\epsilon 26}$-[(2S)-2-amino-6-[[2-[2-[2-[[(4S)-4-carboxy-4-(13-carboxytridecanoylamino)butanoyl]amino]ethoxy]ethoxy]acetyl]amino]hexanoyl]-[$Lys^{18}$,$Glu^{22}$,$Gln^{34}$] (SEQ ID NO: 11)-GLP-1-(7-37)-peptide Chem. 20:

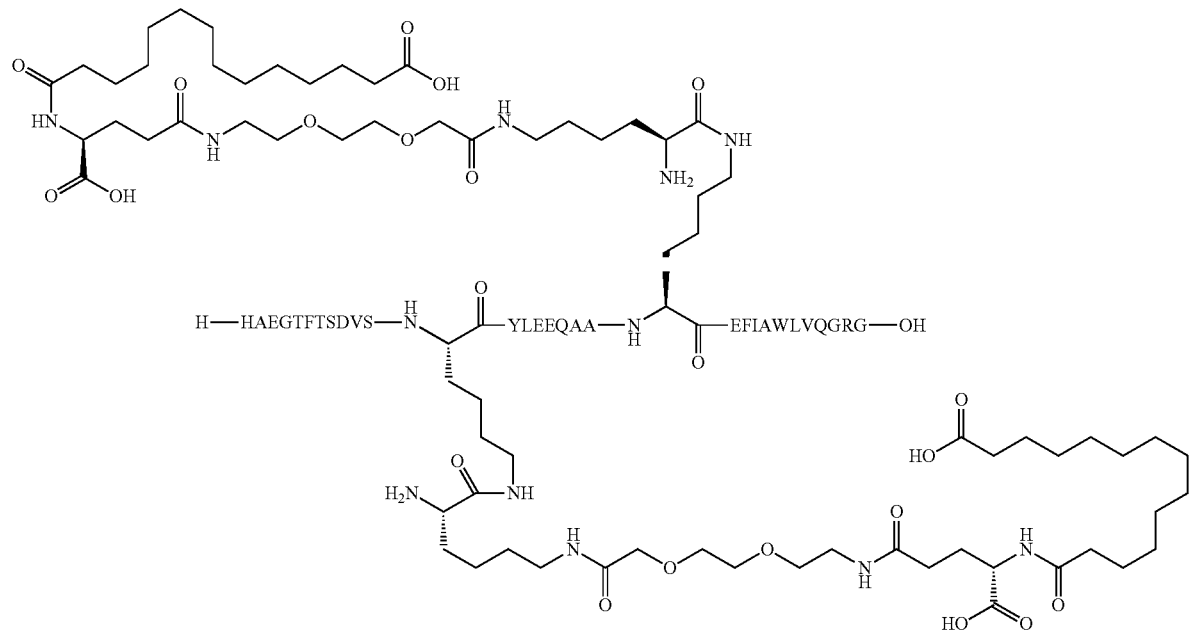

Chem. 20

Preparation Method: SPPS_L; SC_L; CP_M1
LCMS: Method: LCMS_4: Rt=2.11 min m/z: 4754.6; M/3: 1585; M/4: 1189; M/5: 951
UPLC Method: B4_1: Rt=8.25
UPLC Method: A9_1: Rt=9.95

Example 2

$N^{\epsilon 18}$-[(2S)-2-amino-6-[[(4S)-4-carboxy-4-(13-carboxytridecanoylamino)butanoyl]amino]hexanoyl], $N^{\epsilon 26}$-[(2S)-2-amino-6-[[(4S)-4-carboxy-4-(13-carboxytridecanoylamino)butanoyl]amino]hexanoyl]-[Lys$^8$,Glu$^{22}$,Gln$^{34}$] (SEQ ID NO: 11)-GLP-1-(7-37)-peptide Chem. 21

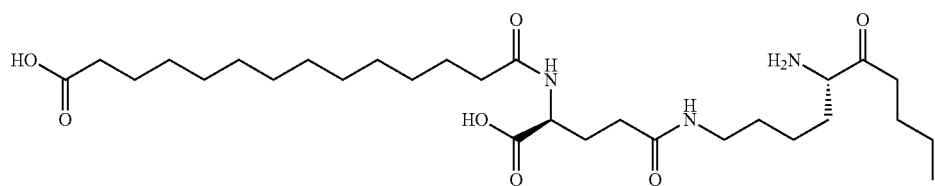

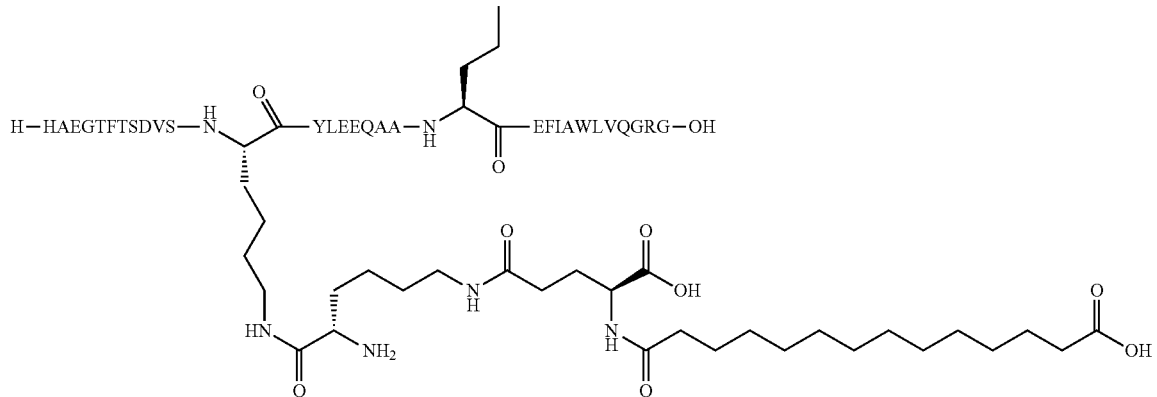

Preparation Method: SPPS_L; SC_L; CP_M1

UPLC method: B4_1: Rt=8.49 min

UPLC method: B9_1: Rt=4.99 min

Example 3

$N^{\epsilon 18}$-[2-[2-[2-[[(2S)-2-amino-6-[[2-[2-[2-[[(4S)-4-carboxy-4-[10-(4-carboxyphenoxyl)decanoylamino]butanoyl]amino]ethoxy]ethoxy]acetyl]amino]hexanoyl]amino]ethoxy]ethoxy]acetyl], $N^{\epsilon 26}$-[2-[2-[2-[[(2S)-2-amino-6-[[2-[2-[2-[[(4S)-4-carboxy-4-[10-(4-carboxyphenoxyl)decanoylamino]butanoyl]amino]ethoxy]ethoxy]acetyl]amino]hexanoyl]amino]ethoxy]ethoxy]acetyl]-[Imp$^7$,Aib$^8$,Lys$^{18}$,Glu$^{22}$,Gln$^{34}$] (SEQ ID NO: 5)-GLP-1-(7-37)-peptide Chem. 22

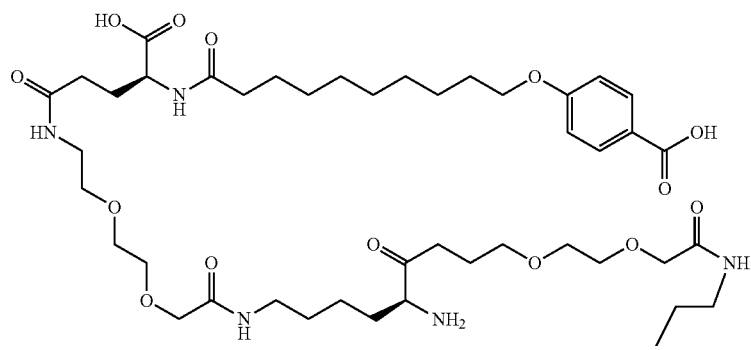

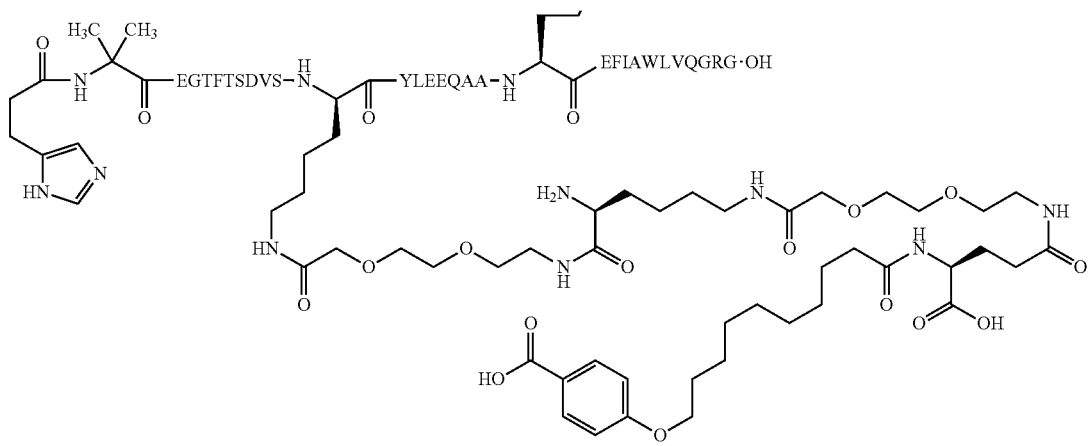

Preparation Method: SPPS_L; SC_L; CP_M1

UPLC Method: B4_1: Rt=8.53 min

UPLC Method: A6_1: Rt=5.02 min

LCMS method: LCMS_4: Rt=2.22 min; m/3=1715; m/4=1286; m/5=1030

Example 4

$N^{\epsilon18}$-[2-[2-[2-[[(2S)-2-amino-6-[[2-[2-[2-[[(4S)-4-carboxy-4-[10-(4-carboxyphenoxyl)decanoylamino]butanoyl]amino]ethoxy]ethoxy]acetyl]amino]hexanoyl]amino]ethoxy]ethoxy]acetyl], $N^{\epsilon31}$-[2-[2-[2-[[(2S)-2-amino-6-[[2-[2-[2-[[(4S)-4-carboxy-4-[10-(4-carboxyphenoxyl)decanoylamino]butanoyl]amino]ethoxy]ethoxy]acetyl]amino]hexanoyl]amino]ethoxy]ethoxy]acetyl]-[Imp$^7$,Lys$^{18}$,Glu$^{22}$,Val$^{25}$, Arg$^{26}$,Lys$^{31}$,Arg$^{34}$] (SEQ ID NO: 6)-GLP-1-(7-37)-peptide Chem. 23

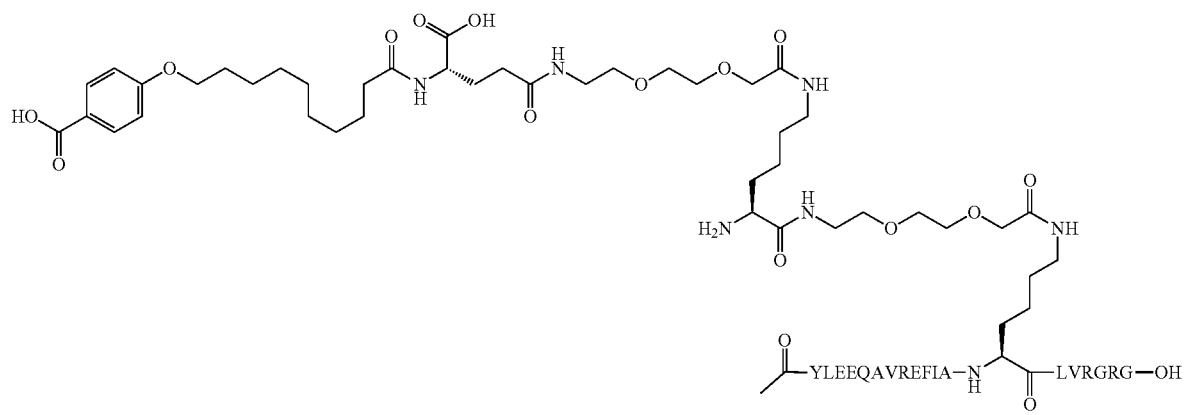

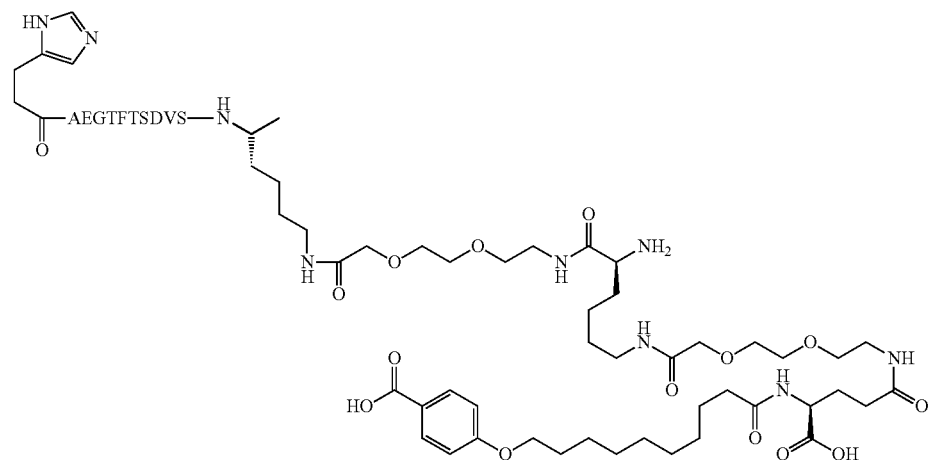

Preparation Method: SPPS_L; SC_L; CP_M1

UPLC Method: B4_1: Rt=7.72 min

UPLC Method: A9_1: Rt=11.71 min

LCMS method; LCMS_4: Rt=2.22 min; m/4=1289; m/5=1031; m/6=860

Example 5

N$^{\epsilon18}$-[(2S)-2-amino-6-[[(2S)-2-amino-6-[[(4S)-4-carboxy-4-[10-(4-carboxyphenoxyl)decanoylamino]butanoyl]amino]hexanoyl]amino]hexanoyl], N$^{\epsilon26}$-[(2S)-2-amino-6-[[(2S)-2-amino-6-[[(4S)-4-carboxy-4-[10-(4-carboxyphenoxyl)decanoylamino]butanoyl]amino]hexanoyl]amino]hexanoyl]-[Aib$^8$,Lys$^{18}$,Glu$^{22}$,Gln$^{34}$] (SEQ ID NO: 9)-GLP-1-(7-37)-peptide Chem. 24

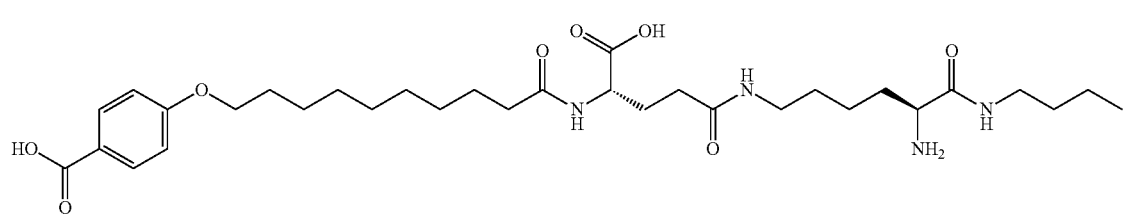

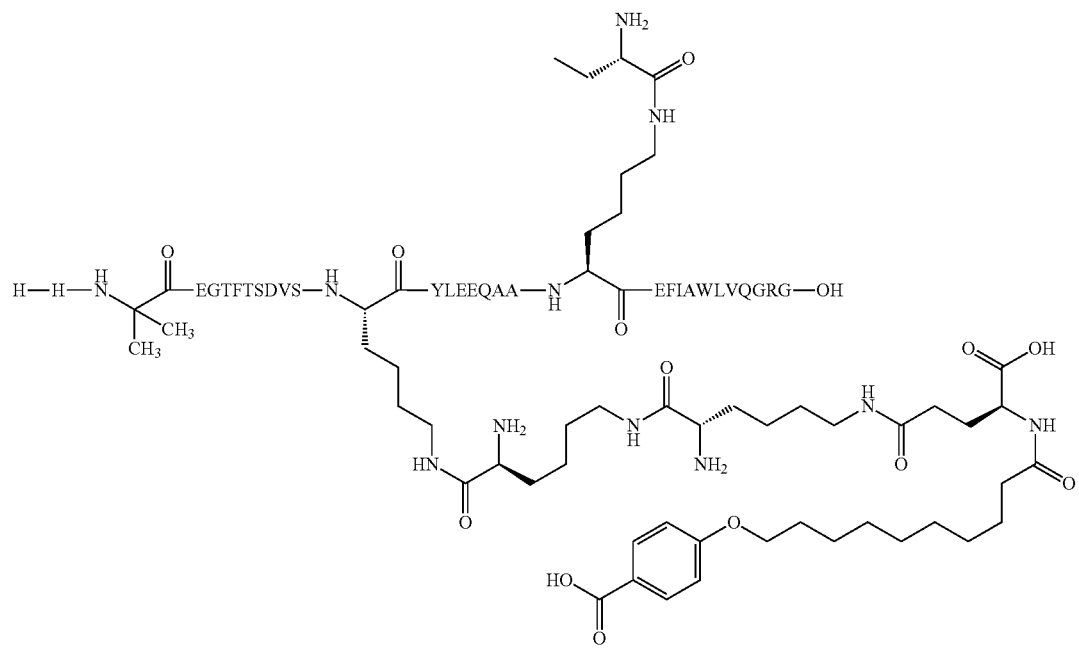

Preparation Method: SPPS_P; SC_P; CP_M1

UPLC Method: A9_1: Rt=10.7 min

UPLC Method: A6_1: Rt=5.6 min

The theoretical molecular mass of 4834.5 Da was confirmed by Method: Maldi_MS: m/z 4833.5

Example 6

$N^{\epsilon 18}$-[(2S)-2-amino-6-[[(2S)-2-amino-6-[[(4S)-4-carboxy-4-[10-(4-carboxyphenoxyl)decanoylamino]butanoyl]amino]hexanoyl]amino]hexanoyl], $N^{\epsilon 26}$-[(2S)-2-amino-6-[[(2S)-2-amino-6-[[(4S)-4-carboxy-4-[10-(4-carboxyphenoxyl)decanoylamino]butanoyl]amino]hexanoyl]amino]hexanoyl]-[Aib$^8$,Lys$^{18}$,Gln$^{34}$] (SEQ ID NO: 12)-GLP-1-(7-37)-peptide Chem. 25

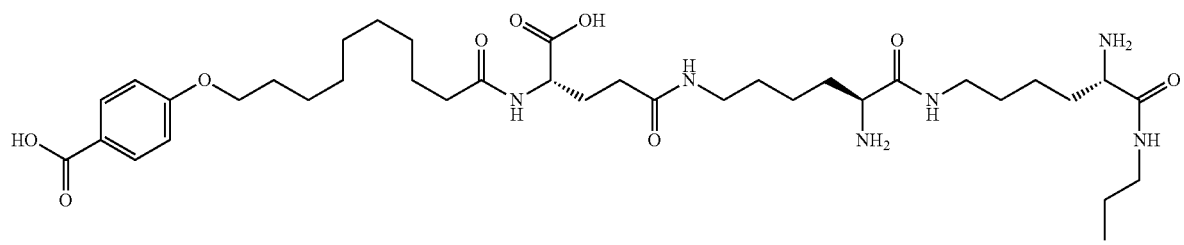

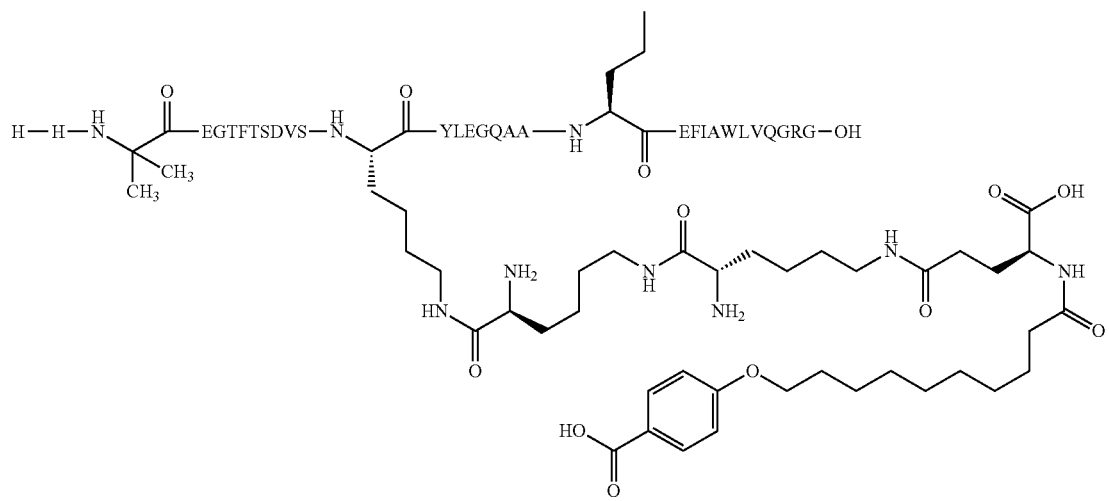

Preparation Method: SPPS_P; SC_P; CP_M1

UPLC Method: B31_1: Rt=14.0 min

UPLC Method: A6_1: Rt=6.2 min

The theoretical molecular mass of 4762 Da was confirmed by Method: Maldi_MS: m/z 4759

Example 7

$N^{\epsilon18}$-[(2S)-2-amino-6-[[(2S)-2-amino-6-[[(4S)-4-carboxy-4-[8-[10-(4-carboxyphenoxyl)decanoylamino]octanoylamino]butanoyl]amino]hexanoyl]amino]hexanoyl], $N^{\epsilon26}$-[(2S)-2-amino-6-[[(2S)-2-amino-6-[[(4S)-4-carboxy-4-[8-[10-(4-carboxyphenoxyl)decanoylamino]octanoylamino]butanoyl]amino]hexanoyl]amino]hexanoyl]-[Aib$^8$, Lys$^{18}$,Glu$^{22}$,Gln$^{34}$] (SEQ ID NO: 9)-GLP-1-(7-37)-peptide Chem. 26

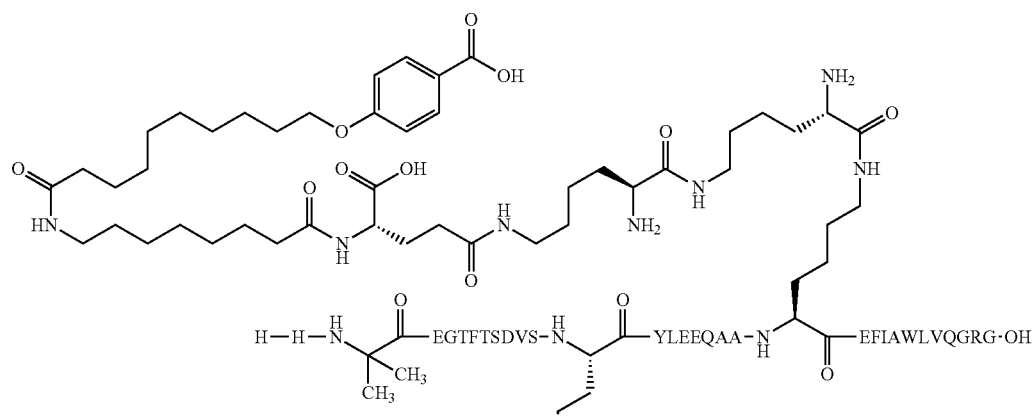

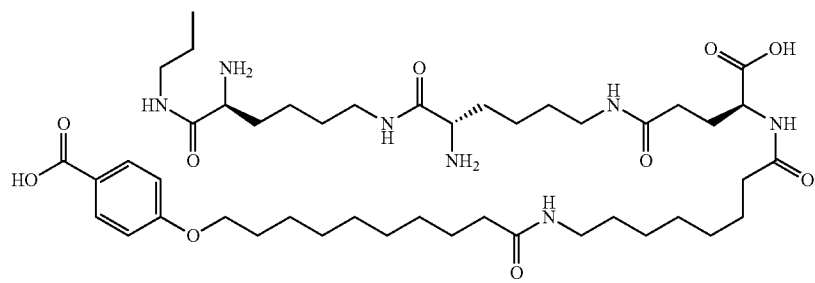

Preparation Method: SPPS_P; SC_P; CP_M1

UPLC Method: B31_1: Rt=17.1 min

UPLC Method: A6_1: Rt=5.9 min

The theoretical molecular mass of 5116.9 Da was confirmed by Method: Maldi_MS: m/z 5114

Example 8

N^ε18-[(2S)-2-amino-6-[[(2S)-2-amino-6-[[(4S)-4-carboxy-4-[12-(4-carboxyphenoxy)dodecanoylamino]butanoyl]amino]hexanoyl]amino]hexanoyl], N^ε26-[(2S)-2-amino-6-[[(2S)-2-amino-6-[[(4S)-4-carboxy-4-[12-(4-carboxyphenoxy)dodecanoylamino]butanoyl]amino]hexanoyl]amino]hexanoyl]-[Aib⁸,Lys¹⁸,Gln³⁴] (SEQ ID NO: 12)-GLP-1-(7-37)-peptide Chem. 27

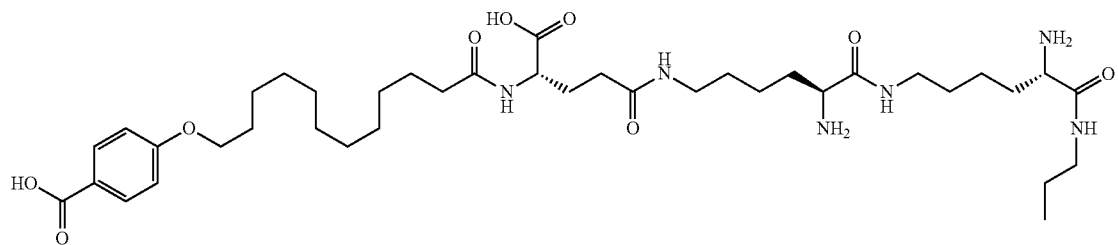

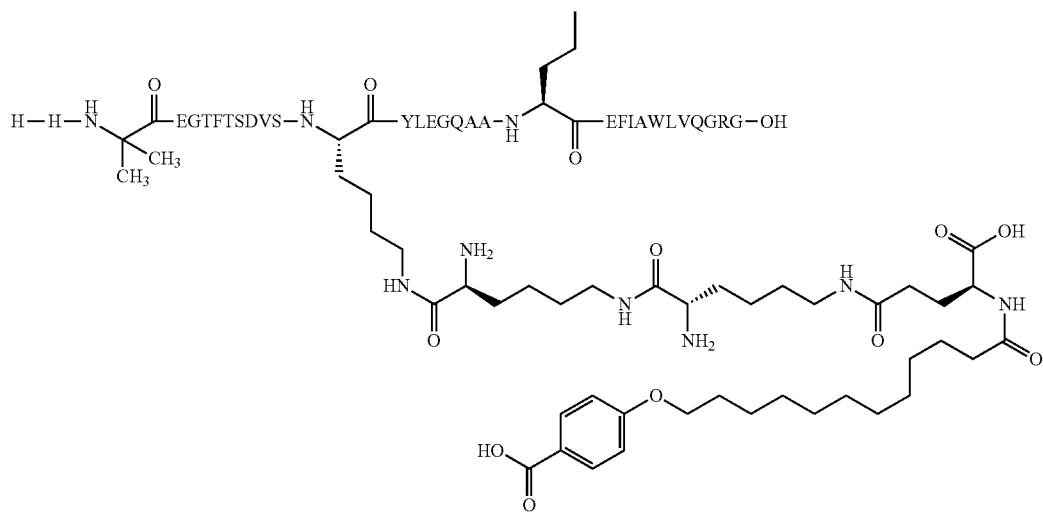

Preparation Method: SPPS_P; SC_P; CP_M1

UPLC Method: B31_1: Rt=17.0 min

UPLC Method: A6_1: Rt=6.9 min

The theoretical molecular mass of 4818.6 Da was confirmed by Method: Maldi_MS: m/z 4817

Example 9

The following compound is prepared and characterised using the above-mentioned general methods, and in analogy with the compounds of the worked examples.

$N^{\epsilon 18}$-[(2S)-2-amino-6-[[2-[2-[2-[[(4S)-4-carboxy-4-[[2-[2-[2-(15-carboxypentadecanoylamino)ethoxy]ethoxy]acetyl]amino]butanoyl]amino]ethoxy]ethoxy]acetyl]amino]hexanoyl], $N^{\epsilon 31}$-[(2S)-2-amino-6-[[2-[2-[2-[[(4S)-4-carboxy-4-[[2-[2-[2-(15-carboxypentadecanoylamino)ethoxy]ethoxy]acetyl]amino]butanoyl]amino]ethoxy]ethoxy]acetyl]amino]hexanoyl]-[Aib$^8$,Lys$^{18}$,Glu$^{22}$,Val$^{25}$,Arg$^{26}$,Lys$^{31}$,Arg$^{34}$] (SEQ ID NO: 6)-GLP-1-(7-37)-peptide

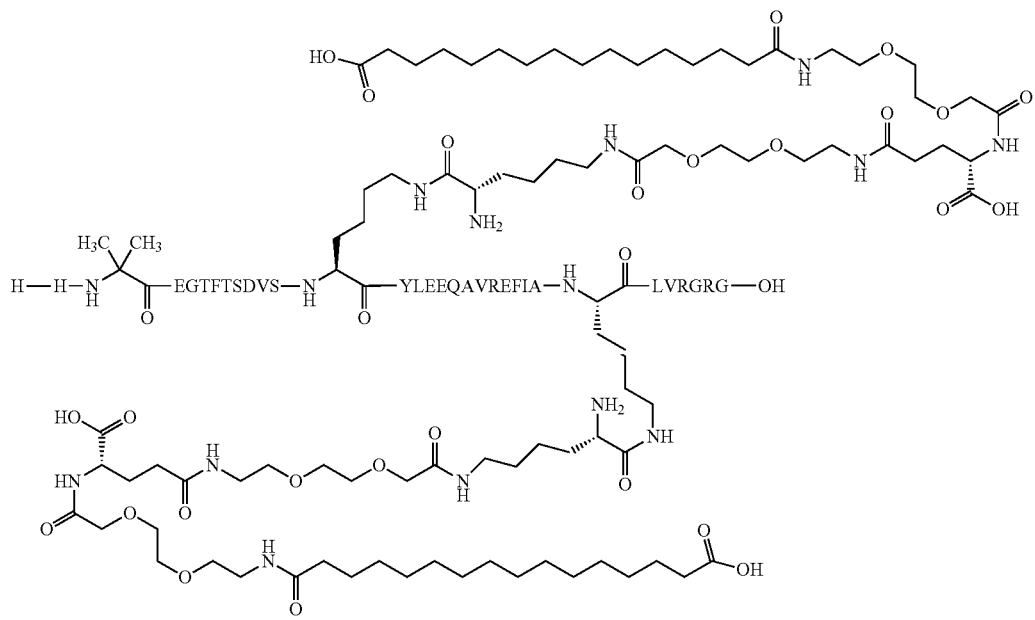

Chem. 28

Example 10

$N^{\epsilon 18}$-[(2S)-2-amino-6-[[(2S)-2-amino-6-[[(4S)-4-carboxy-4-[10-(4-carboxyphenoxyl)decanoylamino]butanoyl]amino]hexanoyl]amino]hexanoyl], $N^{\epsilon 26}$-[(2S)-2-amino-6-[[(2S)-2-amino-6-[[(4S)-4-carboxy-4-[10-(4-carboxyphenoxyl)decanoylamino]butanoyl]amino]hexanoyl]amino]hexanoyl]-[Aib$^8$,Lys$^{18}$,Gln$^{19}$,Glu$^{22}$,Gln$^{34}$] (SEQ ID NO: 10)-GLP-1-(7-37)-peptide

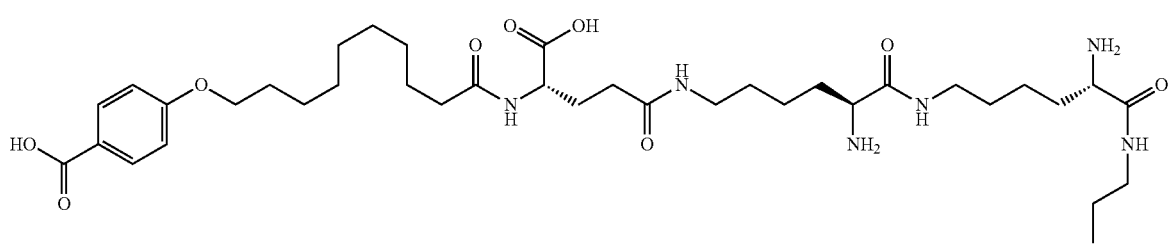

Chem. 29

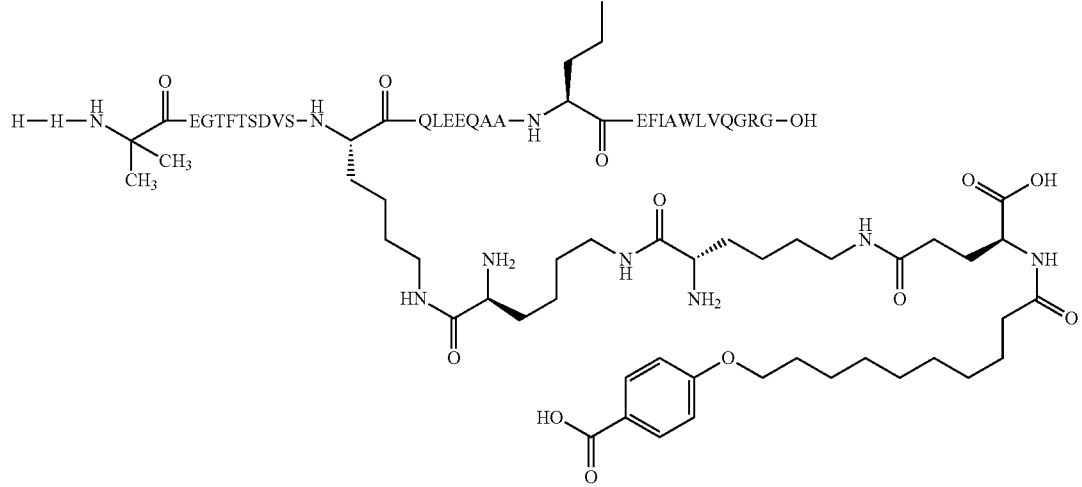

Preparation Method: SPPS_P; SC_P; CP_M1
UPLC Method: B31_1: Rt=14.5 min
UPLC Method: A6_1: Rt=5.2 min
The theoretical molecular mass of 4799.4 Da was confirmed by Method: Maldi_MS: m/z 4799.6

Example 11

$N^{\epsilon 18}$-[(2S)-2-amino-6-[[(2S)-2-amino-6-[[(4S)-4-carboxy-4-(15-carboxypentadecanoylamino)butanoyl]amino]hexanoyl]amino]hexanoyl], $N^{\epsilon 26}$-[(2S)-2-amino-6-[[(2S)-2-amino-6-[[(4S)-4-carboxy-4-(15-carboxypentadecanoylamino)butanoyl]amino]hexanoyl]amino]hexanoyl]-[Aib$^8$,Lys$^{18}$,Gln$^{34}$] (SEQ ID NO: 12)-GLP-1-(7-37)-peptide Chem. 30

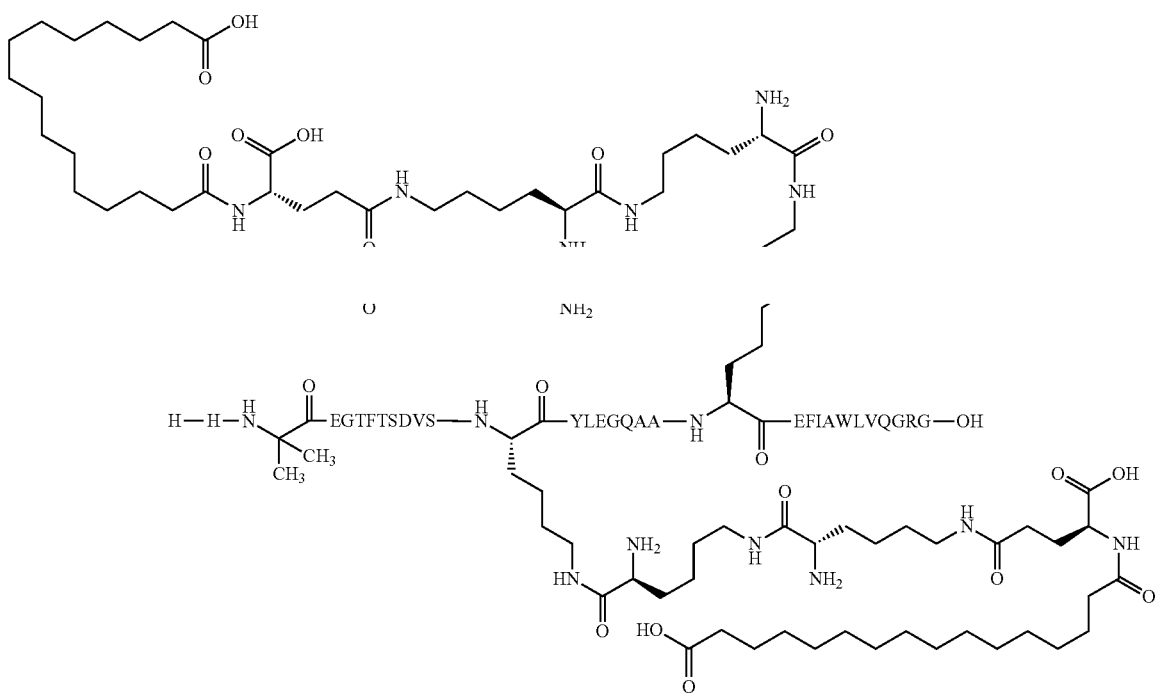

Preparation Method: SPPS_P; SC_P; CP_M1

UPLC Method: B31_1: Rt=17.9 min

UPLC Method: A6_1: Rt=7.6 min

The theoretical molecular mass of 4718.5 Da was confirmed by Method: Maldi_MS: m/z 4716.98

Example 12

$N^{\epsilon 18}$-[(2S)-2-amino-6-[[(2S)-2-amino-6-[[(4S)-4-carboxy-4-(17-carboxyheptadecanoylamino)butanoyl]amino]hexanoyl]amino]hexanoyl], $N^{\epsilon 26}$-[(2S)-2-amino-6-[[(2S)-2-amino-6-[[(4S)-4-carboxy-4-(17-carboxyheptadecanoylamino)butanoyl]amino]hexanoyl]amino]hexanoyl]-[Aib$^8$,Lys$^{18}$,Gln$^{34}$] (SEQ ID NO: 12)-GLP-1-(7-37)-peptide Chem. 31

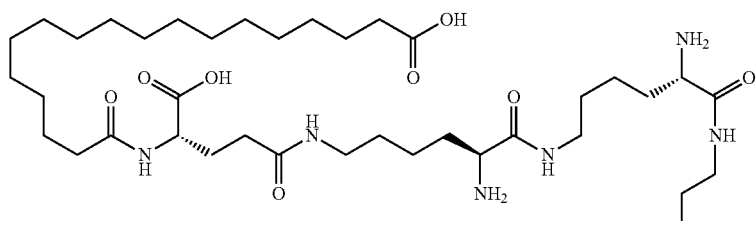

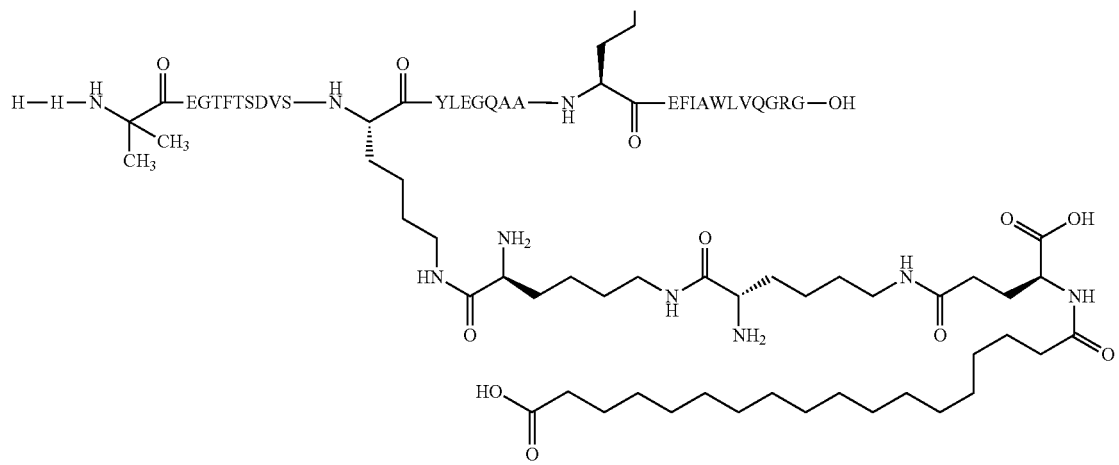

Preparation Method: SPPS_P; SC_P; CP_M1

UPLC Method: B31_1: Rt=19.4 min

UPLC Method: A6_1: Rt=8.5 min

The theoretical molecular mass of 4774.6 Da was confirmed by Method: Maldi_MS: m/z 4773.8

Example 13

$N^{\epsilon 18}$-[(2S)-2-amino-6-[[(4S)-4-carboxy-4-(15-carboxypentadecanoylamino)butanoyl]amino]hexanoyl], $N^{\epsilon 26}$-[(2S)-2-amino-6-[[(4S)-4-carboxy-4-(15-carboxypentadecanoylamino)butanoyl]amino]hexanoyl]-[Aib$^8$,Lys$^{18}$,Gln$^{34}$](SEQ ID NO: 12)-GLP-1-(7-37)-peptide Chem. 32

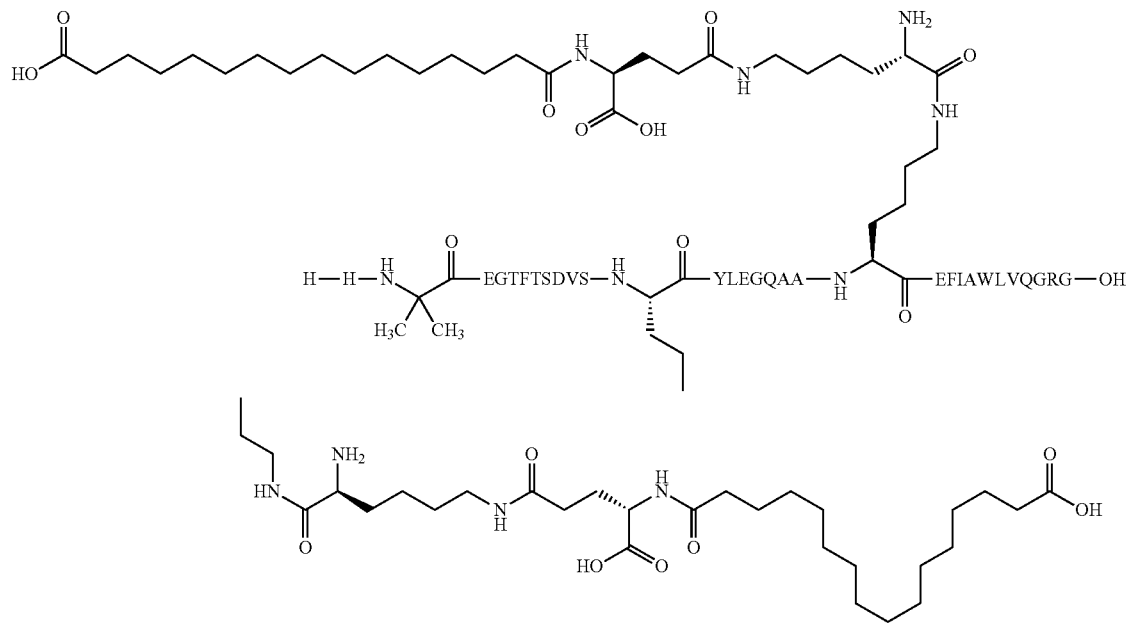

Preparation Method: SPPS_P; SC_P; CP_M1
UPLC method: AP_B4__1: Rt=9.04 min
LCMS method: LCMS_AP: Rt=5.61 min; m/3=1488; m/4=1116

Example 14

$N^{\epsilon 18}$-[(2S)-2-amino-6-[[2-[2-[2-(15-carboxypentadecanoylamino)ethoxy]ethoxy]acetyl]amino]hexanoyl], $N^{\epsilon 26}$-[(2S)-2-amino-6-[[2-[2-[2-(15-carboxypentadecanoylamino)ethoxy]ethoxy]acetyl]amino]hexanoyl]-[Aib$^8$,Lys$^{18}$,Gln$^{34}$] (SEQ ID NO: 12)-GLP-1-(7-37)-peptide Chem. 33

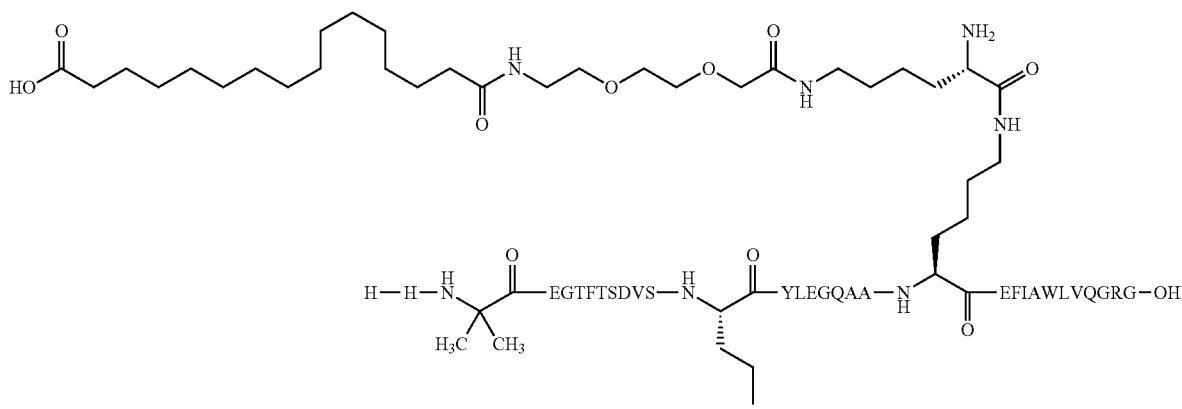

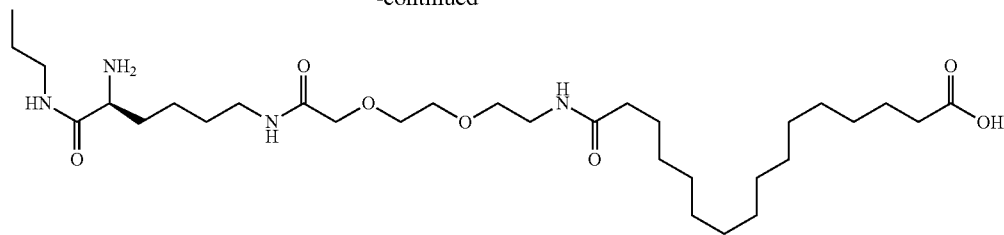

Preparation Method: SPPS_P; SC_P; CP_M1
UPLC method: AP_B4_1: Rt=9.35 min
LCMS method: LCMS_AP: Rt=5.71 min; m/3=1499; m/4=1124

Example 15

$N^{\epsilon 18}$-[(2S)-2-amino-6-[[2-[2-[2-[[(4S)-4-carboxy-4-(15-carboxypentadecanoylamino)butanoyl]amino]ethoxy]ethoxy]acetyl]amino]hexanoyl], $N^{\epsilon 26}$-[(2S)-2-amino-6-[[2-[2-[2-[[(4S)-4-carboxy-4-(15-carboxypentadecanoylamino)butanoyl]amino]ethoxy]ethoxy]acetyl]amino]hexanoyl]-[Aib$^8$,Lys$^{18}$, Gln$^{34}$] (SEQ ID NO: 12)-GLP-1-(7-37)-peptide Chem. 34

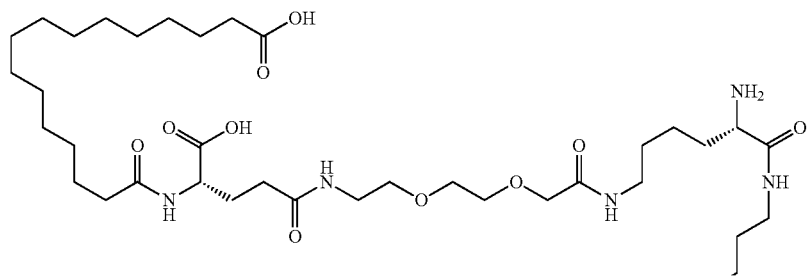

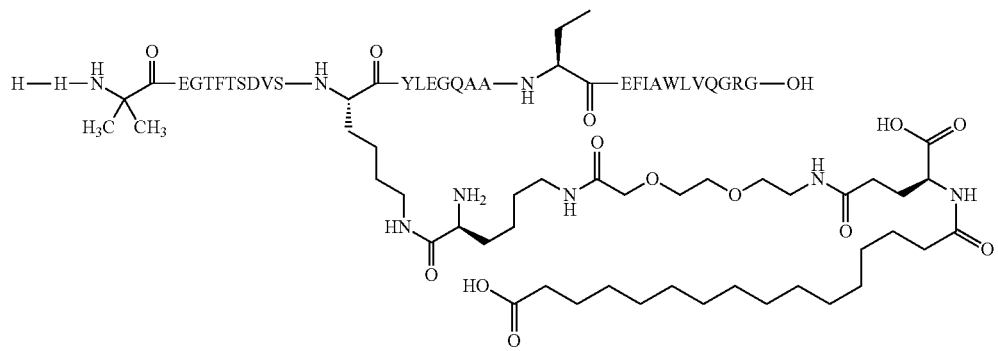

Preparation Method: SPPS_P; SC_P; CP_M1

UPLC method: AP_B4_1: Rt=9.00 min

LCMS method: LCMS_AP: Rt=5.57 min; m/3=1585; m/4=1189

Example 16

The following compound is prepared and characterised using the above-mentioned general methods, and in analogy with the compounds of the worked examples.

$N^{\epsilon 18}$-[(2S)-2-amino-6-[[2-[2-[2-[[(4S)-4-carboxy-4-[10-(4-carboxyphenoxy)decanoylamino]butanoyl]amino]ethoxy]ethoxy]acetyl]amino]hexanoyl], $N^{\epsilon 26}$-[(2S)-2-amino-6-[[2-[2-[2-[[(4S)-4-carboxy-4-[10-(4-carboxyphenoxy)decanoylamino]butanoyl]amino]ethoxy]ethoxy]acetyl]amino]hexanoyl]-[Aib$^8$, Lys$^{18}$,Gln$^{34}$] (SEQ ID NO: 12)-GLP-1-(7-37)-peptide Chem. 35

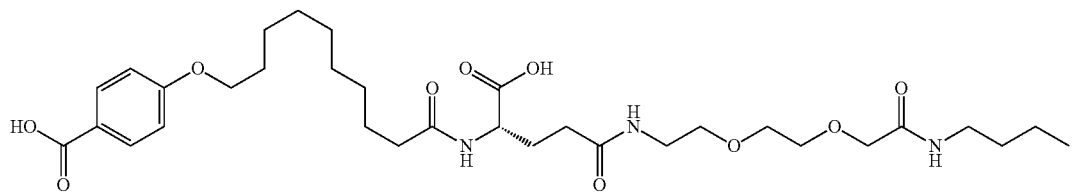

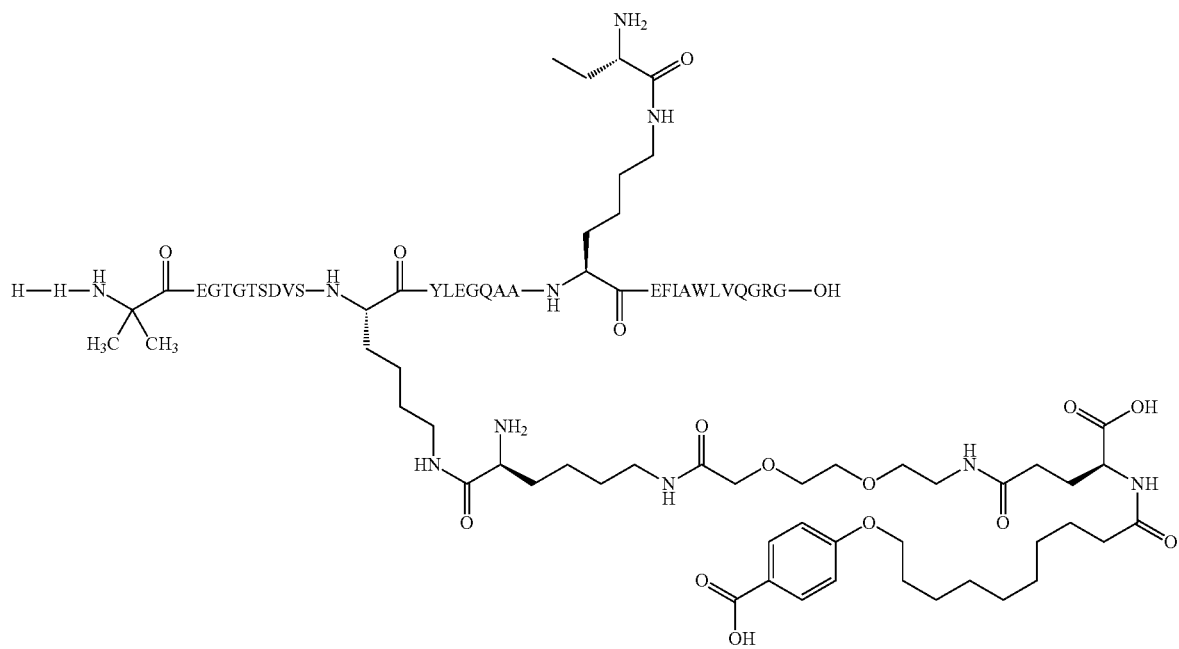

Example 17

The following compound is prepared and characterised using the above-mentioned general methods, and in analogy with the compounds of the worked examples.

$N^{\epsilon 18}$-[(2S)-2-amino-6-[[(2S)-2-amino-6-[[(4S)-4-carboxy-4-[12-(4-carboxyphenoxy)dodecanoylamino]butanoyl]amino]hexanoyl]amino]hexanoyl], $N^{\epsilon 26}$-[(2S)-2-amino-6-[[(2S)-2-amino-6-[[(4S)-4-carboxy-4-[12-(4-carboxyphenoxy)dodecanoylamino]butanoyl]amino]hexanoyl]amino]hexanoyl]-[Aib$^8$,Lys$^{18}$,Glu$^{22}$,Gln$^{34}$] (SEQ ID NO: 9)-GLP-1-(7-37)-peptide Chem. 36

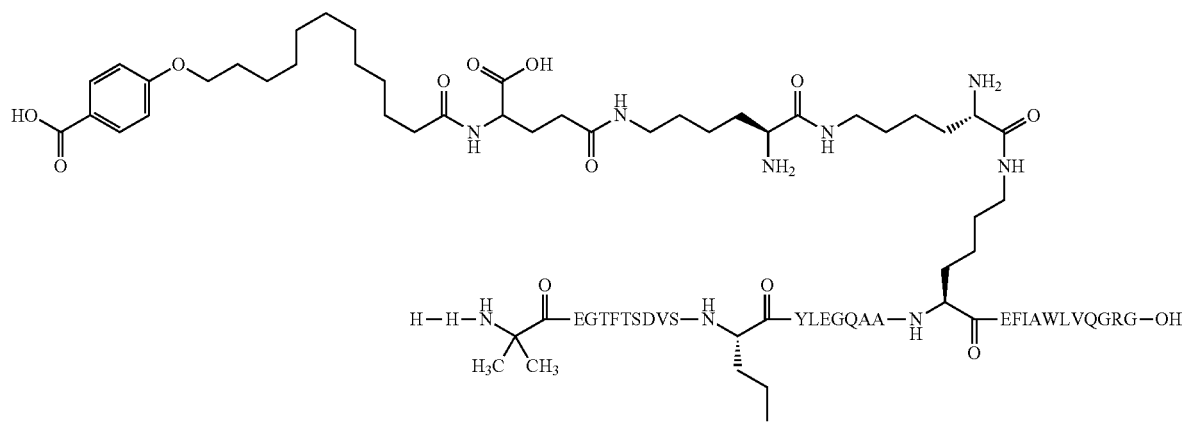

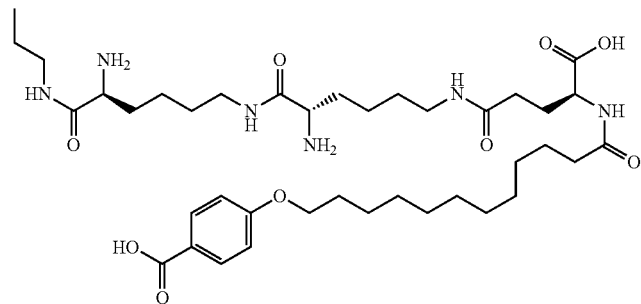

Example 18

The following compound is prepared and characterised using the above-mentioned general methods, and in analogy with the compounds of the worked examples.

N$^{\epsilon 18}$-[(2S)-2-amino-6-[[(2S)-2-amino-6-[[(4S)-4-carboxy-4-(15-carboxypentadecanoylamino)butanoyl]amino]hexanoyl]amino]hexanoyl], N$^{\epsilon 26}$-[(2S)-2-amino-6-[[(2S)-2-amino-6-[[(4S)-4-carboxy-4-(15-carboxypentadecanoylamino)butanoyl]amino]hexanoyl]amino]hexanoyl]-[Aib$^8$,Lys$^{18}$,Glu$^{22}$,Gln$^{34}$] (SEQ ID NO: 9)-GLP-1-(7-37)-peptide Chem. 37

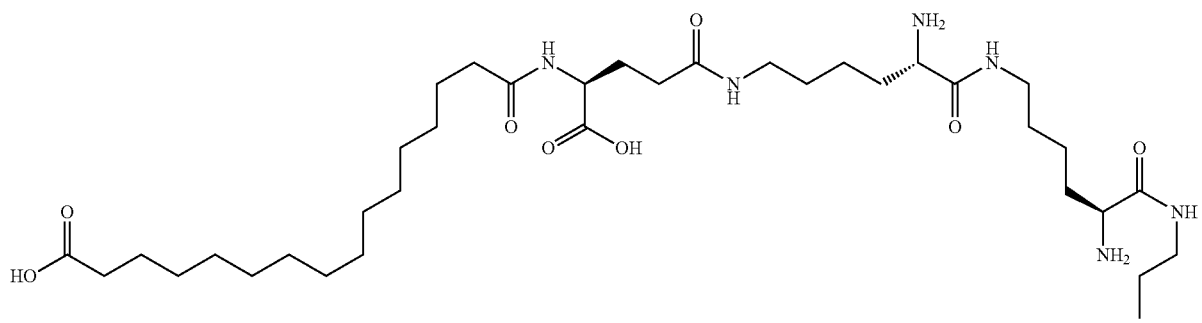

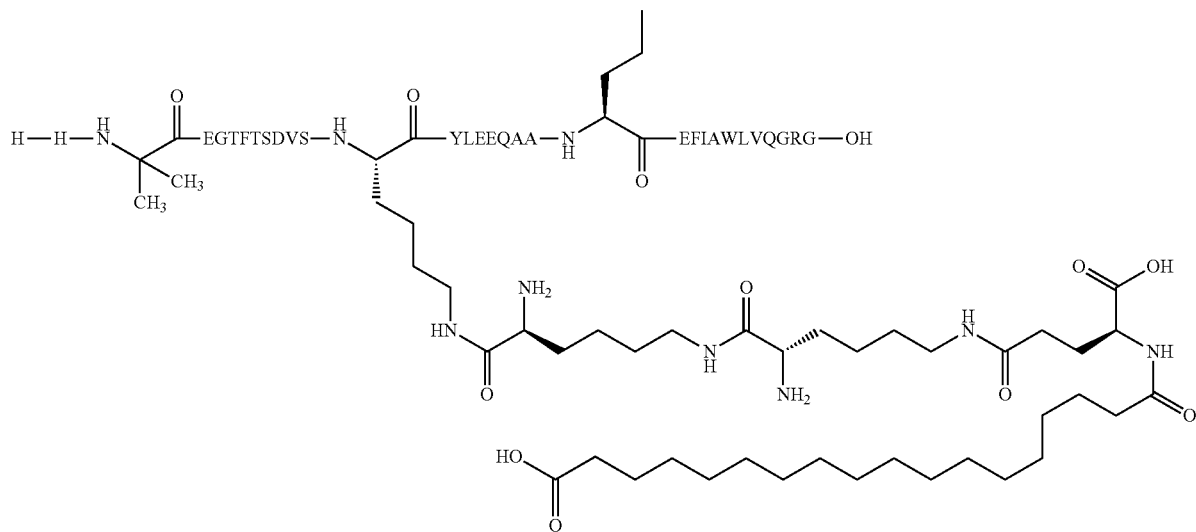

Example 19
N$^{\epsilon18}$-[(2S)-2-amino-6-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl], N$^{\epsilon26}$-[(2S)-2-amino-6-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl]-[Aib$^8$,Lys$^{18}$,Gln$^{34}$] (SEQ ID NO: 12)-GLP-1-(7-37)-peptide
Chem. 38
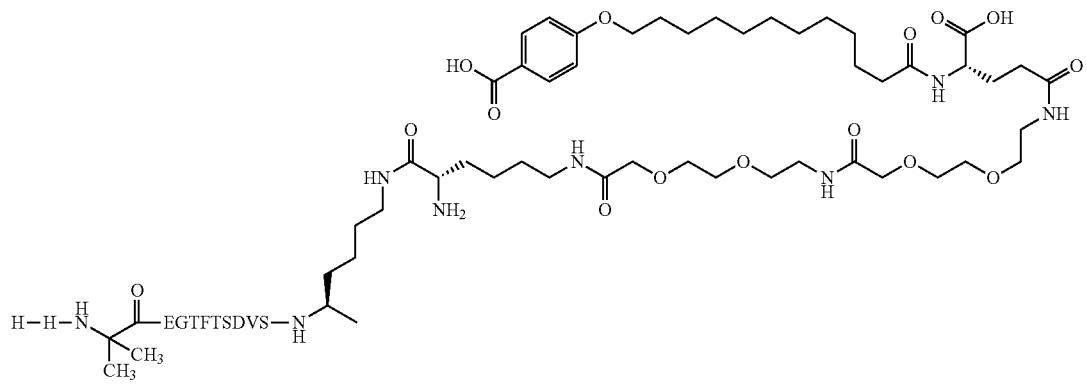
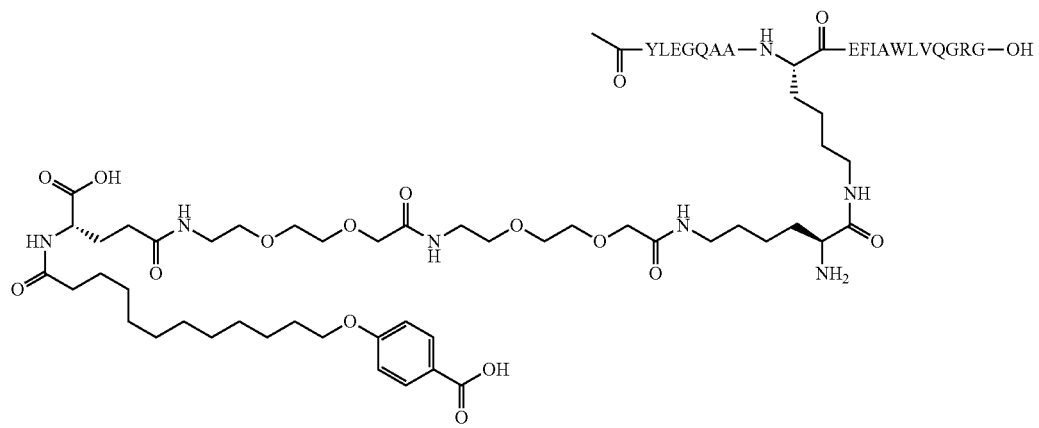

Preparation Method: SPPS_P; SC_P; CP_M1
UPLC Method: A6_1: Rt=8.8 min
The theoretical molecular mass of 5142.8 Da was confirmed by Method: Maldi_MS: m/z 5140.6

Example 20

$N^{\epsilon 18}$-[(2S)-2-amino-6-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]hexanoyl], $N^{\epsilon 26}$-[(2S)-2-amino-6-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]hexanoyl]-[Aib$^8$,Lys$^{18}$,Gln$^{34}$] (SEQ ID NO: 12)-GLP-1-(7-37)-peptide Chem. 39

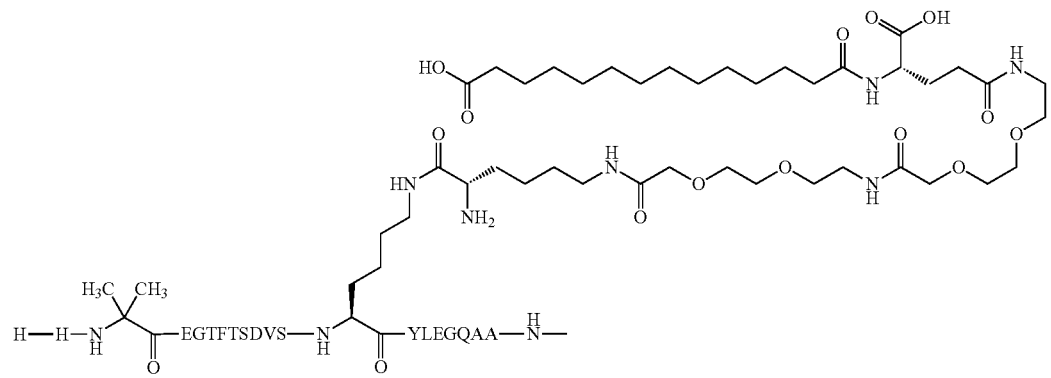

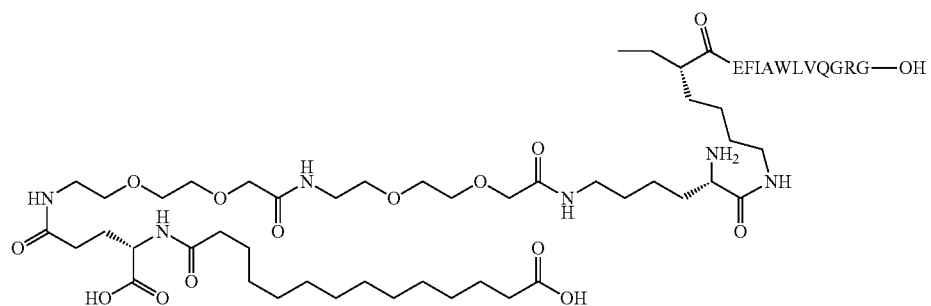

Preparation Method: SPPS_P; SC_P; CP_M1

LCMS method: LCMS_AP: Rt=6.44 min; m/3=1662; m/4=1247

The following compounds are prepared and characterised using the above-mentioned general methods, and in analogy with the compounds of the above examples.

Example 21
N^{ε18}-[(2S)-2-amino-6-[[(4S)-4-carboxy-4-[[4-carboxy-4-(13-carboxytridecanoylamino)butanoyl]amino]butanoyl]amino]hexanoyl], N^{ε26}-[(2S)-2-amino-6-[[(4S)-4-carboxy-4-[[(4S)-4-carboxy-4-(13-carboxytridecanoylamino)butanoyl]amino]butanoyl]amino]hexanoyl]-[Aib⁸,Lys¹⁸,Glu²²,Gln³⁴] (SEQ ID NO: 9)-GLP-1-(7-37)-peptide
Chem.40
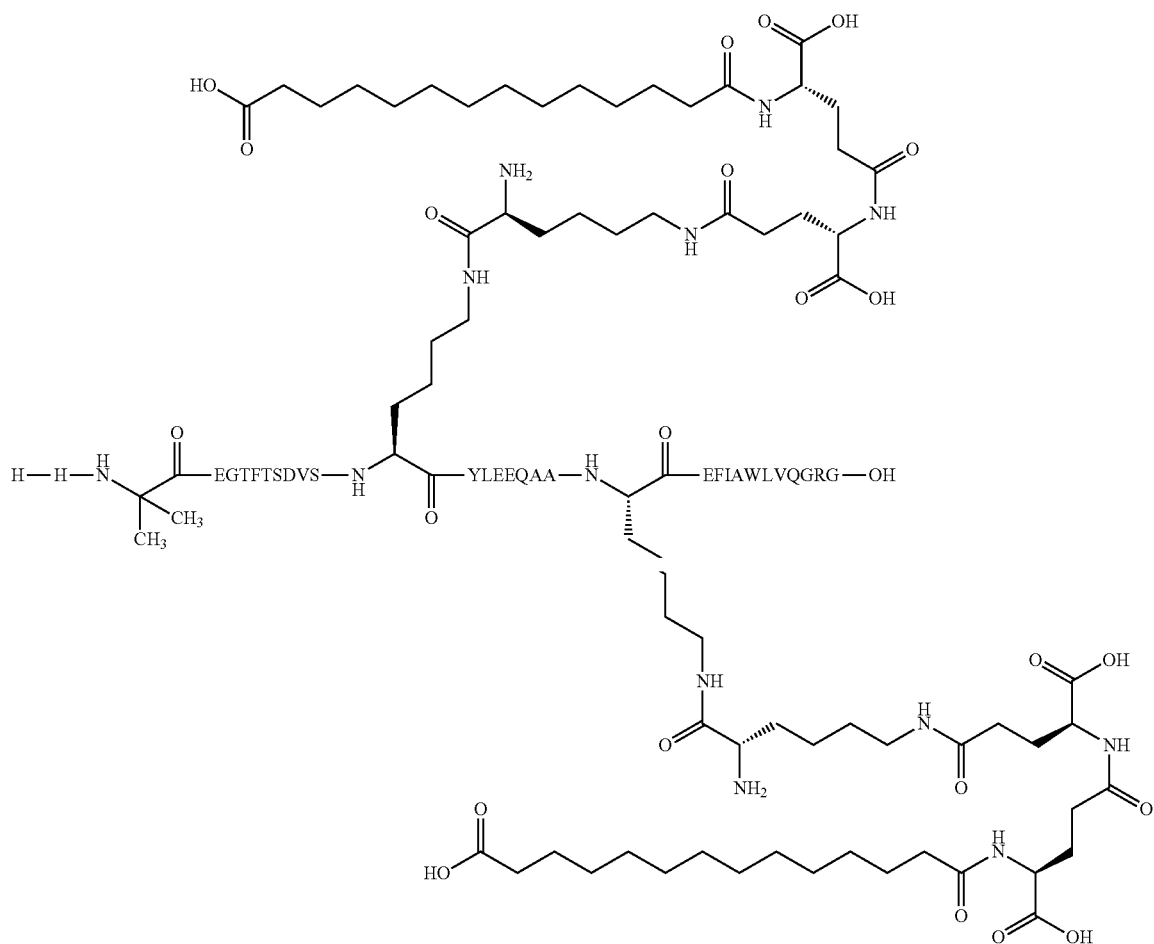

Example 22
$N^{\epsilon 18}$-[(2S)-2-amino-6-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]hexanoyl], $N^{\epsilon 26}$-[(2S)-2-amino-6-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]hexanoyl]-[Aib$^8$,Lys$^{18}$,Glu$^{22}$,Gln$^{34}$] (SEQ ID NO: 9)-GLP-1-(7-37)-peptide
Chem. 41
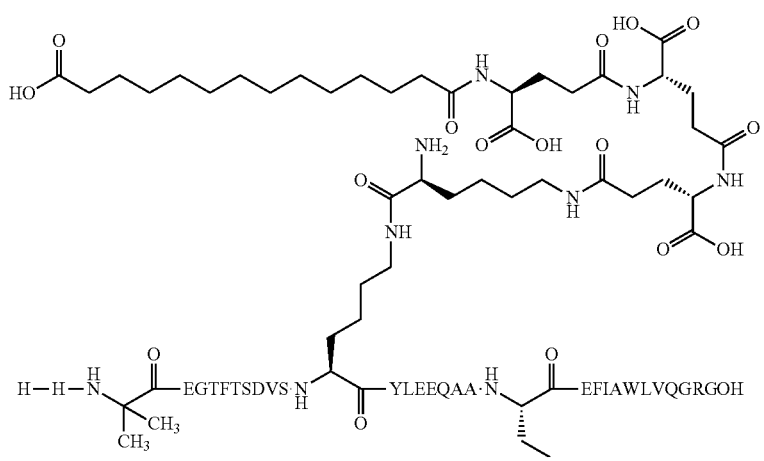
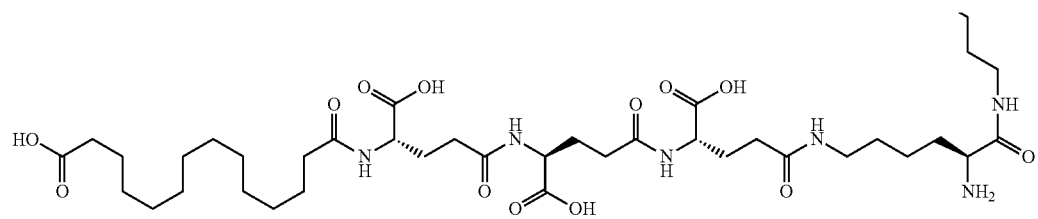

Example 23

$N^{\epsilon 18}$-[(2S)-2-amino-6-[[(2S)-2-amino-6-[[(4S)-4-carboxy-4-(13-carboxytridecanoylamino)butanoyl]amino]hexanoyl]amino]hexanoyl], $N^{\epsilon 26}$-[(2S)-2-amino-6-[[(2S)-2-amino-6-[[(4S)-4-carboxy-4-(13-carboxytridecanoylamino)butanoyl]amino]hexanoyl]amino]hexanoyl]-[Aib$^8$,Lys$^{18}$,Glu$^{22}$,Gln$^{34}$] (SEQ ID NO: 9)-GLP-1-(7-37)-peptide Chem. 42

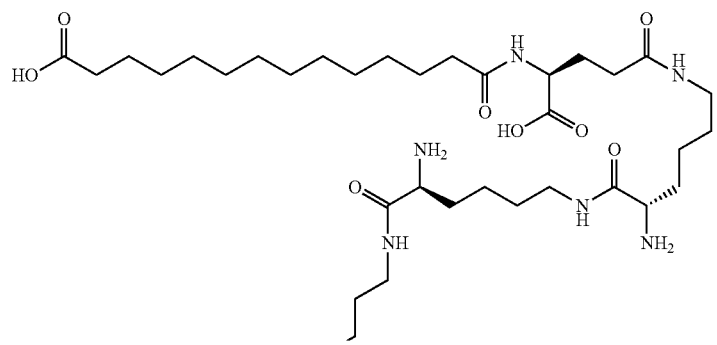

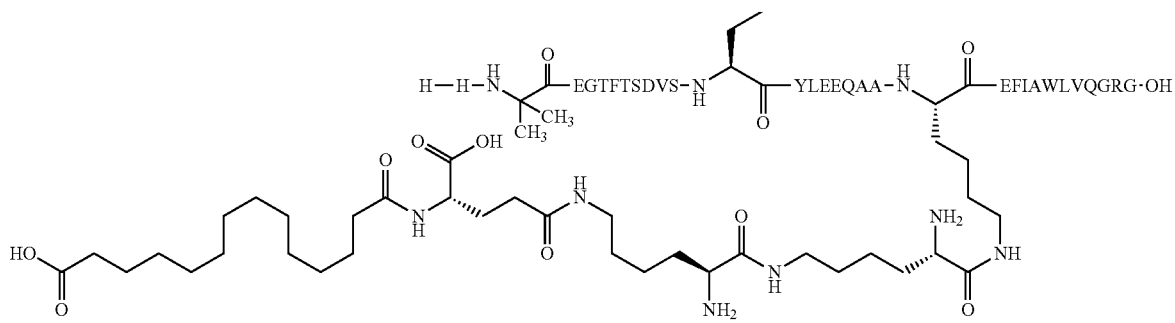

Example 24

$N^{\epsilon 18}$-[(2S)-2-amino-6-[[(4S)-4-carboxy-4-(3-carboxytridecanoylamino)butanoyl]amino]hexanoyl], $N^{\epsilon 26}$-[(2S)-2-amino-6-[[(4S)-4-carboxy-4-(13-carboxytridecanoylamino)butanoyl]amino]hexanoyl]-[Aib$^8$, Lys$^{18}$,Glu$^{22}$,Gln$^{34}$] (SEQ ID NO: 9)-GLP-1 (7-37)-peptide Chem. 43

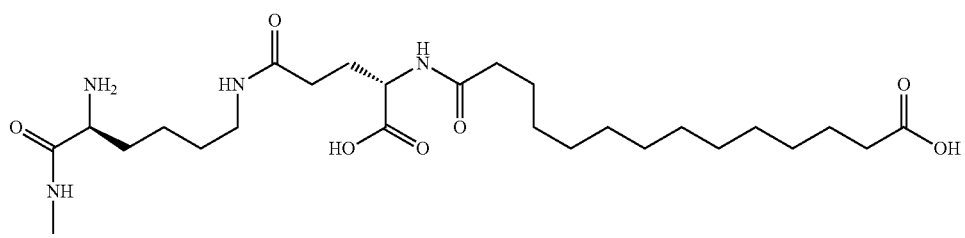

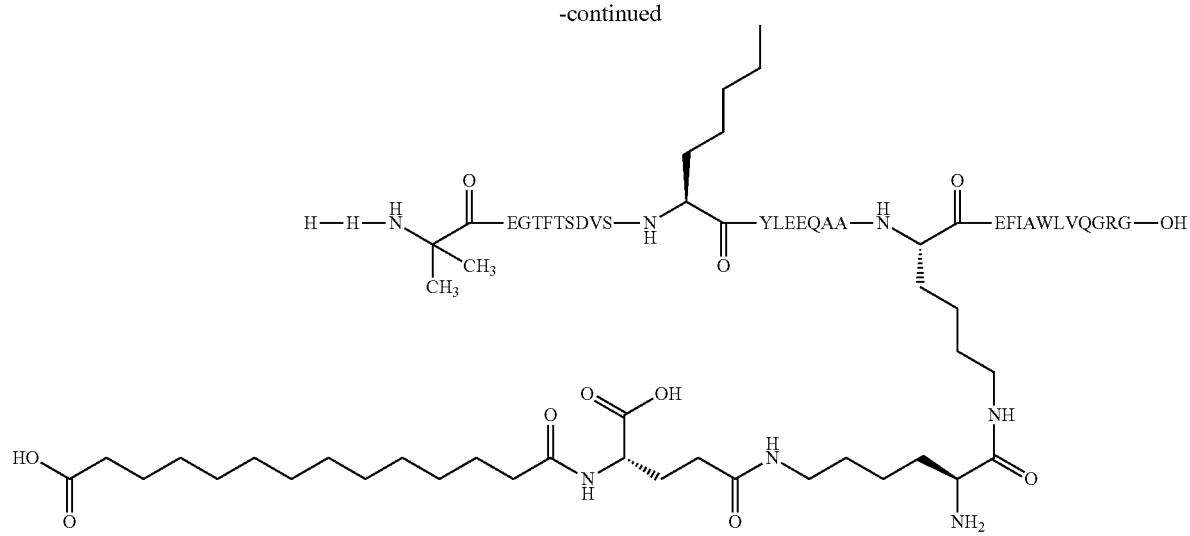
Example 25
N^ε18-[(2S)-2-amino-6-[[2-[2-[2-[[(4S)-4-carboxy-4-(13-carboxytridecanoylamino)butanoyl]amino]ethoxy]ethoxy]acetyl]amino]hexanoyl], N^ε26-[(2S)-2-amino-6-[[2-[2-[2-[[(4S)-4-carboxy-4-(13-carboxytridecanoylamino)butanoyl]amino]ethoxy]ethoxy]acetyl]amino]hexanoyl]-[Aib8,Lys18,Glu22,Gln34] (SEQ ID NO: 9)-OGLE-1-(7-37)-peptide
Chem. 44
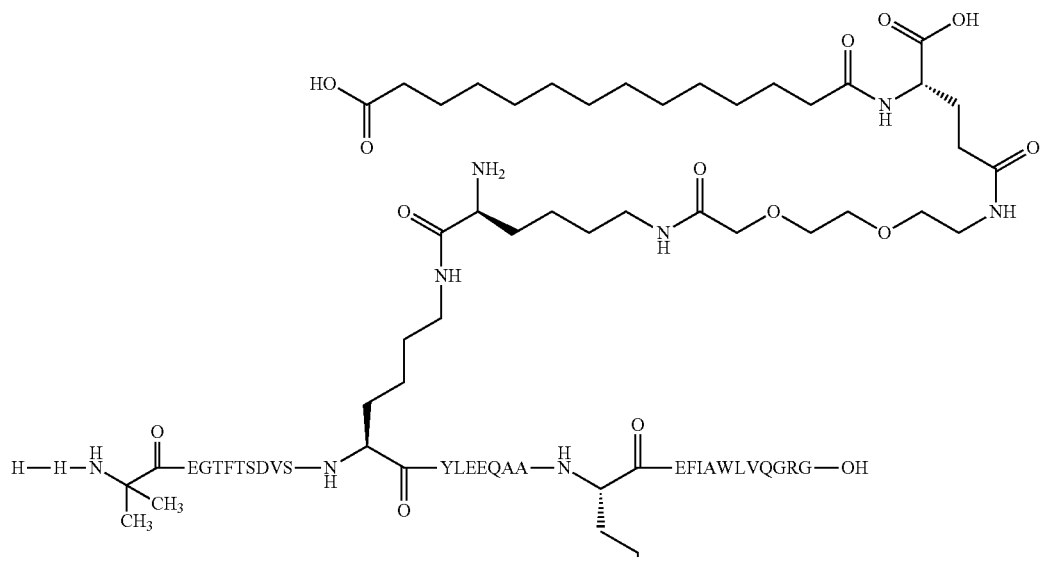
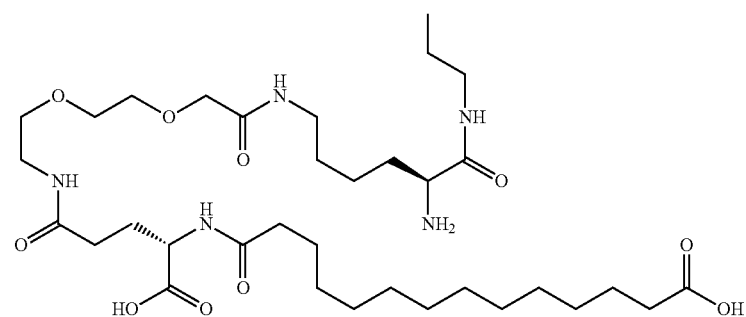

Example 26

$N^{\epsilon 18}$-[(2S)-2-amino-6-[[(4S)-4-carboxy-4-[[(4S)-4-carboxy-4-(15-carboxypentadecanoylamino)butanoyl]amino]butanoyl]amino]hexanoyl], $N^{\epsilon 26}$-[(2S)-2-amino-6-[[(4S)-4-carboxy-4-[[(4S)-4-carboxy-4-(15-carboxypentadecanoylamino)butanoyl]amino]butanoyl]amino]hexanoyl]-[Aib$^8$,Lys$^{18}$,Glu$^{22}$,Gln$^{34}$] (SEQ ID NO: 9)-GLP-1-(7-37)-peptide Chem. 45

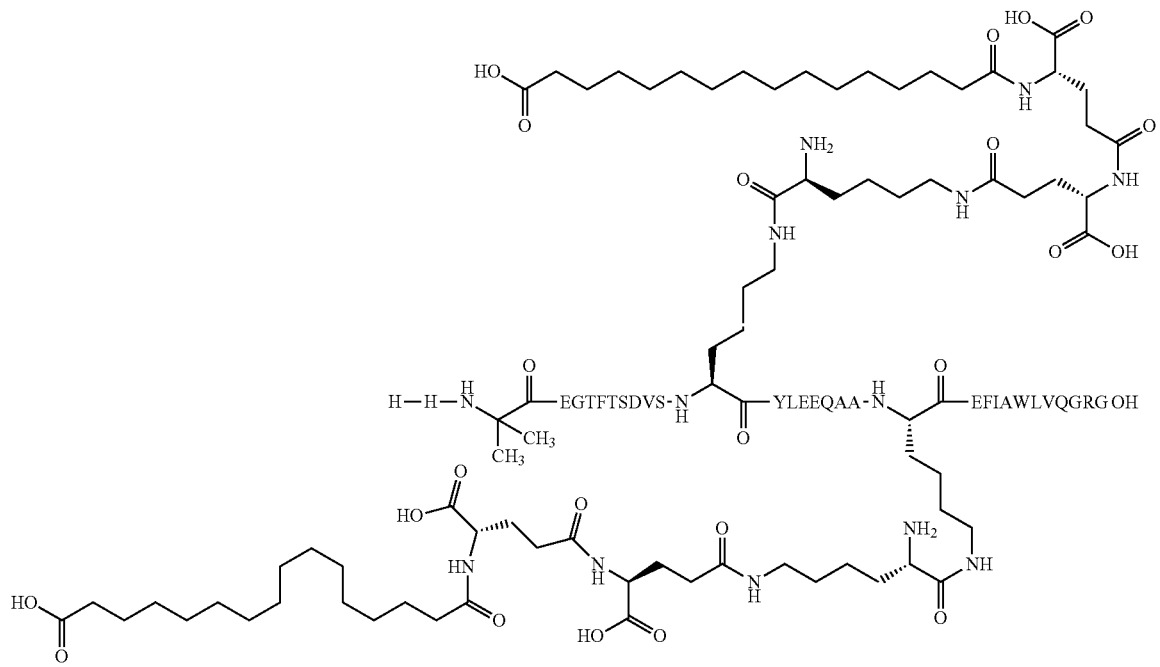

Example 27

$N^{\epsilon 18}$-[(2S)-2-amino-6-[[(4S)-4-carboxy-4-[[(4S)-4-carboxy-4-[[(4S)-4-carboxy-4-(15-carboxypentadecanoylamino)butanoyl]amino]butanoyl]amino]butanoyl]amino]hexanoyl], $N^{\epsilon 26}$-[(2S)-2-amino-6-[[(4S)-4-carboxy-4-[[(4S)-4-carboxy-4-[[(4S)-4-carboxy-4-(15-carboxypentadecanoylamino)butanoyl]amino]butanoyl]amino]butanoyl]amino]hexanoyl]-[Aib$^8$,Lys$^{18}$,Glu$^{22}$,Gln$^{34}$] (SEQ ID NO: 9)-GLP-1-(7-37)-peptide Chem. 46

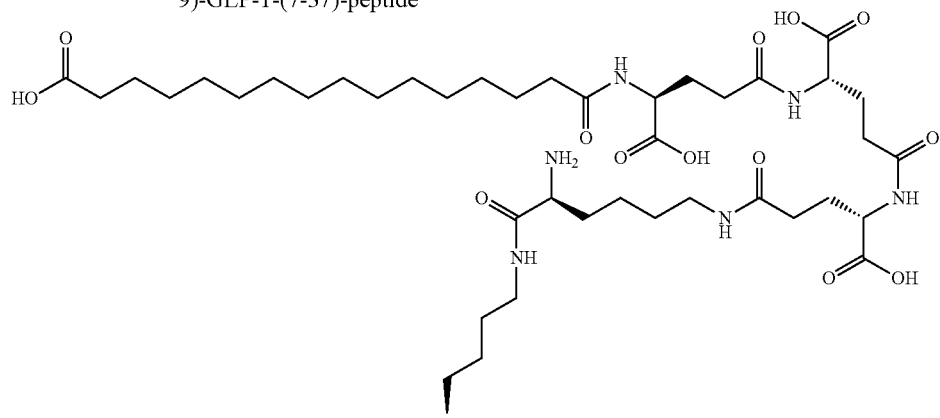

-continued
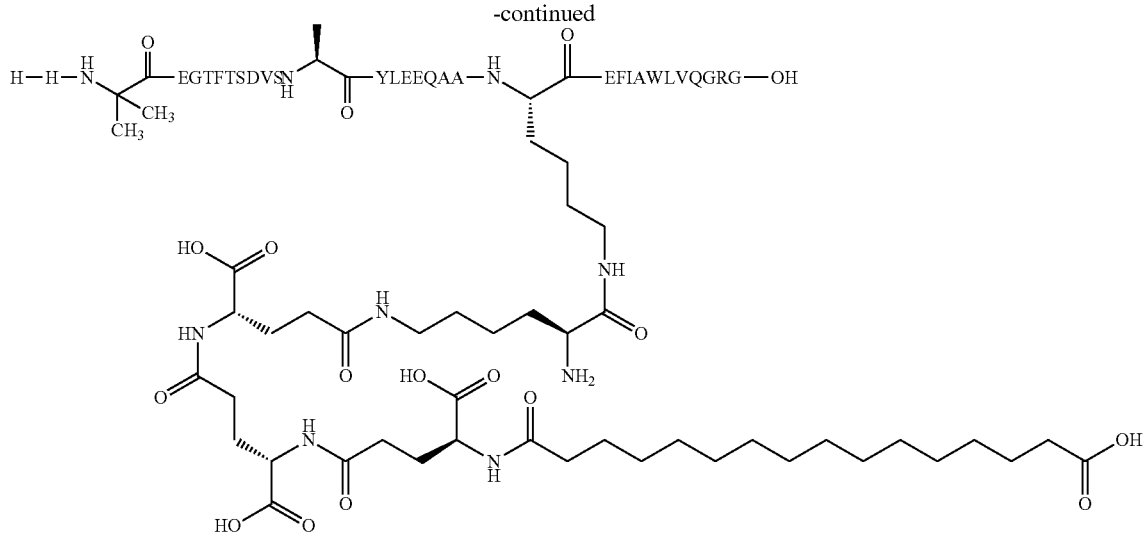
Example 28
$N^{\epsilon 18}$-[(2S)-2-amino-6-[[(4S)-4-carboxy-4-(15-carboxypentadecanoylamino)butanoyl]amino]hexanoyl], $N^{\epsilon 26}$-[(2S)-2-amino-6-[[(4S)-4-carboxy-4-(15-carboxypentadecanoylamino)butanoyl]amino]hexanoyl]-[Aib$^8$,Lys$^{18}$,Glu$^{22}$,Gln$^{34}$](SEQ ID NO: 9)-GLP-1-(7-37)-peptide
Chem. 47
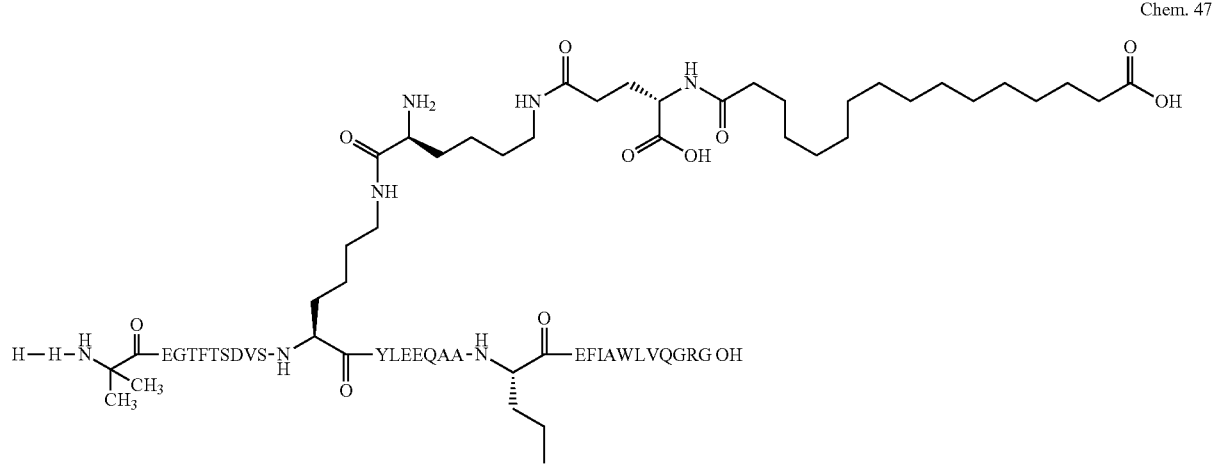
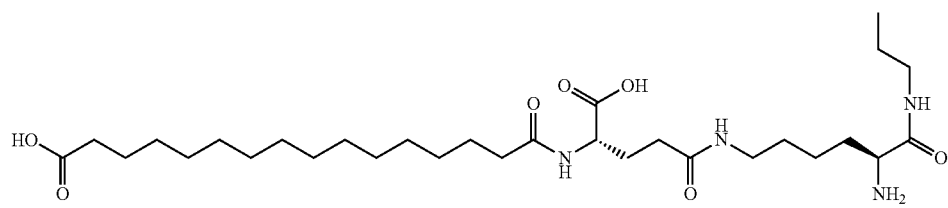

Example 29
$N^{\epsilon 18}$-[(2S)-2-amino-6-[[2-[2-[2-[[(4S)-4-carboxy-4-(15-carboxypentadecanoylamino)butanoyl]amino]ethoxy]ethoxy]acetyl]amino]hexanoyl], $N^{\epsilon 26}$-[(2S)-2-amino-6-[[2-[2-[2-[[(4S)-4-carboxy-4-(15-carboxypentadecanoylamino)butanoyl]amino]ethoxy]ethoxy]acetyl]amino]hexanoyl]-[Aib$^8$,Lys$^{18}$,Glu$^{22}$,Gln$^{34}$] (SEQ ID NO: 9)-GLP-1-(7-37)-peptide
Chem. 48
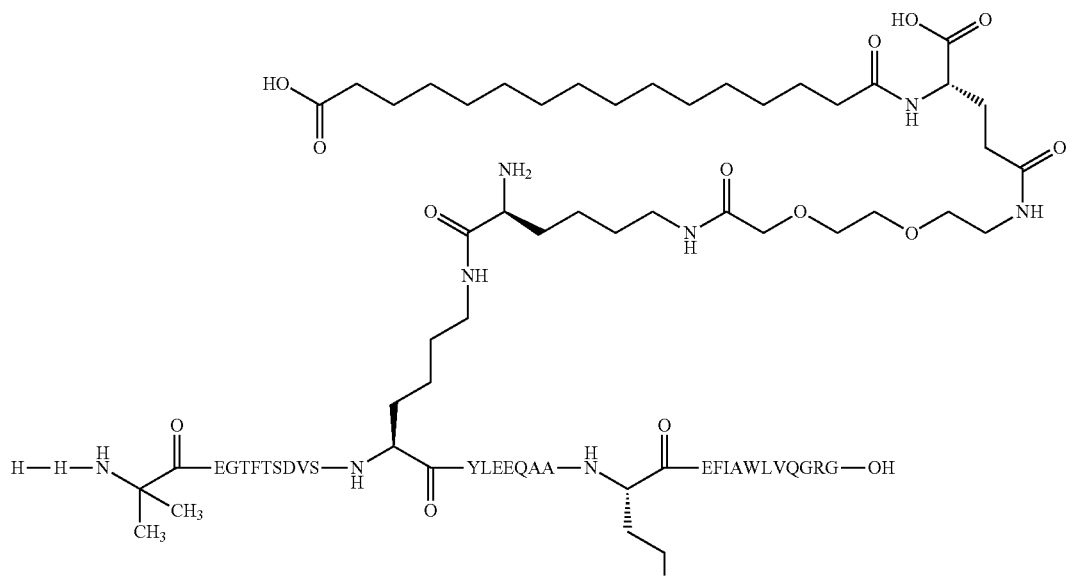
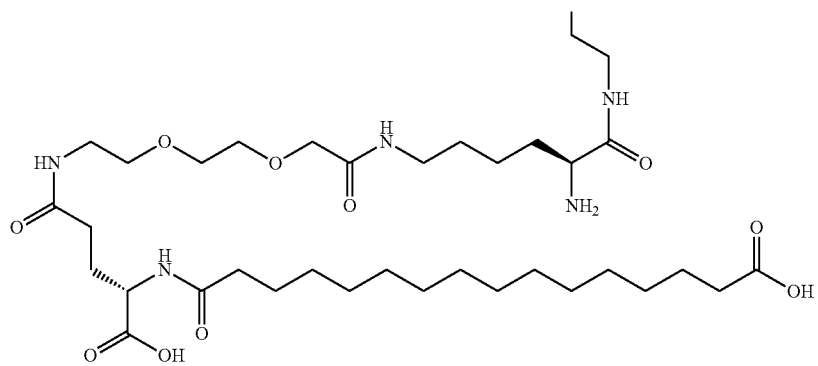

Example 30
N$^{\epsilon 18}$-[(2S)-2-amino-6-[[(4S)-4-carboxy-4-[[(4S)-4-carboxy-4-(17-carboxyheptadecanoylamino)butanoyl]amino]butanoyl]amino]hexanoyl], N$^{\epsilon 26}$-[(2S)-2-amino-6-[[(4S)-4-carboxy-4-[[(4S)-4-carboxy-4-(17-carboxyheptadecanoylamino)butanoyl]amino]butanoyl]amino]hexanoyl]-[Aib$^8$,Lys$^{18}$,Glu$^{22}$,Gln$^{34}$] (SEQ ID NO: 9)-GLP-1-(7-37)-peptide
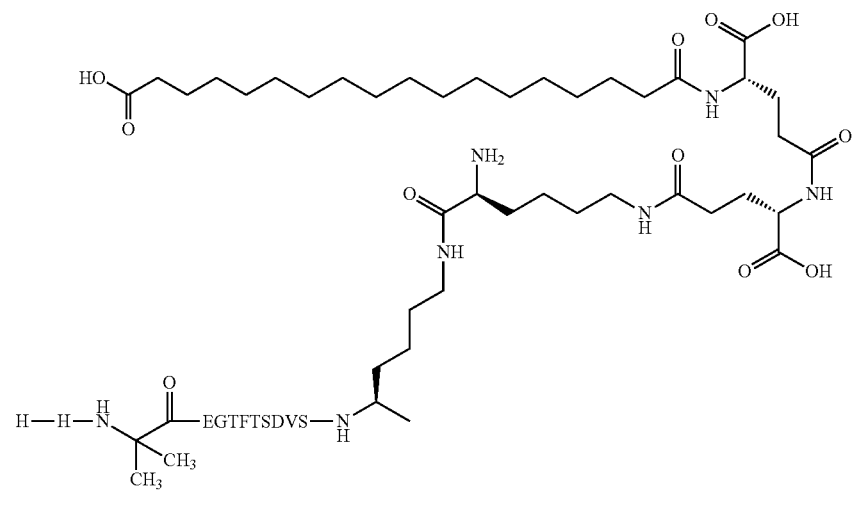
Chem. 49
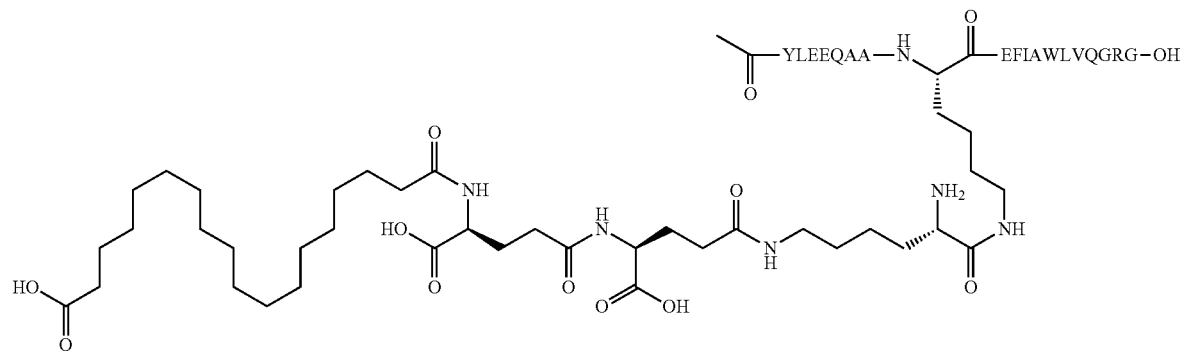

Example 31
N$^{\epsilon 18}$-[(2S)-2-amino-6-[[(4S)-4-carboxy-4-[[4-carboxy-4-[[(4S)-4-carboxy-4-(17-carboxyheptadecanoylamino)butanoyl]amino]butanoyl]amino]butanoyl]amino]hexanoyl, N$^{\epsilon 26}$]-[(2S)-2-amino-6-[[(4S)-4-carboxy-4-[[4-carboxy-4-[[(4S)-4-carboxy-4-(17-carboxyheptadecanoylamino)butanoyl]amino]butanoyl]amino]butanoyl]amino]hexanoyl]-[Aib$^8$, Lys$^{18}$,Glu$^{22}$,Gln$^{34}$] (SEQ ID NO: 9)-GLP-1-(7-37)-peptide
Chem. 50
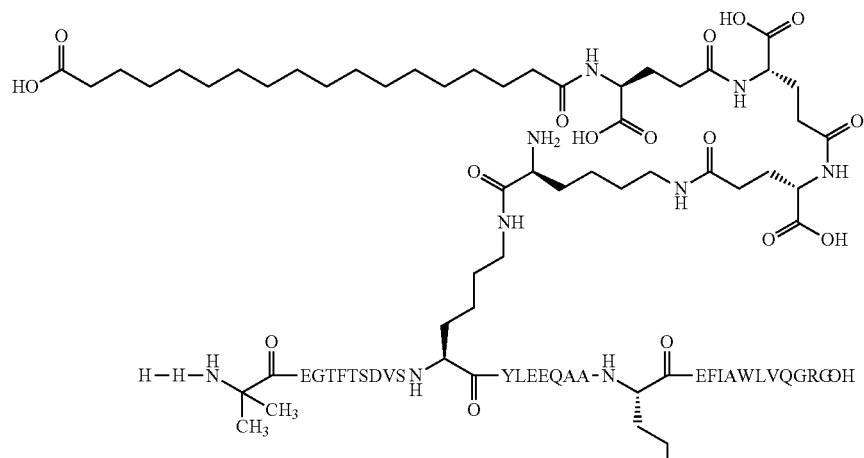
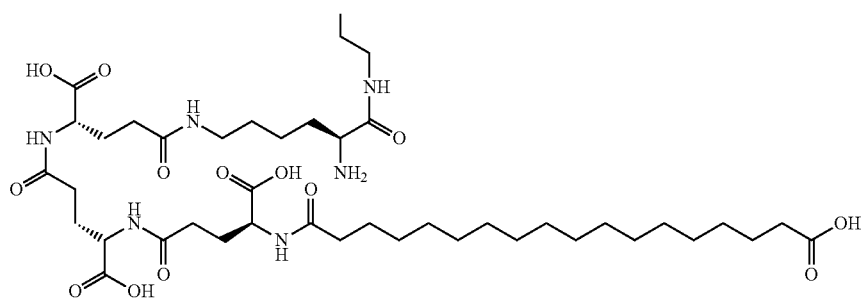

Example 32

N^ε18-[(2S)-2-amino-6-[[(2S)-2-amino-6-[[(4S)-4-carboxy-4-(17-carboxyheptadecanoylamino)butanoyl]amino]hexanoyl]amino]hexanoyl], N^ε26-[(2S)-2-amino-6-[[(2S)-2-amino-6-[[(4S)-4-carboxy-4-(17-carboxyheptadecanoylamino)butanoyl]amino]hexanoyl]amino]hexanoyl]-[Aib^8,Lys^18,Glu^22,Gln^34] (SEQ ID NO: 9)-GLP-1-(7-37)-peptide Chem. 51

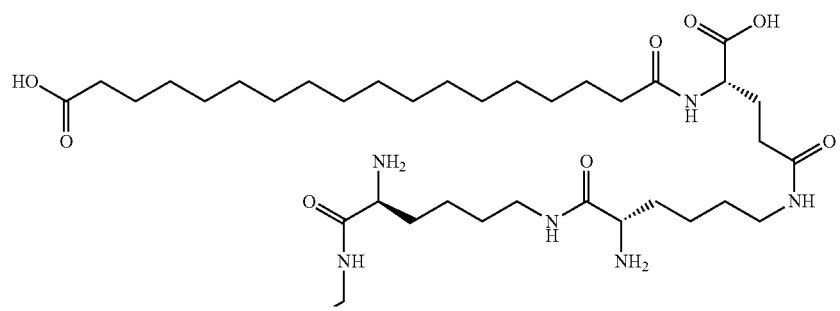

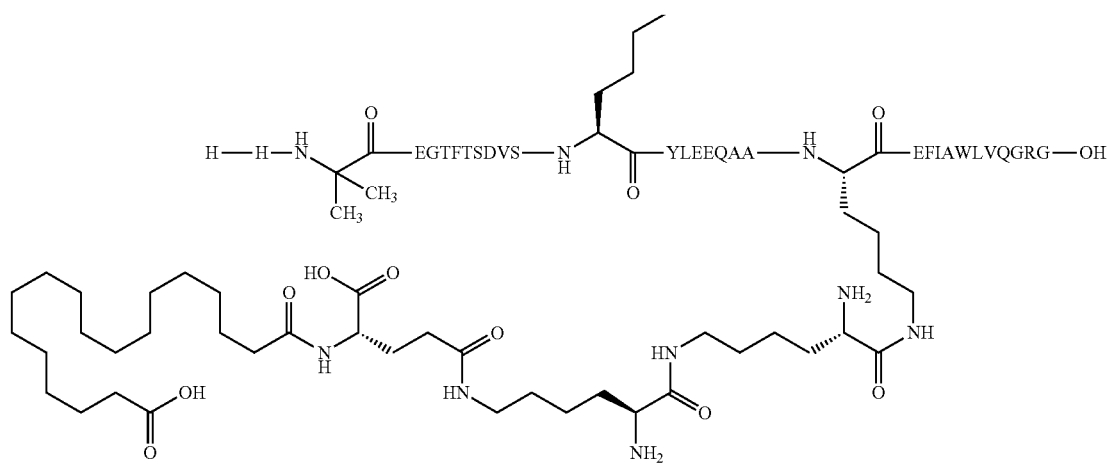

Example 33

N^ε18-[(2S)-2-amino-6-[[(4S)-4-carboxy-4-(17-carboxyheptadecanoylamino)butanoyl]amino]hexanoyl], N^ε26-[(2S)-2-amino-6-[[(4S)-4-carboxy-4-(17-carboxyheptadecanoylamino)butanoyl]amino]hexanoyl]-[Aib^8,Lys^18,Glu^22,Gln^34] (SEQ ID NO: 9)-GLP-1-(7-37)-peptide Chem. 52

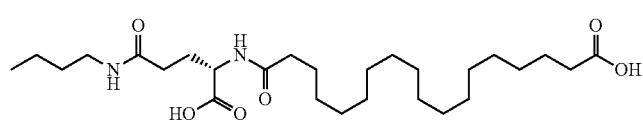

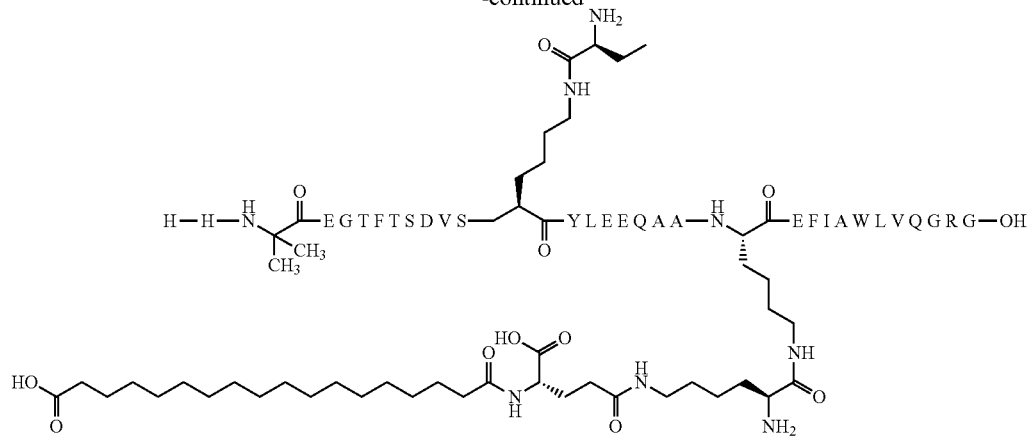
Example 34
N^ε18-[(2S)-2-amino-6-[[2-[2-[2-[[(4S)-4-carboxy-4-(17-carboxyheptadecanoylamino)butanoyl]amino]ethoxy]ethoxy]acetyl]amino]hexanoyl], N^ε26 [(2S)-2-amino-6-[[2-[2-[2-[[(4S)-4-carboxy-4-(17-carboxyheptadecanoylamino)butanoyl]amino]ethoxy]ethoxy]acetyl]amino]hexanoyl]-[Aib8,Lys18,Glu22,Gln34] (SEQ ID NO: 9)-GLP-1-(7-37)-peptide
Chem. 53
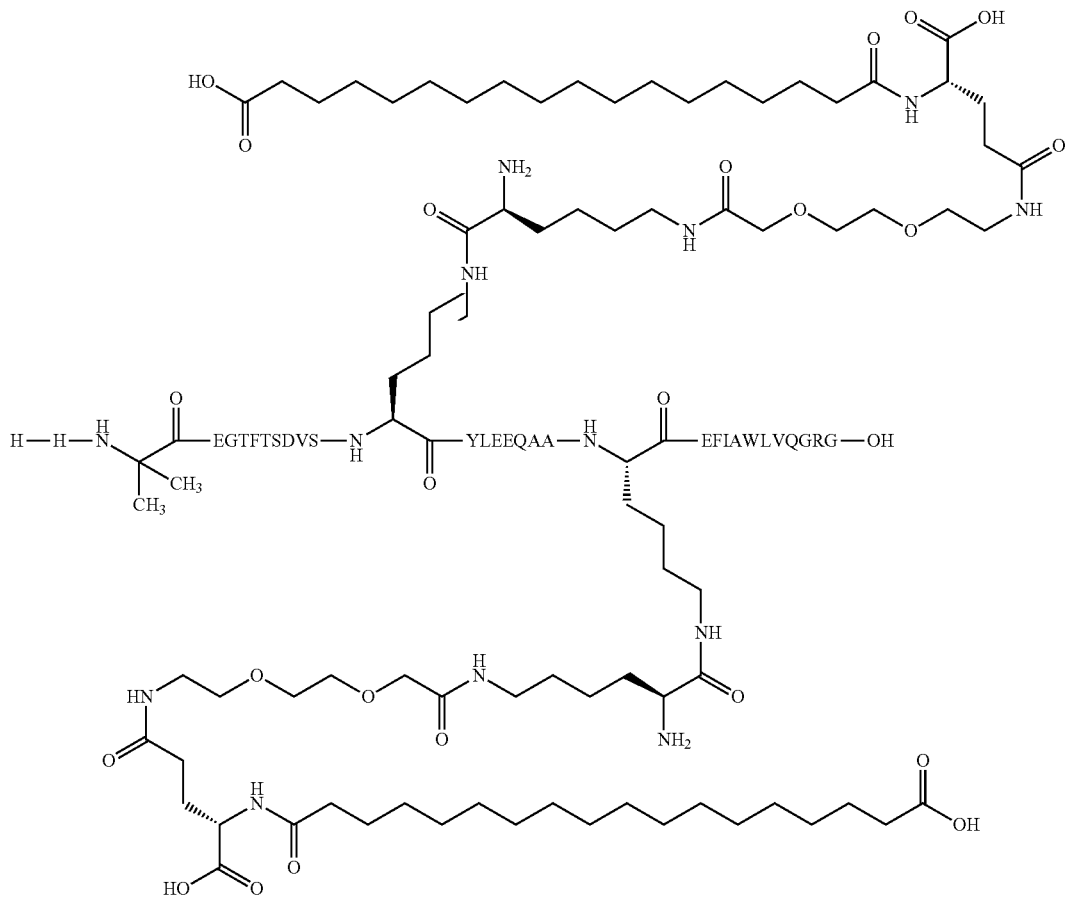

Example 35
Nε$^{18}$-[(2S)-2-amino-6-[[(2S)-2-amino-6-[[(4S)-4-carboxy-4-(19-carboxynonadecanoylamino)butanoyl]amino]hexanoyl]amino]hexanoyl], Nε$^{26}$-[(2S)-2-amino-6-[[(2S)-2-amino-6-[[(4S)-4-carboxy-4-(19-carboxynonadecanoylamino)butanoyl]amino]hexanoyl]amino]hexanoyl]-[Aib$^8$,Lys$^{18}$,Glu$^{22}$,Gln$^{34}$] (SEQ ID NO: 9)-GLP-1-(7-37)-peptide
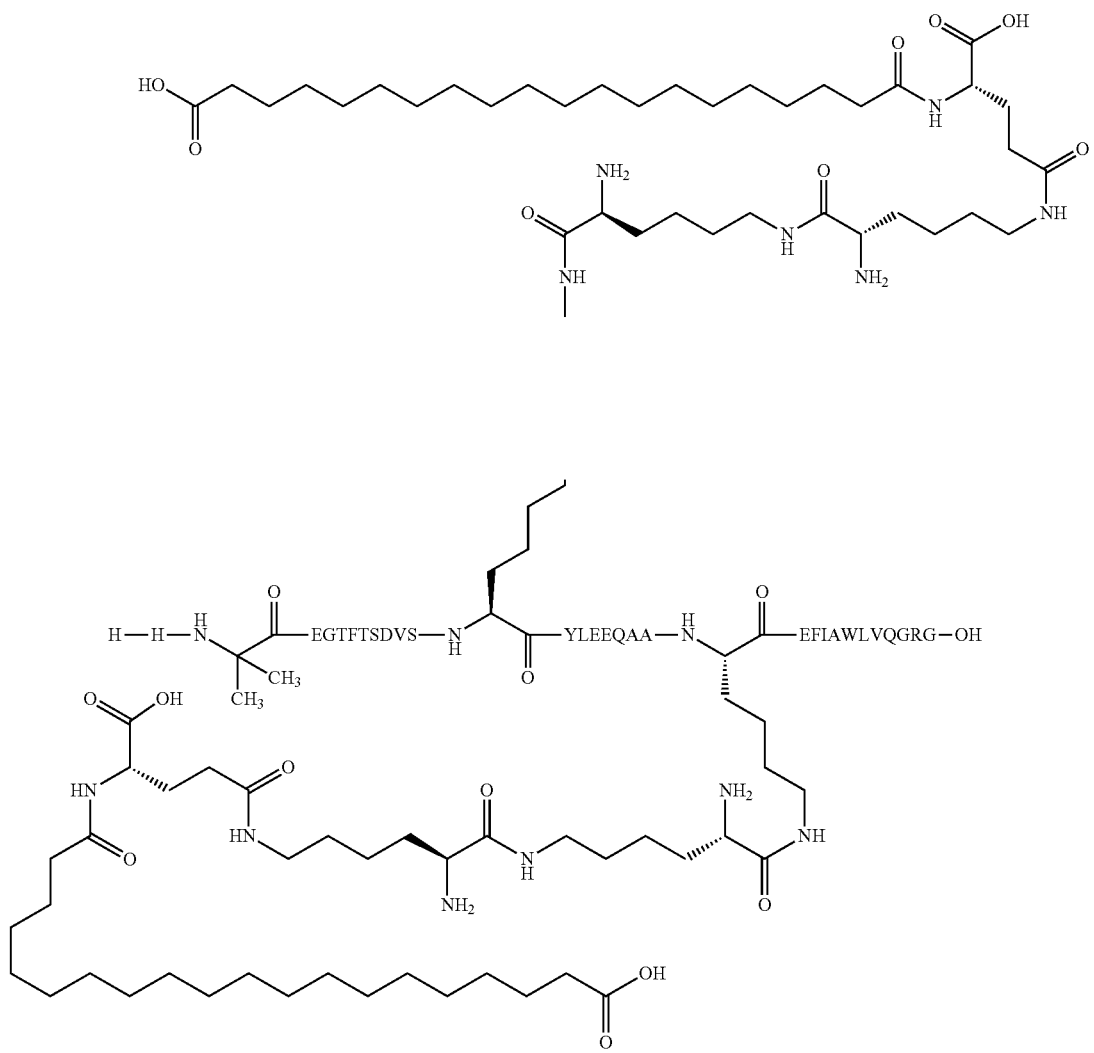
Chem. 54

Example 36

$N^{\epsilon18}$-[(2S)-2-amino-6-[[(4S)-4-carboxy-4-(19-carboxynonadecanoylamino)butanoyl]amino]hexanoyl], $N^{\epsilon26}$-[(2S)-2-amino-6-[[(4S)-4-carboxy-4-(19-carboxynonadecanoylamino)butanoyl]amino]hexanoyl]-[Aib, Lys$^{18}$,Glu$^{22}$,Gln$^{34}$](SEQ ID NO: 9)-GLP-1-(7-37)-peptide Chem. 55

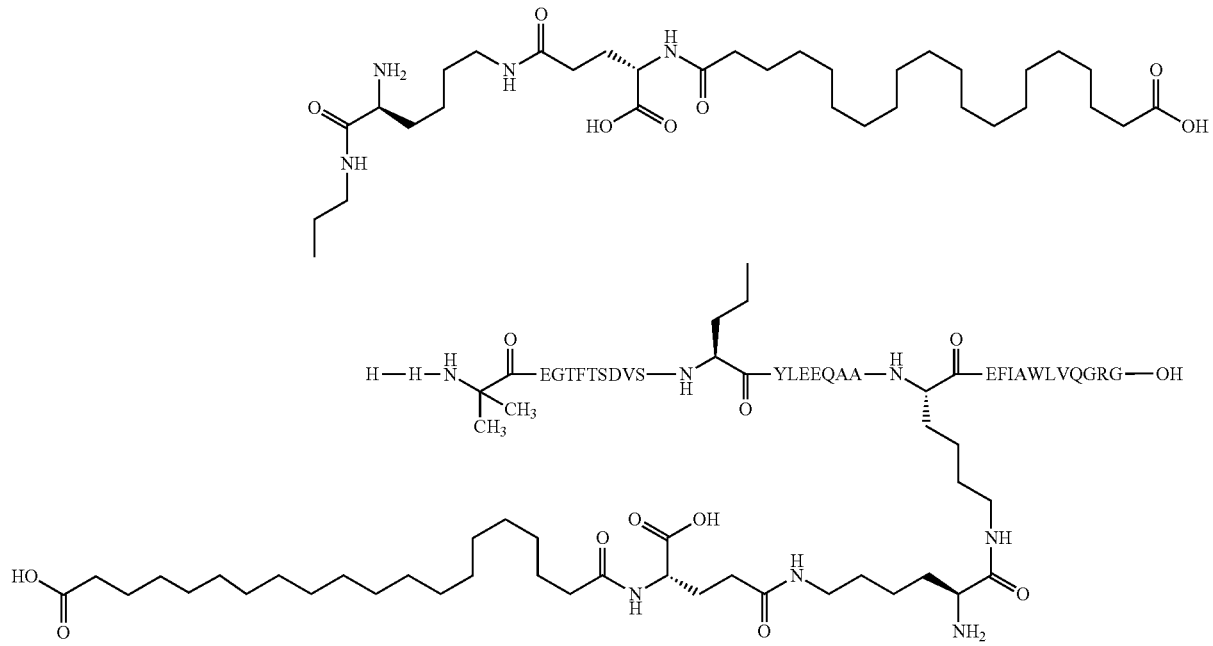

Example 37

$N^{\epsilon18}$-[(2S)-2-amino-6-[[2-[2-[2-[[(4S)-4-carboxy-4-(19-carboxynonadecanoylamino)butanoyl]amino]ethoxy]ethoxy]acetyl]amino]hexanoyl], $N^{\epsilon26}$-[(2S)-2-amino-6-[[2-[2-[2-[[(4S)-4-carboxy-4-(17-carboxyheptadecanoylamino)butanoyl]amino]ethoxy]ethoxy]acetyl]amino]hexanoyl]-[Aib$^8$,Lys$^{18}$, Glu$^{22}$,Gln$^{34}$] (SEQ ID NO: 9)-GLP-1-(7-37)-peptide Chem. 56

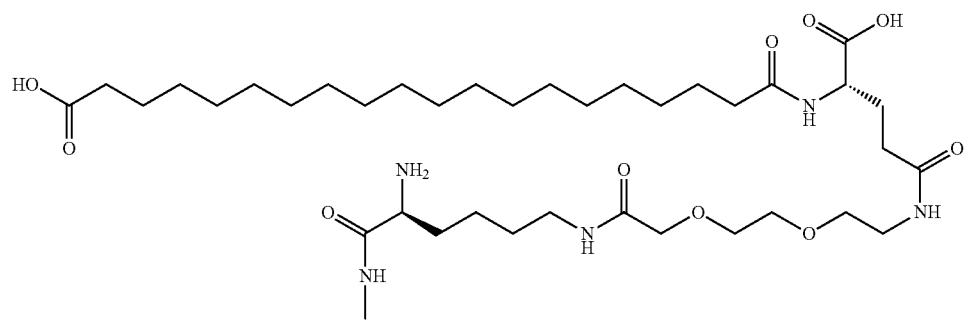

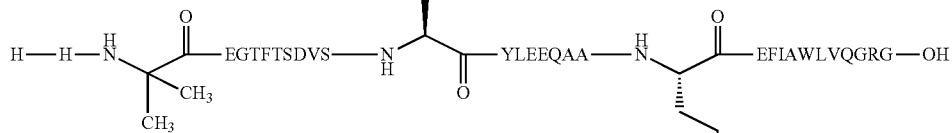
Example 38
$N^{\epsilon 18}$-[(2S)-2-amino-6-[[(4S)-4-carboxy-4-[[4-carboxy-4-[10-(4-carboxyphenoxyl)decanoylamino]butanoyl]amino]butanoyl]amino]hexanoyl], $N^{\epsilon 26}$-[(2S)-2-amino-6-[[(4S)-4-carboxy-4-[[4-carboxy-4-[10-(4-carboxyphenoxyl)decanoylamino]butanoyl]amino]butanoyl]amino]hexanoyl]-[Aib$^8$,Lys$^{18}$,Glu$^{22}$,Gln$^{34}$] (SEQ ID NO: 9)-GLP-1-(7-37)-peptide
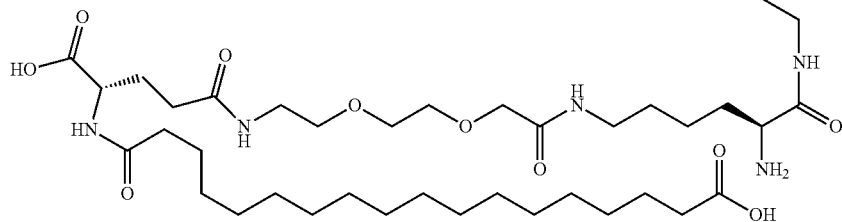
Chem. 57
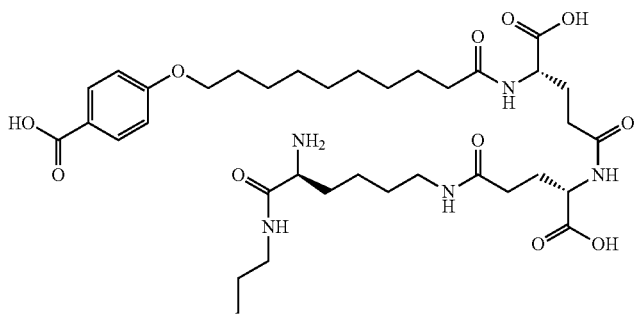
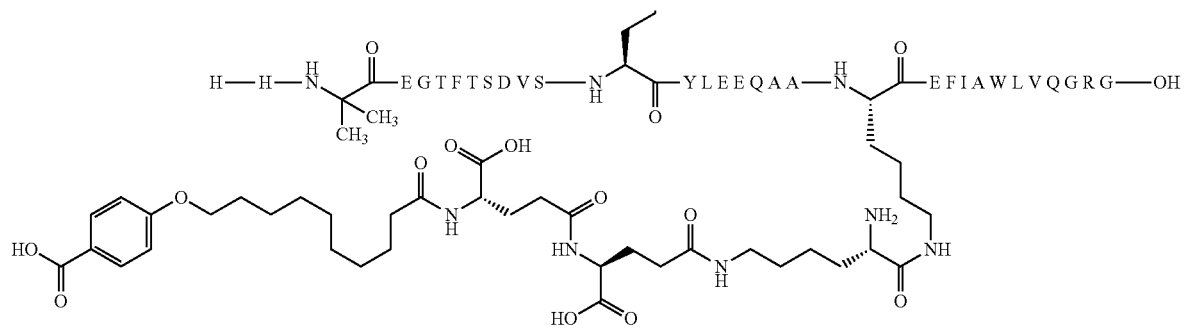

Example 39
N^ε18-[(2S)-2-amino-6-[[(4S)-4-carboxy-4-[[4-carboxy-4-[[(4S)-4-carboxy-4-[10-(4-carboxyphenoxyl)decanoylamino]butanoyl]amino]butanoyl]amino]butanoyl]amino]hexanoyl]N^ε26-[(2S)-2-amino-6-[[(4S)-4-carboxy-4-[[4-carboxy-4-[[4-carboxy-4-[[(4S)-4-carboxy-4-[10-(4-carboxyphenoxyl)decanoylamino]butanoyl]amino]butanoyl]amino]butanoyl]amino]hexanoyl]-[Aib$^8$,Lys$^{18}$,Glu$^{22}$,Gln$^{34}$] (SEQ ID NO: 9)-GLP-1-(7-37)-peptide
Chem. 58
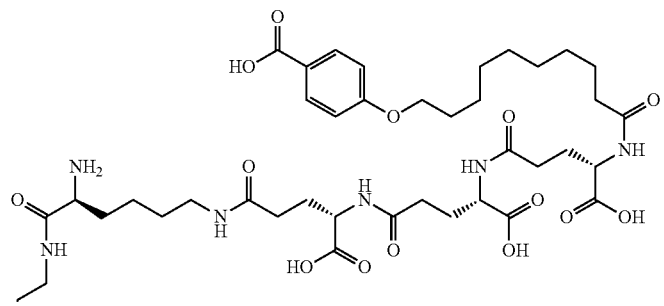
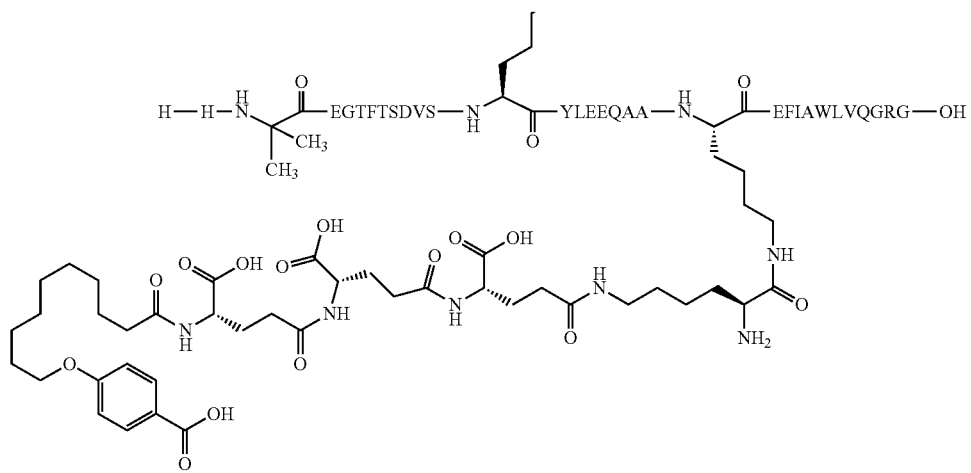

Example 40
$N^{\epsilon 18}$-[(2S)-2-amino-6-[[4-carboxy-4-[[(4S)-4-carboxy-4-[12-(4-carboxyphenoxy)dodecanoylamino]butanoyl]amino]butanoyl]amino]hexanoyl], $N^{\epsilon 26}$-[(2S)-2-amino-6-[[4-carboxy-4-[[(4S)-4-carboxy-4-[12-(4-carboxyphenoxy)dodecanoylamino]butanoyl]amino]butanoyl]amino]hexanoyl]-[Aib8,Lys18,Glu22,Gln34] (SEQ ID NO: 9)-GLP-1-(7-37)-peptide
Chem. 59
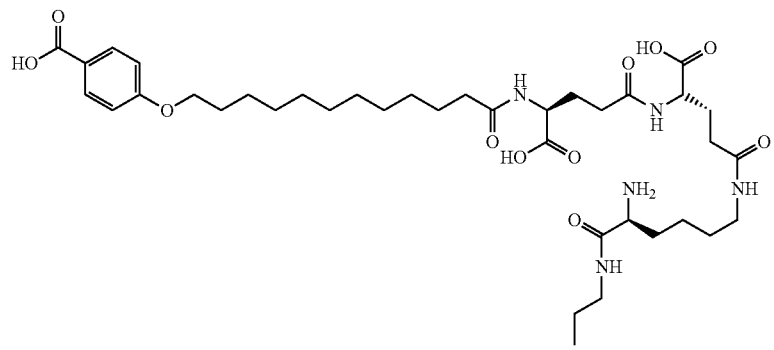
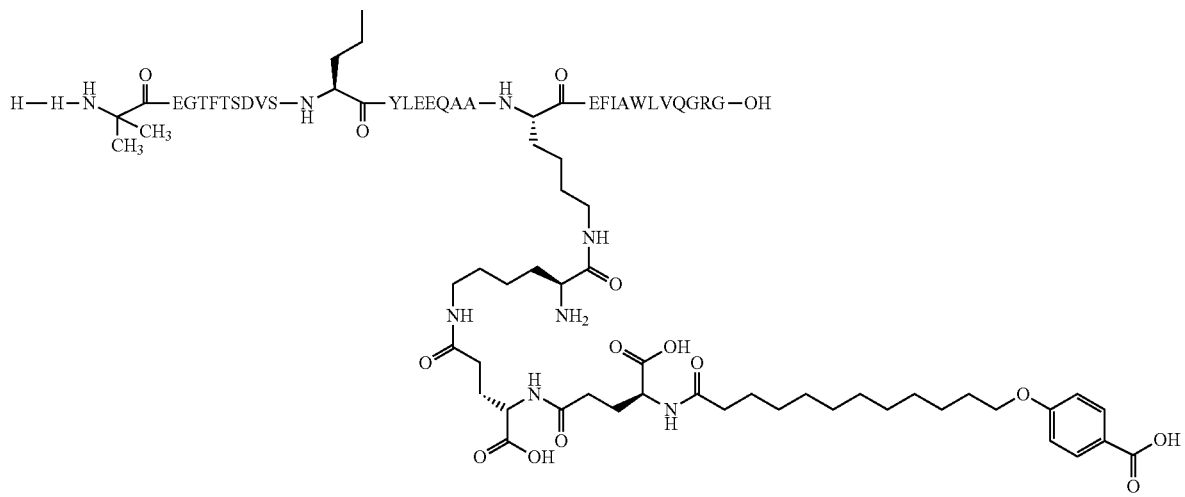

Example 41
$N^{\epsilon 18}$-[(2S)-2-amino-6-[[(4S)-4-carboxy-4-[[4-carboxy-4-[[(4S)-4-carboxy-4-[12-(4-carboxyphenoxy)dodecanoylamino]butanoyl]amino]butanoyl]amino]butanoyl]amino]hexanoyl], $N^{\epsilon 26}$-[(2S)-2-amino-6-[[(4S)-4-carboxy-4-[[4-carboxy-4-[[(4S)-4-carboxy-4-[12-(4-carboxyphenoxy)dodecanoylamino]butanoyl]amino]butanoyl]amino]butanoyl]amino]hexanoyl]-[Aib$^8$,Lys$^{18}$,Glu$^{22}$,Gln$^{34}$] (SEQ ID NO: 9)-GLP-1-(7-37)-peptide
Chem. 60
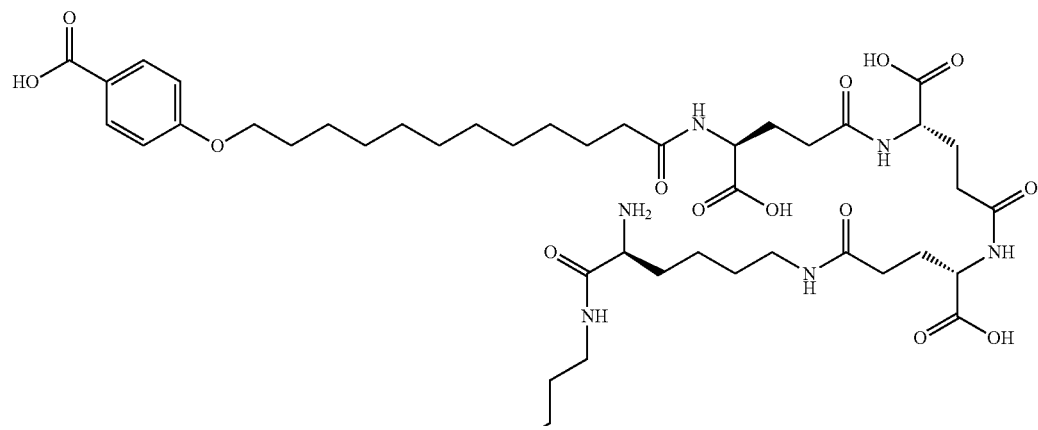
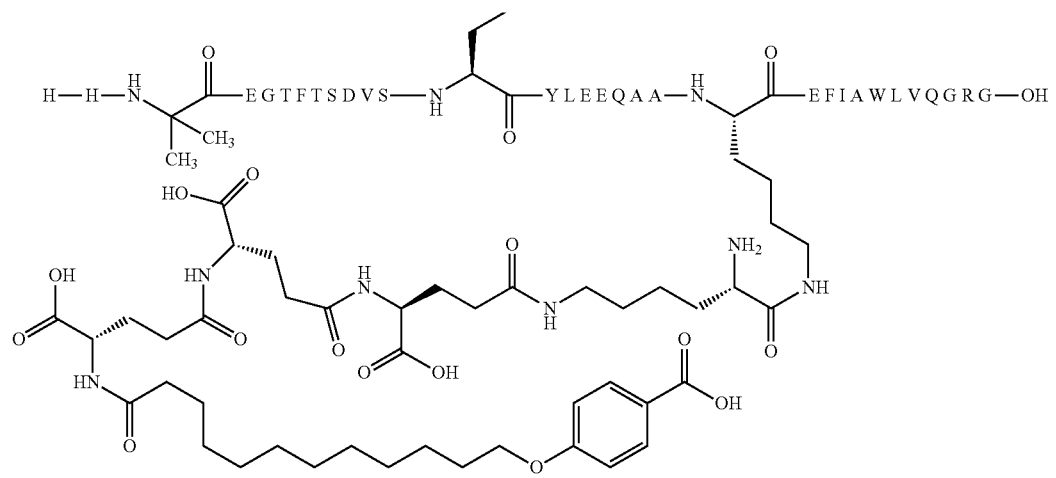

Example 42

N^ε18-[(2S)-2-amino-6-[[(2S)-2-amino-6-[[(4S)-4-carboxy-4-(13-carboxytridecanoylamino)butanoyl]amino]hexanoyl]amino]hexanoyl], N^ε26-[(2S)-2-amino-6-[[(2S)-2-amino-6-[[(4S)-4-carboxy-4-(13-carboxytridecanoylamino)butanoyl]amino]hexanoyl]amino]hexanoyl]-[Aib8,Lys18,Gln34](SEQ ID NO: 12)-GLP-1-(7-37)-peptide Chem. 61

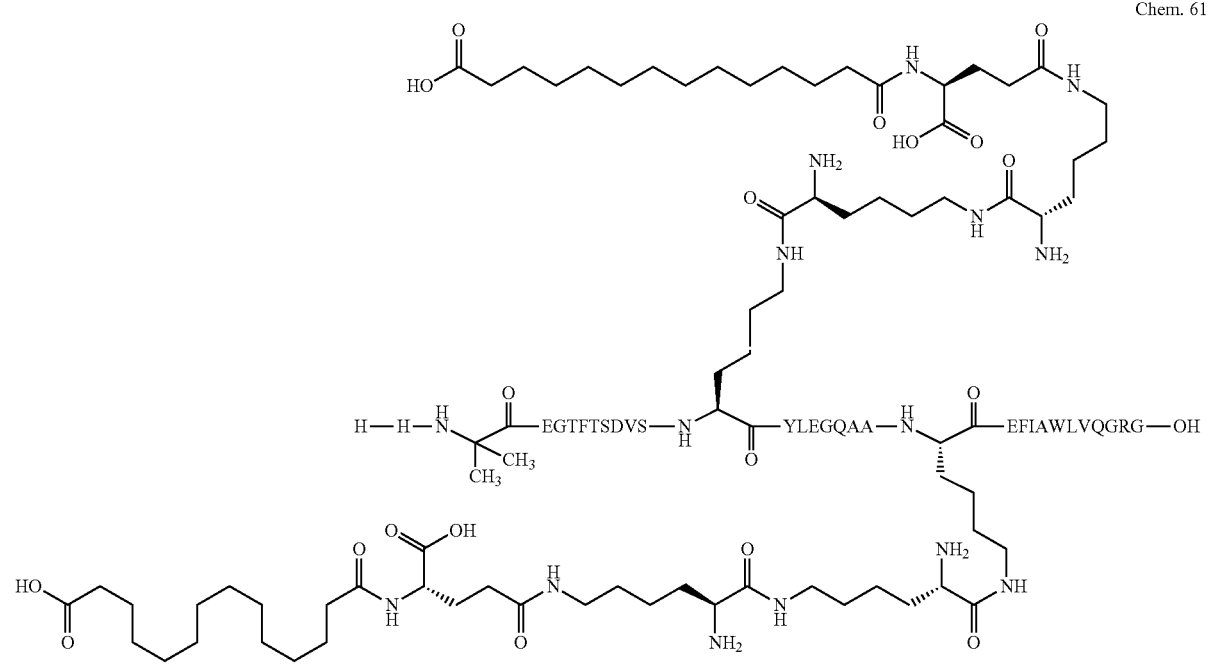

Example 43

N^ε18-[(2S)-2-amino-6-[[(4S)-4-carboxy-4-(13-carboxytridecanoylamino)butanoyl]amino]hexanoyl], N^ε26-[(2S)-2-amino-6-[[(4S)-4-carboxy-4-(13-carboxytridecanoylamino)butanoyl]amino]hexanoyl]-[Aib8,Lys18,Gln34] (SEQ ID NO: 12)-GLP-1-(7-37)-peptide Chem. 62

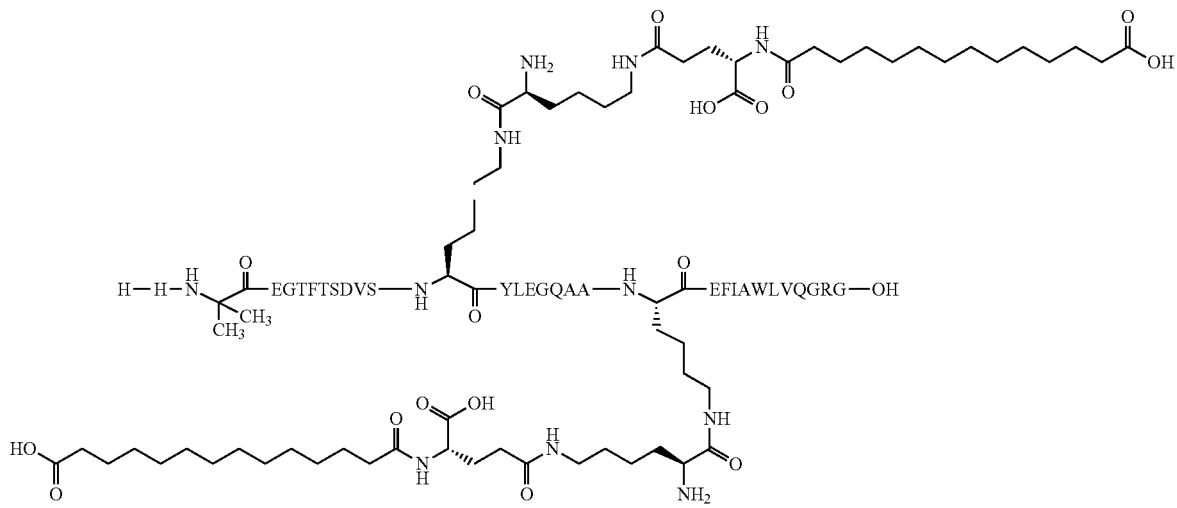

Example 44
N^ε18-[(2S)-2-amino-6-[[2-[2-[2-[[4-carboxy-4-(13-carboxytridecanoylamino)butanoyl]amino]ethoxy]ethoxy]acetyl]amino]hexanoyl], N^ε26-[(2S)-2-amino-6-[[2-[2-[2-[[4-carboxy-4-(13-carboxytridecanoylamino)butanoyl]amino]ethoxy]ethoxy]acetyl]amino]hexanoyl]-[Aib⁸,Lys¹⁸,Gln³⁴] (SEQ ID NO: 12)-GLP-1-(7-37)-peptide
Chem. 63
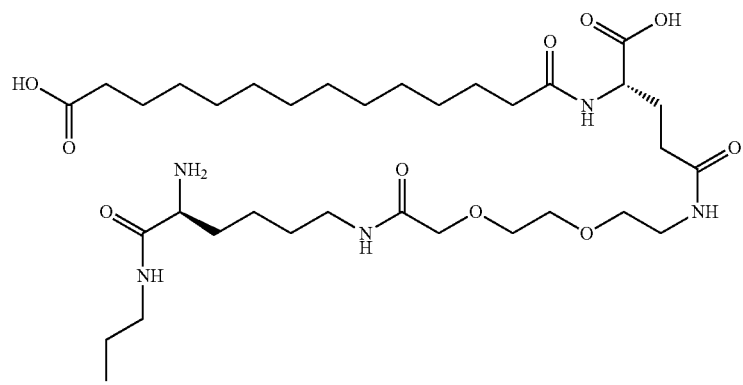
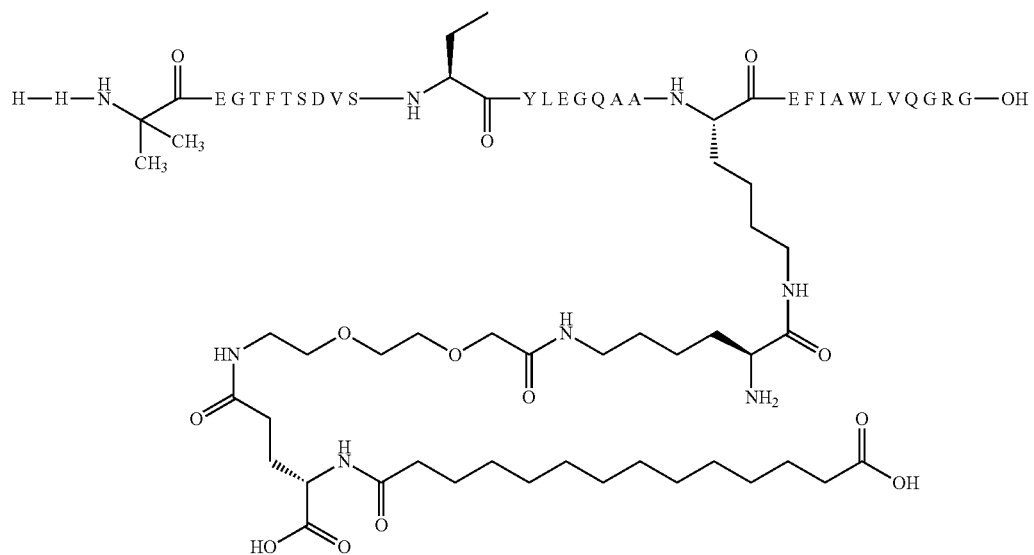

Example 45

$N^{\epsilon 18}$-[(2S)-2-amino-6-[[(4S)-4-carboxy-4-(17-carboxyheptadecanoylamino)butanoyl]amino]hexanoyl], $N^{\epsilon 26}$-[(2S)-2-amino-6-[[(4S)-4-carboxy-4-(17-carboxyheptadecanoylamino)butanoyl]amino]hexanoyl]-[Aib$^8$,Lys$^{18}$,Gln$^{34}$](SEQ ID NO: 12)-GLP-1-(7-37)-peptide Chem. 64

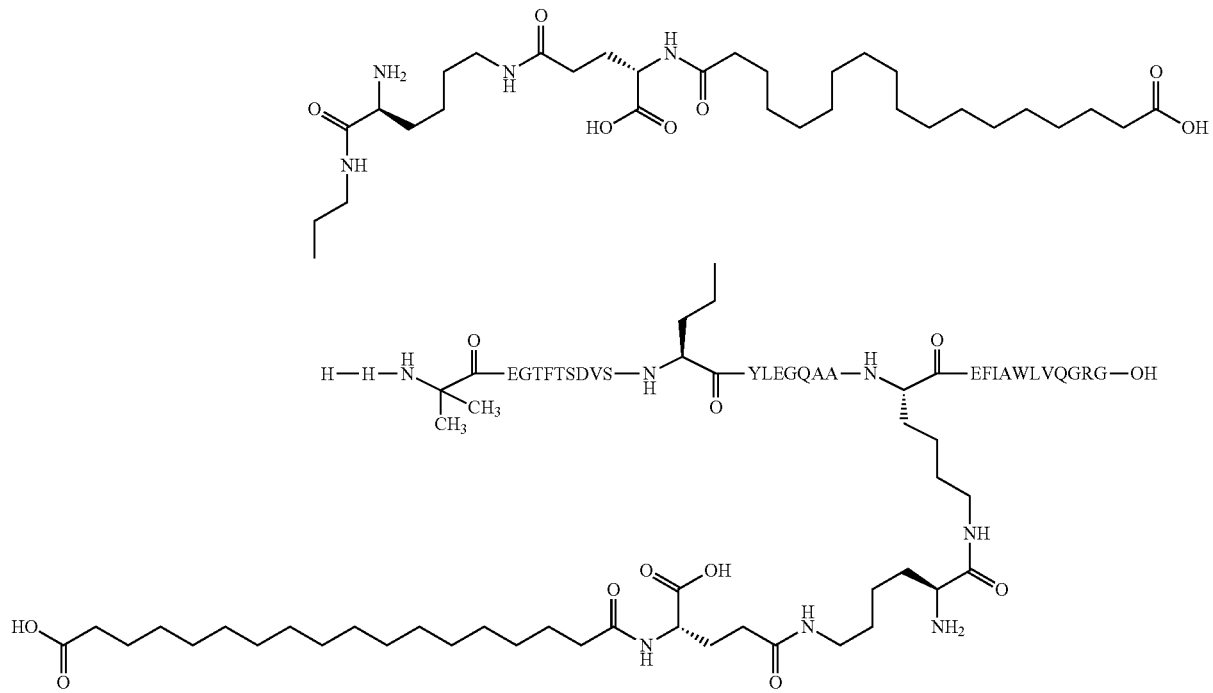

Example 46

$N^{\epsilon 18}$-[(2S)-2-amino-6-[[2-[2-[2-[[4-carboxy-4-(17-carboxyheptadecanoylamino)butanoyl]amino]ethoxy]ethoxy]acetyl]amino]hexanoyl], $N^{\epsilon 26}$-[(2S)-2-amino-6-[[2-[2-[2-[[4-carboxy-4-(17-carboxyheptadecanoylamino)butanoyl]amino]ethoxy]ethoxy]acetyl]amino]hexanoyl]-[Aib$^8$,Lys$^{18}$,Gln$^{34}$] (SEQ ID NO: 12)-GLP-1-(7-37)-peptide Chem. 65

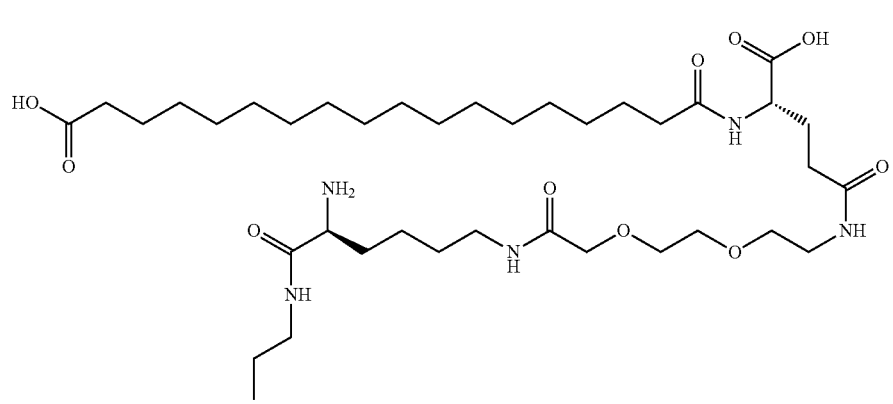

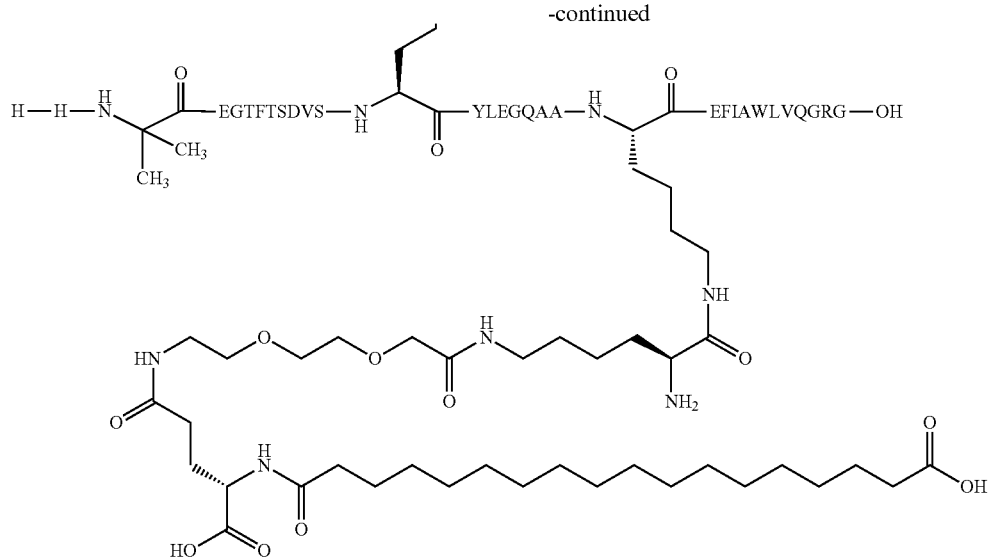
Example 47
N$^{\epsilon 18}$-[(2S)-2-amino-6-[[(2S)-2-amino-6-[[(4S)-4-carboxy-4-(19-carboxynonadecanoylamino)butanoyl]amino]hexanoyl]amino]hexanoyl], N$^{\epsilon 26}$-[(2S)-2-amino-6-[[(2S)-2-amino-6-[[(4S)-4-carboxy-4-(19-carboxynonadecanoylamino)butanoyl]amino]hexanoyl]amino]hexanoyl]-[Aib$^8$,Lys$^{18}$,Gln$^{34}$] (SEQ ID NO: 12)-GLP-1-(7-37)-peptide
Chem. 66
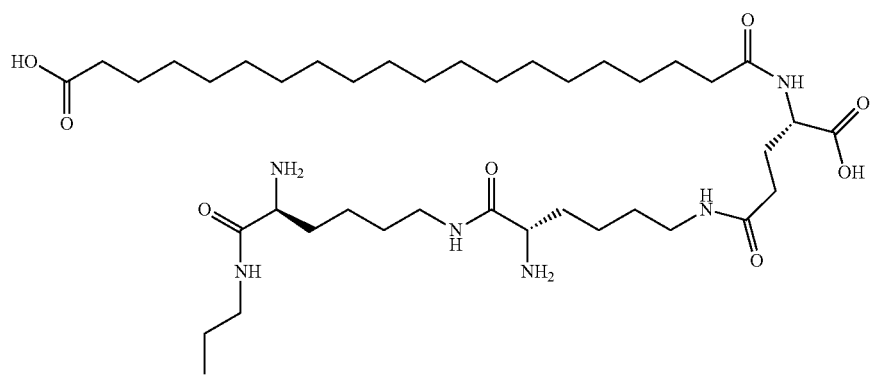

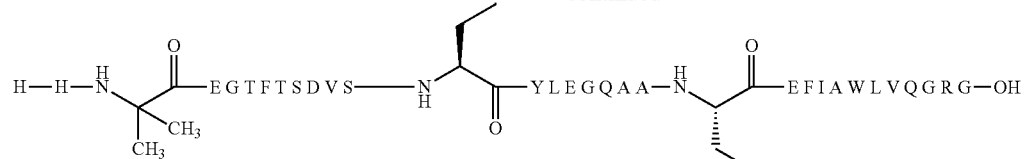
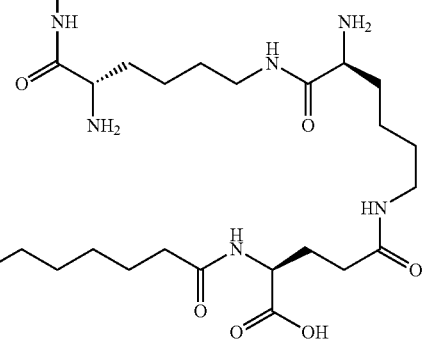
Example 48
N$^{\epsilon 18}$-[(2S)-2-amino-6-[[(4S)-4-carboxy-4-(19-carboxynonadecanoylamino)butanoyl]amino]hexanoyl], N$^{\epsilon 26}$-[(2S)-2-amino-6-[[(4S)-4-carboxy-4-(19-carboxynonadecanoylamino)butanoyl]amino]hexanoyl]-[Aib$^8$,Lys$^{18}$,Gln$^{34}$](SEQ ID NO: 12)-GLP-1-(7-37)-peptide
Chem. 67
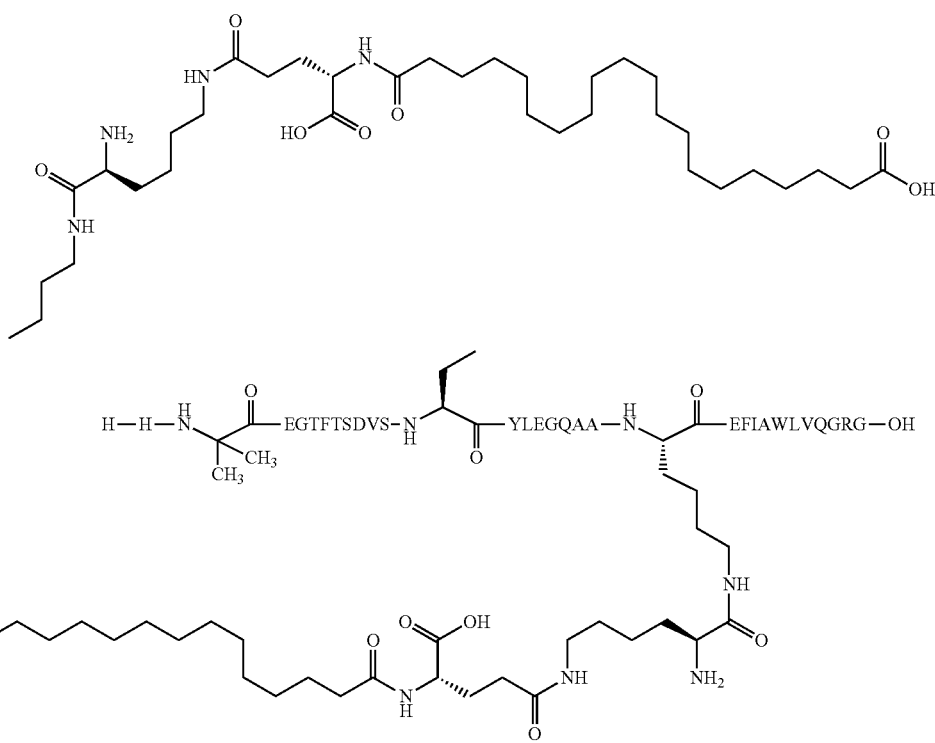

Example 49
$N^{\epsilon18}$-[(2S)-2-amino-6-[[2-[2-[2-[[4-carboxy-4-(19-carboxynonadecanoylamino)butanoyl]amino]ethoxy]ethoxy]acetyl]amino]hexanoyl], $N^{\epsilon26}$-[(2S)-2-amino-6-[[2-[2-[2-[[4-carboxy-4-(17-carboxyheptadecanoylamino)butanoyl]amino]ethoxy]ethoxy]acetyl]amino]hexanoyl]-[Aib$^8$,Lys$^{18}$,Gln$^{34}$] (SEQ ID NO: 12)-GLP-1-(7-37)-peptide
Chem. 68
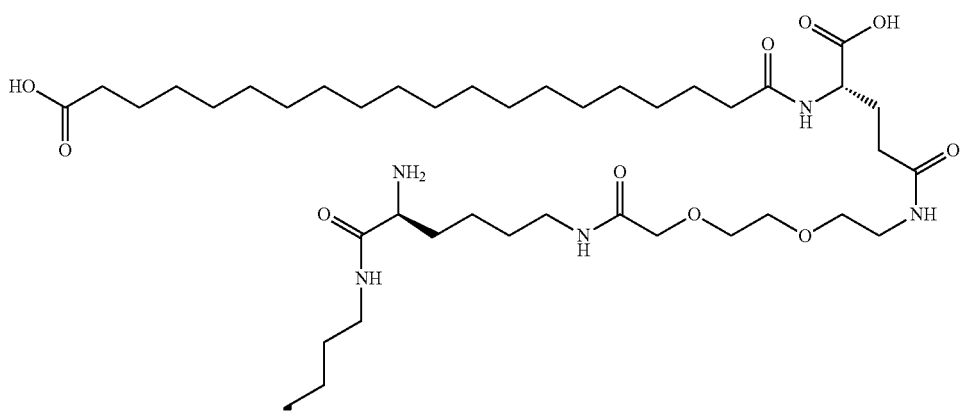
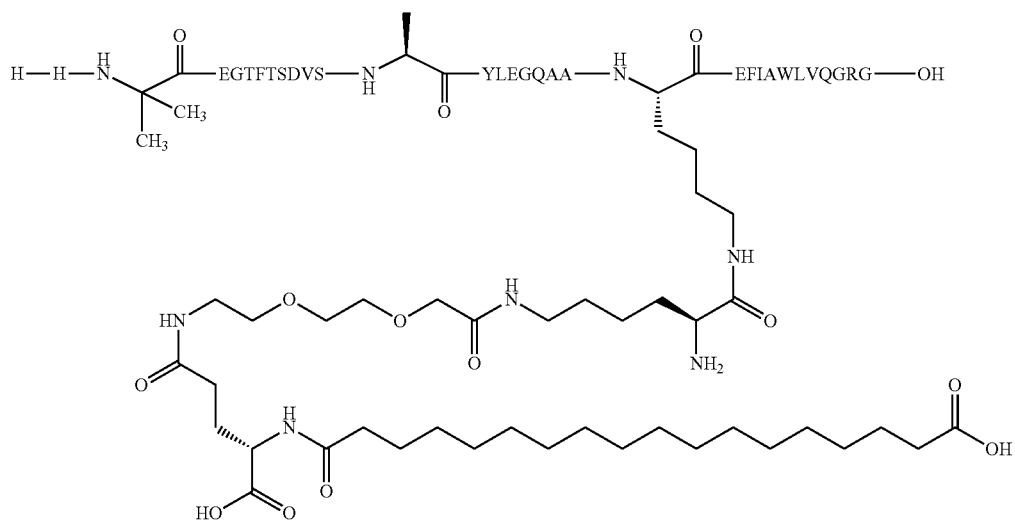

Example 50
$N^{\epsilon18}$-[(2S)-2-amino-6-[[2-[2-[2-[[4-carboxy-4-[12-(4-carboxyphenoxy)dodecanoylamino]butanoyl]amino]ethoxy]ethoxy]acetyl]amino]hexanoyl], $N^{\epsilon26}$-[(2S)-2-amino-6-[[2-[2-[2-[[4-carboxy-4-[12-(4-carboxyphenoxy)dodecanoylamino]butanoyl]amino]ethoxy]ethoxy]acetyl]amino]hexanoyl]-[Aib$^8$,Lys$^{18}$,Gln$^{34}$] (SEQ ID NO: 12)-GLP-1-(7-37)-peptide
Chem. 69
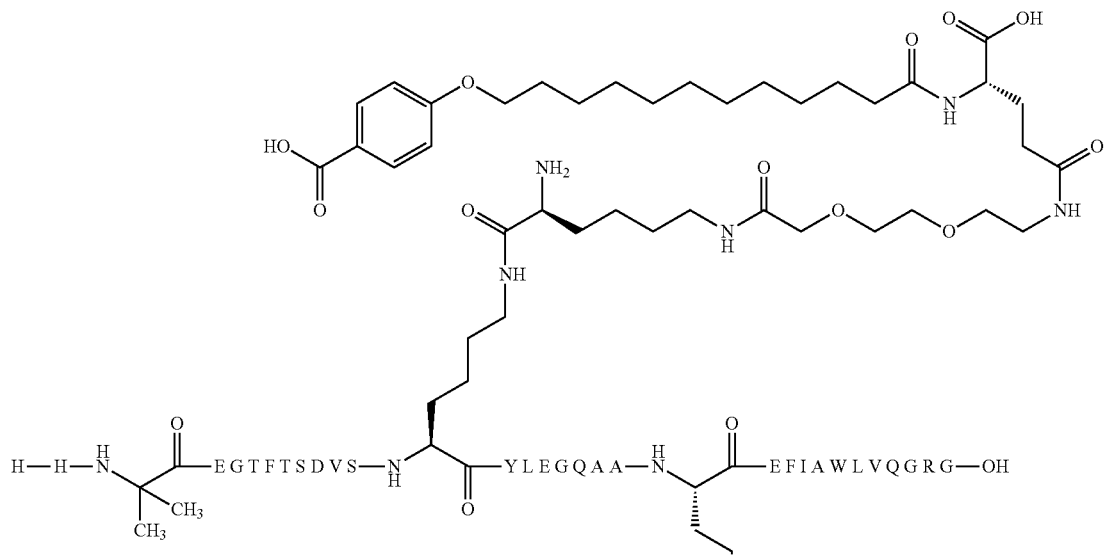
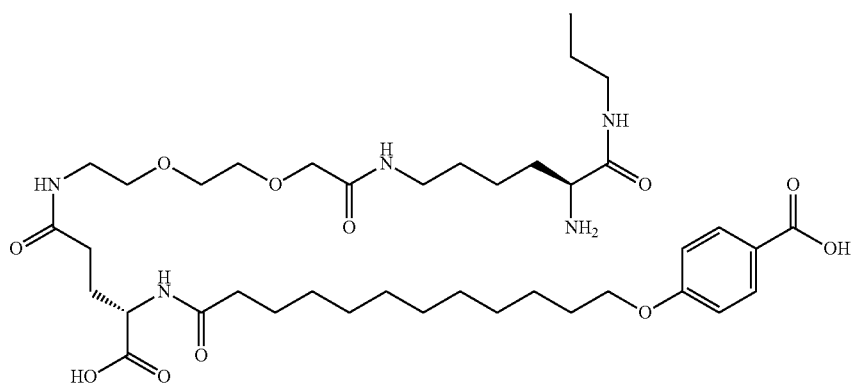

Example 51
$N^{\epsilon 18}$-[(2S)-2-amino-6-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]hexanoyl], $N^{\epsilon 26}$-[(2S)-2-amino-6-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]hexanoyl]-[Aib$^8$,Lys$^{18}$,Glu$^{22}$,Gln$^{34}$] (SEQ ID NO: 9)-GLP-1-(7-37)-peptide
Chem. 70
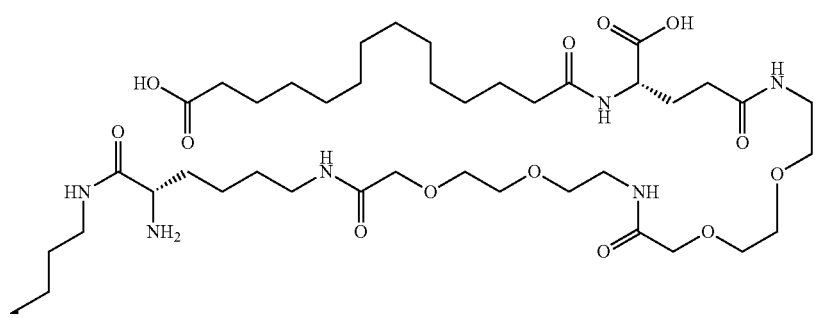
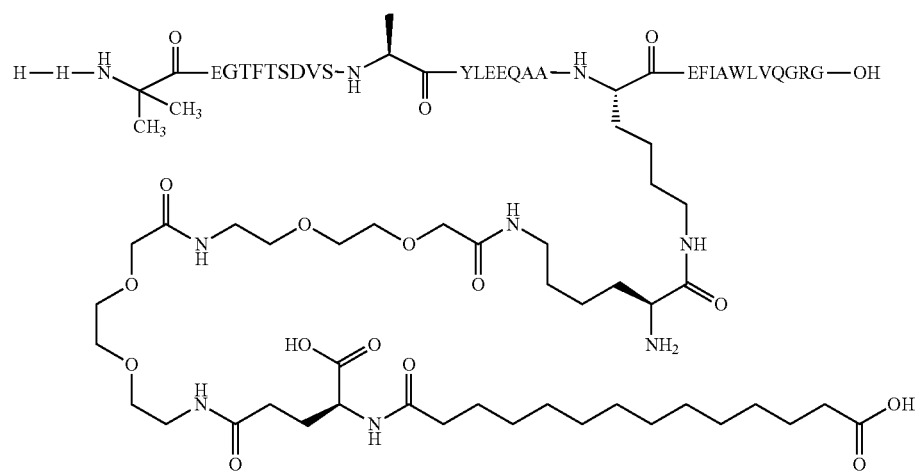

Example 52
$N^{\epsilon 18}$-[(2S)-2-amino-6-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]hexanoyl], $N^{\epsilon 26}$-[(2S)-2-amino-6-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]hexanoyl]-[Aib$^8$,Lys$^{18}$,Glu$^{22}$,Gln$^{34}$] (SEQ ID NO: 9)-GLP-1-(7-37)-peptide
Chem. 71
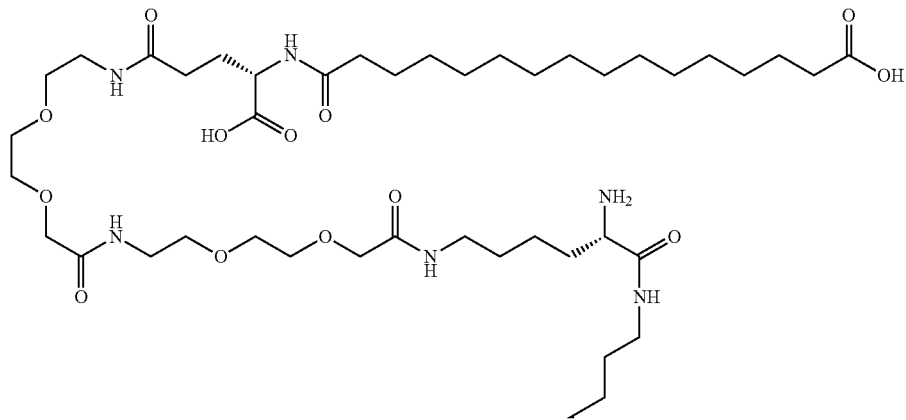
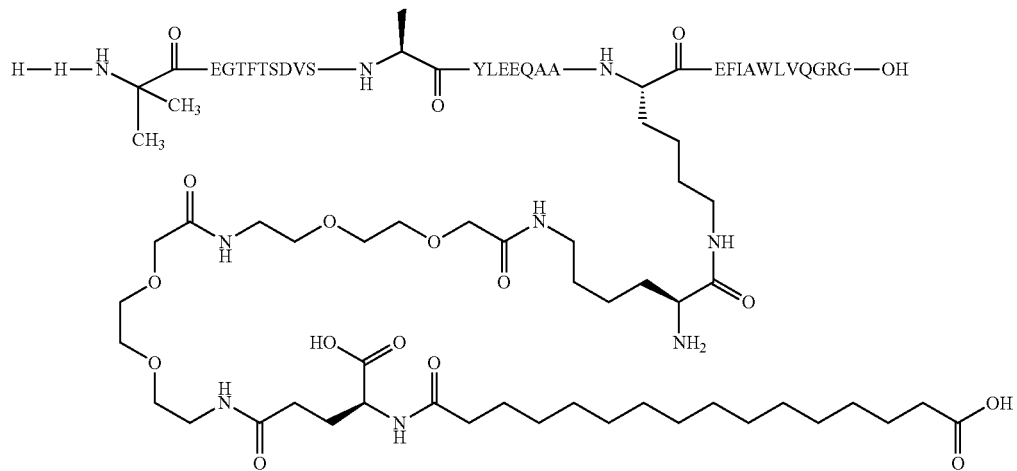

Example 53
N$^{\epsilon 18}$-[(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy yl]amino]hexanoyl], N$^{\epsilon 26}$-[(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy yl]amino]hexanoyl]-[Aib$^8$,Lys$^{18}$,Glu$^{22}$,Gln$^{34}$] (SEQ ID NO: 9)-GLP-1-(7-37)-peptide
Chem. 72
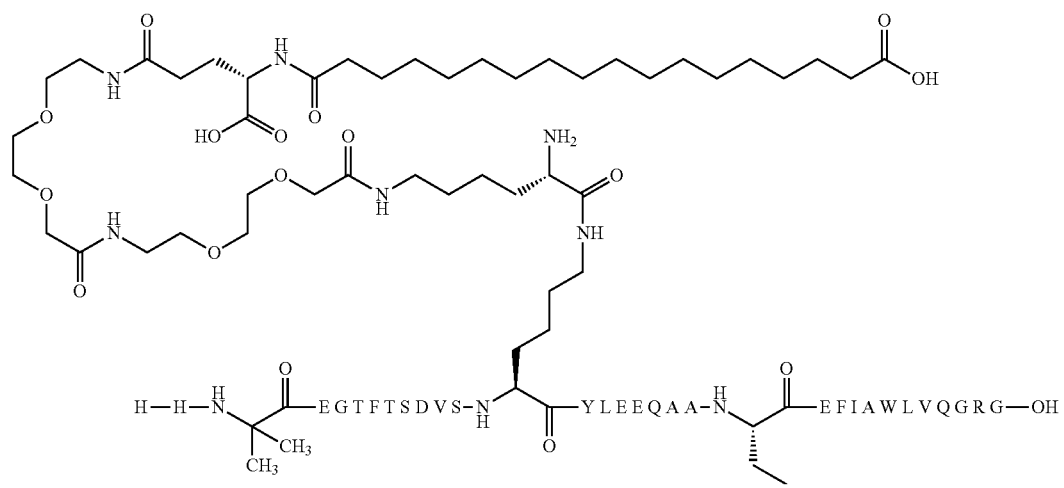
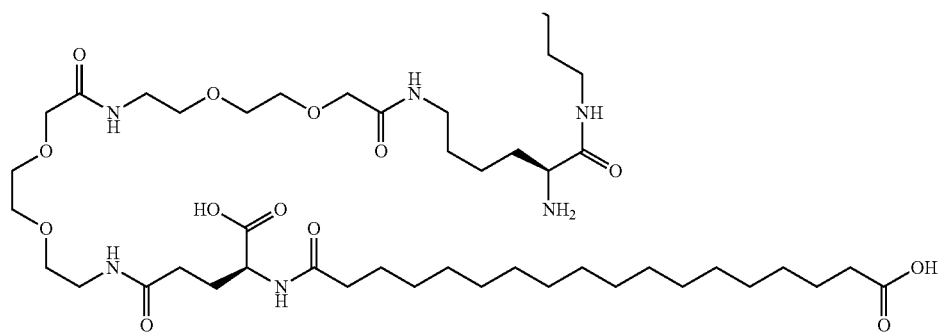

Example 54
N^ε18-[(2S)-2-amino-6-[[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl]amino]hexanoyl], N^ε26-[(2S)-2-amino-6-[[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl]amino]hexanoyl]-[Aib⁸,Lys¹⁸,Glu²²,Gln³⁴] (SEQ ID NO: 9)-GLP-1-(7-37)-peptide
Chem. 73
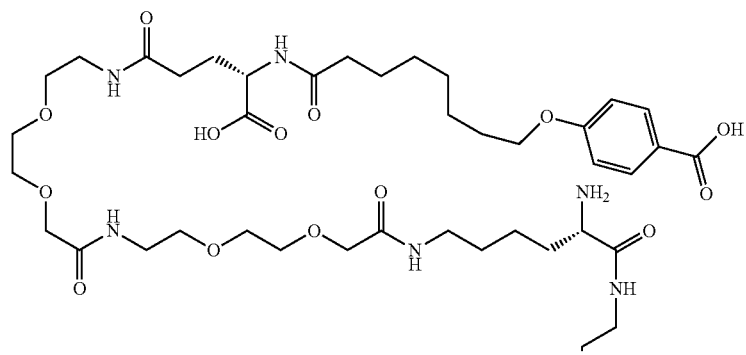
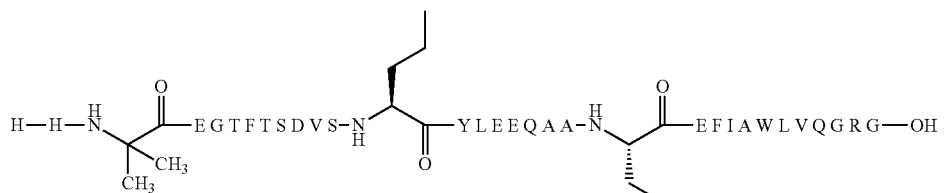
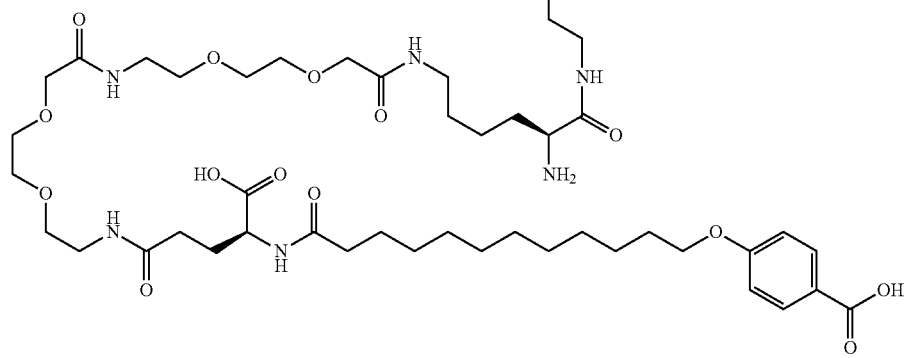

Example 55
$N^{\epsilon 18}$-[(2S)-2-amino-6-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl], $N^{\epsilon 26}$-[(2S)-2-amino-6-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl]-[Aib$^8$,Lys$^{18}$,Glu$^{22}$,Gln$^{34}$] (SEQ ID NO: 9)-GLP-1-(7-37)-peptide
Chem. 74
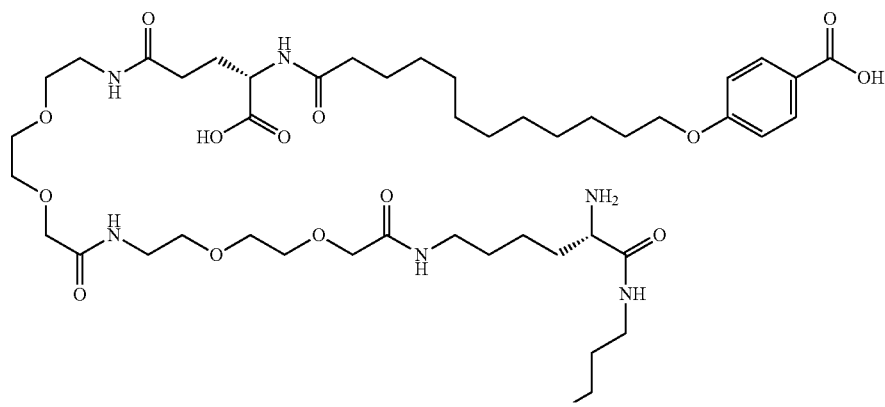
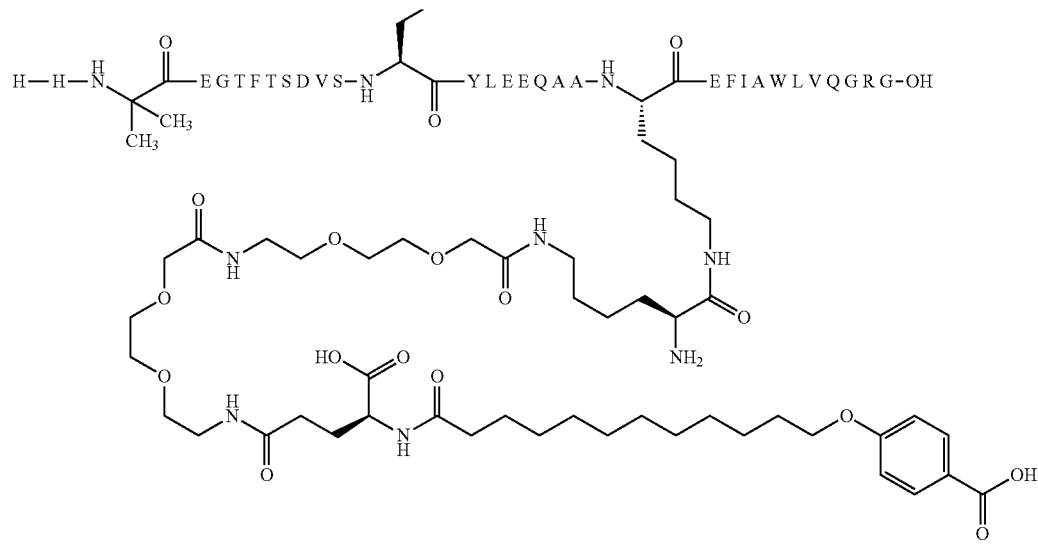

Example 56
N^ε18-[(2S)-2-amino-6-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]hexanoyl], N^ε26-[(2S)-2-amino-6-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]hexanoyl]-[Aib^8,Lys^18,Gln^34] (SEQ ID NO: 12)-GLP-1-(7-37)-peptide
Chem. 75
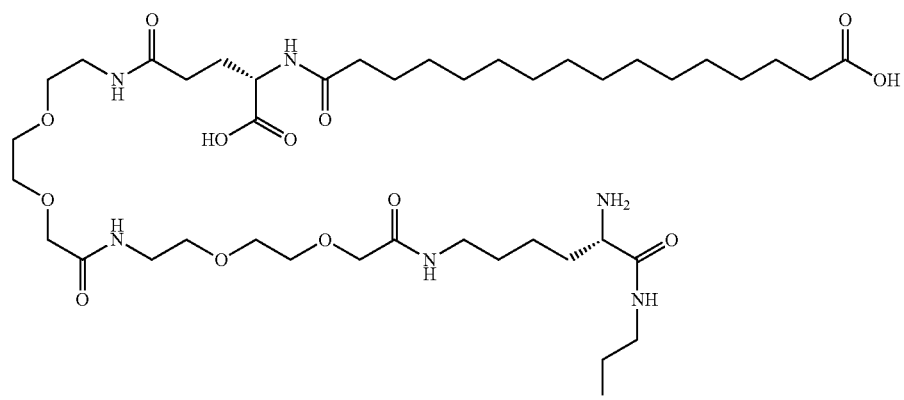
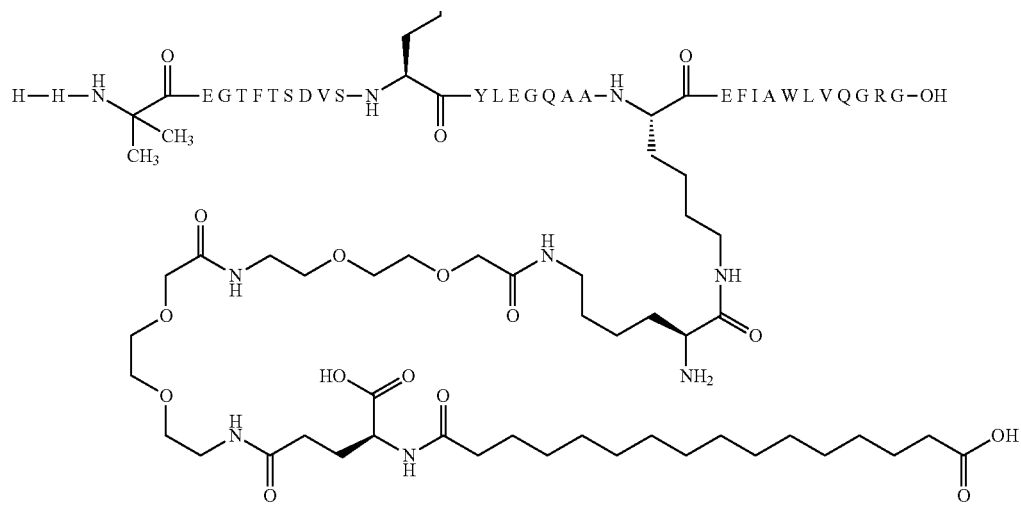

Example 57
N$^{\epsilon 18}$-[(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl], N$^{\epsilon 26}$-[(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl]-[Aib$^8$,Lys$^{18}$,Gln$^{34}$] (SEQ ID NO: 12)-GLP-1-(7-37)-peptide
Chem. 76
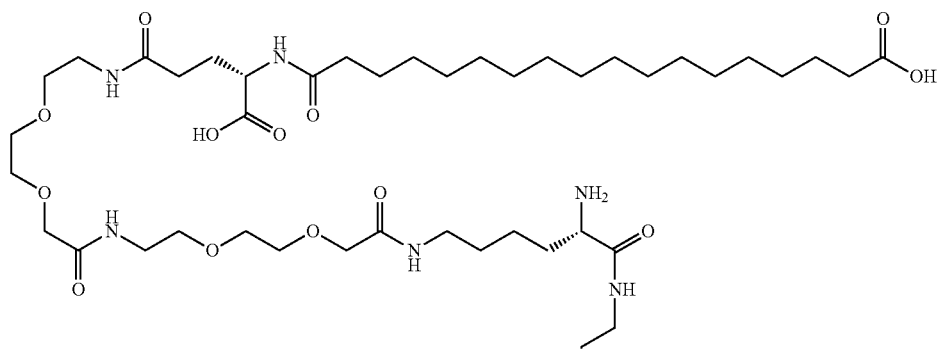
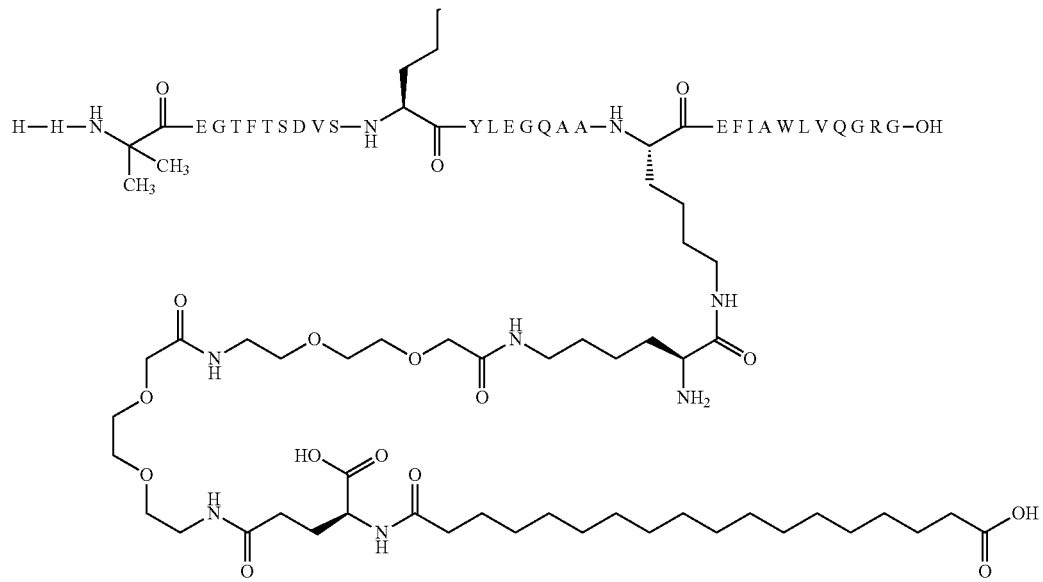

Example 58
N^ε18-[(2S)-2-amino-6-[[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl]amino]hexanoyl], N^ε26-[(2S)-2-amino-6-[[2-[2-[2-[[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl]amino]hexanoyl]-[Aib^8,Lys^18,Gln^34] (SEQ ID NO: 12)-GLP-1-(7-37)-peptide
Chem. 77
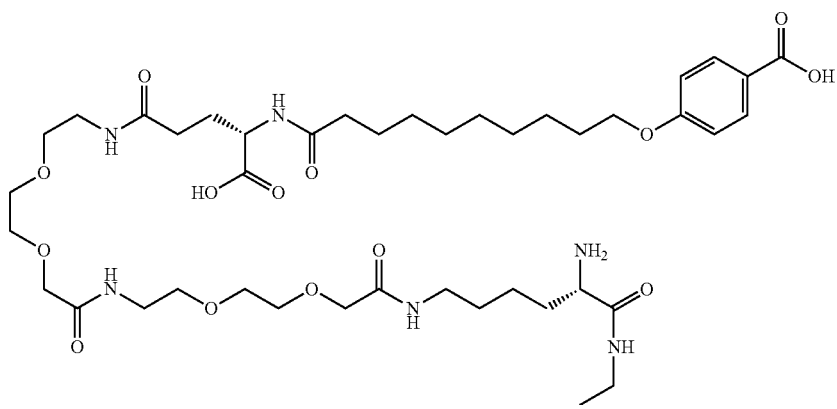
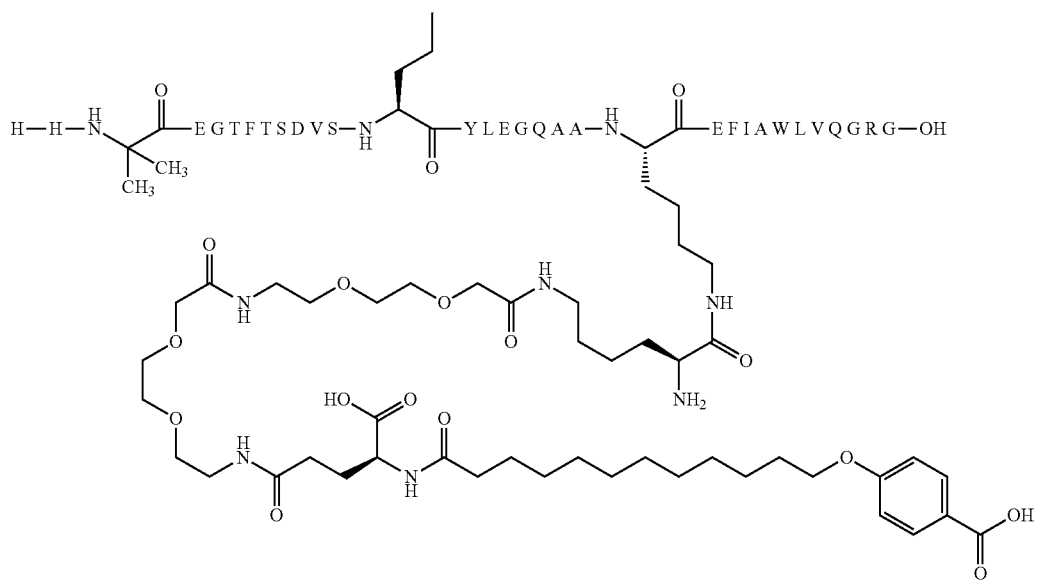

BIOLOGICAL METHODS

Example 59

In Vitro Potency

The purpose of this example is to test the activity, or potency, of the GLP-1 derivatives in vitro.

The potencies of the GLP-1 derivatives of Examples 1-8, 10-15, and 19 were determined as described below, i.e. as the stimulation of the formation of cyclic AMP (cAMP) in a medium containing membranes expressing the human GLP-1 receptor.

Principle

Purified plasma membranes from a stable transfected cell line, BHK467-12A (tk-ts13), expressing the human GLP-1 receptor were stimulated with the GLP-1 derivative in question, and the potency of cAMP production was measured using the AlphaScreen™ cAMP Assay Kit from Perkin Elmer Life Sciences. The basic principle of The AlphaScreen Assay is a competition between endogenous cAMP and exogenously added biotin-cAMP. The capture of cAMP is achieved by using a specific antibody conjugated to acceptor beads.

Cell Culture and Preparation of Membranes

A stable transfected cell line and a high expressing clone were selected for screening. The cells were grown at 5% $CO_2$ in DMEM, 10% FCS, 1% Pen/Strep (Penicillin/Streptomycin) and 1.0 mg/ml of the selection marker G418.

Cells at approximate 80% confluence were washed 2× with PBS and harvested with Versene (aqueous solution of the tetrasodium salt of ethylenediaminetetraacetic acid), centrifuged 5 min at 1000 rpm and the supernatant removed. The additional steps were all made on ice. The cell pellet was homogenised by the Ultrathurax for 20-30 sec. in 10 ml of Buffer 1 (20 mM Na-HEPES, 10 mM EDTA, pH=7.4), centrifuged 15 min at 20,000 rpm and the pellet resuspended in 10 ml of Buffer 2 (20 mM Na-HEPES, 0.1 mM EDTA, pH=7.4). The suspension was homogenised for 20-30 sec and centrifuged 15 min at 20,000 rpm. Suspension in Buffer 2, homogenisation and centrifugation was repeated once and the membranes were resuspended in Buffer 2. The protein concentration was determined and the membranes stored at −80° C. until use.

The assay was performed in ½-area 96-well plates, flat bottom (Costar cat. no:3693). The final volume per well was 50 µl.

Solutions and Reagents

AlphaScreen cAMP Assay Kit from Perkin Elmer Life Sciences (cat. No: 6760625M); containing Anti-cAMP Acceptor beads (10 U/µl), Streptavidin Donor beads (10 U/µl) and Biotinylated-cAMP (133 U/µl).

AlphaScreen Buffer, pH=7.4: 50 mM TRIS-HCl (Sigma, cat.no: T3253); 5 mM HEPES (Sigma, cat.no: H3375); 10 mM $MgCl_2$, $6H_2O$ (Merck, cat.no: 5833); 150 mM NaCl (Sigma, cat.no: S9625); 0.01% Tween (Merck, cat.no: 822184). The following was added to the AlphaScreen Buffer prior to use (final concentrations indicated): BSA (Sigma, cat. no. A7906): 0.1%; IBMX (Sigma, cat. no. 15879): 0.5 mM; ATP (Sigma, cat. no. A7699): 1 mM; GTP (Sigma, cat. no. G8877): 1 uM.

cAMP standard (dilution factor in assay=5): cAMP Solution: 5 µL of a 5 mM cAMP-stock+495 µL AlphaScreen Buffer.

Suitable dilution series in AlphaScreen Buffer were prepared of the cAMP standard as well as the GLP-1 derivative to be tested, e.g. the following eight concentrations of the GLP-1 compound: $10^{-7}$, $10^{-8}$, $10^{-9}$, $10^{-10}$, $10^{-12}$, $10^{-13}$ and $10^{-14}$M, and a series from, e.g., $10^{-6}$ to $3\times10^{-11}$ of cAMP.

Membrane/Acceptor Beads

Use hGLP-1/BHK 467-12A membranes; 3 µg/well corresponding to 0.6 mg/ml (the amount of membranes used pr. well may vary)

"No membranes": Acceptor Beads (2 units/well final) in AlphaScreen buffer "3 µg/well membranes": membranes+Acceptor Beads (2 units/well final) in AlphaScreen buffer Add 10 µl "No membranes" to the cAMP standard (per well in duplicates) and the positive and negative controls Add 10 µl "3 µg/well membranes" to the GLP-1 derivatives (per well in duplicates/triplicates)

Pos. Control: 10 µl "no membranes"+10 µl AlphaScreen Buffer

Neg. Control: 10 µl "no membranes"+10 µl cAMP Stock Solution (50 µM)

As the beads are sensitive to direct light, any handling was in the dark (as dark as possible), or in green light. All dilutions were made on ice.

Procedure
1. Make the AlphaScreen Buffer.
2. Dissolve and dilute the GLP-1 derivatives/cAMP standard in AlphaScreen Buffer.
3. Make the Donor Beads solution (by mixing streptavidin donor beads (2 units/well) and biotinylated cAMP (1.2 units/well) and incubate 20-30 min. in the dark at RT.
4. Add the cAMP/GLP-1 derivatives to the plate: 10 µl per well.
5. Prepare membrane/Acceptor Beads solution and add this to the plates: 10 µl per well.
6. Add the Donor Beads: 30 µl per well.
7. Wrap the plate in aluminium foil and incubate on the shaker for 3 hours (very slowly) at RT.
8. Count on AlphaScreen—each plate pre incubates in the AlphaScreen for 3 minutes before counting.

Results

The $EC_{50}$ [nM] values were calculated using the GraphPad Prism software (version 5).

The potency of all derivatives in vitro was confirmed. 13 derivatives had an in vitro potency corresponding to an $EC_{50}$ of 1200 pM or below; 11 derivatives had a still further improved potency corresponding to an $EC_{50}$ at 500 pM or below; 7 derivatives were very potent corresponding to an $EC_{50}$ at 200 pM or below; and 2 derivatives had a very good potency corresponding to an $EC_{50}$ of 100 pM or below.

For comparison, compound no. 13 in Table 1 of Journal of Medicinal Chemistry (2000), vol. 43, no. 9, p. 1664-669 (GLP-1(7-37) acylated at $K^{26,34}$ with bis-C12-diacid) had an in vitro potency corresponding to an $EC_{50}$ of 1200 pM.

If desired, the fold variation in relation to GLP-1 may be calculated as $EC_{50}$ (GLP-1)/$EC_{50}$ (analogue)–3693.2.

Example 60

GLP-1 Receptor Binding

The purpose of this experiment is to investigate the binding to the GLP-1 receptor of the GLP-1 derivatives, and how the binding is potentially influenced by the presence of albumin. This is done in an in vitro experiment as described below.

The binding affinity of the GLP-1 derivatives of Examples 1-8, 10-15, and 19 to the human GLP-1 receptor was measured by way of their ability to displace of $^{125}$I-GLP-1 from the receptor. In order to test the binding of the derivatives to the receptor in the presence of albumin, the assay was performed with a low concentration of albumin (0.005% —corresponding to the residual amount thereof in the tracer), as well as with a high concentration of albumin (2.0% added). A shift in the binding affinity, $IC_{50}$, is an indication that the derivative in question binds to albumin, and thereby a prediction of a potential protracted pharmacokinetic profile of the derivative in question in animal models.

Conditions
Species (in vitro): Hamster
Biological End Point: Receptor Binding
Assay Method: SPA
Receptor: GLP-1 receptor
Cell Line: BHK tk-ts13
Cell Culture and Preparation of Membranes A stable transfected cell line and a high expressing clone were selected for screening. The cells were grown at 5% $CO_2$ in DMEM, 10% FCS, 1% Pen/Strep (Penicillin/Streptomycin) and 1.0 mg/ml of the selection marker G418.

Cells at approximate 80% confluence were washed 2× with PBS and harvested with Versene (aqueous solution of the tetrasodium salt of ethylenediaminetetraacetic acid), centrifuged 5 min at 1000 rpm and the supernatant removed. The additional steps were all made on ice. The cell pellet was homogenised by the Ultrathurax for 20-30 sec. in a suitable amount of Buffer 1 (20 mM Na-HEPES, 10 mM EDTA, pH=7.4) but e.g. 10-20 ml, centrifuged 15 min at 20,000 rpm and the pellet resuspended in a suitable amount of Buffer 2 (20 mM Na-HEPES, 0.1 mM EDTA, pH=7.4) but e.g. 10-20 ml. The suspension was homogenised for 20-30 sec and centrifuged 15 min at 20,000 rpm. Suspension in Buffer 2, homogenisation and centrifugation was repeated once more and the membranes were resuspended in Buffer 2. The protein concentration was determined and the membranes stored at −80° C. until use.

SPA Binding Assay:

Test compounds, membranes, SPA-particles and $[^{125}I]$-GLP-1 (7-36)$NH_2$ were diluted in assay buffer. 25 ul (microliter) of test compounds are added to Optiplate. HSA ("high albumin" experiment containing 2% HSA), or buffer ("low albumin" experiment containing 0.005% HSA), was added (50 ul). 5-10 ug protein/sample was added (50 ul) corresponding to 0.1-0.2 mg protein/ml (to be preferably optimised for each membrane preparation). SPA-particles (Wheatgerm agglutinin SPA beads, Perkin Elmer, #RPNQ0001) were added in an amount of 0.5 mg/well (50 ul). The incubation was started with $[^{125}I]$-GLP-1 (7-36)$NH_2$ (final concentration 0.06 nM corresponding to 49.880 DPM, 25 ul). The plates were sealed with PlateSealer and incubated for 120 minutes at 30° C. while shaking. The plates were centrifuged (1500 rpm, 10 min) and counted in Topcounter.

Assay buffer:
50 mM HEPES
5 mM EGTA
5 mM MgCl2
0.005% Tween 20
pH 7.4
HSA was SIGMA A1653
Calculations The $IC_{50}$ value was read from the curve as the concentration which displaces 50% of $^{125}I$-GLP-1 from the receptor, and the ratio of $[(IC_{50}/nM)$ high HSA$]/[(IC_{50}/nM)$ low HSA$]$ was determined.

Generally, the binding to the GLP-1 receptor at low albumin concentration should be as good as possible, corresponding to a low $IC_{50}$ value.

The $IC_{50}$ value at high albumin concentration is a measure of the influence of albumin on the binding of the derivative to the GLP-1 receptor. As is known, the GLP-1 derivatives also bind to albumin. This is a generally desirable effect, which extends their lifetime in plasma. Therefore, the $IC_{50}$ value at high albumin will generally be higher than the $IC_{50}$ value at low albumin, corresponding to a reduced binding to the GLP-1 receptor, caused by albumin binding competing with the binding to the GLP-1 receptor.

A high ratio ($IC_{50}$ value (high albumin)/$IC_{50}$ value (low albumin)) may therefore be taken as an indication that the derivative in question binds well to albumin (may have a long half-life), and also per se binds well to the GLP-1 receptor (the $IC_{50}$ value (high albumin) is high, and the $IC_{50}$ value (low albumin) is low).

Results

The following results were obtained, where "ratio" refers to $[(IC_{50}/nM)$ high HSA$]/[(IC_{50}/nM)$ low HSA$])$:

All derivatives had a ratio above 10; 13 derivatives were above 50; 11 derivatives were above 100; 8 derivatives above 500; and 4 derivatives had a ratio above 1000.

Furthermore as regards $IC_{50}$ (low albumin), all derivatives had an $IC_{50}$ (low albumin) below 35 nM; 14 derivatives were below 15 nM; 13 derivatives were below 10 nM; 12 derivatives were below 5.0 nM; 10 derivatives were below 1.0 nM; and 6 derivatives were below 0.50 nM.

Finally as regards $IC_{50}$ (high albumin), 10 derivatives were below 1000 nM; 7 derivatives were below 500 nM; and 3 derivatives were below 250 nM.

Example 61

Estimate of Oral Bioavailability—Gut Injection in Rat (Sodium Caprate)

The purpose of this experiment is to estimate the oral bioavailability of the GLP-1 derivatives. To this end, the exposure in plasma after direct injection into the intestinal lumen of the GLP-1 derivatives is studied in vivo in rats, as described in the following. The GLP-1 derivatives are tested in a concentration of 1000 uM in a solution of 55 mg/ml sodium caprate.

32 male Sprague Dawley rats with a body weight upon arrival of approximately 240 g are obtained from Taconic (Denmark) and assigned to the different treatments by simple randomisation, 4 rats per group. The rats are fasted for approximately 18 hours before the experiment and taken into general anaesthesia (Hypnorm/Dormicum).

The GLP-1 derivatives are administered in the jejunum either in the proximal part (10 cm distal for the duodenum) or in the mid-intestine (50 cm proximal for the cecum). A PE50-catheter, 10 cm long was inserted into the jejunum, forwarded at least 1.5 cm into the jejunum, and secured before dosing by ligature around the gut and the catheter with 3/0 suture distal to tip to prevent leak or catheter displacement. Catheter is placed without syringe and needle and 2 ml saline is administered into abdomen before closing the incision with wound clips.

100 μl of the respective GLP-1 derivative is injected into the jejunal lumen through the catheter with a 1 ml syringe. Subsequently, 200 μl of air is pushed into the jejunal lumen with another syringe to "flush" the catheter. This syringe is leaved connected to the catheter to prevent flow back into the catheter.

Blood samples (200 ul) are collected at desired intervals (usually at times 0, 10, 30, 60, 120 and 240 min) into EDTA tubes from the tail vein and centrifuged 5 minutes, 10000G, at 4° C. within 20 minutes. Plasma (75 ul) is separated to Micronic tubes, immediately frozen, and kept at −20° C. until analyzed for plasma concentration of the respective GLP-1 derivative with LOCI (Luminescent Oxygen Channeling Immunoassay), generally as described for the determination of insulin by Poulsen and Jensen in Journal of Biomolecular Screening 2007, vol. 12, p. 240-247. The donor beads are coated with streptavidin, while acceptor beads are conjugated with a monoclonal antibody recognising a mid-/C-terminal epitope of the peptide. Another monoclonal antibody, specific for the N-terminus, is biotinylated. The three reactants are combined with the analyte and form a two-sited immuno-complex. Illumination of the complex releases singlet oxygen atoms from the donor beads, which are channeled into the acceptor beads and trigger chemiluminescence which is measured in an Envision plate reader. The amount of light is proportional to the concentration of the compound.

After the blood sampling the rats are sacrificed under anaesthesia and the abdomen is opened to verify correct catheter placement.

The mean (n=4) plasma concentrations (pmol/l) are determined as a function of time. The ratio of plasma concentration (pmol/l) divided by the concentration of the dosing solution (pmol/l) is calculated for each treatment, and the results for t=30 min (30 minutes after the injection of the compound in the jejunum) are assessed (dose-corrected exposure at 30 min) as a surrogate measure of intestinal bioavailability. The dose-corrected exposure is expected to correlate with the actual bioavailability.

Dose-corrected exposure at 30 min refers to (the plasma concentration 30 minutes after injection of the compound in the jejunum (pM)), divided by (the concentration of the compound in the dosing solution ($\mu$M)).

Example 62

Estimate of Oral Bioavailability—Gut Injection and Oral Gavage in Rat (SNAC)

The purpose of this experiment is to estimate the oral bioavailability of the GLP-1 derivatives in a rat model. In brief, a liquid solution of the GLP-1 derivative in sodium N-[8-(2-hydroxybenzoyl)amino]caprylate (SNAC) is administered by gut injection (to the intestines), or by oral gavage (to the stomach), and the subsequent exposure in plasma of the GLP-1 derivative is measured.

A 250 mg/ml stock solution of SNAC was prepared by dissolving SNAC (12.5 g) in highly pure laboratory water (MilliQ) (50.0 ml). The pH was adjusted to about 8.5 with 1 N NaOH (aq).

Solutions with about 1000 uM (800-1200 uM) of the GLP-1 derivatives of Examples 5-8, 11-13, and 15, respectively, in 250 mg/ml SNAC were prepared by dissolving the desired amount of the respective GLP-1 derivative in the SNAC stock solution. The concentration of the GLP-1 derivative was determined prior to administration by a state-of-the-art method, such as CLND-HPLC (chemiluminescent nitrogen detection for HPLC).

32 male Sprague Dawley rats with a body weight upon arrival of approximately 240 g were obtained from Taconic (Denmark) and assigned to the different treatments by simple randomisation, 8 rats per group. All rats were fasted on grids for approximately 18 hours before the experiment.

For gut injection, on the day of experiment, rats were taken into general anaesthesia (Hypnorm/Dormicum) and remained anaesthetized during the entire experiment. The GLP-1 derivatives of Examples 5-7 were administered in the proximal part of the jejunum (10 cm distal for the duodenum). A PE50-catheter, 10 cm long, was inserted into the jejunum, forwarded at least 1.5 cm into the jejunum, and secured before dosing by ligature around the gut. Furthermore, the catheter was provided with a 3/0 suture distal to tip to prevent leak or catheter displacement. The catheter was placed without syringe and needle and 2 ml saline was administered into abdomen before closing the incision with wound clips.

100 $\mu$l SNAC solution of the respective GLP-1 derivative was injected into the jejunal lumen through the catheter with a 1 ml syringe. Subsequently, 200 $\mu$l of air was pushed into the jejunal lumen with another syringe to "flush" the catheter. This syringe was leaved connected to the catheter to prevent flow back into the catheter.

Blood samples (200 ul) were collected at desired intervals (usually at times 0, 30, 60, 120 and 180 min) into EDTA tubes from the tail vein.

For oral gavage, the animals were conscious during the entire experiment.

100 $\mu$l SNAC solution of the GLP-1 derivatives of Examples 5-8, 11-13, and 15, respectively, was administered by oral gavage directly to the stomach.

Blood samples (200 ul) were collected at desired intervals (usually at times 0, 30, 60, 120 and 180 min) into EDTA tubes from the sublingual plexus.

All obtained blood samples were kept on ice and centrifuged for 5 minutes, 10000G, at 4° C. within 20 minutes. Plasma (75 ul) was separated to Micronic tubes, immediately frozen, and kept at −20° C. until analyzed for plasma concentration of the respective GLP-1 derivative with LOCI (Luminescent Oxygen Channeling Immunoassay), generally as described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immuno-complex. Illumination of the complex released singlet oxygen atoms from the donor beads, which were channeled into the acceptor beads and triggered chemiluminescence which was measured in an Envision plate reader. The amount of light was proportional to the concentration of the compound.

After the blood sampling all rats were sacrificed under anaesthesia and the abdomen of the gut injection rats was opened to verify correct catheter placement.

The mean (n=8) plasma concentrations (pmol/l) were determined as a function of time. The AUC of the plasma exposure (pmol/l) vs time curve, from time 30 to 180 (min), was dose-corrected, i.e., divided by the amount (dose) of the derivative in the dosed solution (pmol). The thus dose-corrected AUC of plasma exposure from time 30-180 min (having the unit of min×pM/pmol=min/L) was used as a surrogate measure of bioavailability—a measure to rank the derivatives with regards to their absorption in the rat model.

The following results were obtained:

For the gut injection experiment, the AUC of the dose-corrected plasma exposure from time 30 to 180 min for the tested GLP-1 derivatives was in the range of 170 to 322 min×pM/pmol. Two of the three tested compounds were above 250 min×pM/pmol.

For the oral gavage experiment, the AUC of the dose-corrected plasma exposure from time 30 to 180 min for the tested GLP-1 derivatives was in the range of 18 to 75 min× pM/pmol. Of the eight tested compounds six were above 20, four were above 40, and two were above 60 min×pM/pmol.

Example 63

Effect on Blood Glucose and Body Weight—PD Db/Db Mice

The purpose of the study is to verify the effect of the GLP-1 derivatives on blood glucose (BG) and body weight (BW) in a diabetic setting.

The GLP-1 derivatives are tested in a dose-response study in an obese, diabetic mouse model (db/db mice) as described in the following.

Fifty db/db mice (Taconic, Denmark), fed from birth with the diet NIH31 (NIH 31M Rodent Diet, commercially available from Taconic Farms, Inc., US, see www.taconic.com), are enrolled for the study at the age of 7-9 weeks The mice are given free access to standard chow (e.g. Altromin 1324, Brogaarden, Gentofte, Denmark) and tap water and kept at 24° C.

After 1-2 weeks of acclimatisation, the basal blood glucose is assessed twice on two consecutive days (i.e. at 9 am). The 8 mice with the lowest blood glucose values are excluded from the experiments. Based on the mean blood glucose values, the remaining 42 mice are selected for further experimentation and allocated to 7 groups (n=6) with matching blood glucose levels. The mice are used in experiments with duration of 5 days for up to 4 times. After the last experiment the mice are euthanised.

The seven groups receive treatment as follows:
1: Vehicle, s.c.
2: GLP-1 derivative, 0.3 nmol/kg, s.c.
3: GLP-1 derivative, 1.0 nmol/kg, s.c.
4: GLP-1 derivative, 3.0 nmol/kg, s.c.
5: GLP-1 derivative, 10 nmol/kg, s.c.
6: GLP-1 derivative, 30 nmol/kg, s.c.
7: GLP-1 derivative, 100 nmol/kg, s.c.
Vehicle: 50 mM sodium phosphate, 145 mM sodium chloride, 0.05% tween 80, pH 7.4.

The GLP-1 derivative is dissolved in the vehicle, to concentrations of 0.05, 0.17, 0.5, 1.7, 5.0 and 17.0 nmol/ml. Animals are dosed s.c. with a dose-volume of 6 ml/kg (i.e. 300 μl per 50 g mouse).

On the day of dosing, blood glucose is assessed at time–½ h (8.30 am), where after the mice are weighed. The GLP-1 derivative is dosed at approximately 9 am (time 0). On the day of dosing, blood glucose is assessed at times 1, 2, 4 and 8 h (10 am, 11 am, 1 pm and 5 pm).

On the following days, the blood glucose is assessed at time 24 and 48 h after dosing (and if desired also at time 72, and 96 h after dosing), i.e. at 9 am on day 2 and 3, and if desired at 9 am on day 4 and 5). On each day, the mice are weighed following blood glucose sampling.

The mice are weighed individually on a digital weight.

Samples for the measurement of blood glucose are obtained from the tail tip capillary of conscious mice. Blood, 10 μl, is collected into heparinised capillaries and transferred to 500 μl glucose buffer (EKF system solution, Eppendorf, Germany). The glucose concentration is measured using the glucose oxidase method (glucose analyser Biosen 5040, EKF Diagnostic, GmbH, Barleben, Germany). The samples are kept at room temperature for up to 1 h until analysis. If analysis had to be postponed, samples are kept at 4° C. for a maximum of 24 h.

$ED_{50}$ is the dose giving rise to half-maximal effect in nmol/kg. This value is calculated on the basis of the ability of the derivatives to lower body weight as well as the ability to lower blood glucose, as explained below.

$ED_{50}$ for body weight is calculated as the dose giving rise to half-maximum effect on delta BW 24 hours following the subcutaneous administration of the derivative. For example, if the maximum decrease in body weight after 24 hours is 4.0 g, then $ED_{50}$ bodyweight would be that dose in nmol/kg which gives rise to a decrease in body weight after 24 hours of 2.0 g. This dose ($ED_{50}$ body weight) may be read from the dose-response curve.

$ED_{50}$ for blood glucose is calculated as the dose giving rise to half-maximum effect on AUC delta BG 8 hours following the subcutaneous administration of the analogue.

The $ED_{50}$ value may only be calculated if a proper sigmoidal dose-response relationship exists with a clear definition of the maximum response. Thus, if this would not be the case the derivative in question is re-tested in a different range of doses until the sigmoidal dose-response relationship is obtained.

Example 64

Effect on Food Intake—PD LYD Pigs

The purpose of this experiment is to investigate the effect of GLP-1 derivatives on food intake in pigs. This is done in a pharmacodynamic (PD) study as described below, in which food intake is measured 1, 2, 3, and 4 days after administration of a single dose of the GLP-1 derivative, as compared to a vehicle-treated control group.

Female Landrace Yorkshire Duroc (LYD) pigs, approximately 3 months of age, weighing approximately 30-35 kg were used (n=3-4 per group). The animals were housed in a group for 1-2 weeks during acclimatisation to the animal facilities. During the experimental period the animals were placed in individual pens from Monday morning to Friday afternoon for measurement of individual food intake. The animals were fed ad libitum with pig fodder (Svinefoder, Antonio) at all times both during the acclimatisation and the experimental period. Food intake was monitored on line by logging the weight of fodder every 15 minutes. The system used was Mpigwin (Ellegaard Systems, Faaborg, Denmark).

The GLP-1 derivatives were dissolved in a phosphate buffer (50 mM phosphate, 0.05% tween 80, pH 8) at concentrations of 12, 40, 120, 400 or 1200 nmol/ml corresponding to doses of 0.3, 1, 3, 10 or 30 nmol/kg. The phosphate buffer served as vehicle. Animals were dosed with a single subcutaneous dose of the GLP-1 derivative or vehicle (dose volume 0.025 ml/kg) on the morning of day 1, and food intake was measured for 3-4 days after dosing. On the last day of each study, 3-4 days after dosing, a blood sample for measurement of plasma exposure of the GLP-1 derivative was taken from the heart in anaesthetized animals. The animals were thereafter euthanized with an intra-cardial overdose of pentobarbitone. Plasma content of the GLP-1 derivatives was analysed using ELISA or a similar antibody based assay.

Food intake was calculated as mean±SEM 24 h food intake on each of the 3-4 study days. Statistical comparisons of the 24 hour food intake in the vehicle vs. GLP-1 derivative group on the 4 days were done using one-way or two-way-ANOVA repeated measures, followed by Bonferroni post-test.

The derivatives of Examples 1, 5, and 6 were tested as described above in a dosage of 3 nM/kg. Two of the derivatives significantly reduced the food intake as compared to the vehicle-treated group on day 1 (0-24 h) and day 2 (24-48 h). One of these also significantly reduced the food intake on day 3 (48-72 h) and day 4 (72-96 h). As expected, the food intake reducing effect of the derivatives diminished from day to day in the study period, depending on the terminal half-life of the derivative.

Example 65

Half-Life in Rat—PK Rat

The purpose of this Example is to investigate half-life in vivo in rat.

In vivo pharmacokinetic studies in rats were performed with three GLP-1 derivatives (compounds of the Examples 5, 7, and 11), as described in the following.

Male Sprague Dawley rats of same age with a body weight from 400 to 600 g were obtained from Taconic (Denmark) and assigned to the treatments by simple randomisation on body weight, approximately 3-6 rats per group, so that all animals in each group were of similar body weight.

The GLP-1 derivatives (approximately 6 nmole/ml) were dissolved in 50 mM sodium phosphate, 145 mM sodium chloride, 0.05% tween 80, pH 7.4. Intravenous injections (1.0 ml/kg) of the compounds were given through a catheter implanted in the right jugular vein. Blood was sampled from vena sublingualis for 5 days post dosing. Blood samples (200 µl) were collected in EDTA buffer (8 mM) and then centrifuged at 4° C. and 10000 G for 5 minutes. Plasma samples were kept at −20° C. until analyzed for plasma concentration of the respective GLP-1 compound.

The plasma concentrations of the GLP-1 compounds were determined using a Luminescence Oxygen Channeling Immunoasssay (LOCI), generally as described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immuno-complex. Illumination of the complex released singlet oxygen atoms from the donor beads, which were channeled into the acceptor beads and triggered chemiluminescence which was measured in an Envision plate reader. The amount of light was proportional to the concentration of the compound.

Plasma concentration-time profiles were analyzed using WinNonlin (ver. 5.0, Pharsight Inc., Mountain View, Calif., USA), and the half-life ($T_{1/2}$) calculated using individual plasma concentration-time profiles from each animal.

All tested derivatives had a half-life above 10 hours, two were above 15, and one was above 20 hours.

Example 66

Half-Life in Minipigs—PK Minipig

The purpose of this study was to determine the protraction in vivo of the GLP-1 derivatives after i.v. administration to minipigs, i.e. the prolongation of their time of action. This was done in a pharmacokinetic (PK) study, where the terminal half-life of the derivative in question was determined. By terminal half-life was generally meant the period of time it takes to halve a certain plasma concentration, measured after the initial distribution phase.

Male Göttingen minipigs (Ellegaard Göttingen Minipigs A/S, Dalmose, Denmark), approximately 7-14 months of age and weighing from approximately 16-35 kg, were used in the studies. The minipigs were housed individually and fed restrictedly once or twice daily with SDS minipig diet (Special Diets Services, Essex, UK). After at least 2 weeks of acclimatisation two permanent central venous catheters were implanted in vena cava caudalis or cranialis in each animal. The animals were allowed 1 week recovery after the surgery, and were then used for repeated pharmacokinetic studies with a suitable wash-out period between dosings.

The animals were fasted for approximately 18 h before dosing and for at least 4 h after dosing, but has ad libitum access to water during the whole period.

The GLP-1 derivatives of Examples 5, 6, 8, and 11 were dissolved in 50 mM sodium phosphate, 145 mM sodium chloride, 0.05% tween 80, pH 7.4 to a concentration of usually from 20-60 nmol/ml.

Intravenous injections (the volume corresponding to usually 1-2 nmol/kg) of the compounds were given through one catheter, and blood was sampled at predefined time points for up till 13 days post dosing (preferably through the other catheter). Blood samples were collected in EDTA buffer (8 mM) and then centrifuged at 4° C. and 1942 G for 10 minutes.

Plasma was pippetted into Micronic tubes on dry ice, and kept at −20° C. until analyzed for plasma concentration of the respective GLP-1 compound using ELISA or a similar antibody based assay or LC-MS. Individual plasma concentration-time profiles were analyzed by a non-compartmental model in WinNonlin v. 5.0 (Pharsight Inc., Mountain View, Calif., USA), and the resulting terminal half-lives (harmonic mean) determined.

The following results were obtained: All derivatives had a terminal half-life of above 5 hours; 3 derivatives above 25 hours; and 1 derivative above 50 hours.

While certain features of the invention have been illustrated and described herein, many modifications, substitutions, changes, and equivalents will now occur to those of ordinary skill in the art. It is, therefore, to be understood that the appended claims were intended to cover all such modifications and changes as fall within the true spirit of the invention.

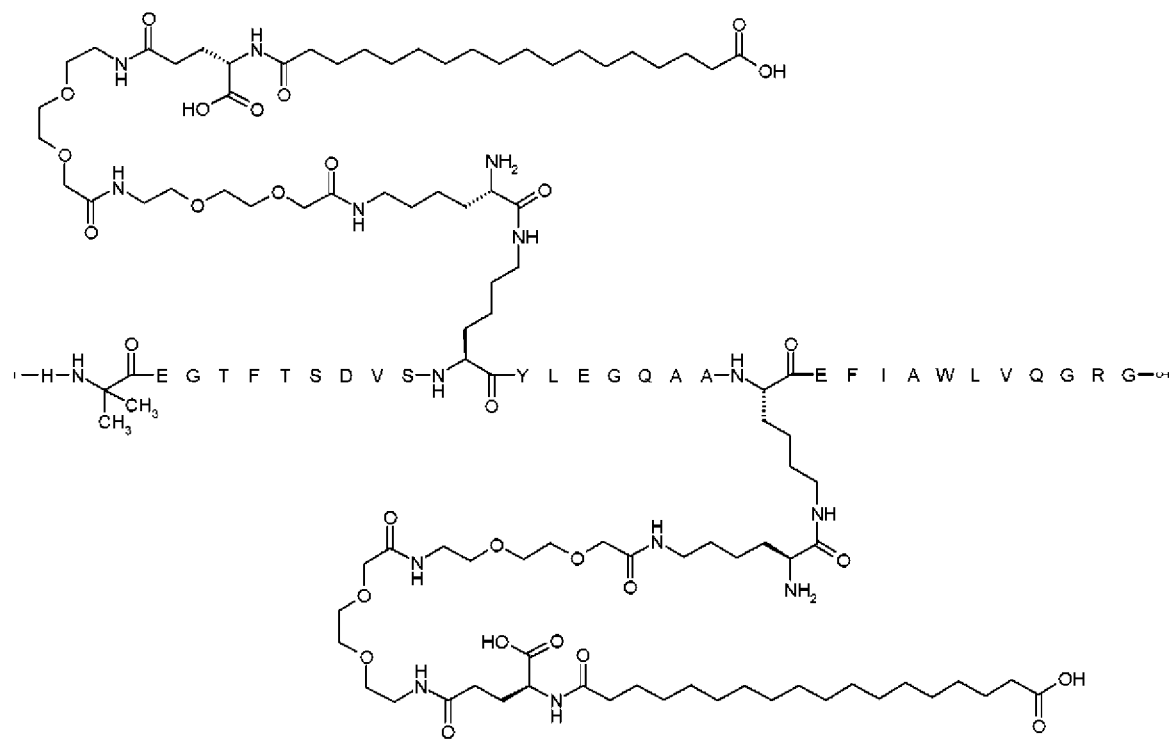

The invention claimed is:

1. A derivative of a GLP-1 analogue, which analogue comprises a first K residue at a position corresponding to position 18 of GLP-1(7-37) (SEQ ID NO: 1), a second K residue at position 22, 26, 27, 30, 31, 34 or 37, and a maximum of seven amino acid changes as compared to GLP-1(7-37), which derivative comprises two protracting moieties attached to said first and second K residue, respectively, via a linker, wherein the protracting moiety is selected from Chem. 2, and Chem. 1:

$$HOOC—C_6H_4—O—(CH_2)_y—CO—* \quad \text{Chem. 2}$$

$$HOOC—(CH_2)_x—CO—*, \quad \text{Chem. 1}$$

in which x is an integer in the range of 6-18, and y is an integer in the range of 3-17; and the linker comprises $$*—NH—(CH_2)_q—CH[(CH_2)_w—NH_2]—CO—*, \quad \text{Chem. 3}$$

wherein q is an integer in the range of 0-5, and w is an integer in the range of 0-5;

or a pharmaceutically acceptable salt, amide, or ester thereof.

2. The derivative of claim 1, wherein the analogue comprises a GLP-1 analogue of Formula I:

$Xaa_7$-$Xaa_8$-Glu-Gly-Thr-$Xaa_{12}$-Thr-Ser-Asp-$Xaa_{16}$-Ser-Lys-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$ (SEQ ID NO: 8), wherein $Xaa_7$ is L-histidine, imidazopropionyl, α-hydroxy-histidine, D-histidine, desamino-histidine, 2-amino-histidine, β-hydroxy-histidine, homohistidine, $N^α$-acetyl-histidine, $N^α$-formyl-histidine, α-fluoromethyl-histidine, α-methyl-histidine, 3-pyridylalanine, 2-pyridylalanine, or 4-pyridylalanine;

$Xaa_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{12}$ is Phe or Leu;

$Xaa_{16}$ is Val or Leu;

$Xaa_{19}$ is Tyr or Gln;

$Xaa_{20}$ is Leu or Met;

$Xaa_{22}$ is Gly, Glu, Lys, or Aib;

$Xaa_{23}$ is Gln, Glu, or Arg;

$Xaa_{25}$ is Ala or Val;

$Xaa_{26}$ is Val, His, Lys, or Arg;

$Xaa_{27}$ is Glu, Leu, or Lys;

$Xaa_{30}$ is Ala, Glu, Lys, or Arg;

$Xaa_{31}$ is Trp, Lys, or His $Xaa_{33}$ is Val or Lys;

$Xaa_{34}$ is Lys, Glu, Asn, Gly, Gln, Arg, His, or absent;

$Xaa_{35}$ is Gly, Aib, or absent;

$Xaa_{36}$ is Arg, Gly, Lys, or absent;

$Xaa_{37}$ is Gly, Ala, Glu, Pro, Lys, Arg, or absent; and $Xaa_{38}$ is Ser, Gly, Ala, Glu, Pro, Lys, Arg, or absent.

3. The derivative of claim 1, wherein x is 10, 12, 14, 16, or 18.

4. The derivative of claim 3, wherein y is 7, 8, 9, or 11.

5. The derivative of claim 4, wherein the analogue comprises no K residues other than the first and the second K residue.

6. The derivative of claim 5, wherein a carboxylic acid group of the C-terminal amino acid of the analogue is converted into carboxylic acid amide.

7. A compound selected from the following:
Chem. 20
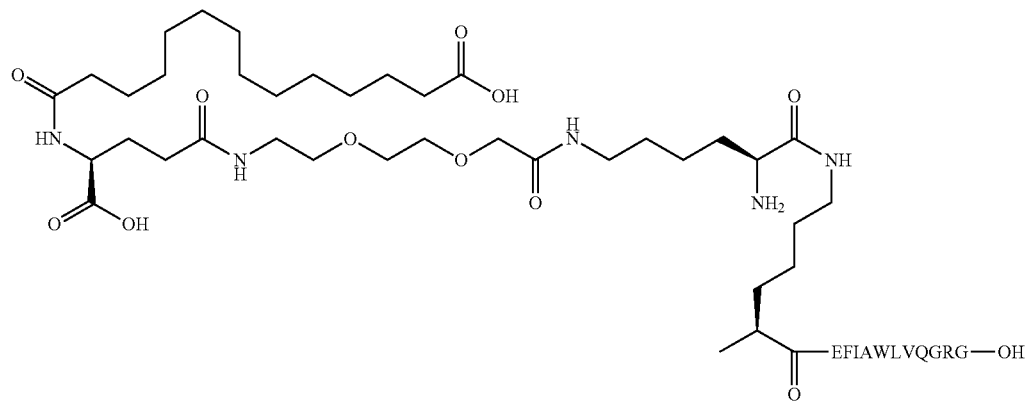
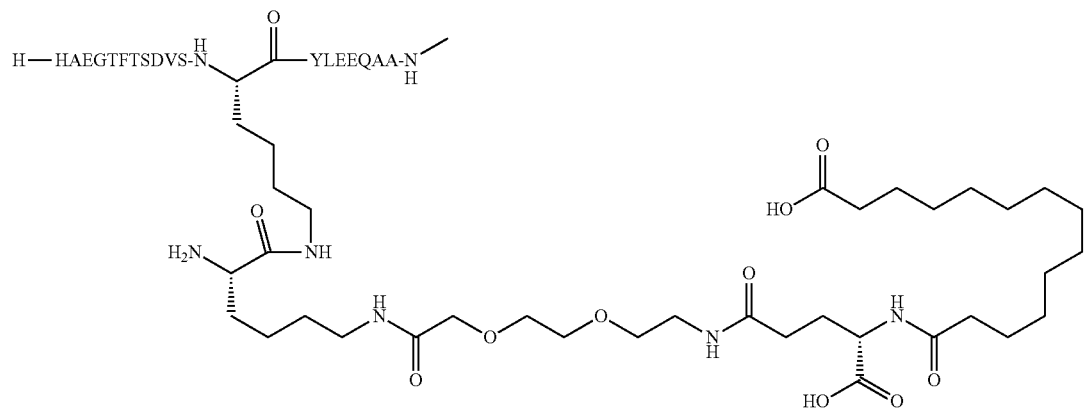
wherein the amino acid sequence is that of SEQ ID NO: 11,
Chem. 21
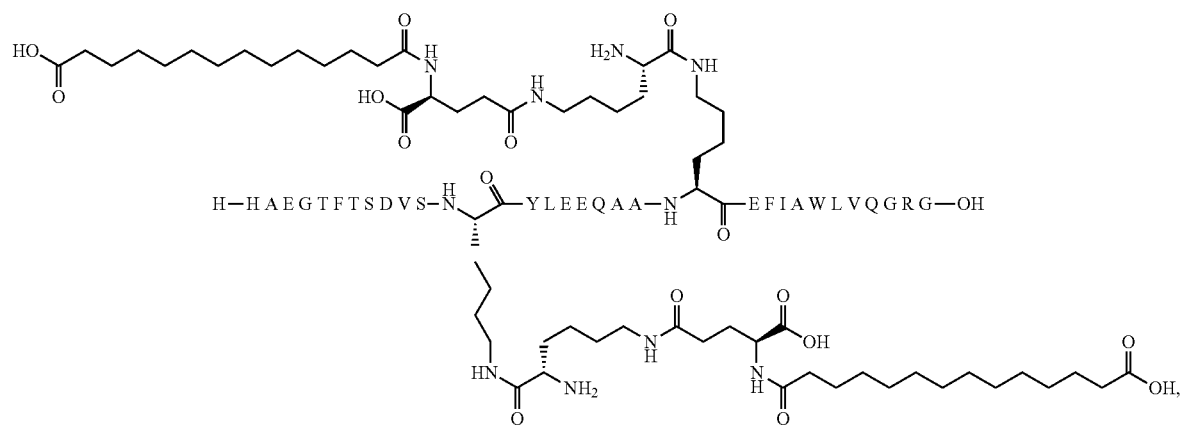

wherein the amino acid sequence is that of SEQ ID NO: 11,
Chem. 22
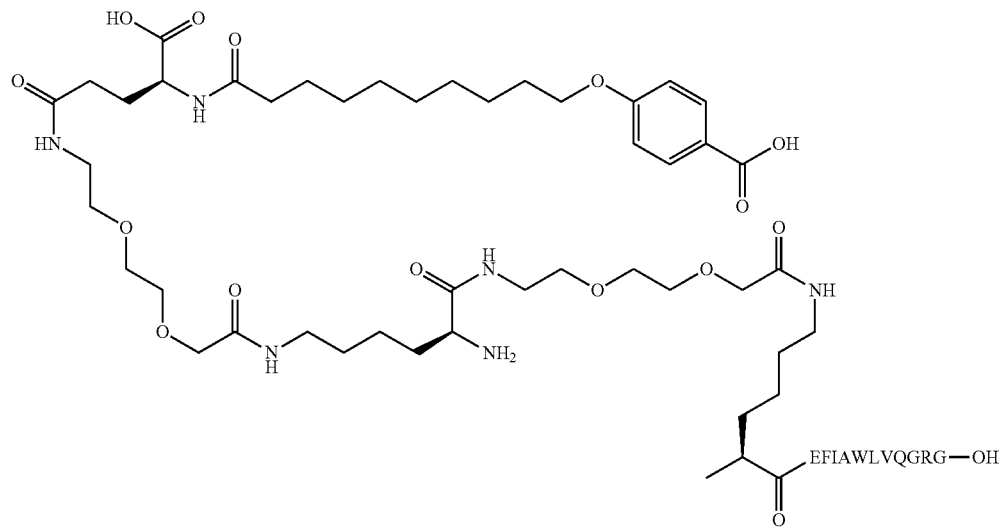
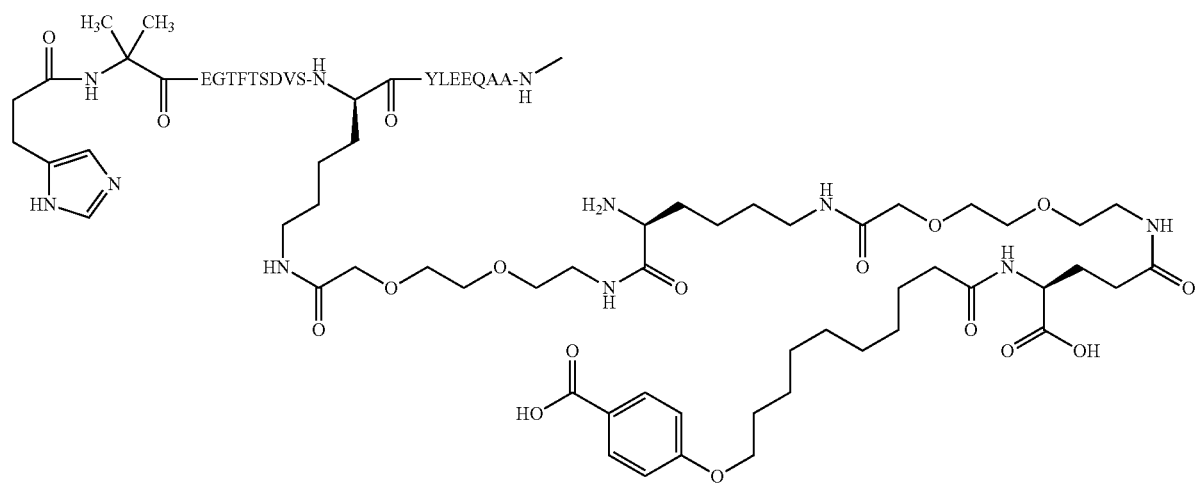
wherein the amino acid sequence is that of SEQ ID NO: 5,
Chem. 23
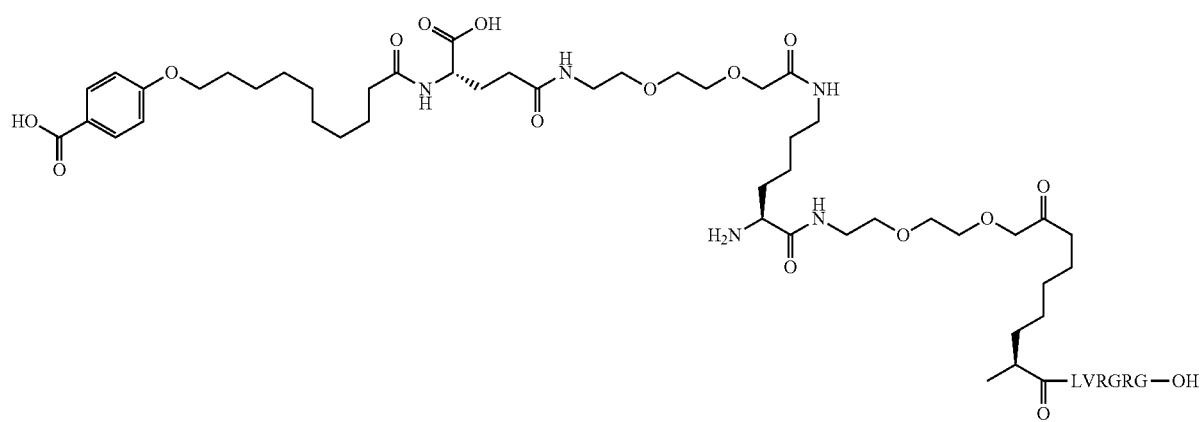

-continued
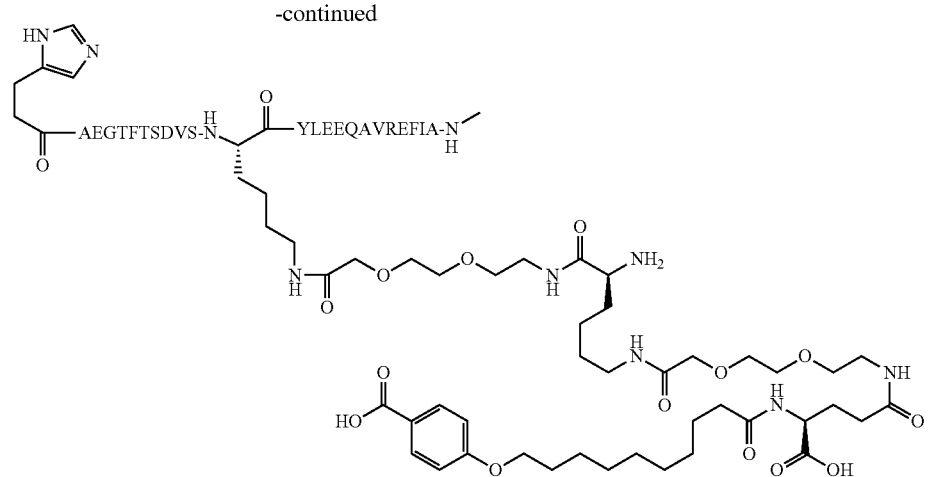
wherein the amino acid sequence is that of SEQ ID NO: 6,
Chem. 24
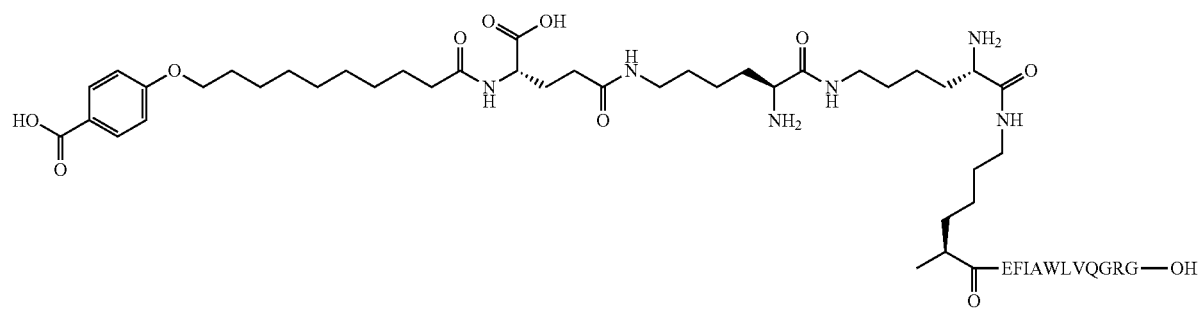
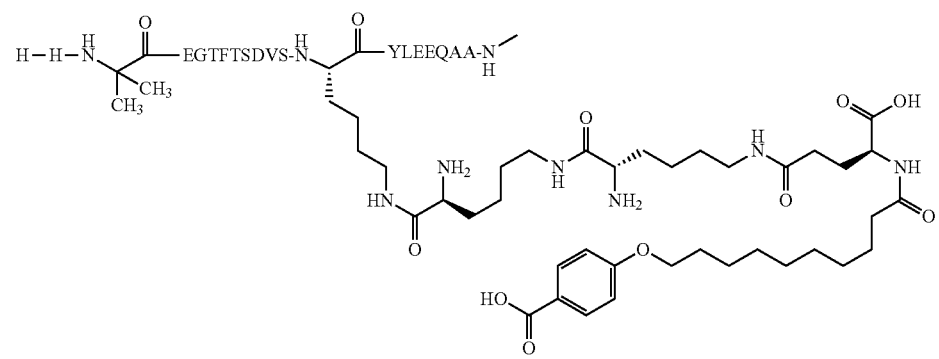

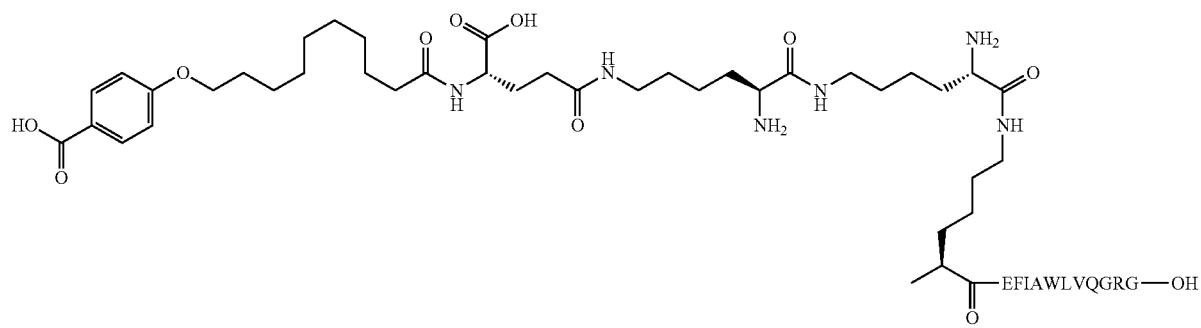
wherein the amino acid sequence is that of SEQ ID NO: 9,
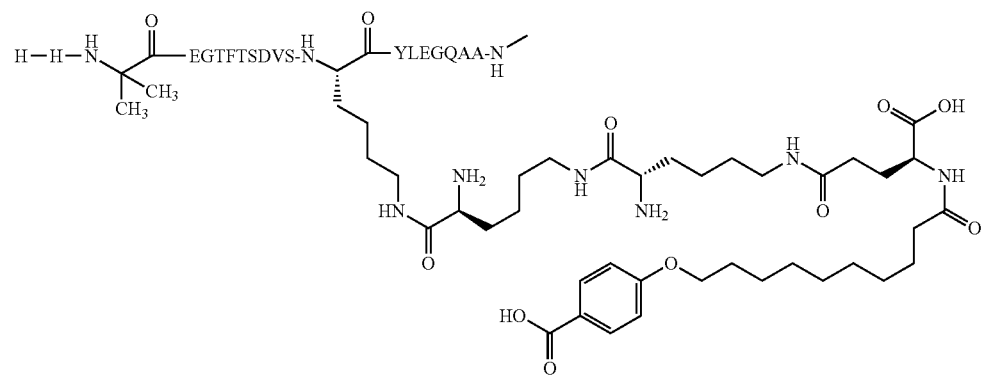
wherein the amino acid sequence is that of SEQ ID NO: 12,
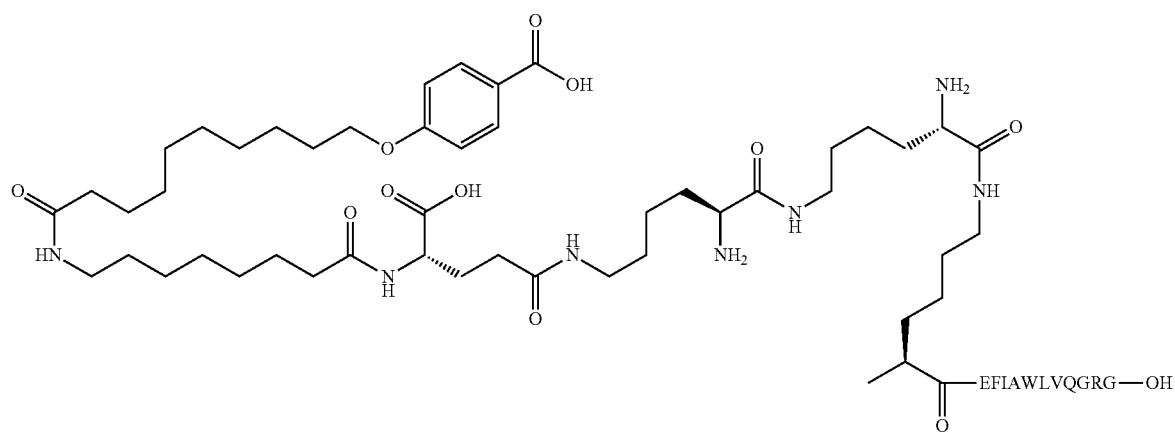

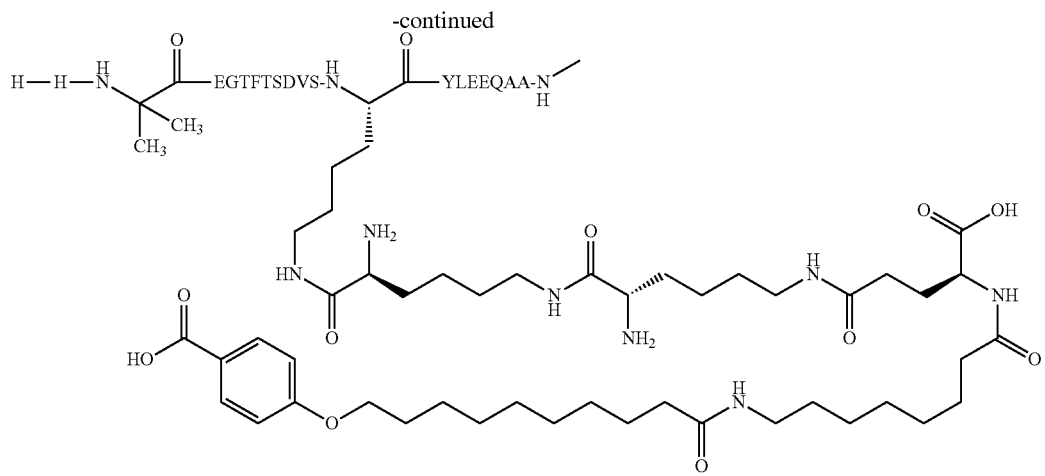
wherein the amino acid sequence is that of SEQ ID NO: 9,
Chem. 27
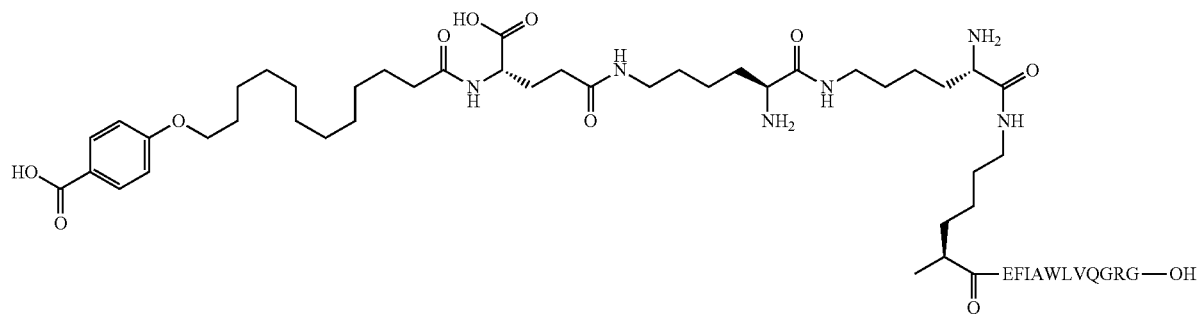
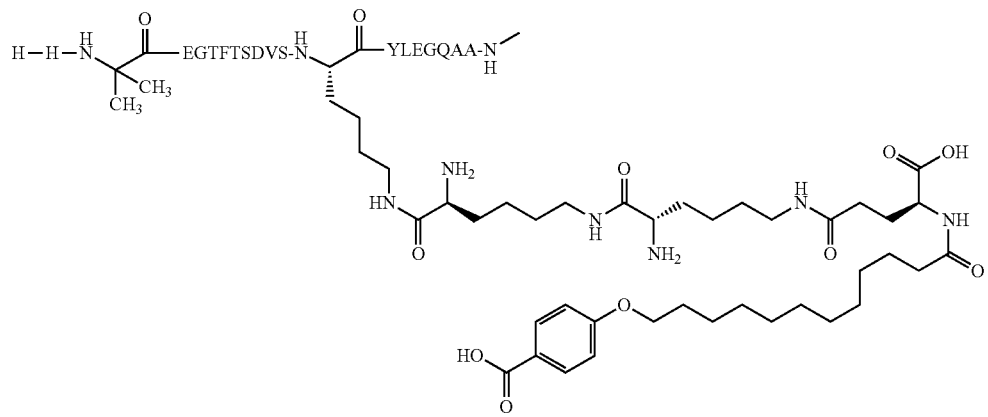

wherein the amino acid sequence is that of SEQ ID NO: 12,
Chem. 28
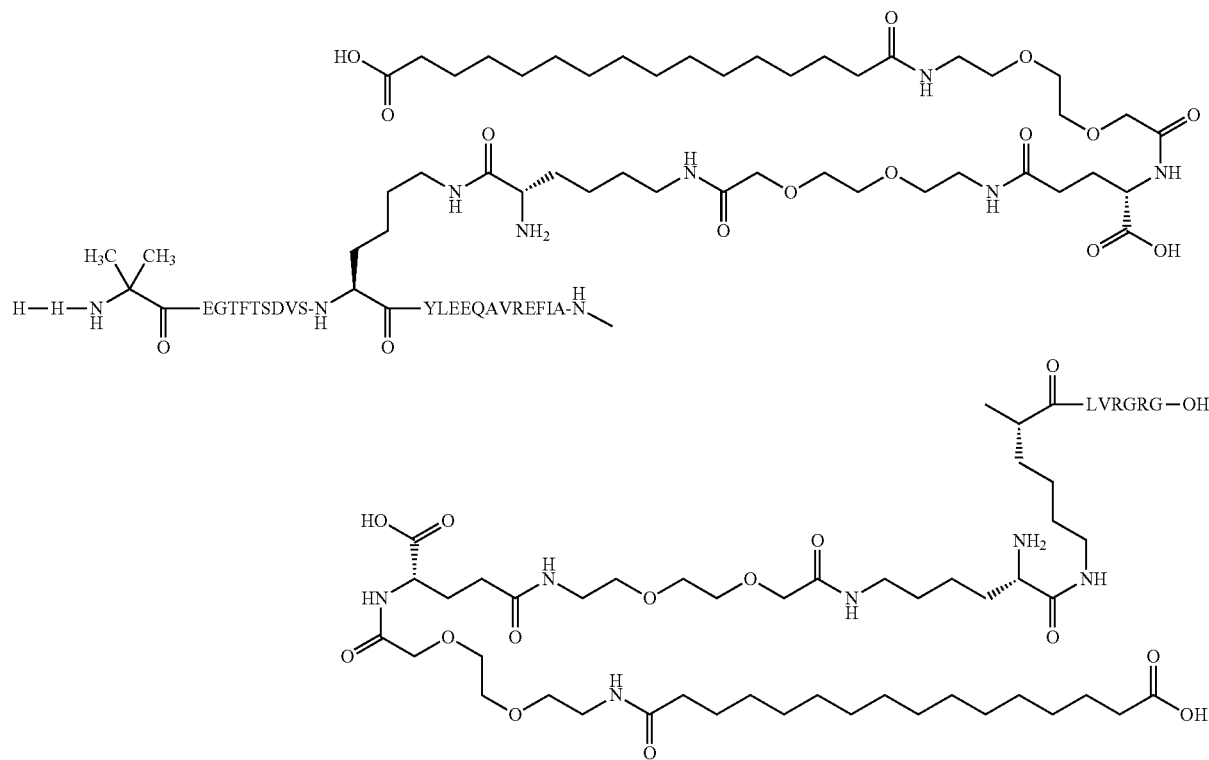
wherein the amino acid sequence is that of SEQ ID NO: 6,
Chem. 29
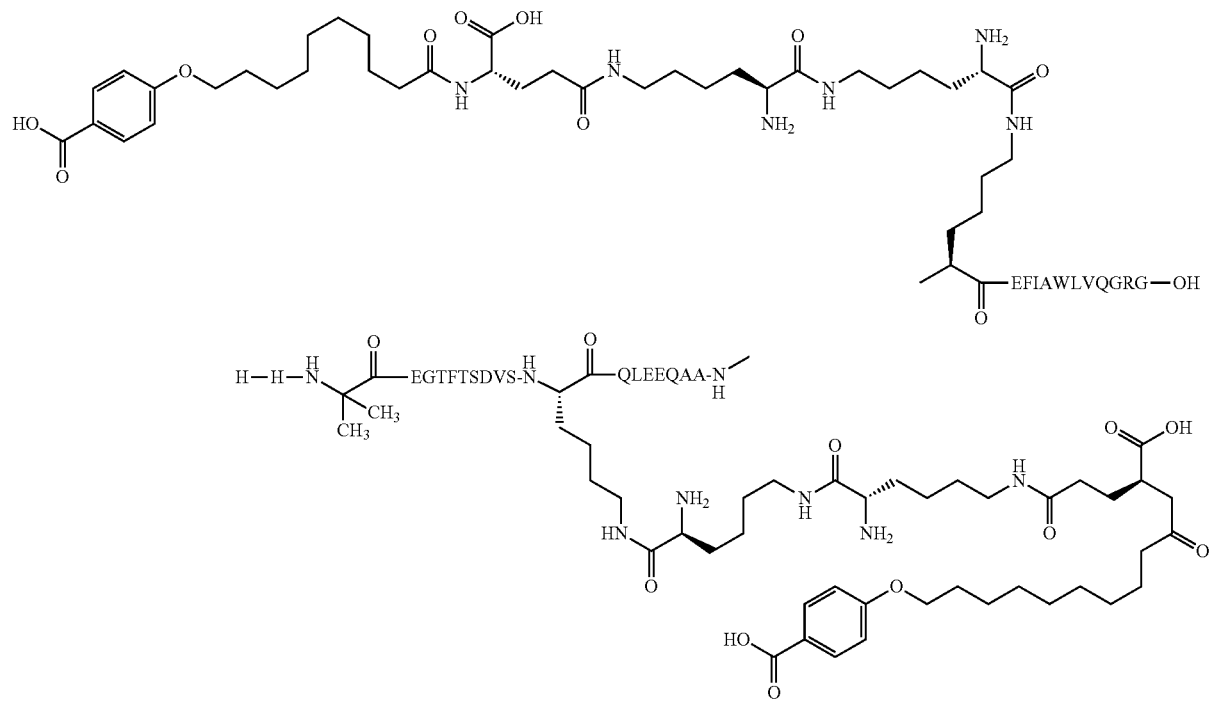

wherein the amino acid sequence is that of SEQ ID NO: 10,
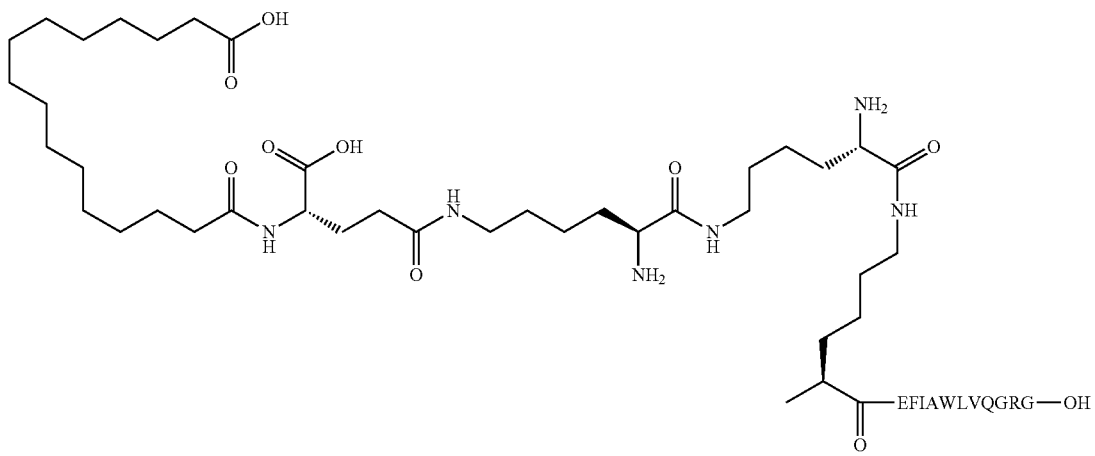
Chem. 30
wherein the amino acid sequence is that of SEQ ID NO: 12,
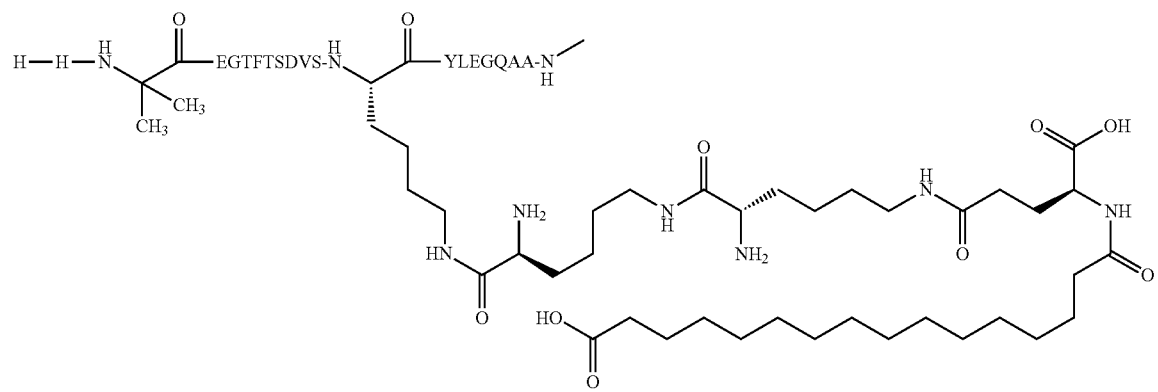
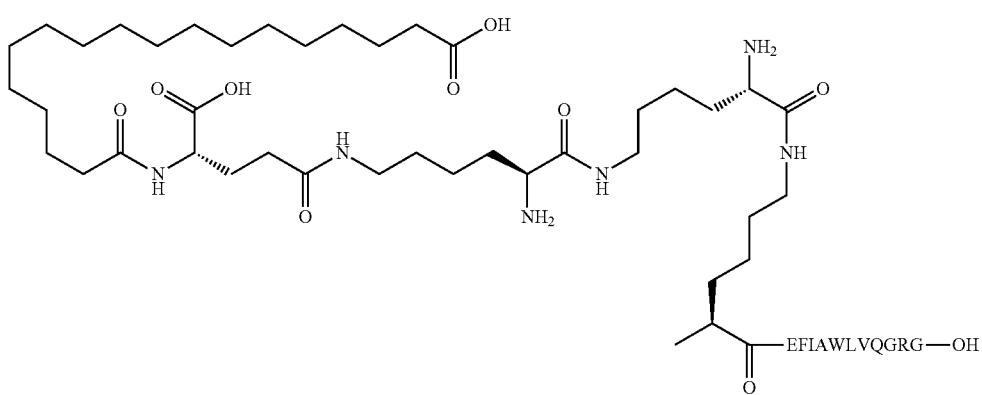
Chem. 31

-continued
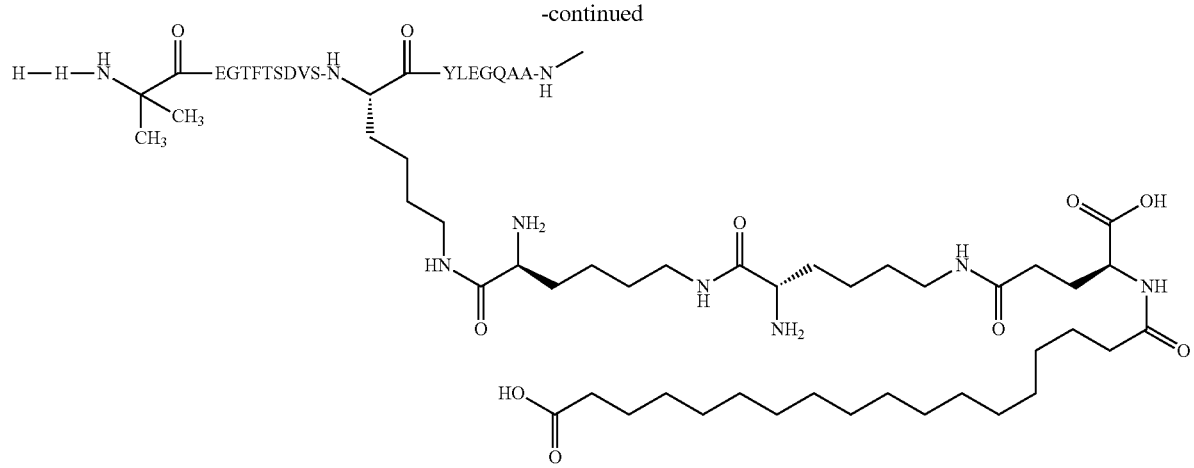
wherein the amino acid sequence is that of SEQ ID NO: 12,
Chem. 32
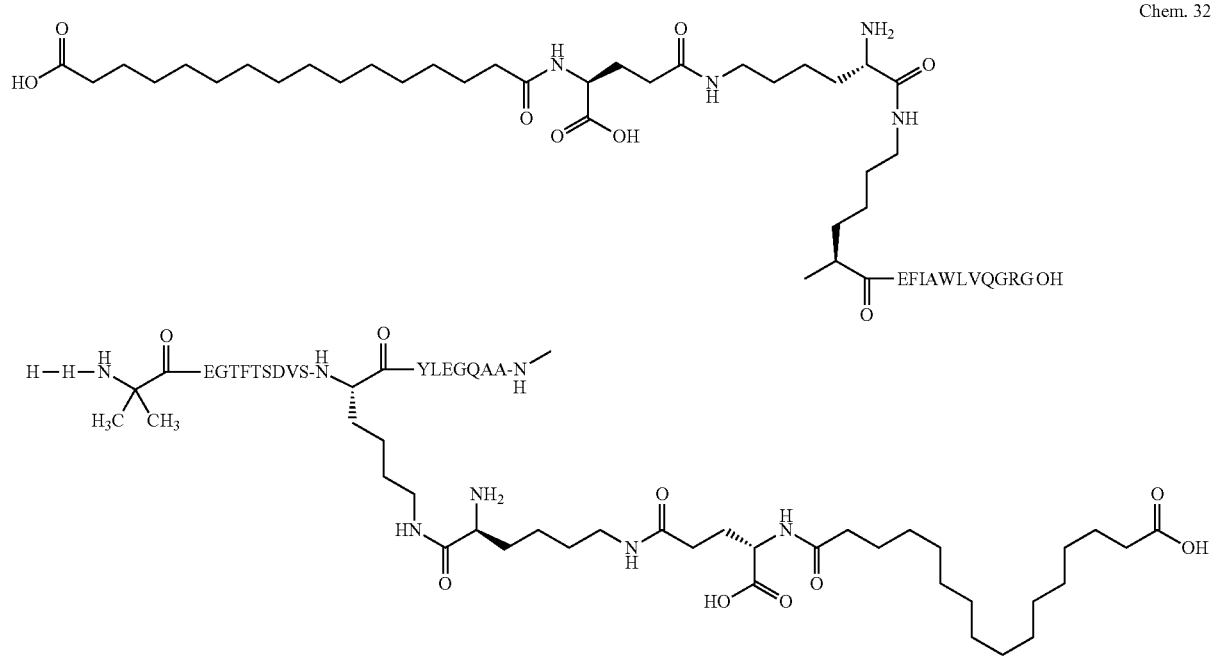
wherein the amino acid sequence is that of SEQ ID NO: 12,
Chem. 33
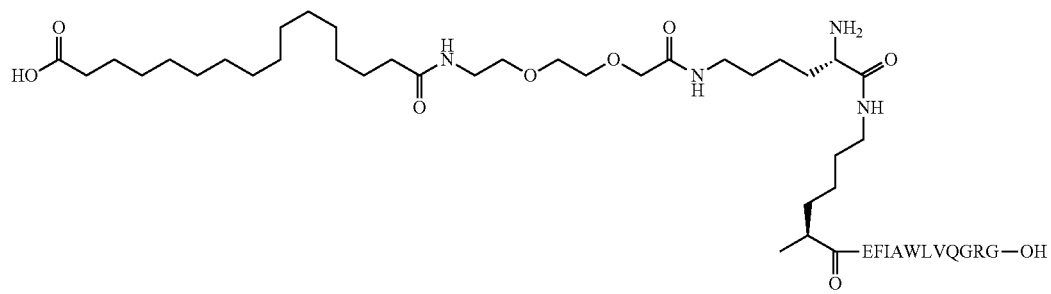

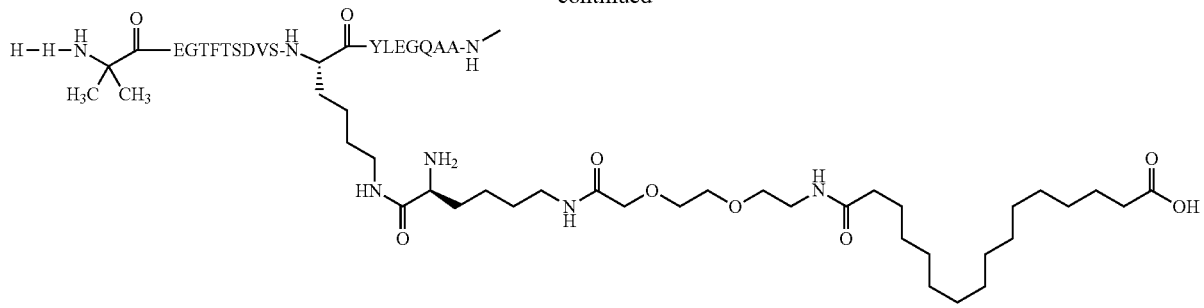
wherein the amino acid sequence is that of SEQ ID NO: 12,
Chem. 34
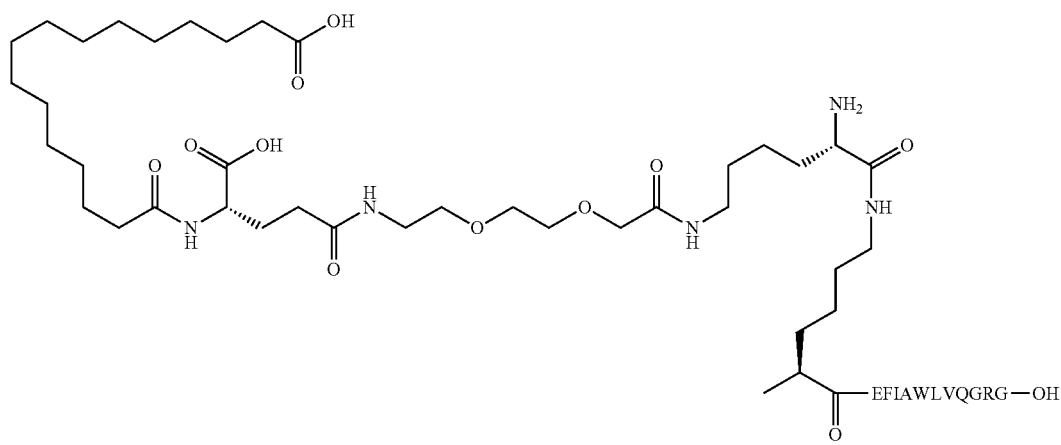
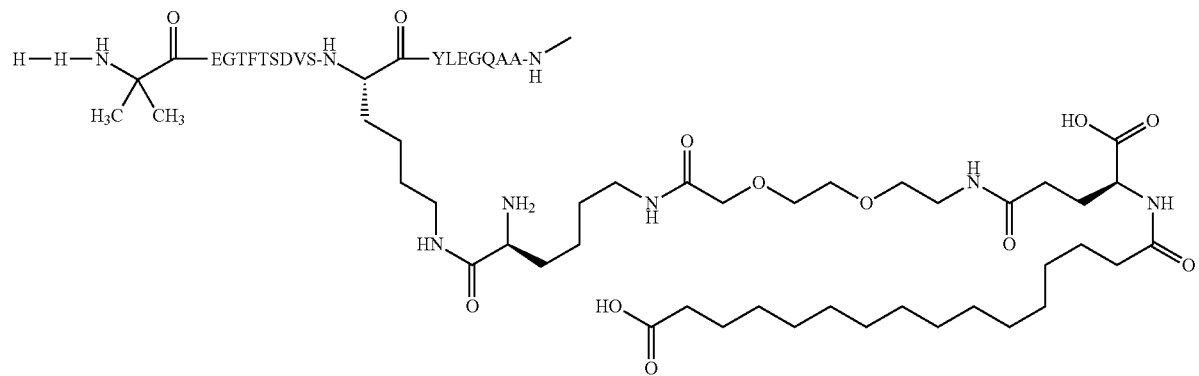
wherein the amino acid sequence is that of SEQ ID NO: 12,
Chem. 35
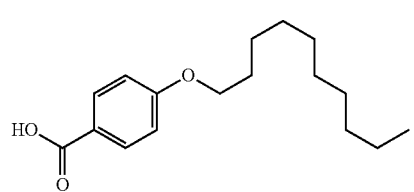

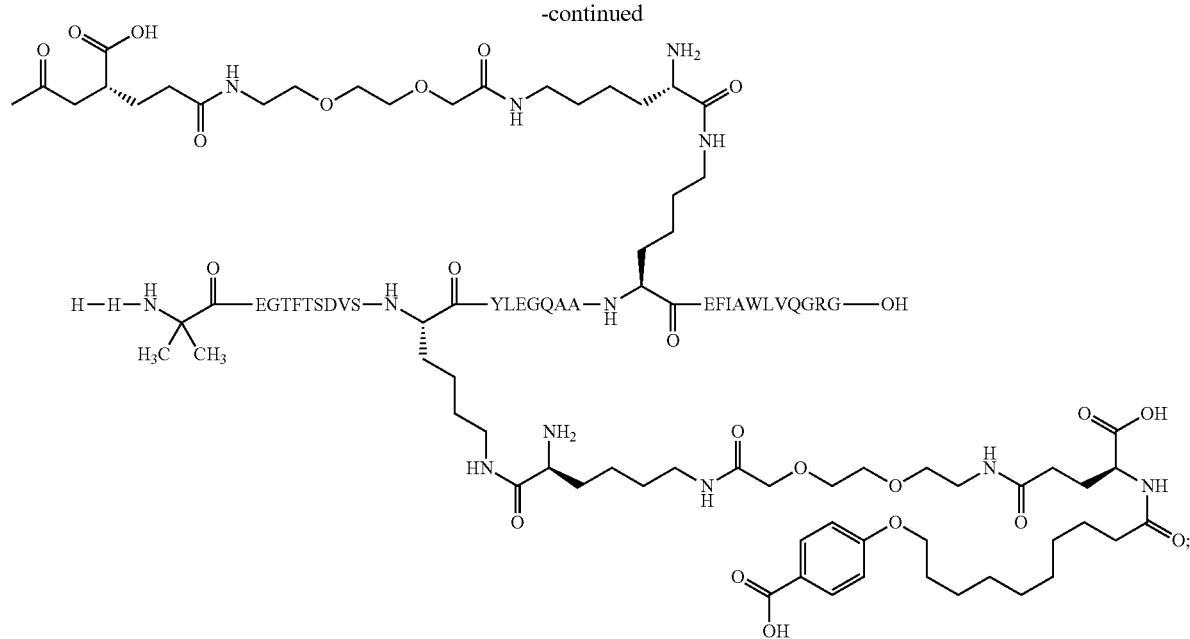
-continued
wherein the amino acid sequence is that of SEQ ID NO: 12,
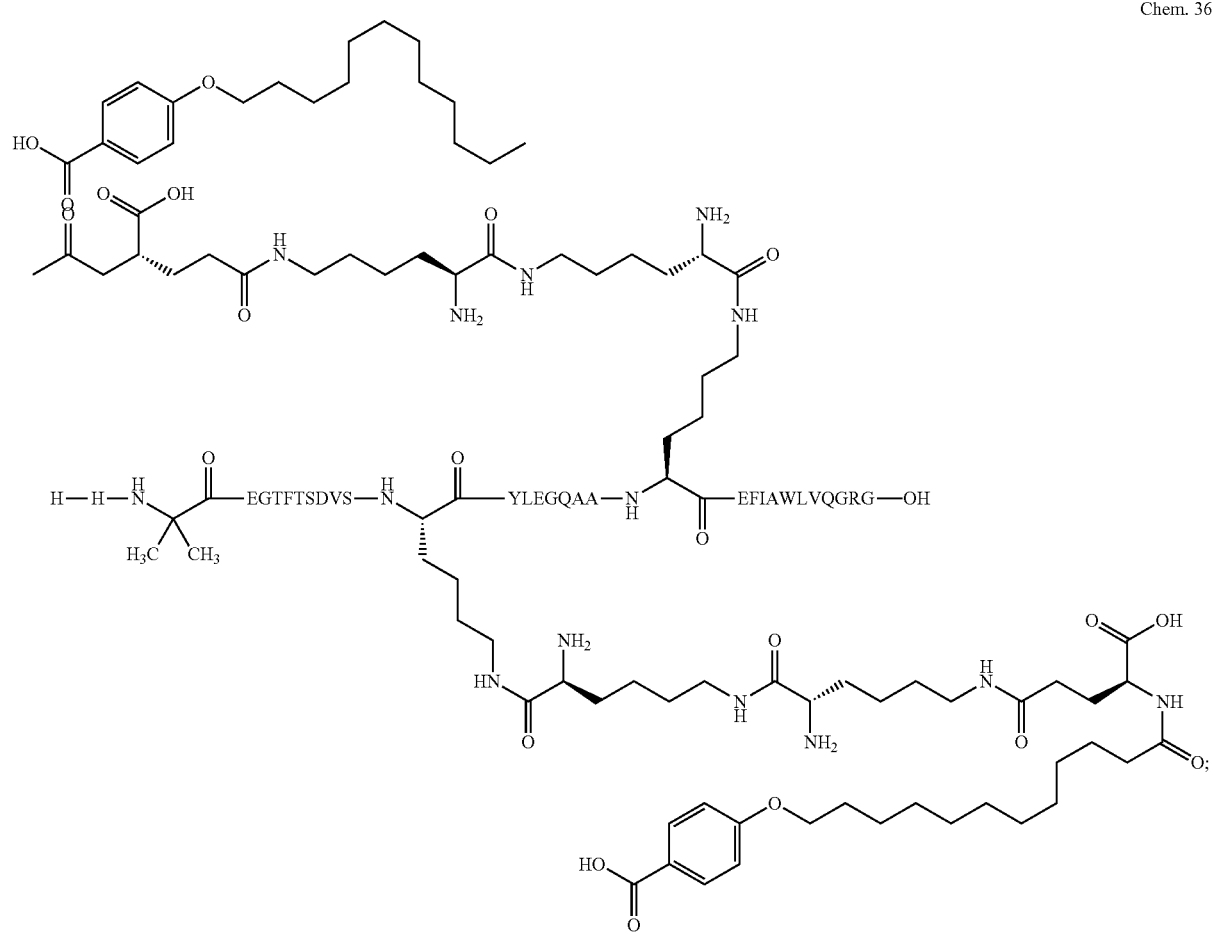
Chem. 36 wherein the amino acid sequence is that of SEQ ID NO: 9,
Chem. 37
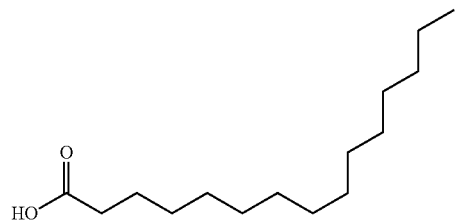
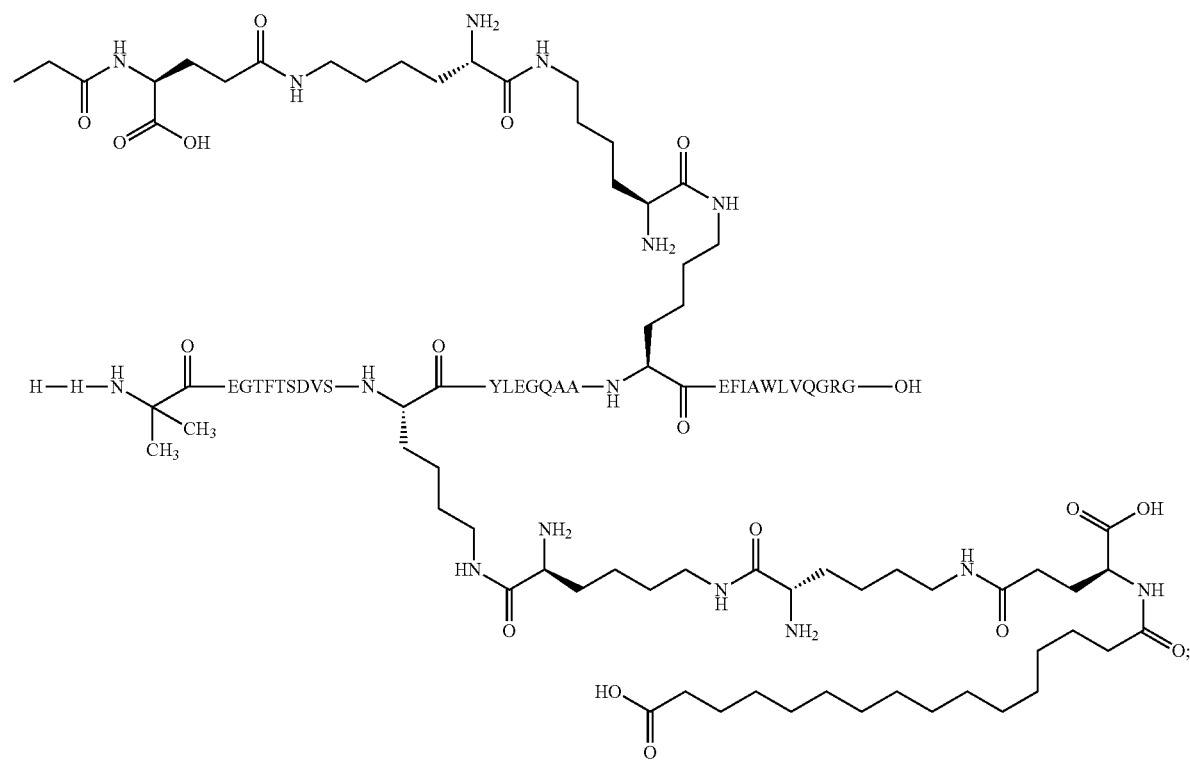
wherein the amino acid sequence is that of SEQ ID NO: 9,

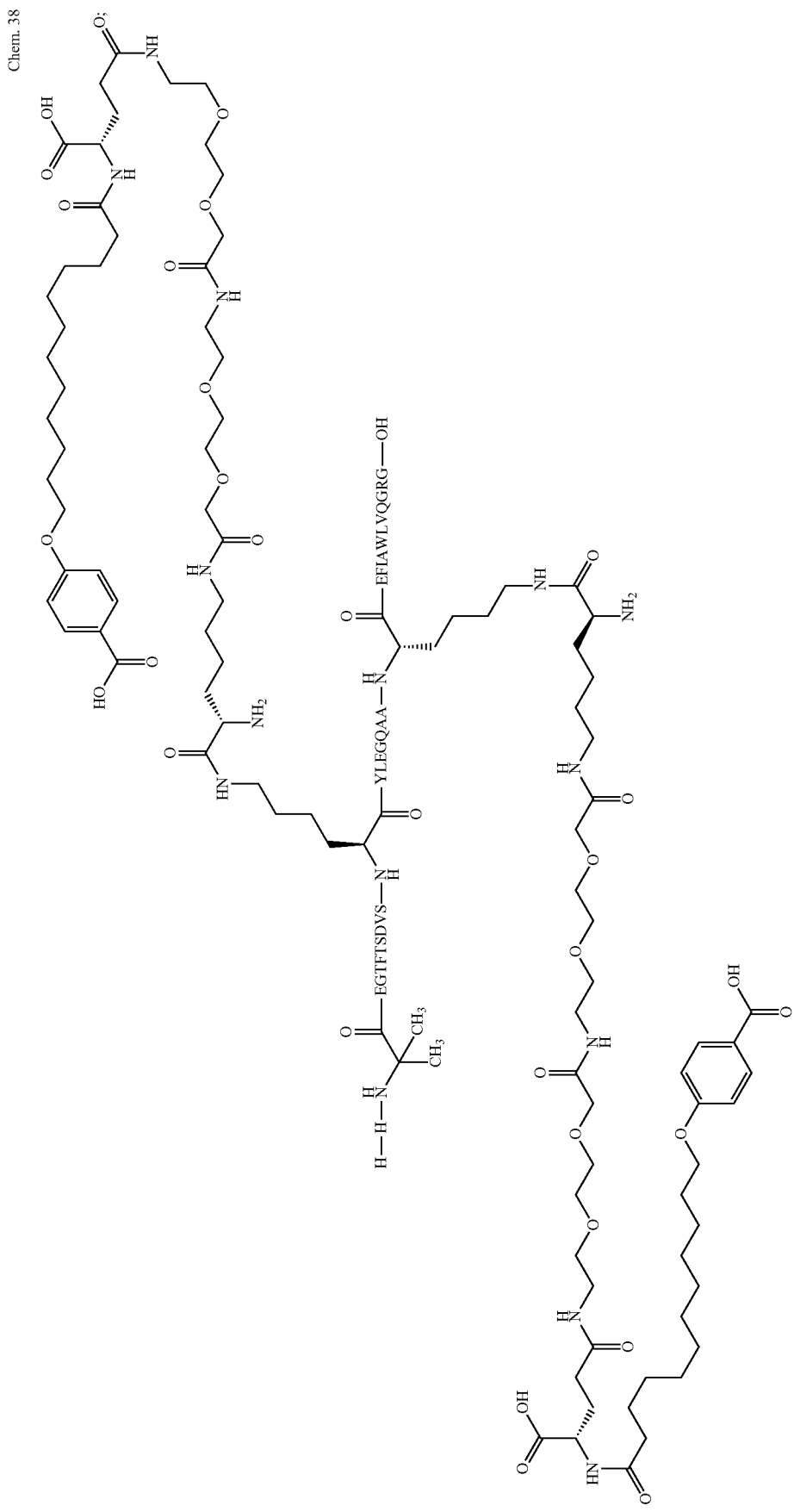

wherein the amino acid sequence is that of SEQ ID NO: 12,
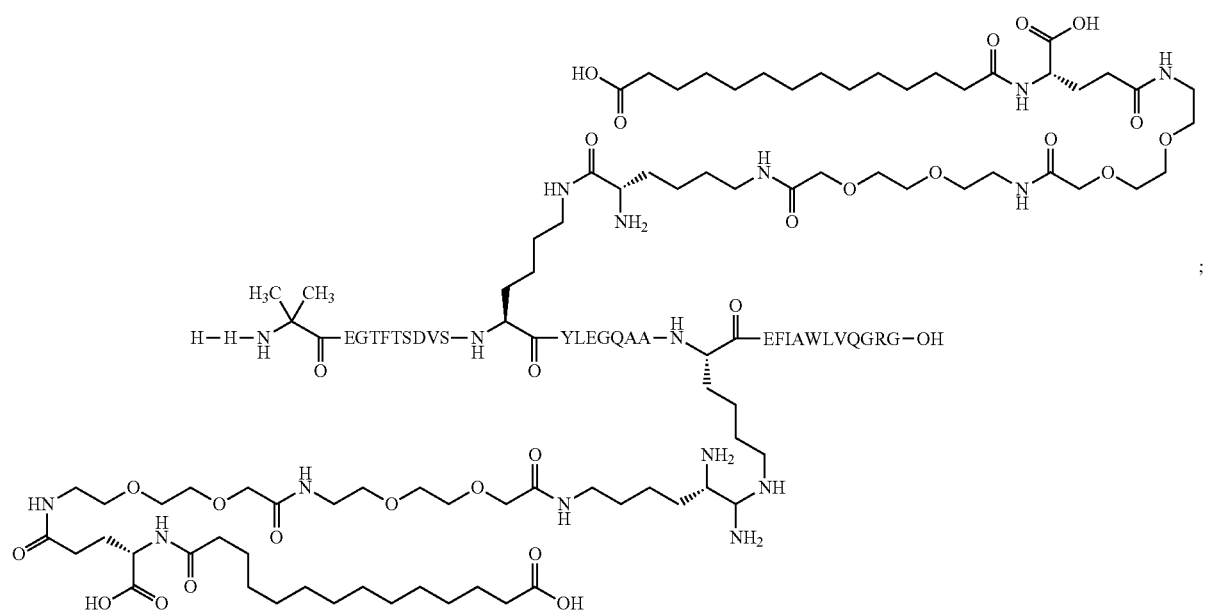
Chem.39
wherein the amino acid sequence is that of SEQ ID NO:12,
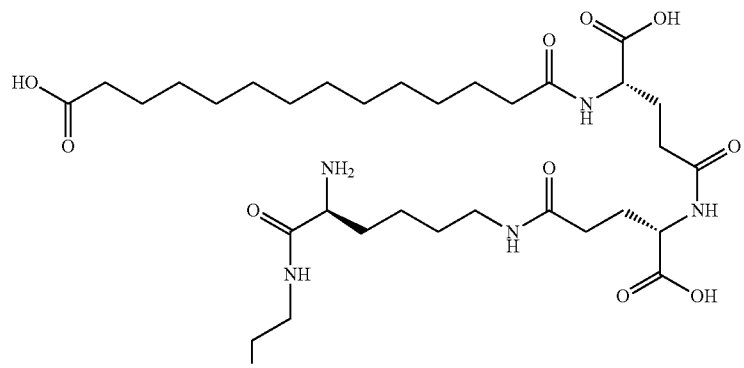
Chem. 40

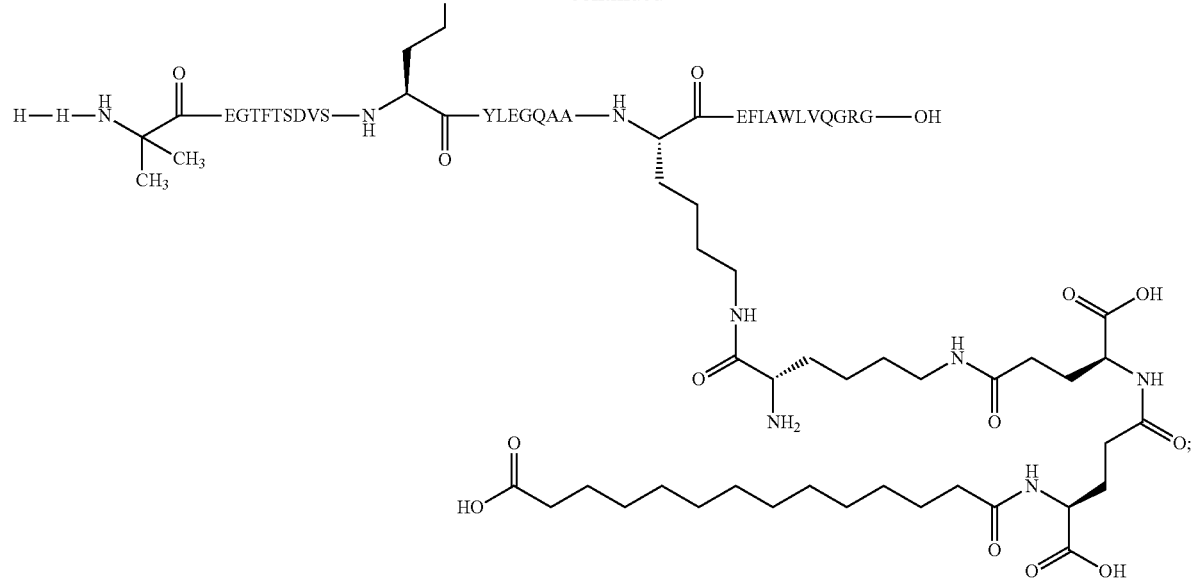
wherein the amino acid sequence is that of SEQ ID NO: 9,
Chem. 41
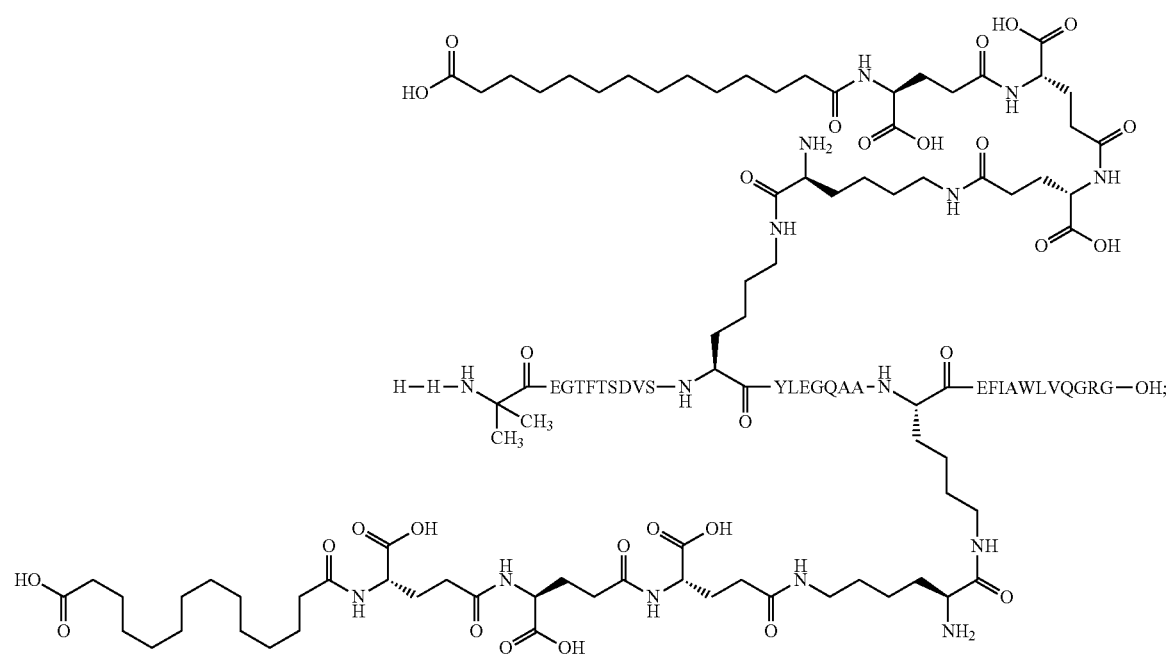

wherein the amino acid sequence is that of SEQ ID NO: 9,
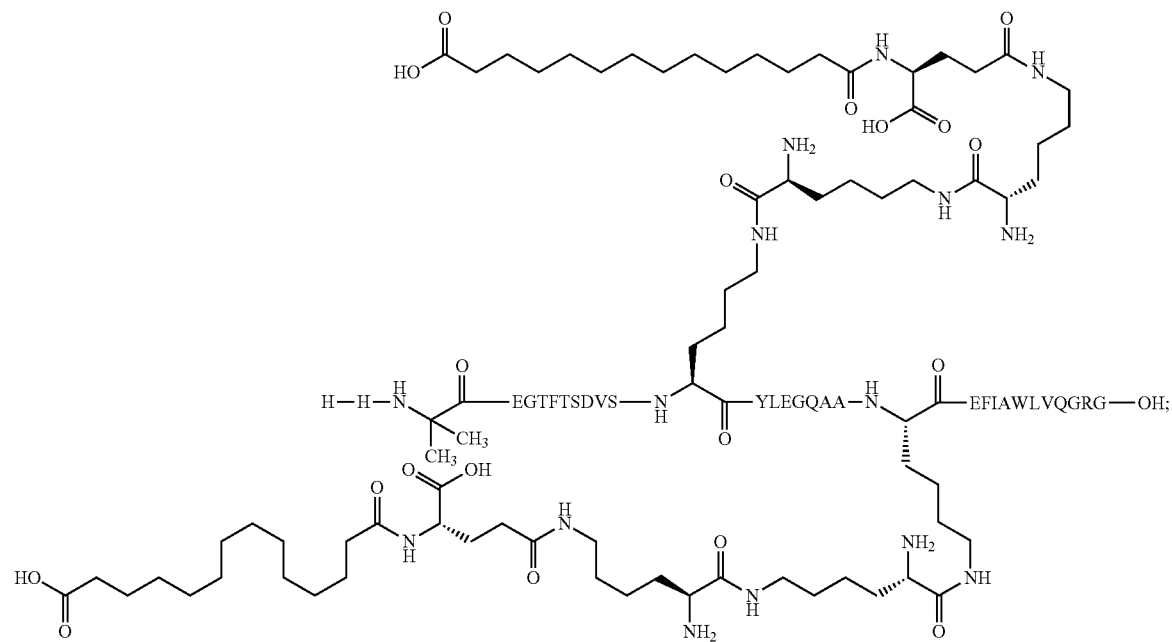
wherein the amino acid sequence is that of SEQ ID NO: 9,

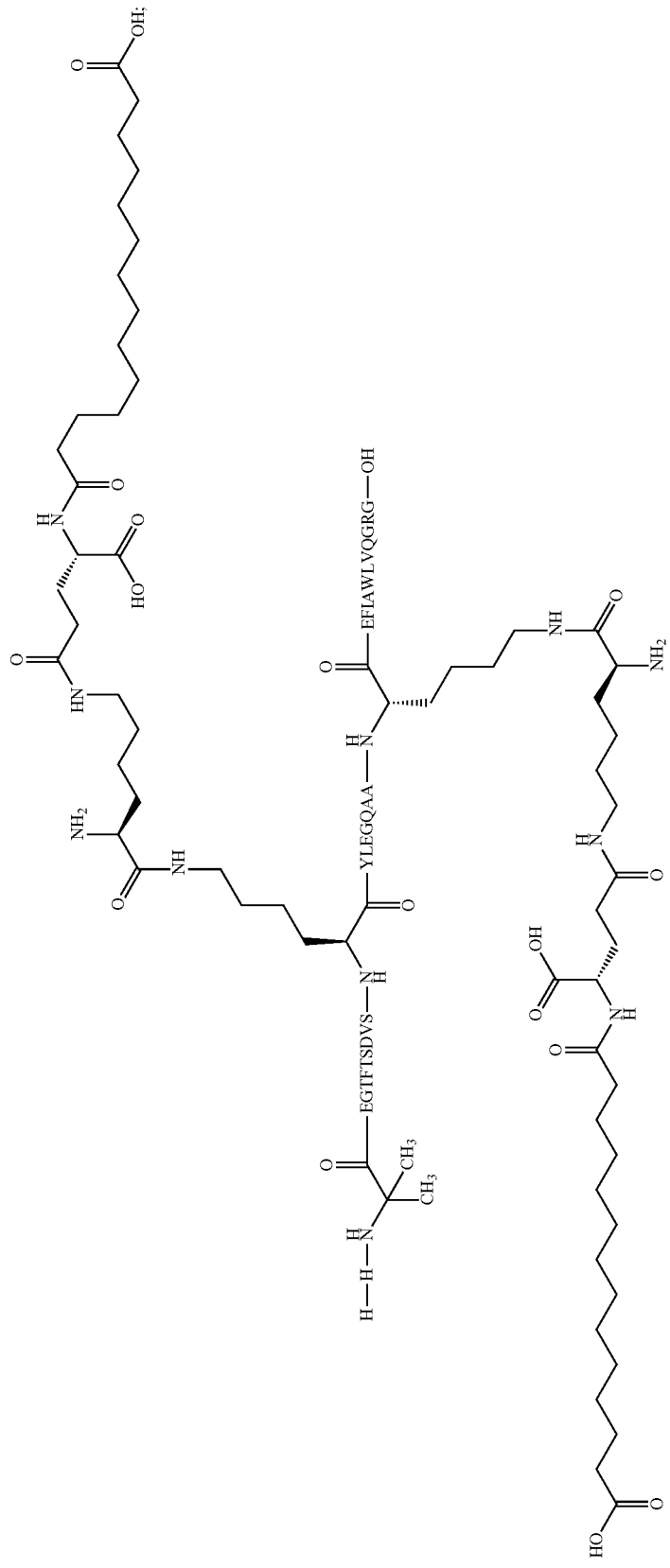
Chem 43 wherein the amino acid sequence is that of SEQ ID NO: 9,
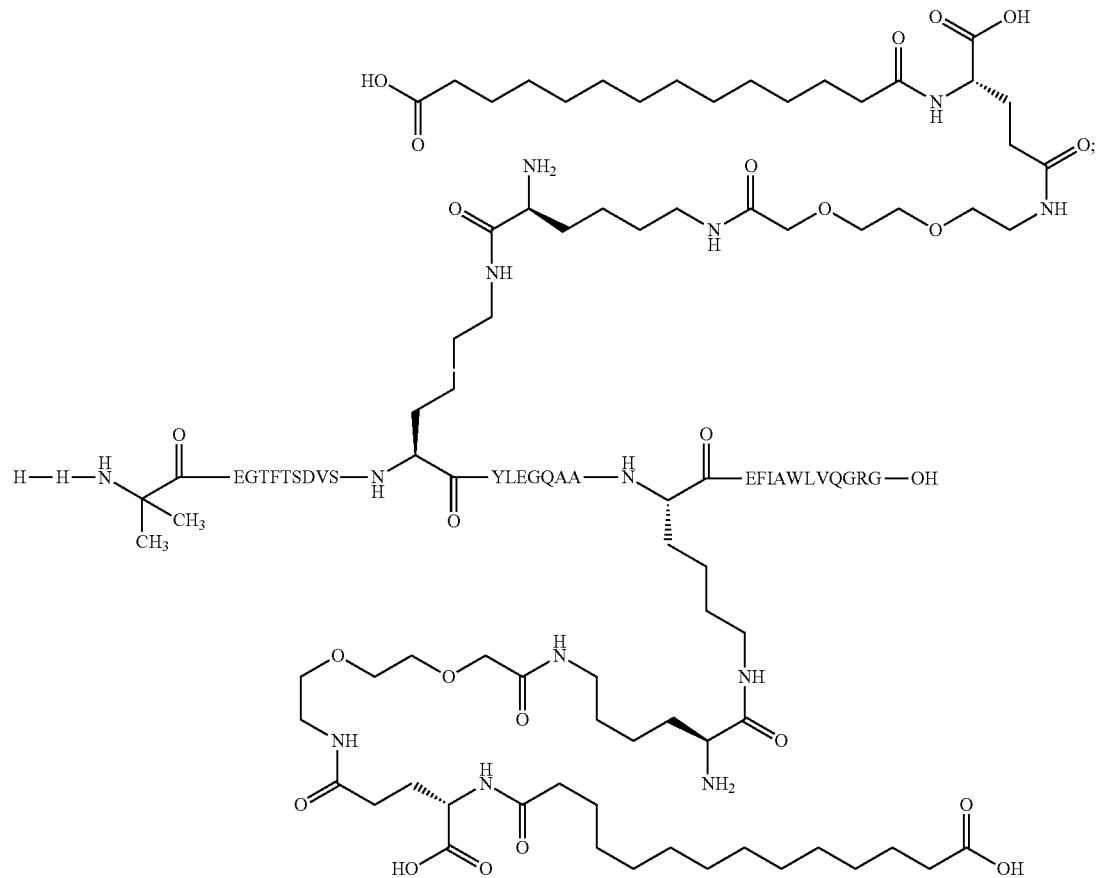
wherein the amino acid sequence is that of SEQ ID NO: 9,
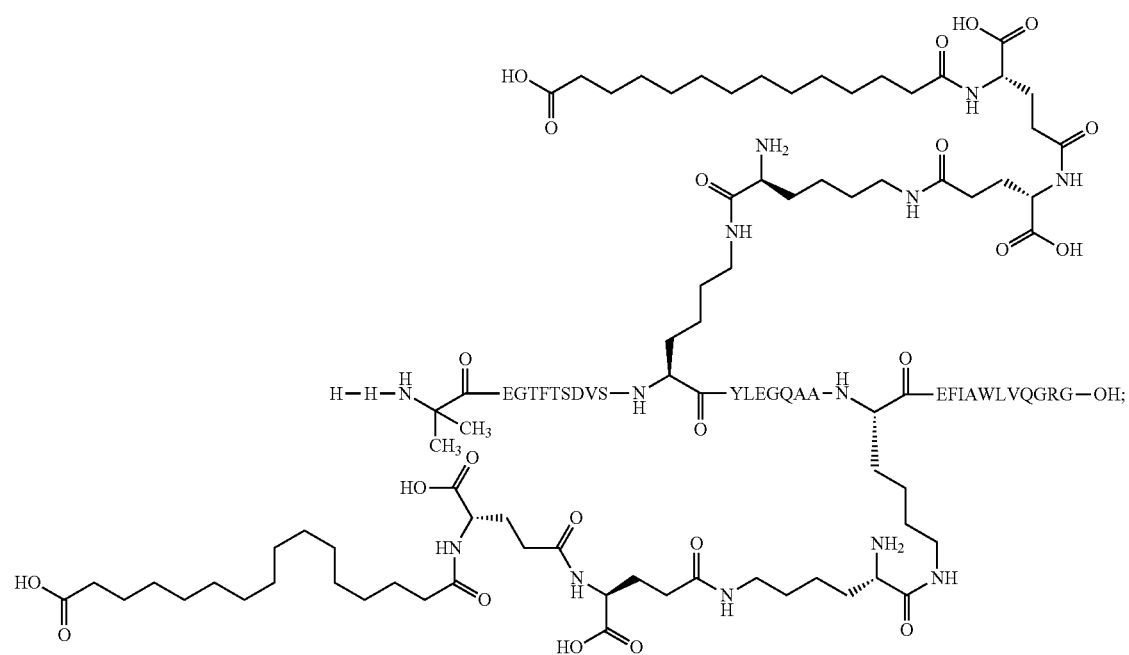

wherein the amino acid sequence is that of SEQ ID NO: 9,
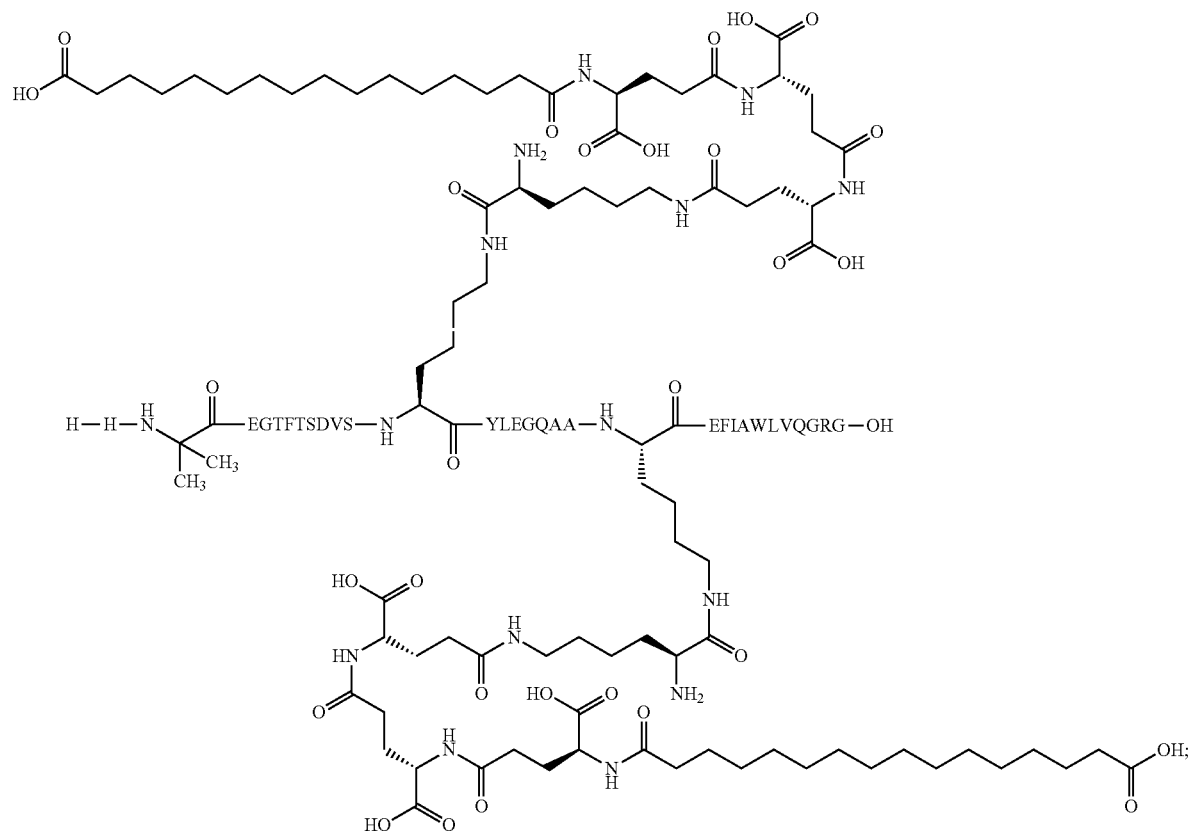
Chem. 46
wherein the amino acid sequence is that of SEQ ID NO: 9,

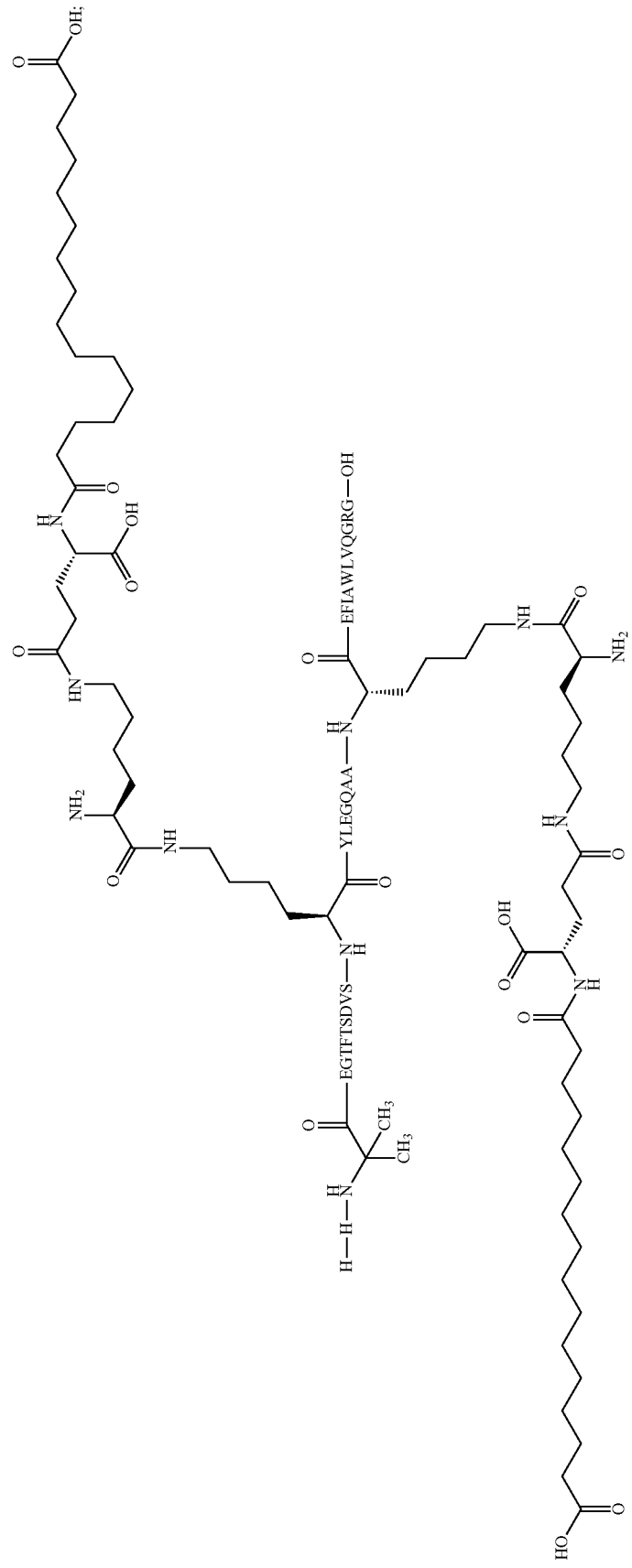
Chem. 47 wherein the amino acid sequence is that of SEQ ID NO: 9,
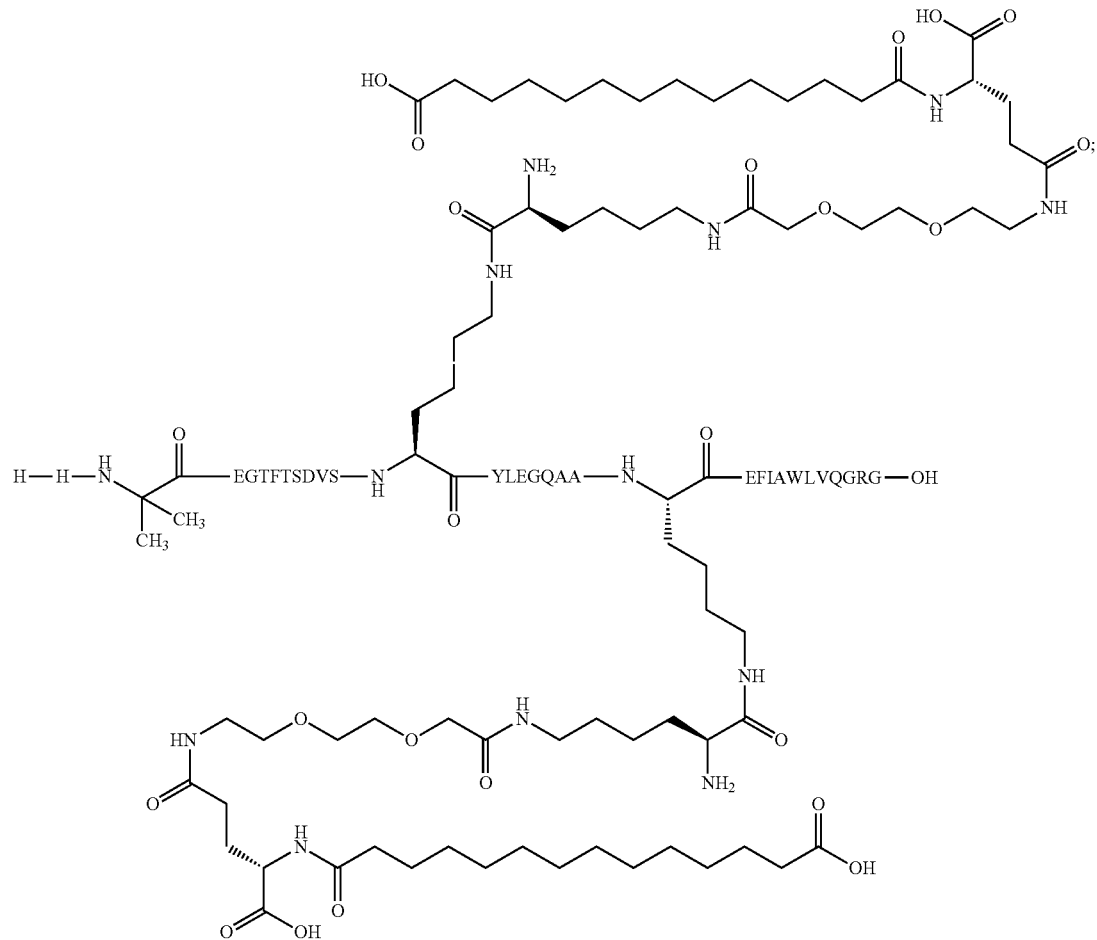
Chem. 48
wherein the amino acid sequence is that of SEQ ID NO: 9,
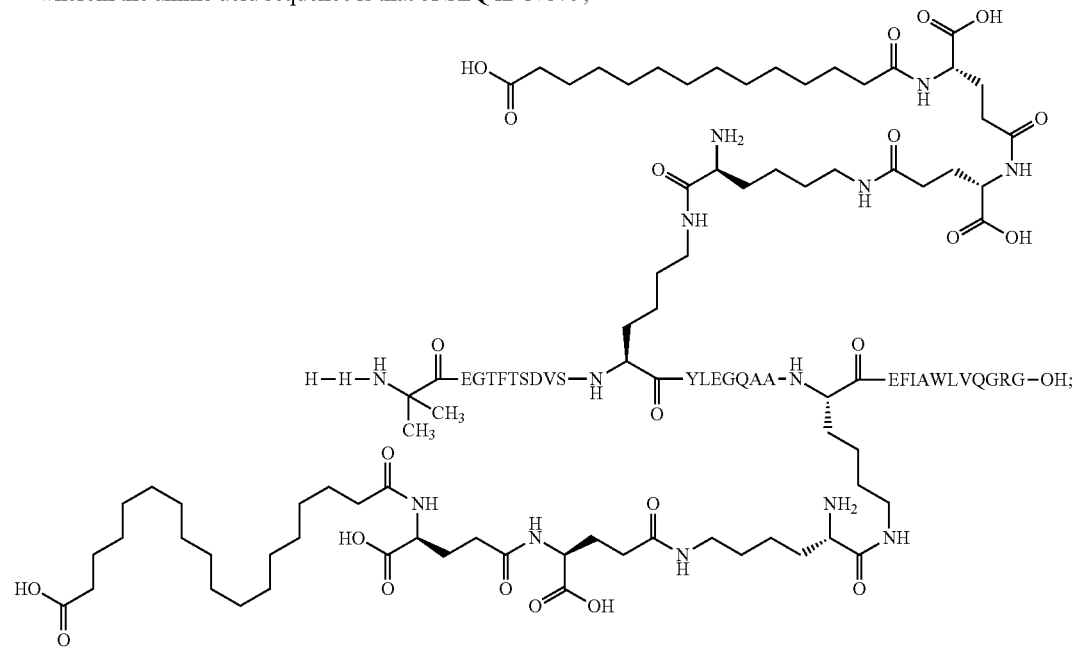
Chem. 49 wherein the amino acid sequence is that of SEQ ID NO: 9,
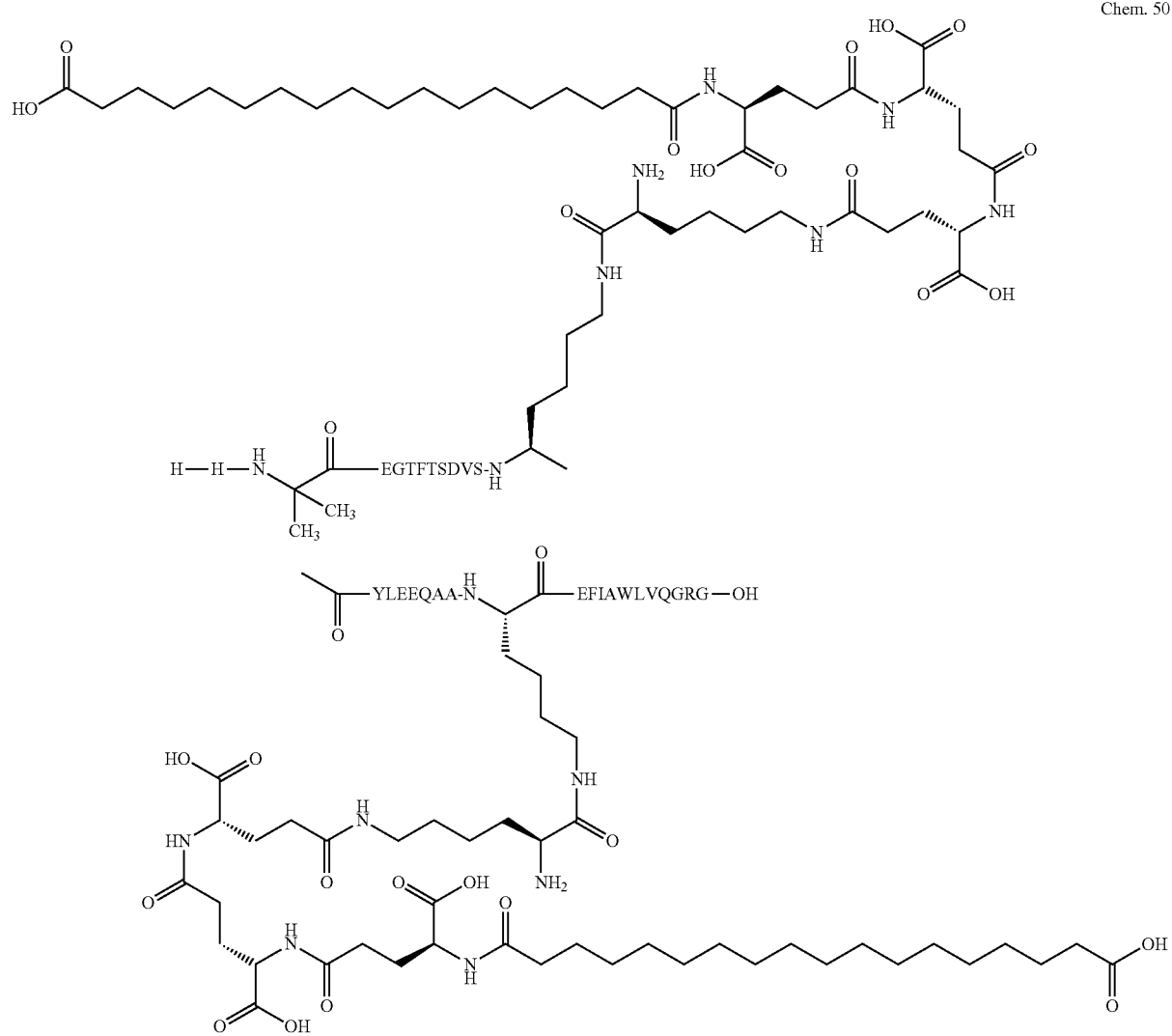
Chem. 50
wherein the amino acid sequence is that of SEQ ID NO: 9,
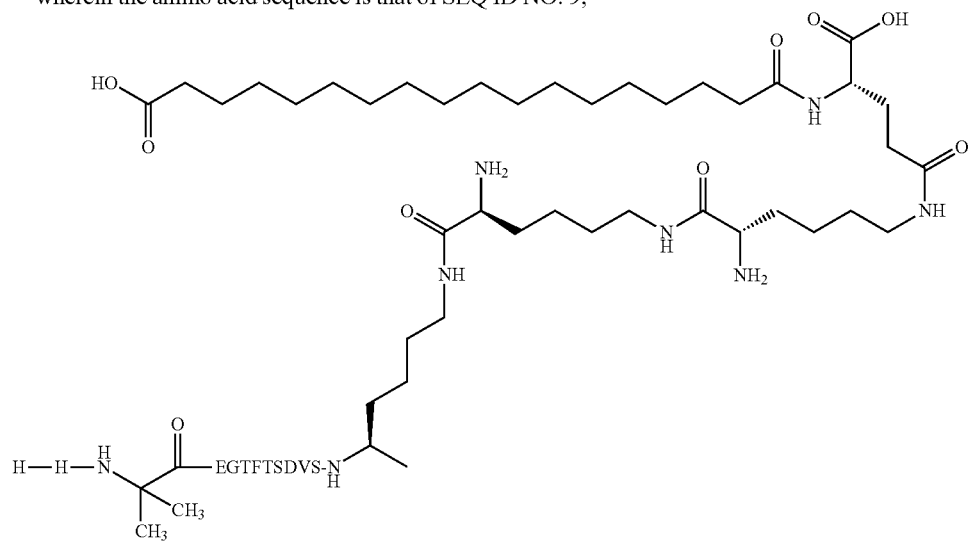
Chem. 51

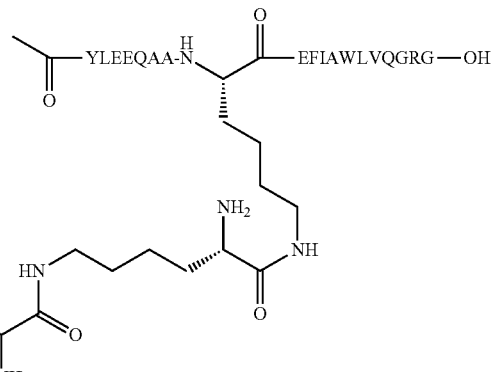
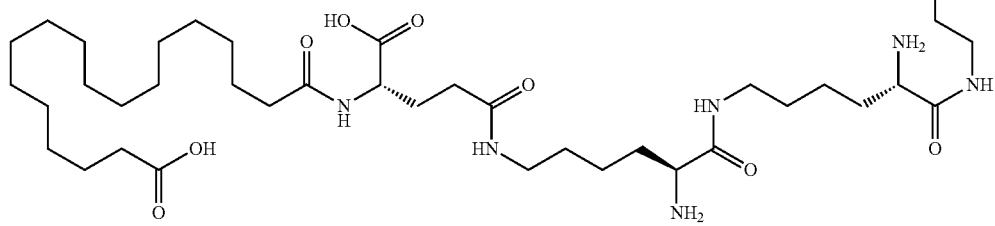
wherein the amino acid sequence is that of SEQ ID NO: 9,
Chem. 52
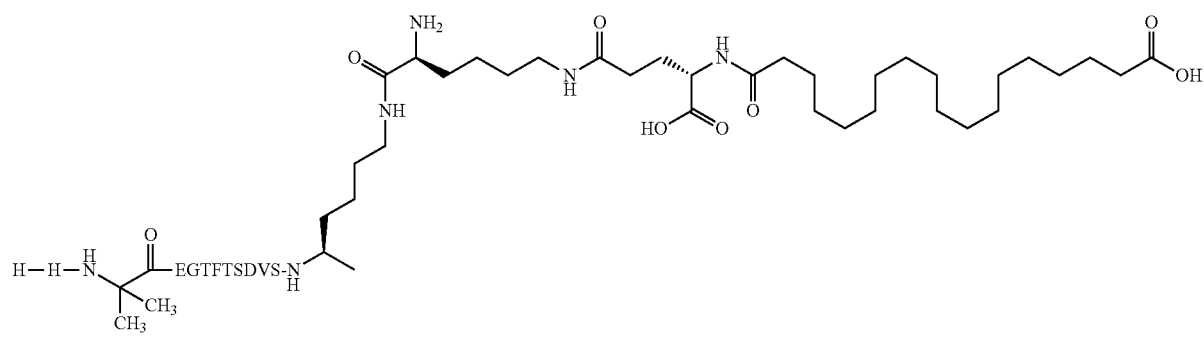
wherein the amino acid sequence is that of SEQ ID NO: 9,
Chem. 53
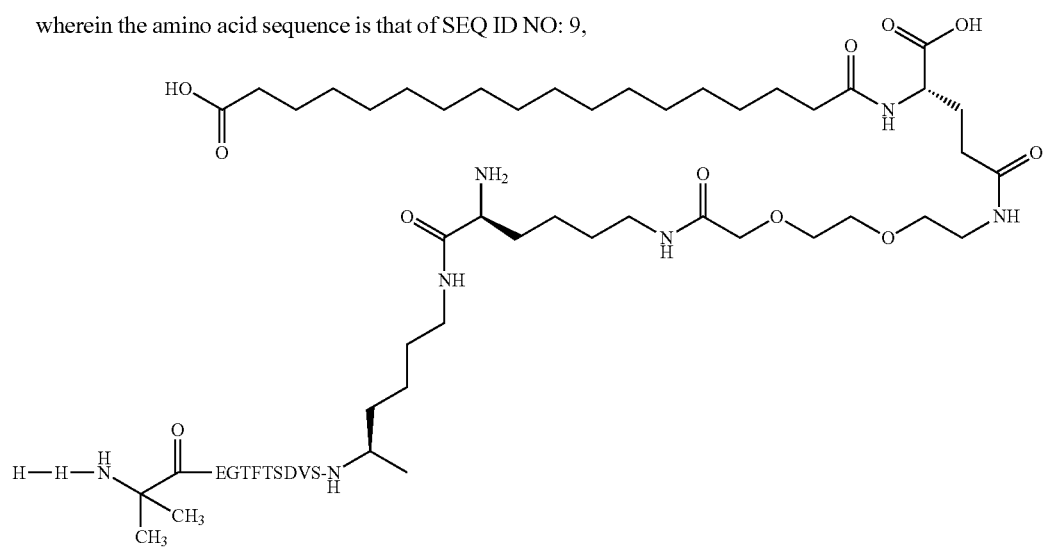

-continued
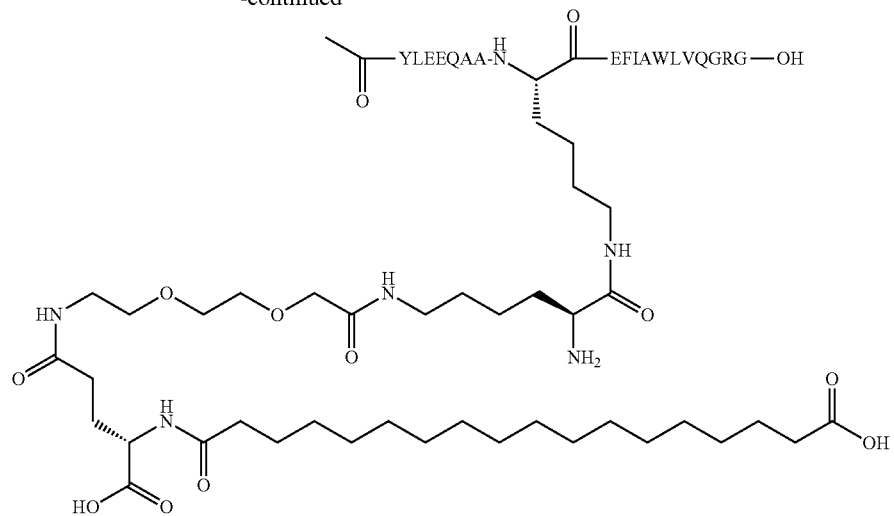
wherein the amino acid sequence is that of SEQ ID NO: 9,
Chem. 54
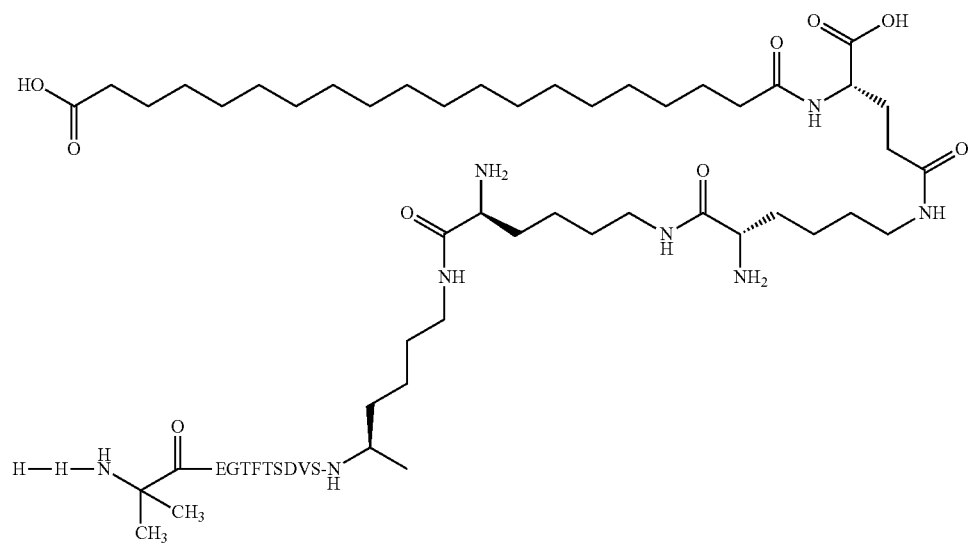
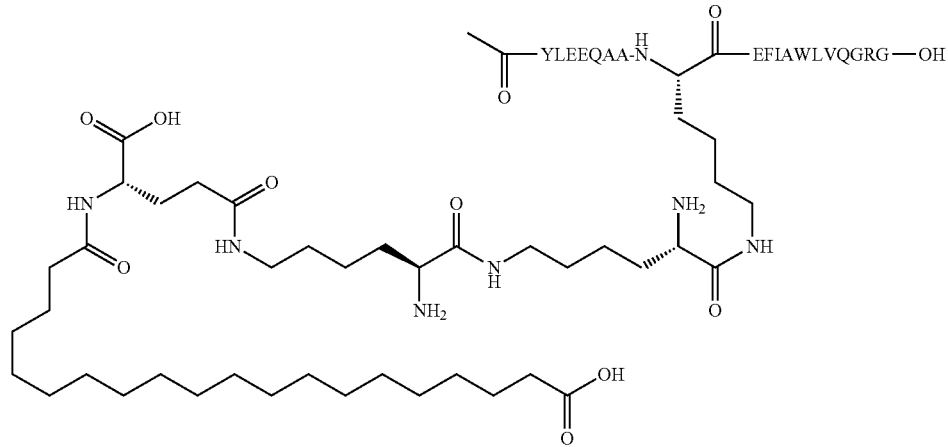

wherein the amino acid sequence is that of SEQ ID NO: 9,
Chem. 55
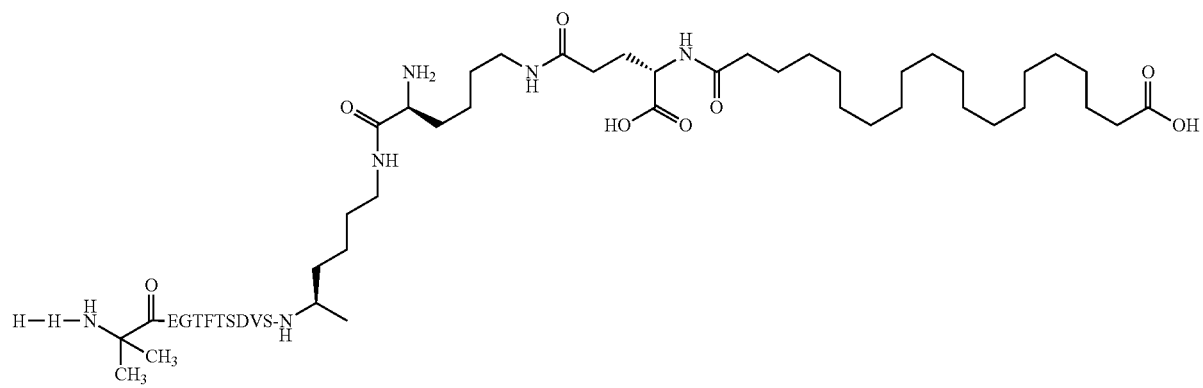
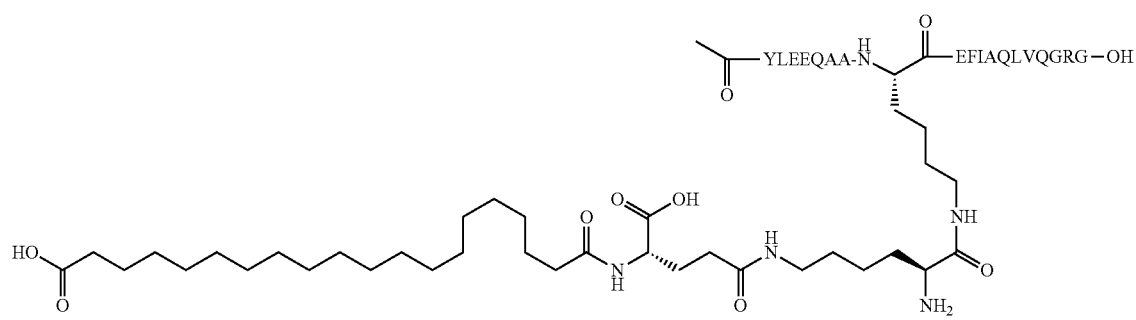
wherein the amino acid sequence is that of SEQ ID NO: 9,
Chem. 56
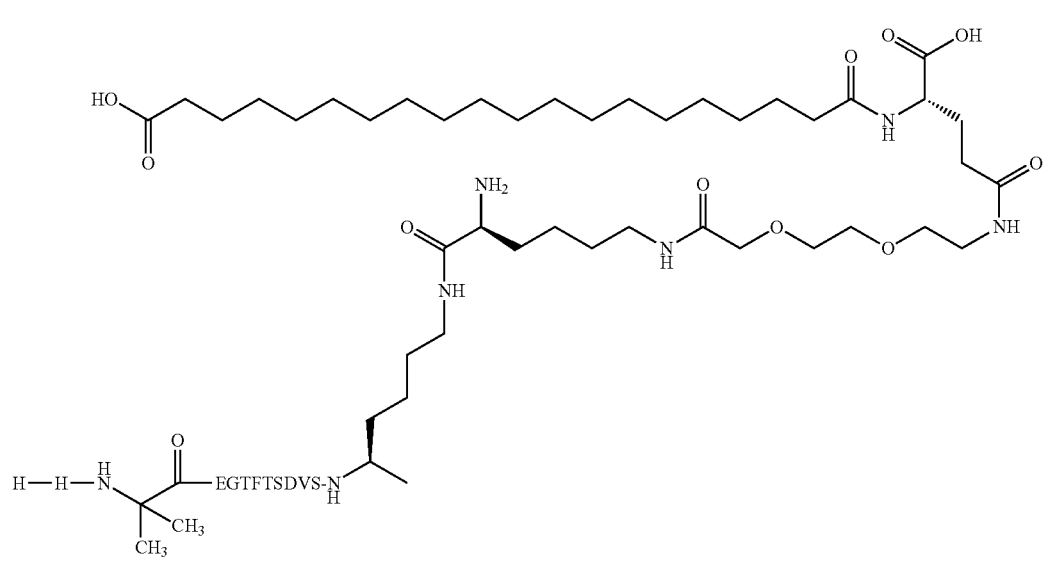

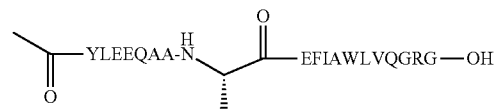
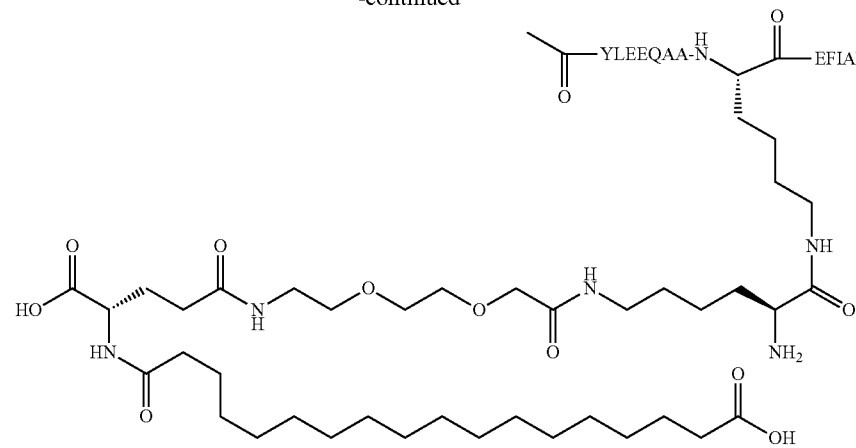
wherein the amino acid sequence is that of SEQ ID NO: 9,
Chem. 57
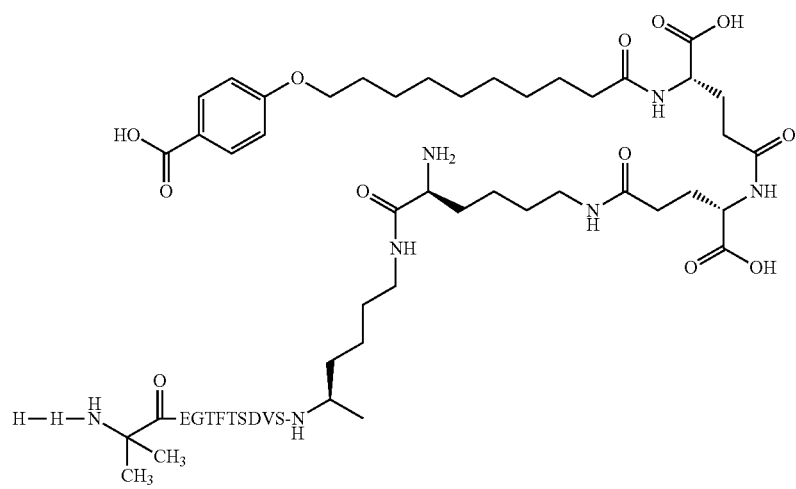
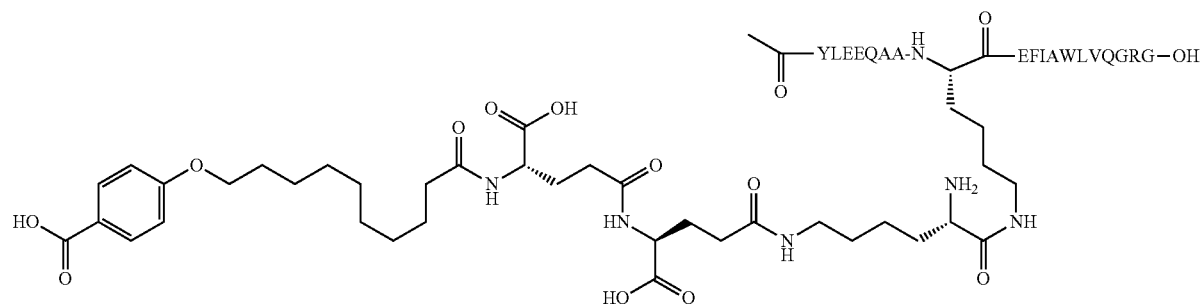

wherein the amino acid sequence is that of SEQ ID NO: 9,
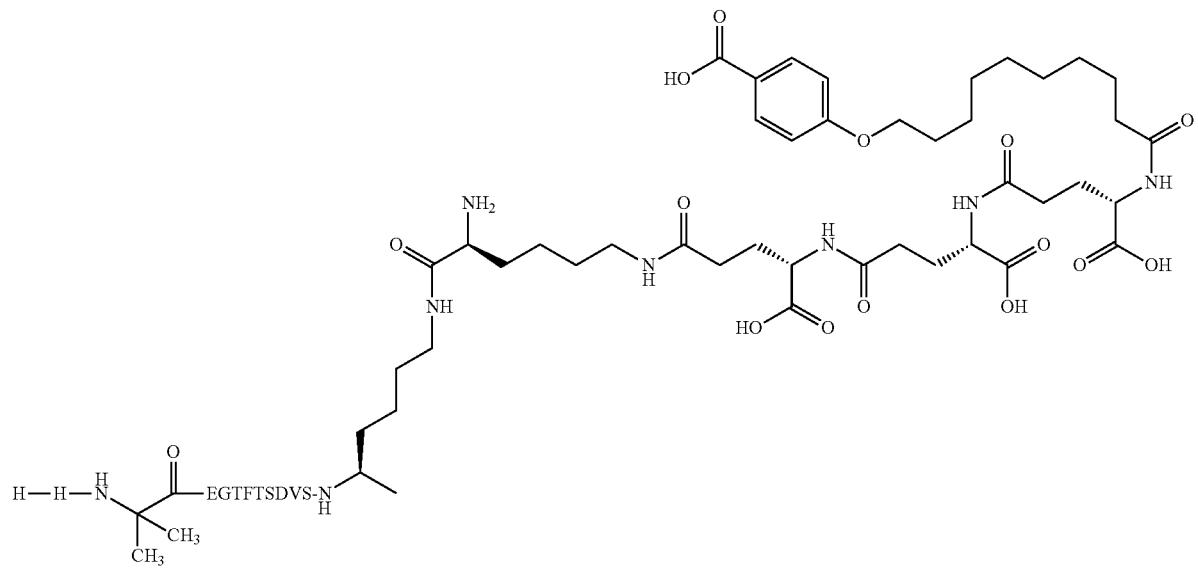
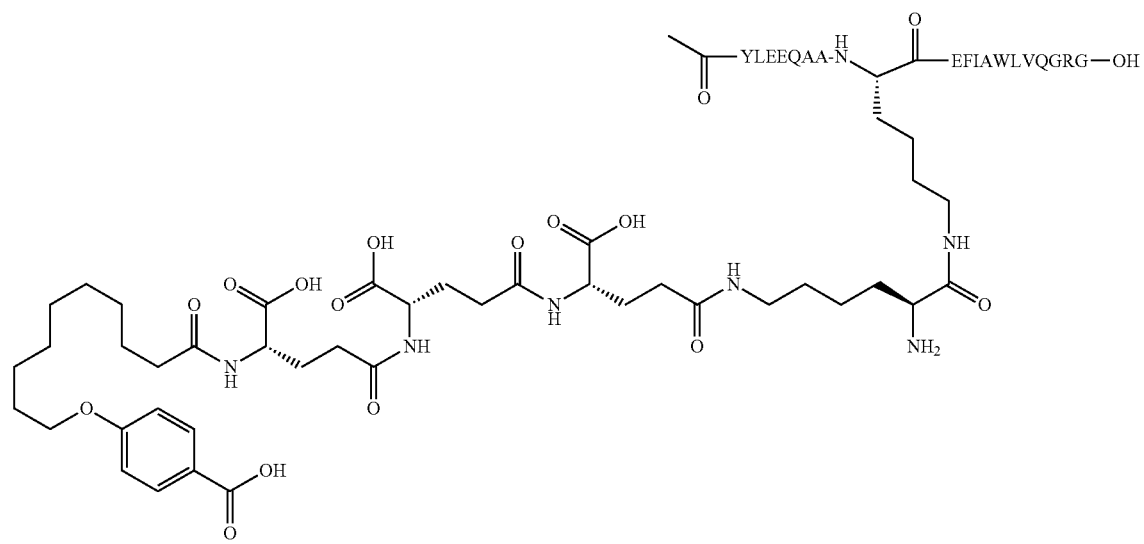

wherein the amino acid sequence is that of SEQ ID NO: 9,
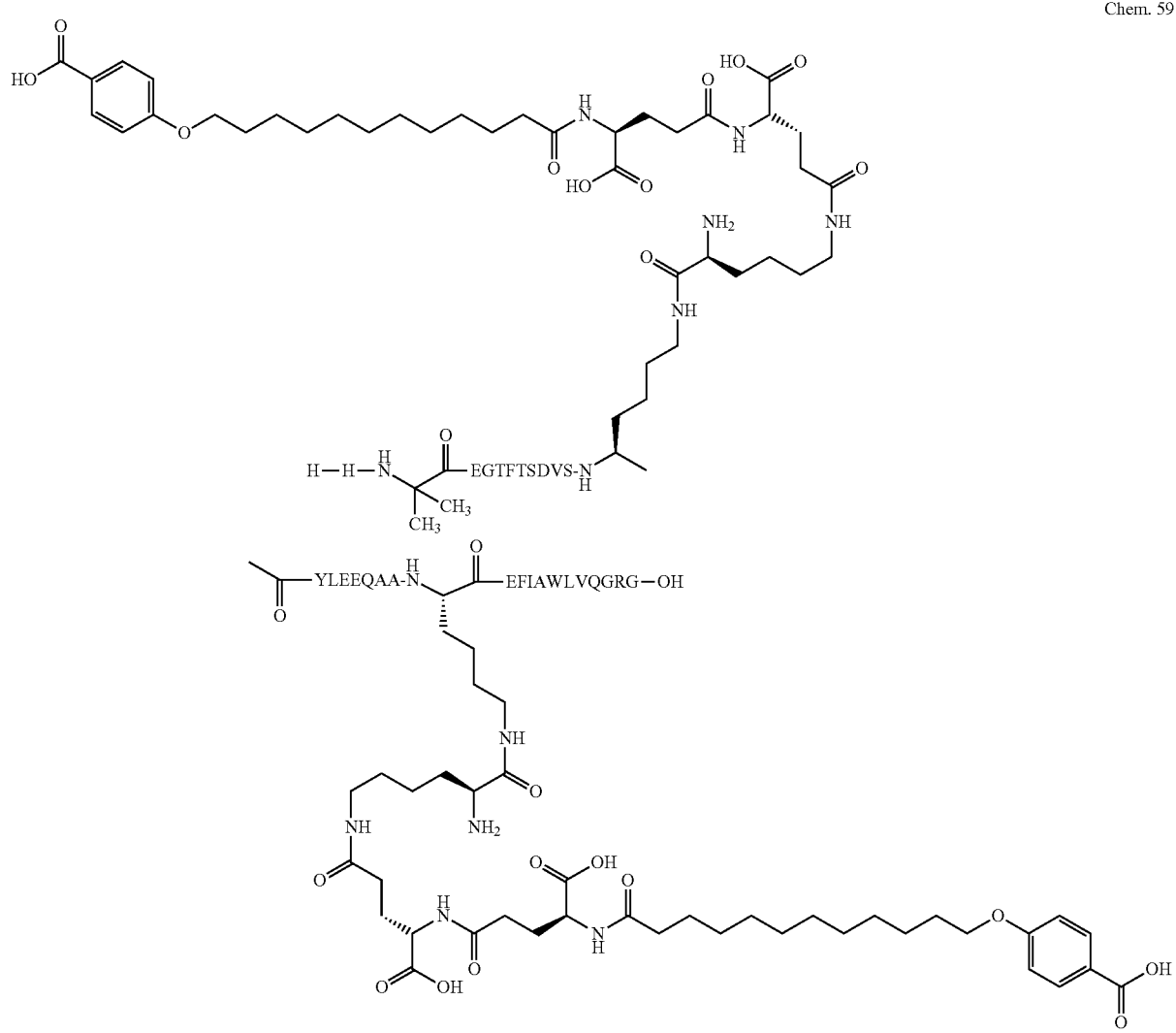
wherein the amino acid sequence is that of SEQ ID NO: 9,
Chem. 60:
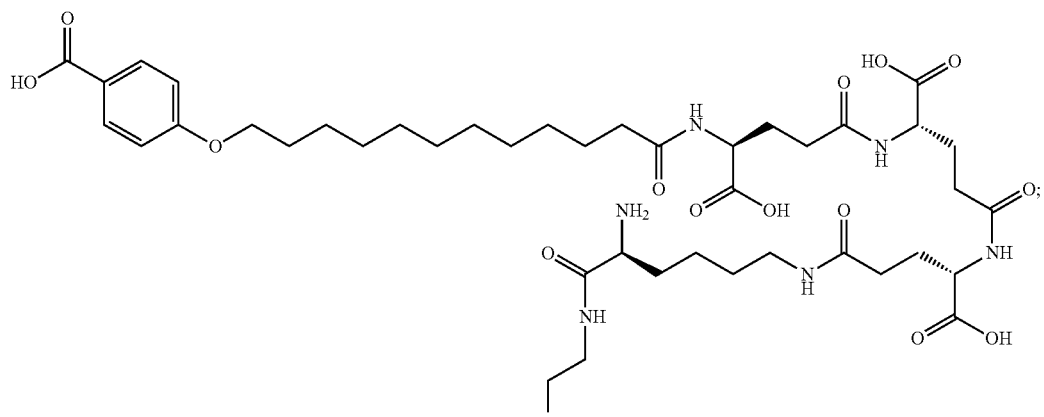

-continued
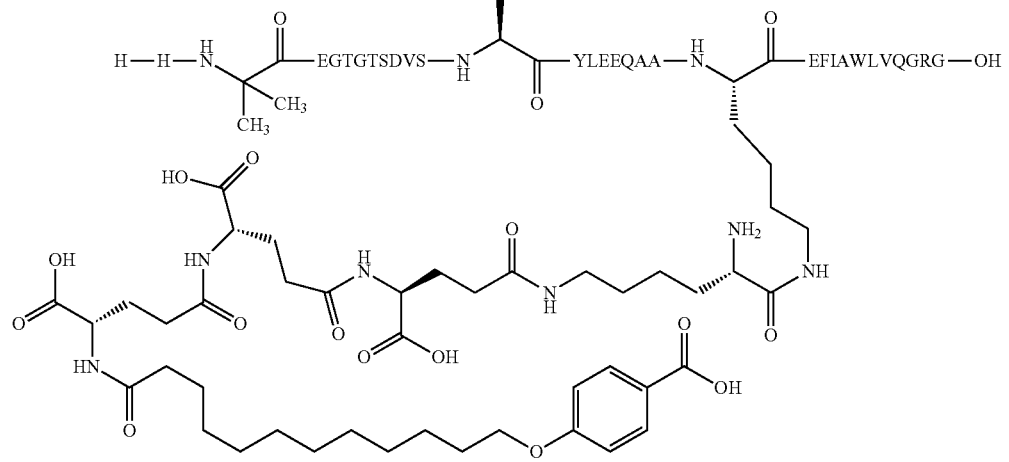
wherein the amino acid sequence is that of SEQ ID NO: 9,
Chem. 61
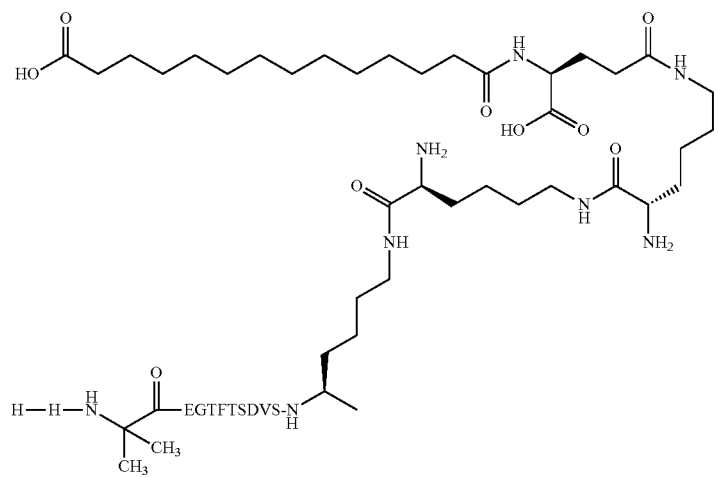
wherein the amino acid sequence is that of SEQ ID NO: 12,
Chem. 62:
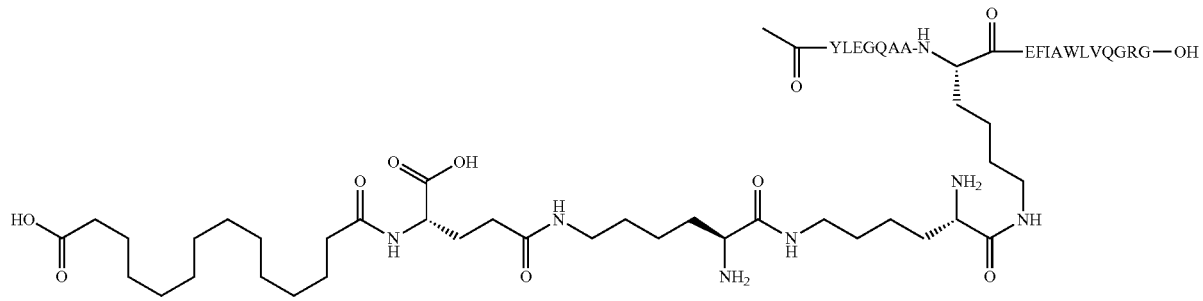

Chem. 62
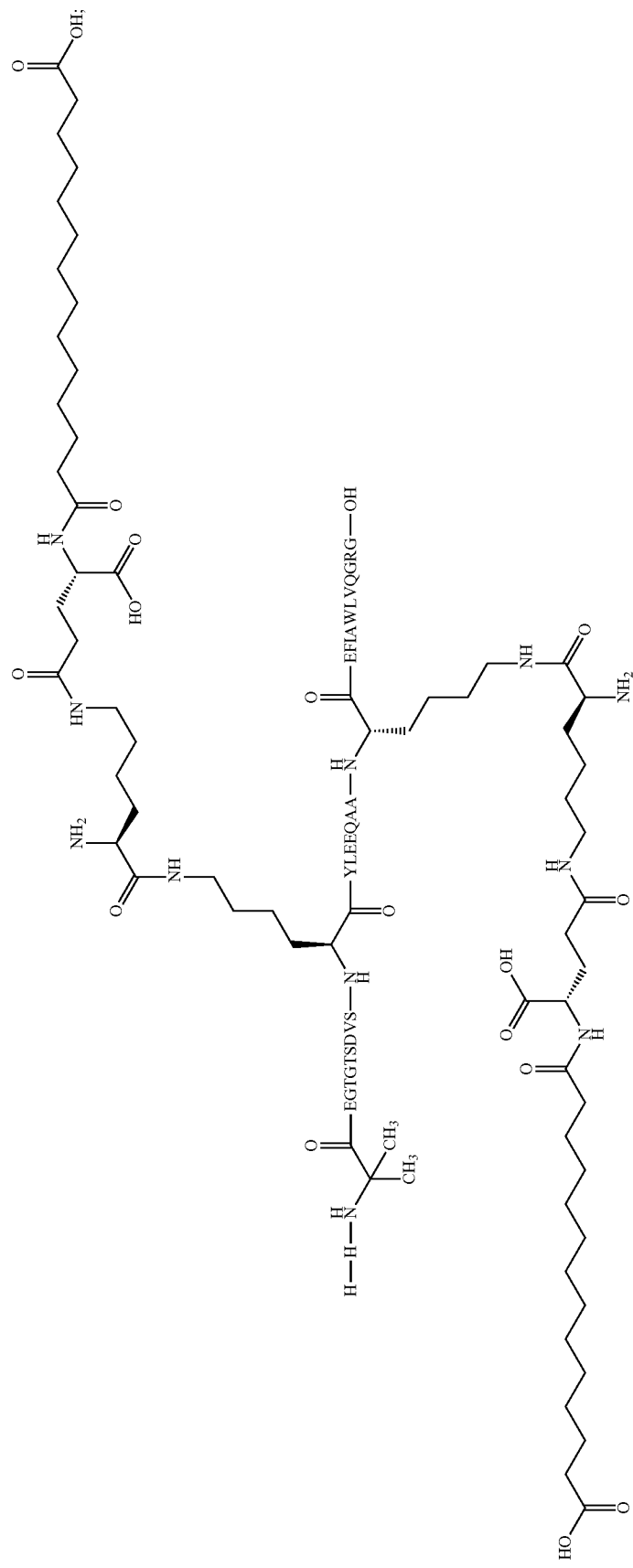

wherein the amino acid sequence is that of SEQ ID NO: 12,
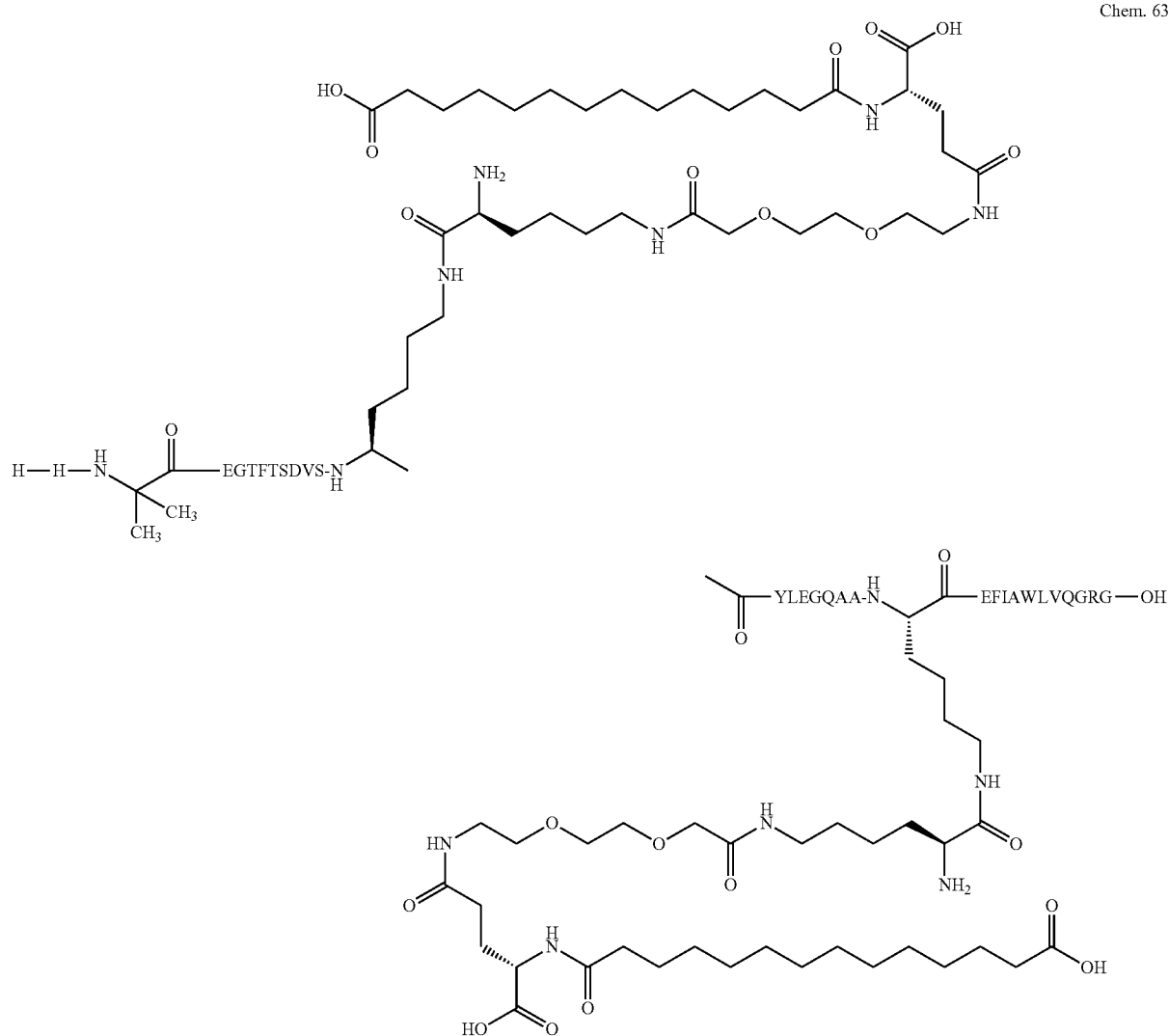
wherein the amino acid sequence is that of SEQ ID NO: 12,
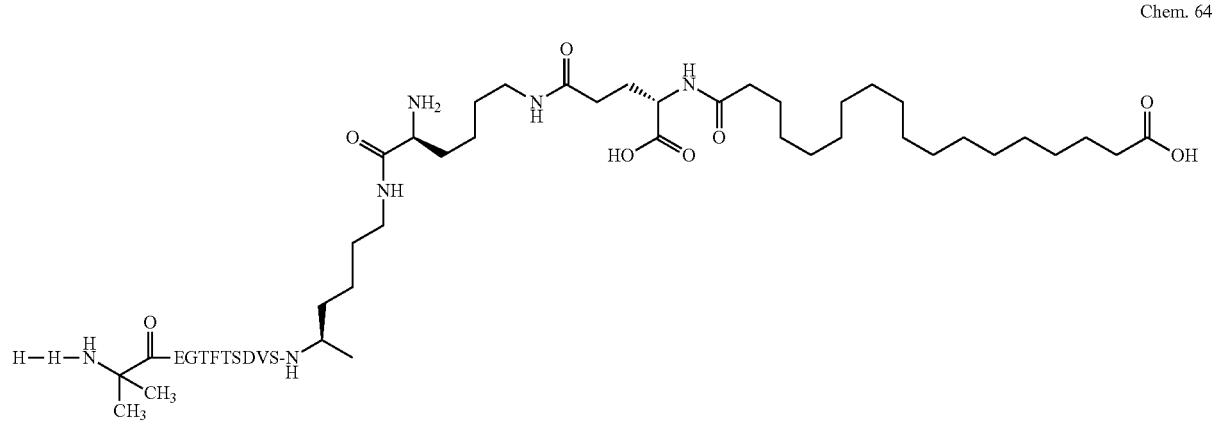

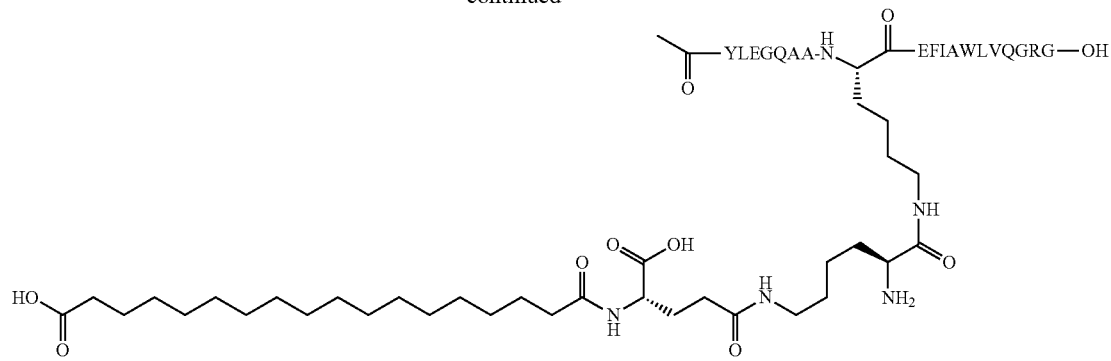
wherein the amino acid sequence is that of SEQ ID NO: 12,
Chem. 65
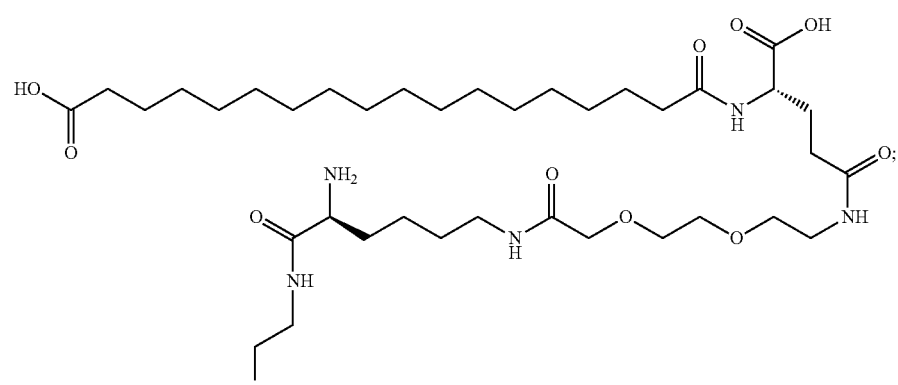
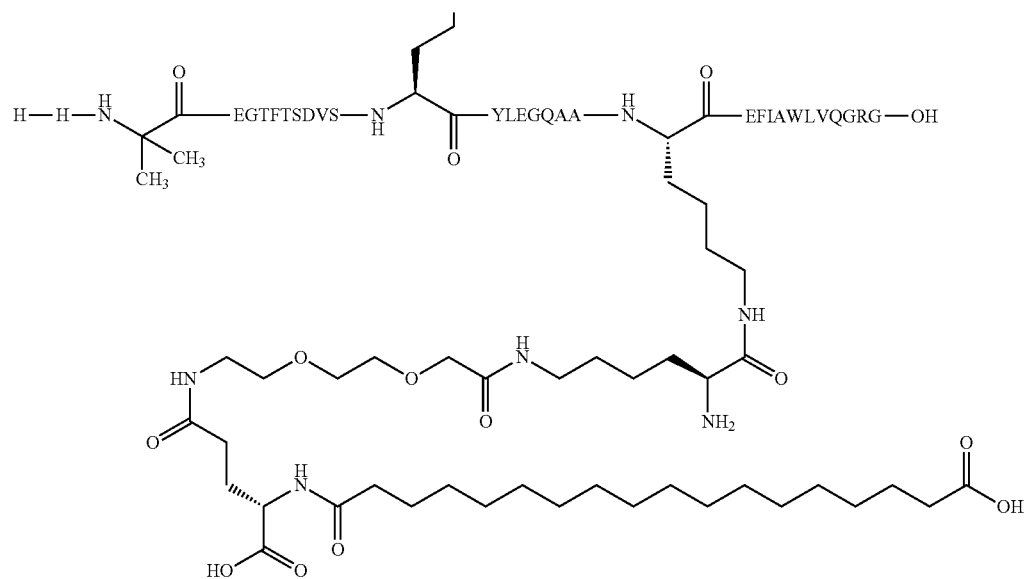

wherein the amino acid sequence is that of SEQ ID NO: 12,
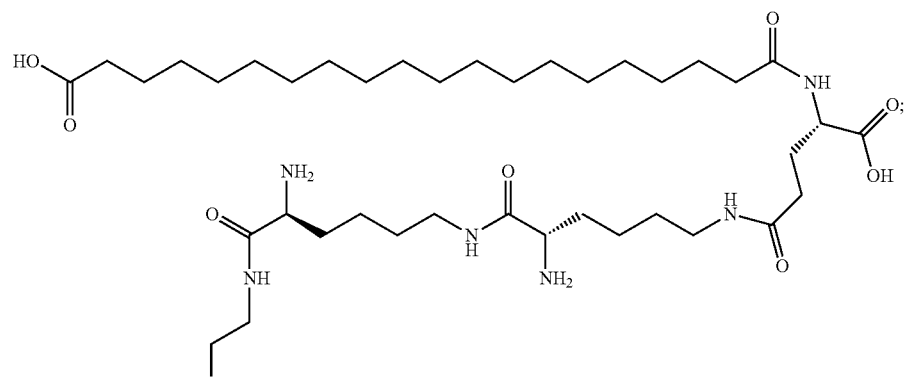
Chem. 66
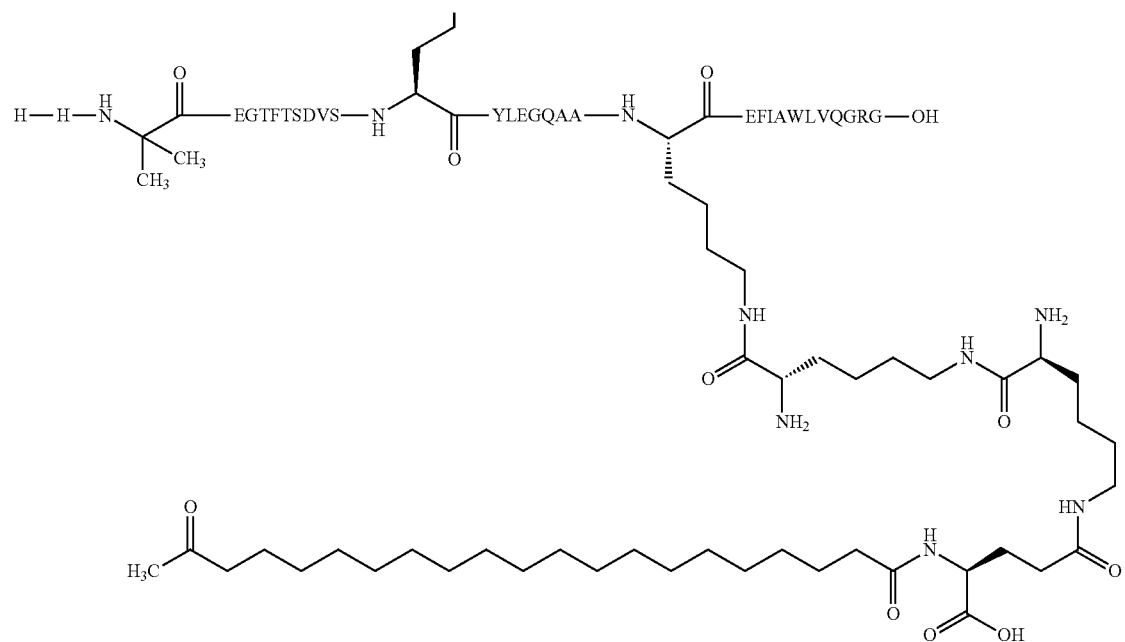
wherein the amino acid sequence is that of SEQ ID NO: 12,

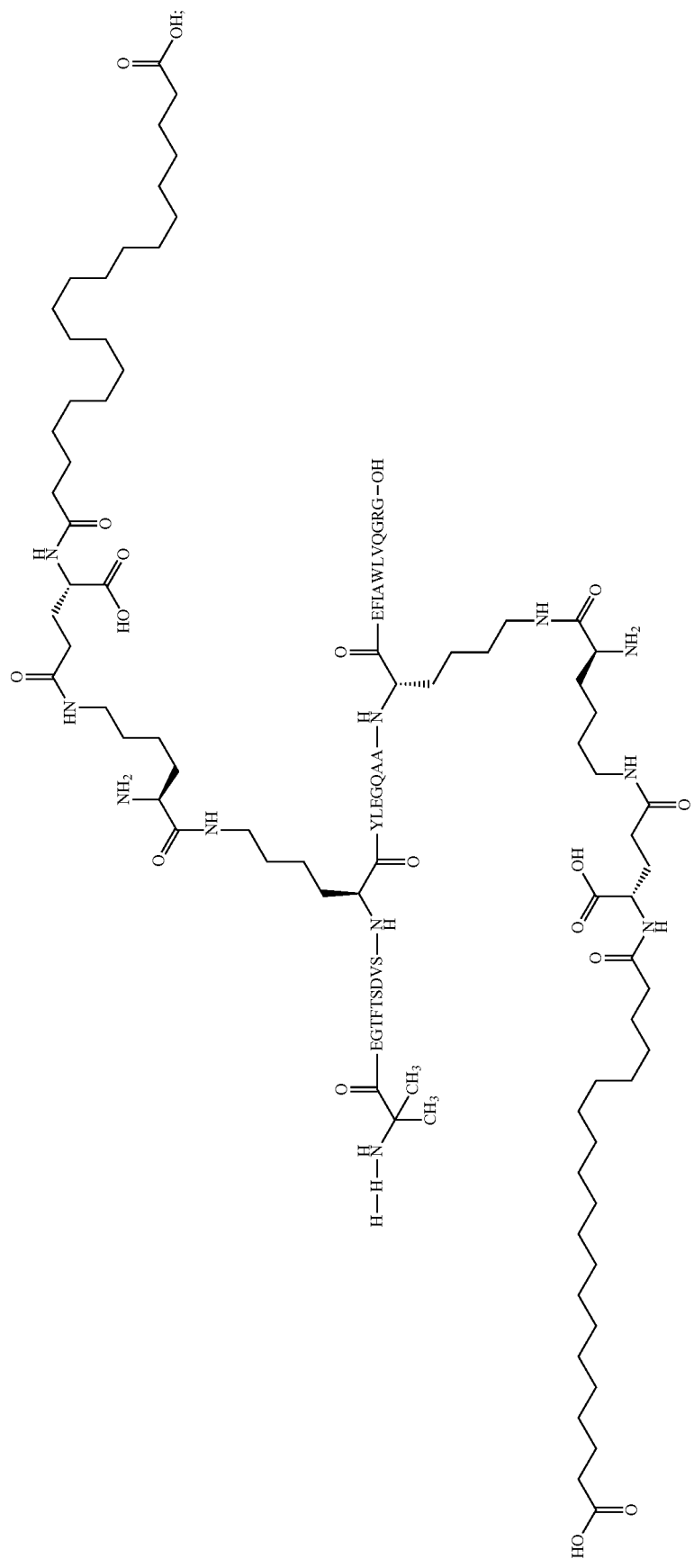
Chem. 67 wherein the amino acid sequence is that of SEQ ID NO: 12,
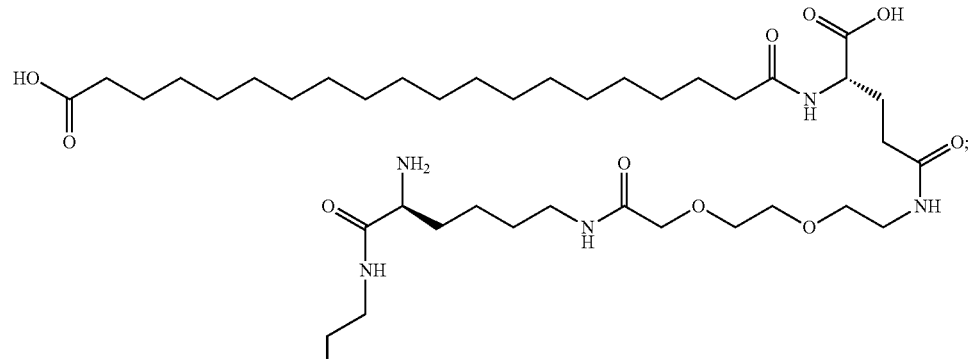
Chem. 68
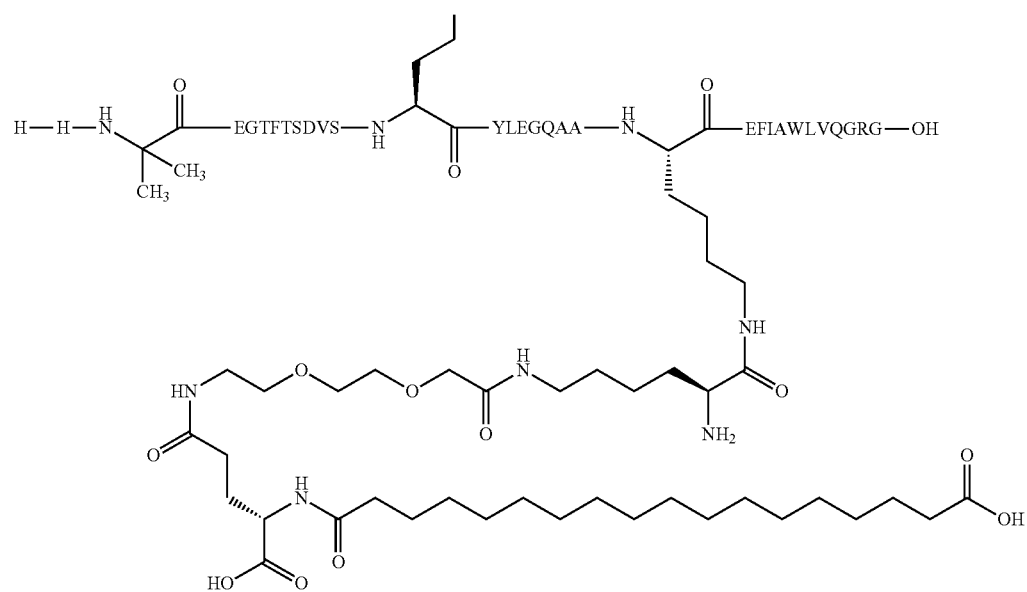
wherein the amino acid sequence is that of SEQ ID NO: 12,
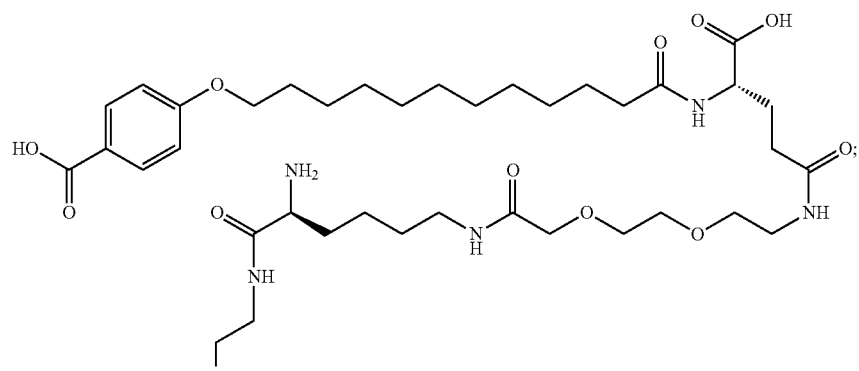
Chem. 69

-continued
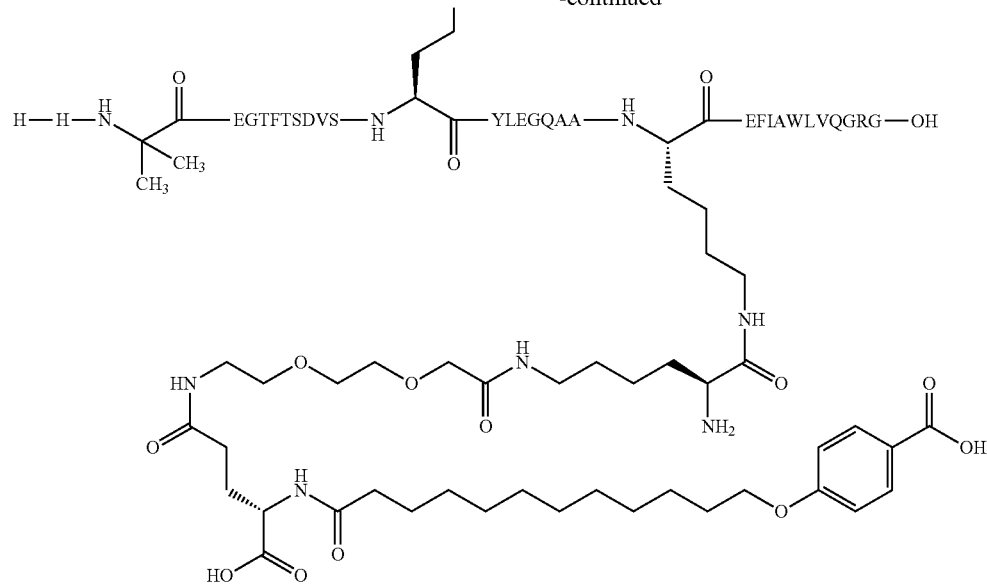
wherein the amino acid sequence is that of SEQ ID NO: 12,
Chem. 70
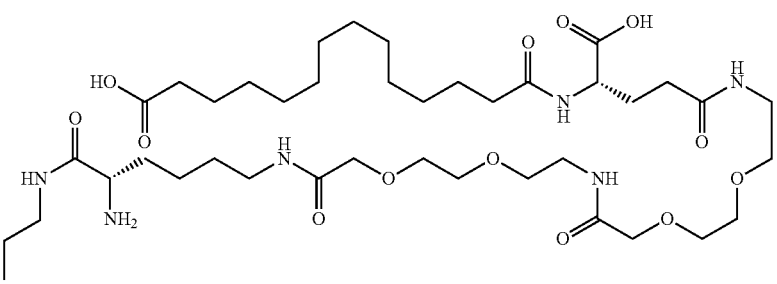
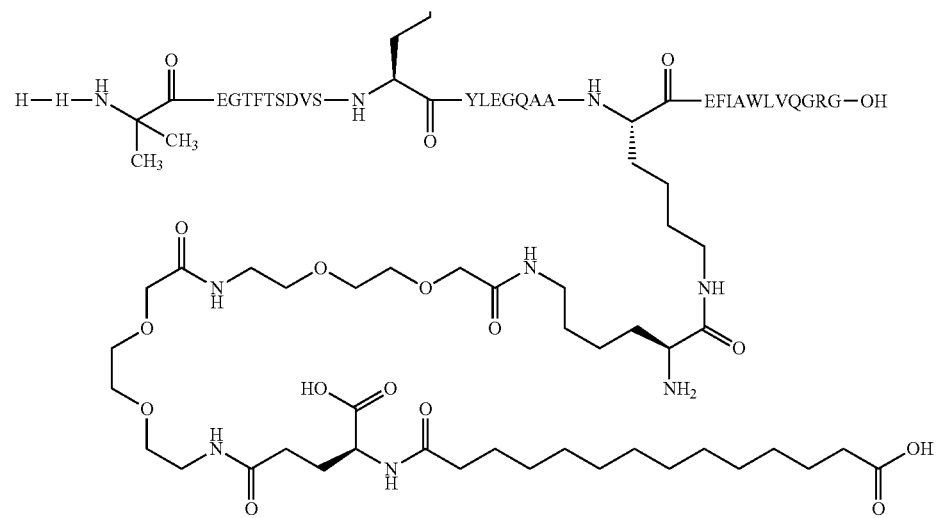
;

wherein the amino acid sequence is that of SEQ ID NO: 9,
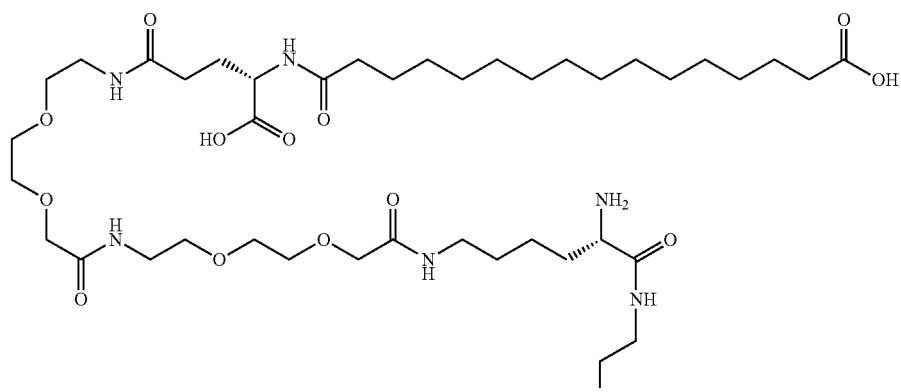
Chem. 71
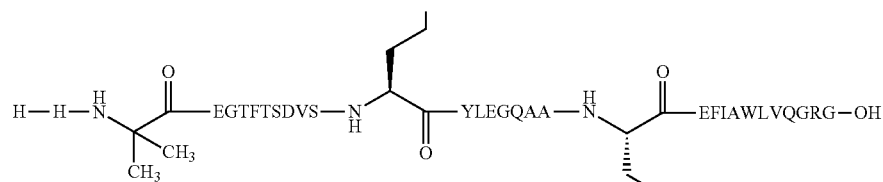
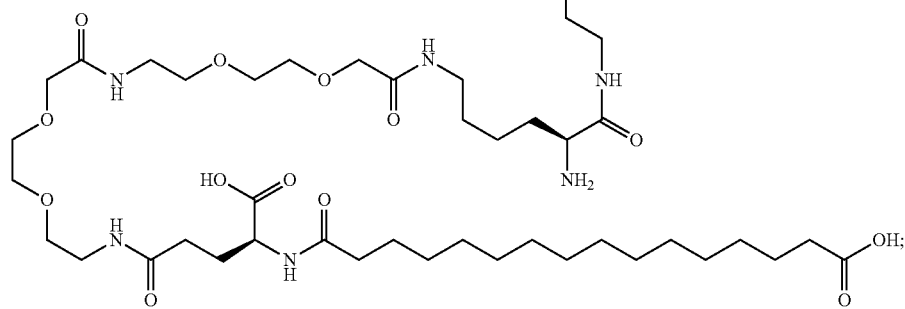
wherein the amino acid sequence is that of SEQ ID NO: 9,
Chem. 72
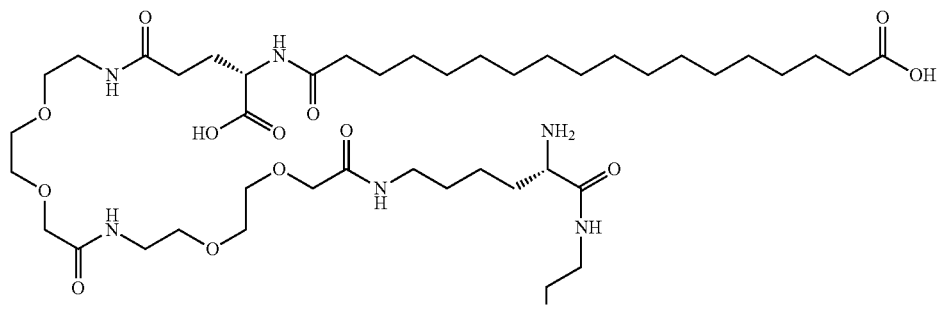

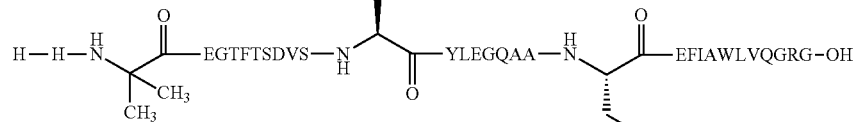
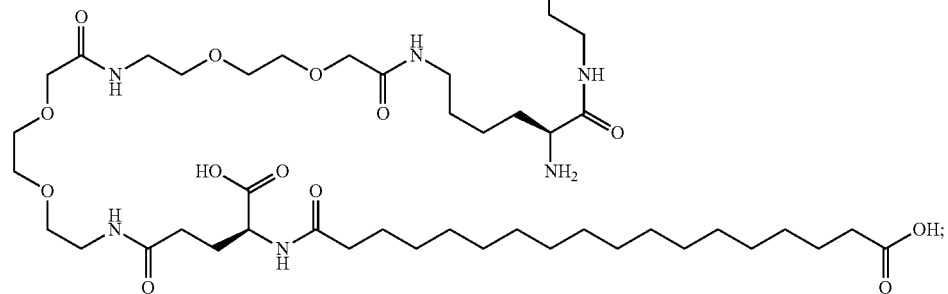
wherein the amino acid sequence is that of SEQ ID NO: 9,
Chem. 73
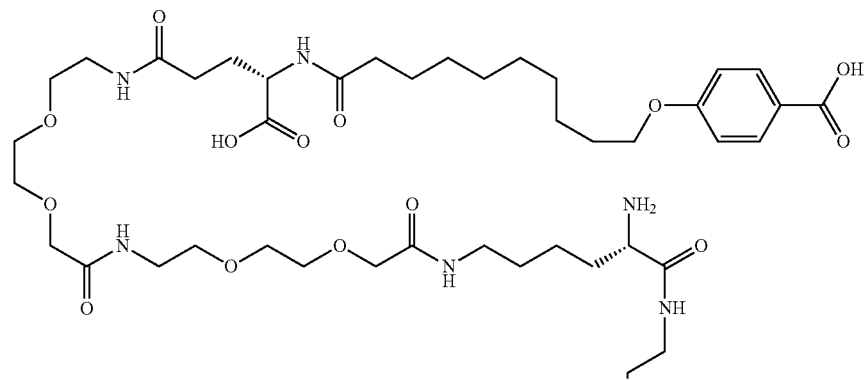
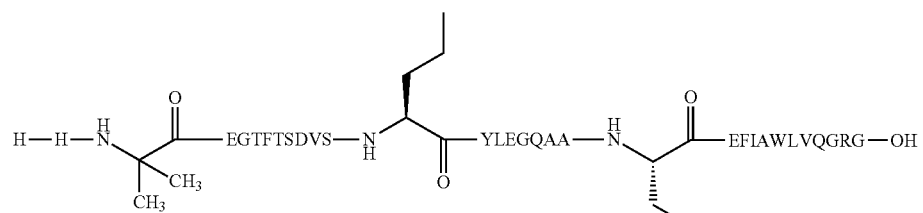
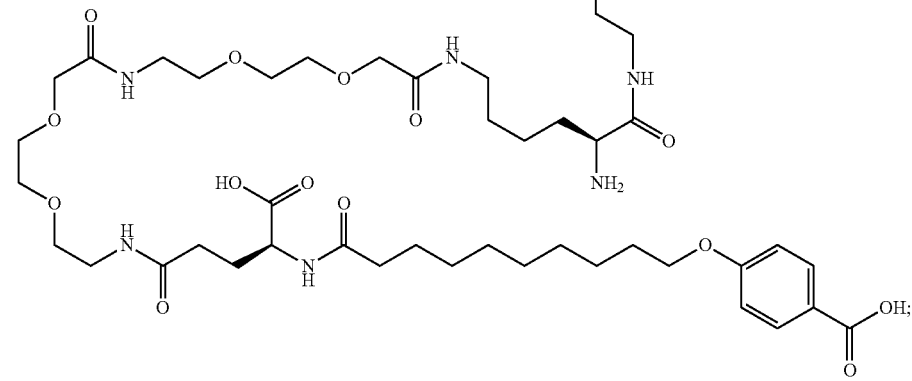

wherein the amino acid sequence is that of SEQ ID NO: 9,
Chem. 74
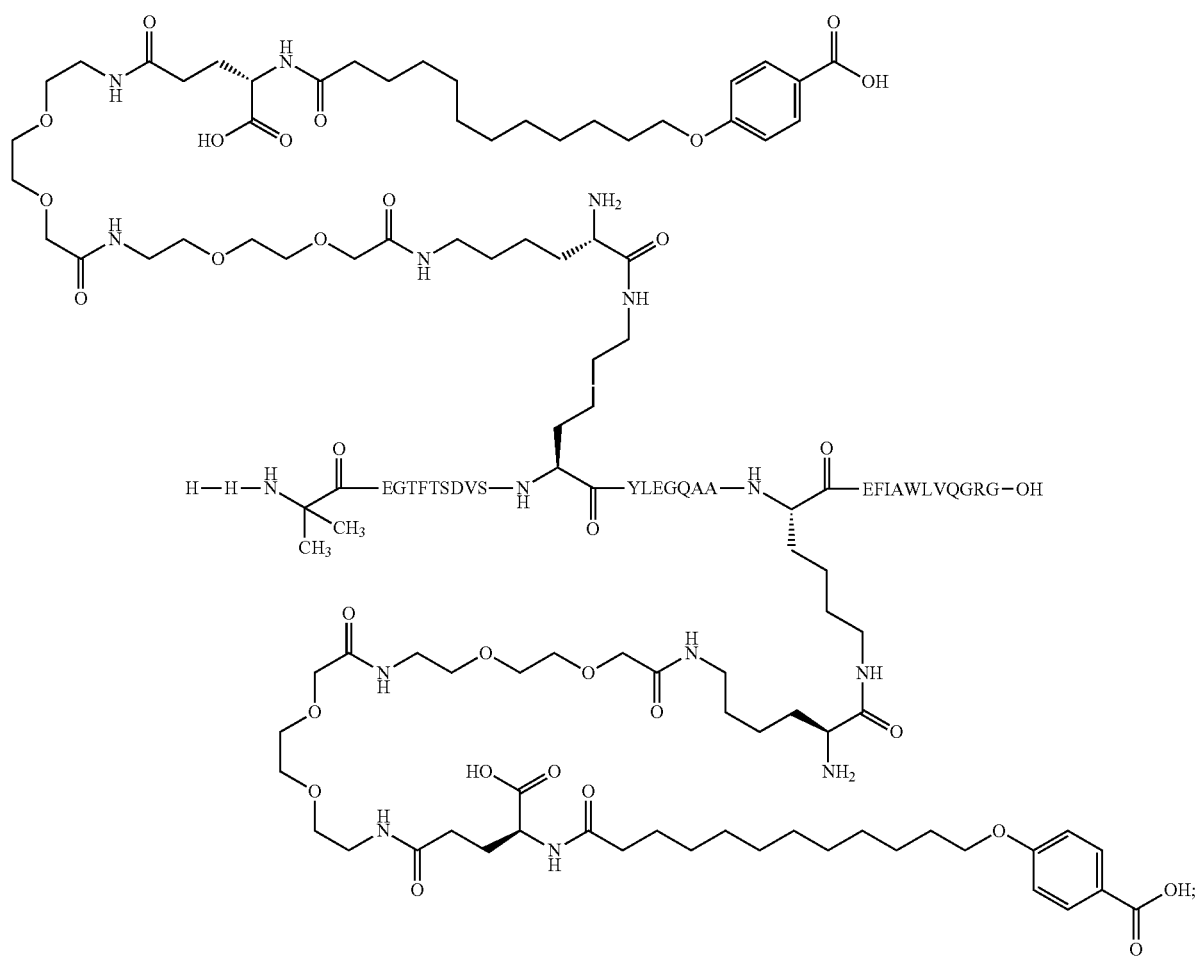
wherein the amino acid sequence is that of SEQ ID NO: 9,
Chem.75
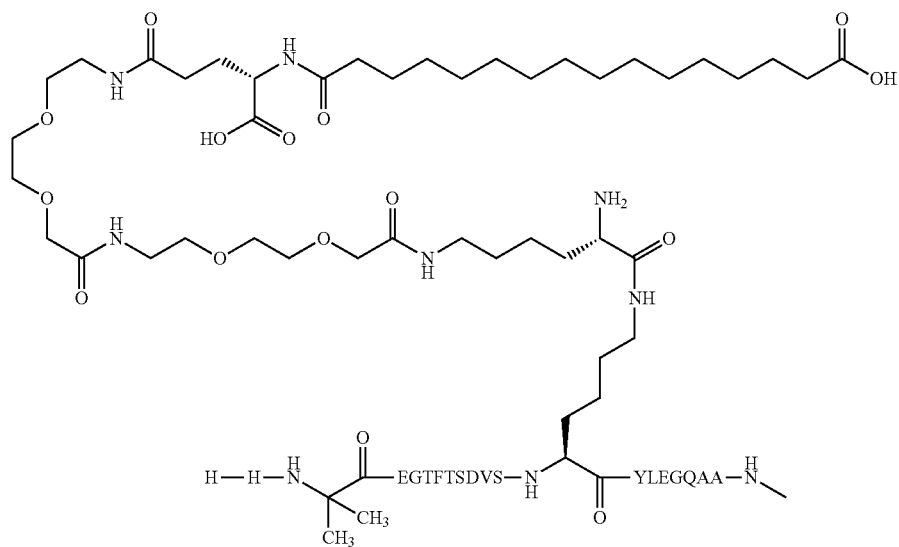

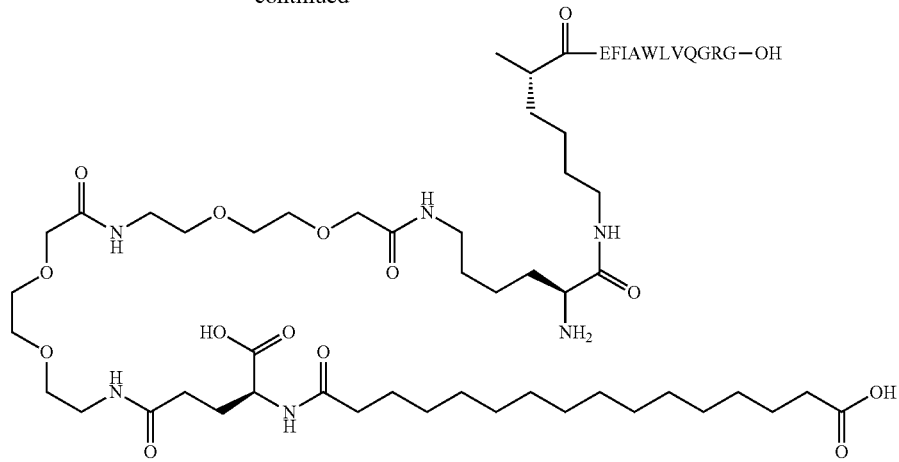
wherein the amino acid sequence is that of SEQ ID NO: 12,
Chem. 76
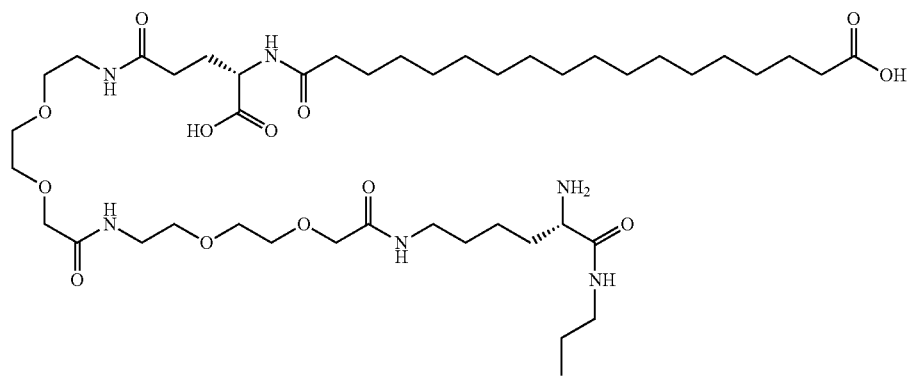
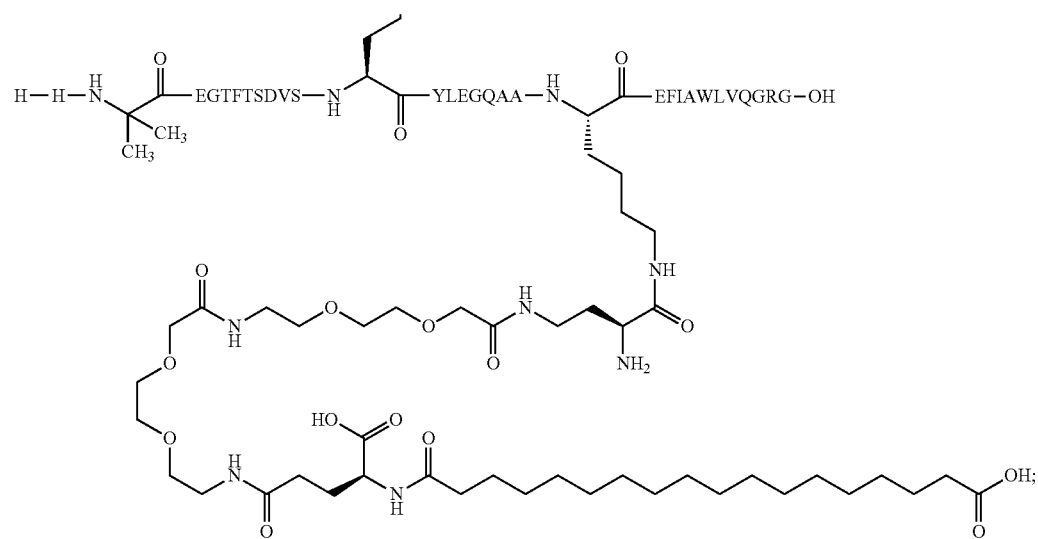

wherein the amino acid sequence is that of SEQ ID NO: 12, or

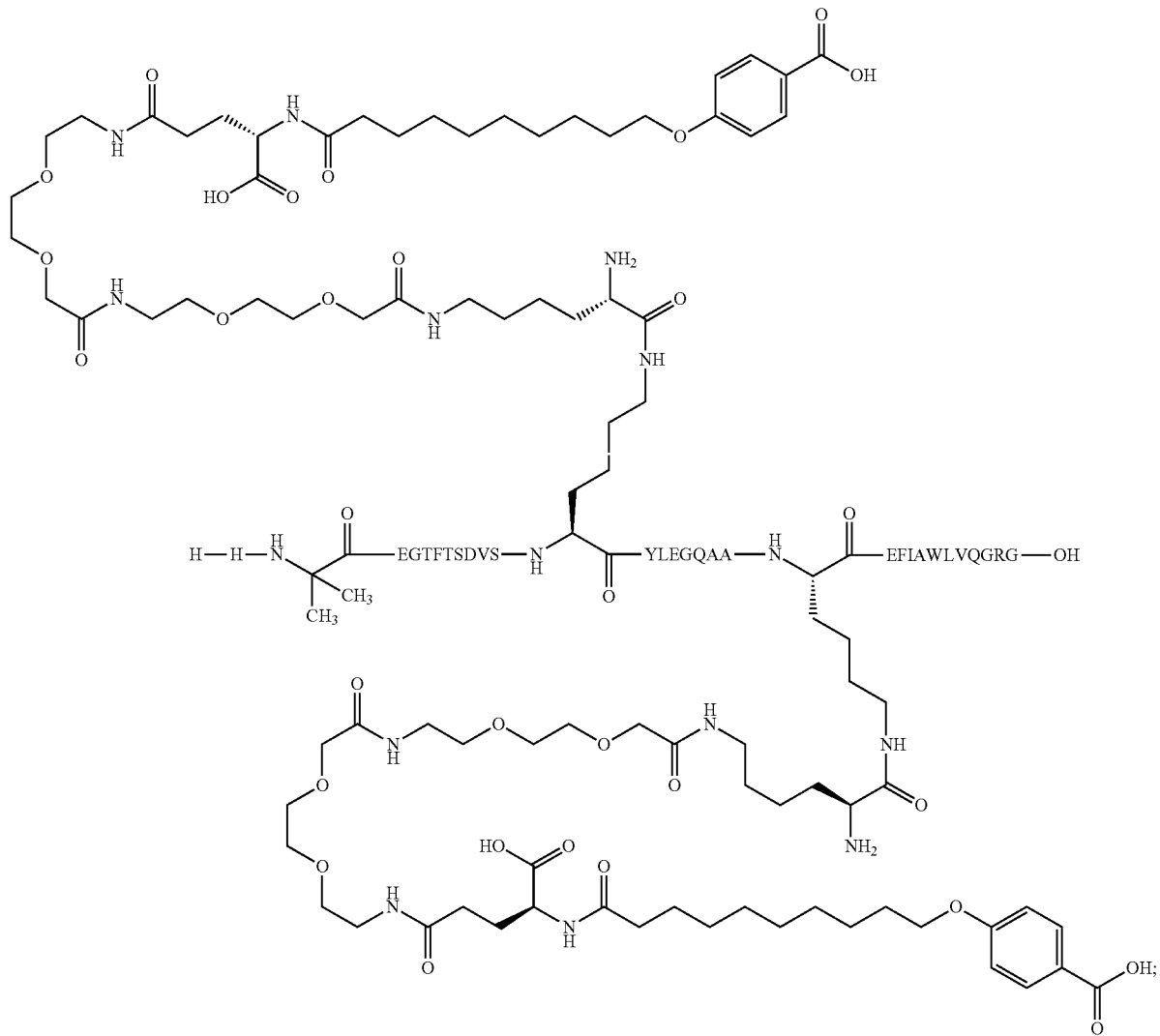

Chem. 77 wherein the amino acid sequence is that of SEQ ID NO: 12; or a pharmaceutically acceptable salt, amide, or ester of any of the foregoing compounds.

8. A pharmaceutical composition comprising a derivative of claim 1 and a pharmaceutically acceptable excipient.

9. A method for treating diabetes in a subject, said method comprising administering to said subject a therapeutically effective amount of a pharmaceutical composition according to claim 8.

10. The derivative of claim 2, wherein x is 10, 12, 14, 16, or 18.

11. The derivative of claim 10, wherein y is 7, 8, 9, or 11.

12. The derivative of claim 11, wherein the analogue comprises no K residues other than the first and the second K residue.

13. The derivative of claim 12, wherein a carboxylic acid group of the C-terminal amino acid of the analogue is converted into carboxylic acid amide.

14. A pharmaceutical composition comprising a derivative of claim 2 and a pharmaceutically acceptable excipient.

15. A method for treating diabetes in a subject, said method comprising administering to said subject a therapeutically effective amount of a pharmaceutical composition according to claim 14.

16. A pharmaceutical composition comprising a derivative of claim 7 and a pharmaceutically acceptable excipient.

17. A method for treating diabetes in a subject, said method comprising administering to said subject a therapeutically effective amount of a pharmaceutical composition according to claim 16.

18. The derivative of claim 5, wherein the second K residue is at position 26 or 31.

19. The derivative of claim 2, wherein
Xaa$_7$ is L-histidine or imidazopropionyl;
Xaa$_8$ is Ala, Gly, Val, or Aib;
Xaa$_{12}$ is Phe;
Xaa$_{16}$ is Val;
Xaa$_{19}$ is Tyr;
Xaa$_{20}$ is Leu;
Xaa$_{22}$ is Gly, Glu or Lys;

$Xaa_{23}$ is Gln;
$Xaa_{25}$ is Ala or Val;
$Xaa_{26}$ is Val, Lys, or Arg;
$Xaa_{27}$ is Glu or Lys;
$Xaa_{30}$ is Ala or Lys;
$Xaa_{31}$ is Trp or Lys;
$Xaa_{33}$ is Val;
$Xaa_{34}$ is Lys, Gln, Arg, or absent;
$Xaa_{35}$ is Gly, or absent;
$Xaa_{36}$ is Arg, or absent;
$Xaa_{37}$ is Gly, Lys, or absent; and
$Xaa_{38}$ is Ser, or absent.

20. The derivative of claim 19, wherein
$Xaa_{8}$ is Aib;
$Xaa_{25}$ is Ala or Val;
$Xaa_{26}$ is Val, Lys, or Arg;
$Xaa_{27}$ is Glu or Lys;
$Xaa_{30}$ is Ala or Lys;
$Xaa_{31}$ is Trp or Lys;
$Xaa_{34}$ is Gln;
$Xaa_{35}$ is Gly, or absent;
$Xaa_{36}$ is Arg, or absent;
$Xaa_{37}$ is Gly, Lys, or absent; and
$Xaa_{38}$ is Ser, or absent.

21. The derivative of claim 20, wherein
$Xaa_{22}$ is Glu.

22. The derivative of claim 20, wherein
$Xaa_{22}$ is Gly or Glu;
$Xaa_{27}$ is Glu;
$Xaa_{30}$ is Ala;
$Xaa_{37}$ is Gly or absent; and
the second K residue is at position 26 or 31.

23. The derivative of claim 21, wherein
$Xaa_{27}$ is Glu;
$Xaa_{30}$ is Ala;
$Xaa_{37}$ is Gly or absent; and
the second K residue is at position 26 or 31.

24. The compound of claim 7 which is Chem. 24:

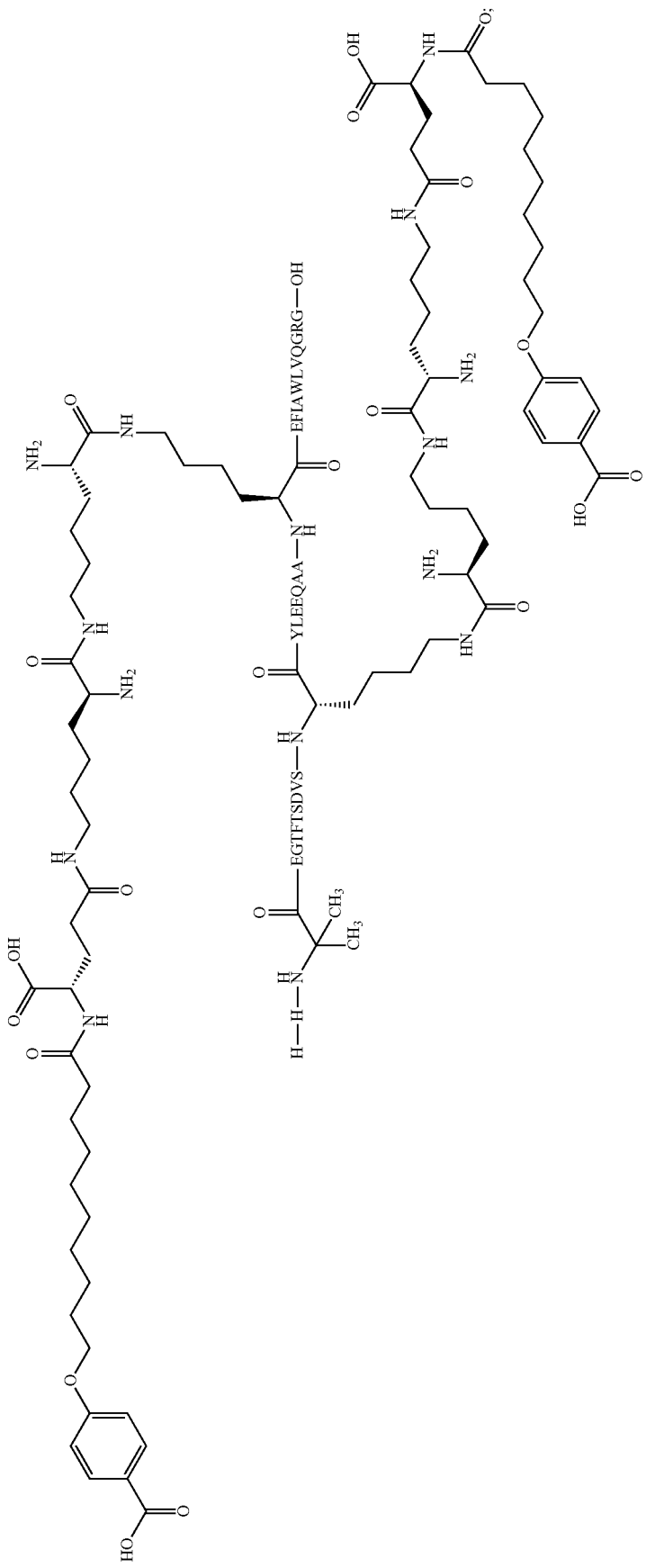

wherein the amino acid sequence is that of SEQ ID NO: 9.

25. The compound of claim 7 which is Chem. 38:

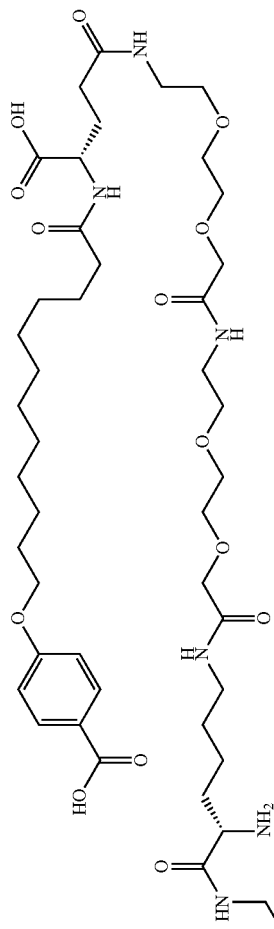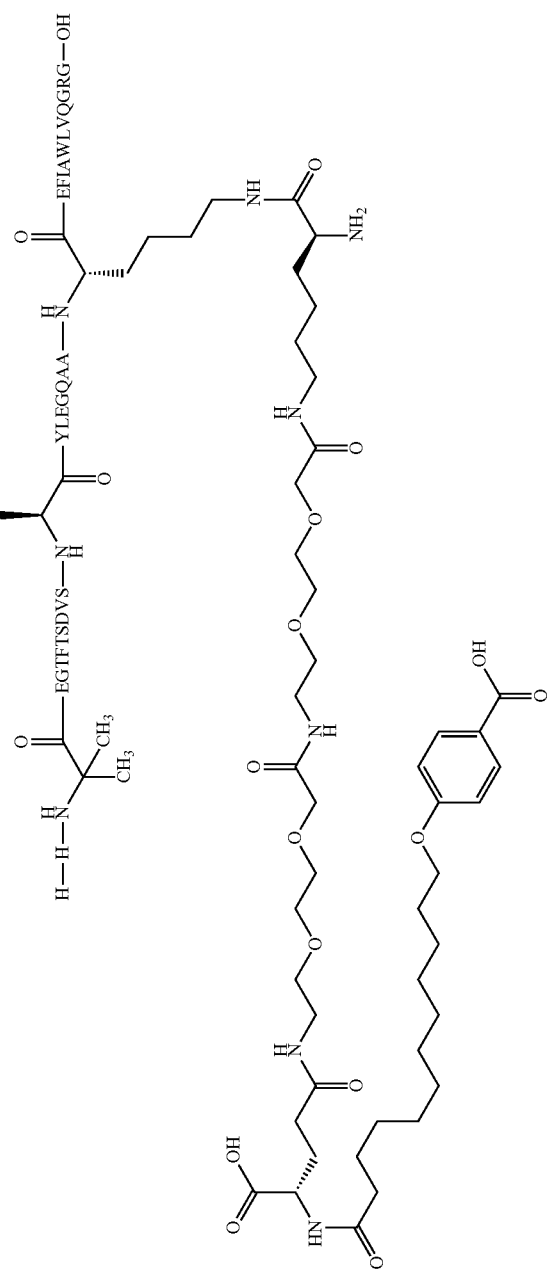

wherein the amino acid sequence is that of SEQ ID NO: 12.
26. The compound of claim 7 which is Chem. 39:
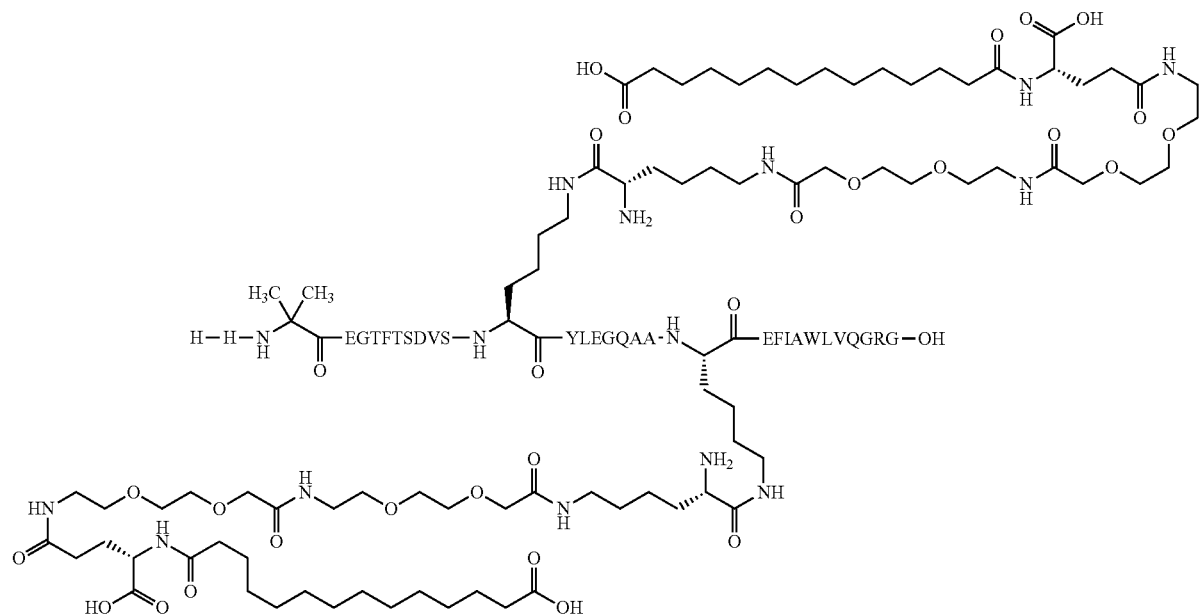
wherein the amino acid sequence is that of SEQ ID NO: 12.
* * * * *

UNITED STATES PATENT AND TRADEMARK OFFICE
CERTIFICATE OF CORRECTION

PATENT NO.         : 9,006,178 B2                                Page 1 of 21
APPLICATION NO.    : 13/883946
DATED              : April 14, 2015
INVENTOR(S)        : Jacob Kofoed et al.

It is certified that error appears in the above-identified patent and that said Letters Patent is hereby corrected as shown below:

At column 179-180, claim number 7, chem. number 20, please replace with

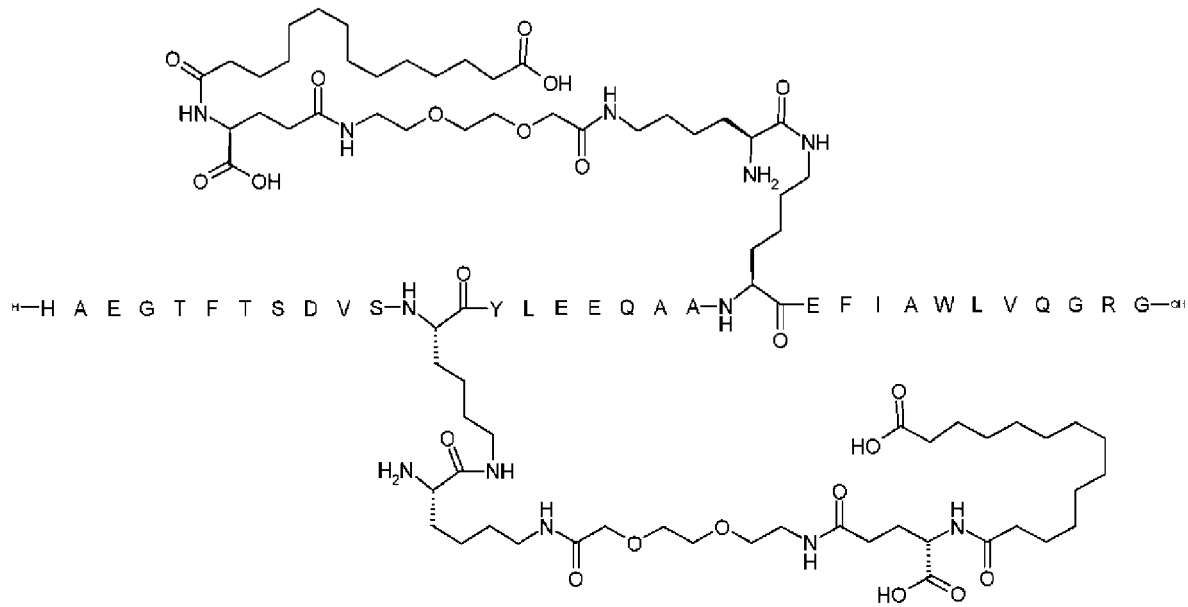

Signed and Sealed this
Fifth Day of April, 2016

Michelle K. Lee
*Director of the United States Patent and Trademark Office*

CERTIFICATE OF CORRECTION (continued)
U.S. Pat. No. 9,006,178 B2

At column 181-182, claim number 7, chem. number 22, please replace with

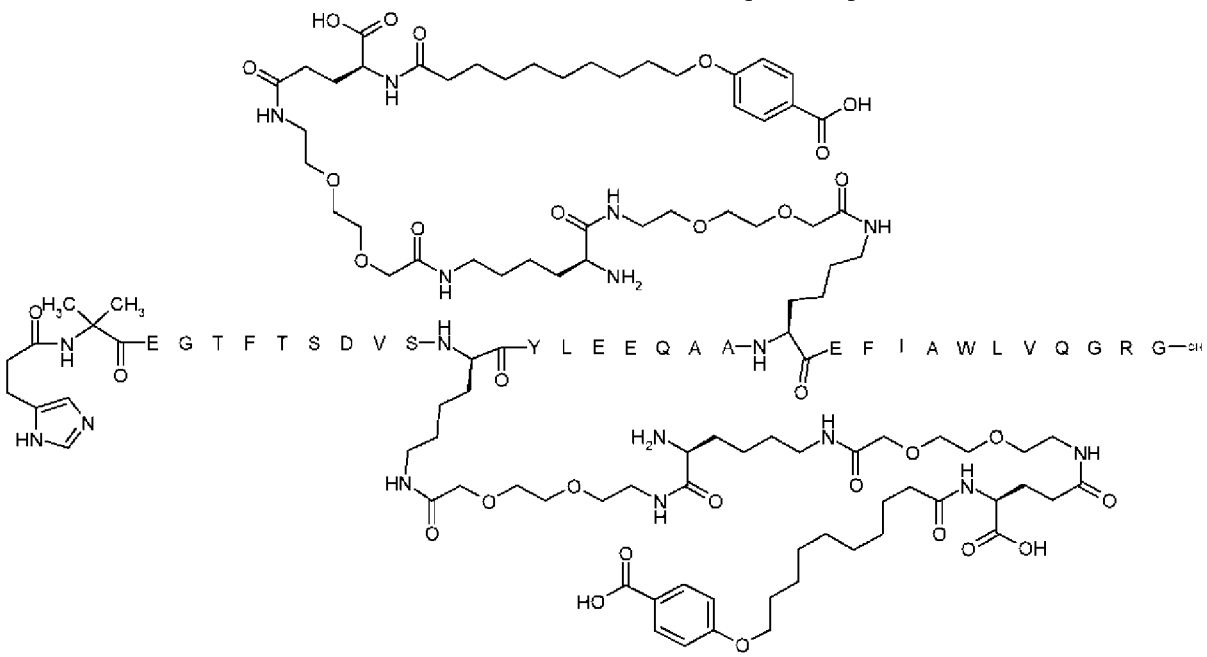

At column 181-182, claim number 7, chem. number 23, please replace with

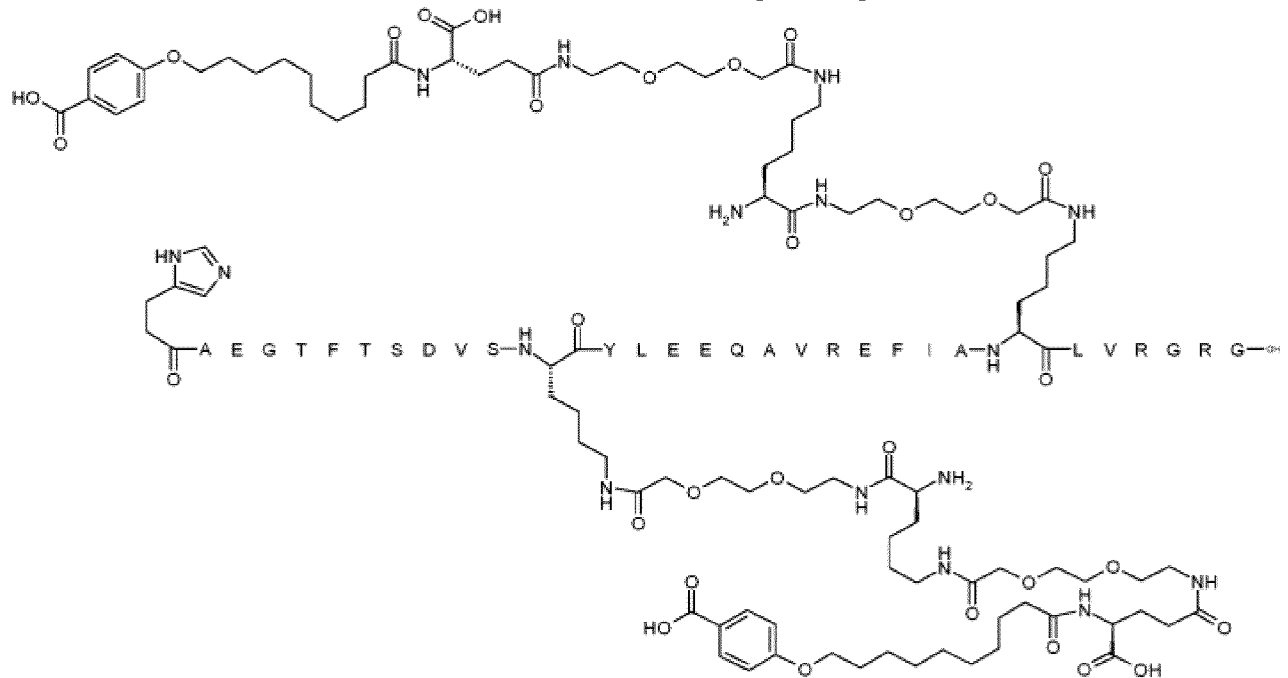

CERTIFICATE OF CORRECTION (continued)  
U.S. Pat. No. 9,006,178 B2

Page 3 of 21

At column 183-184, claim number 7, chem. number 24, please replace with

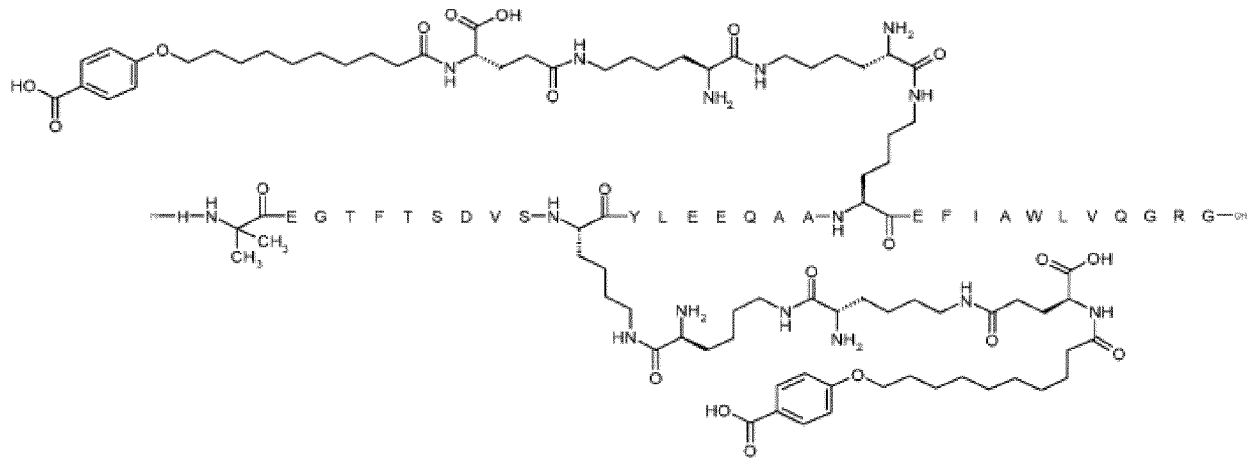

At column 185-186, claim number 7, chem. number 25, please replace with

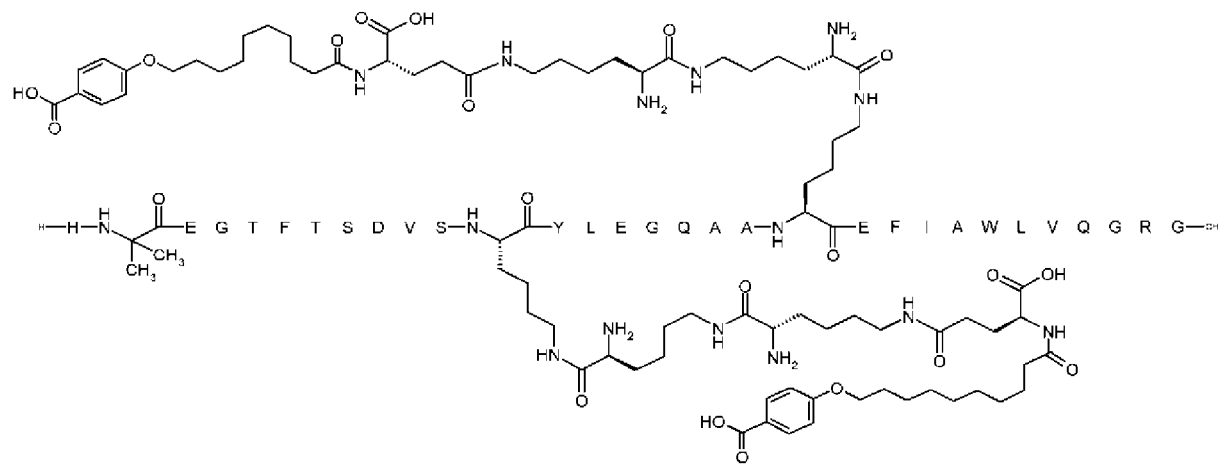

At column 185-186, claim number 7, chem. number 26, please replace with

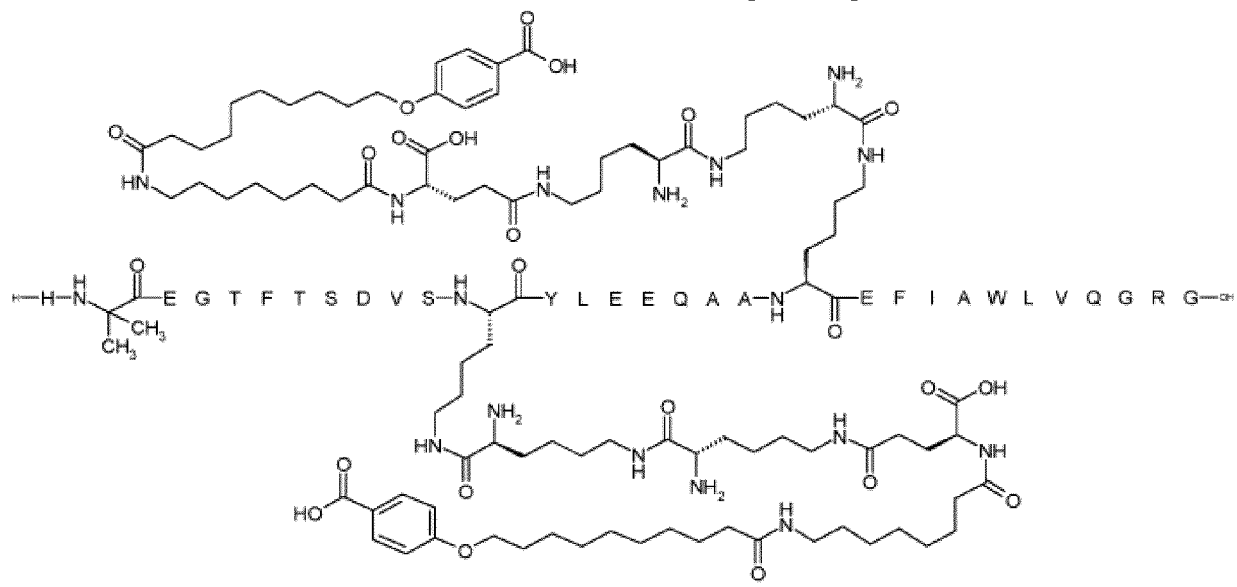

CERTIFICATE OF CORRECTION (continued)
U.S. Pat. No. 9,006,178 B2

At column 187-188, claim number 7, chem. number 27, please replace with

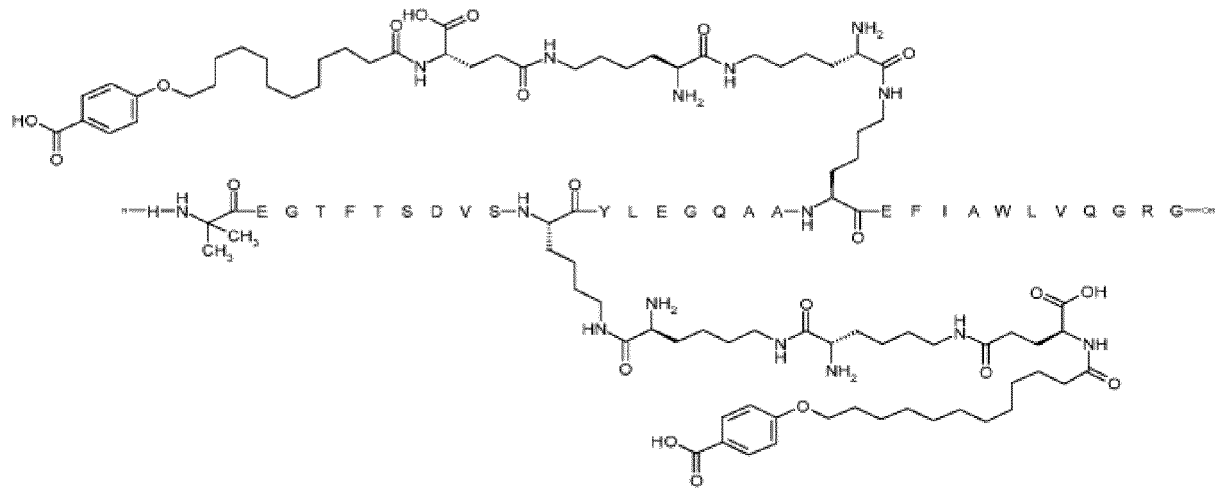

At column 189-190, claim number 7, chem. number 28, please replace with

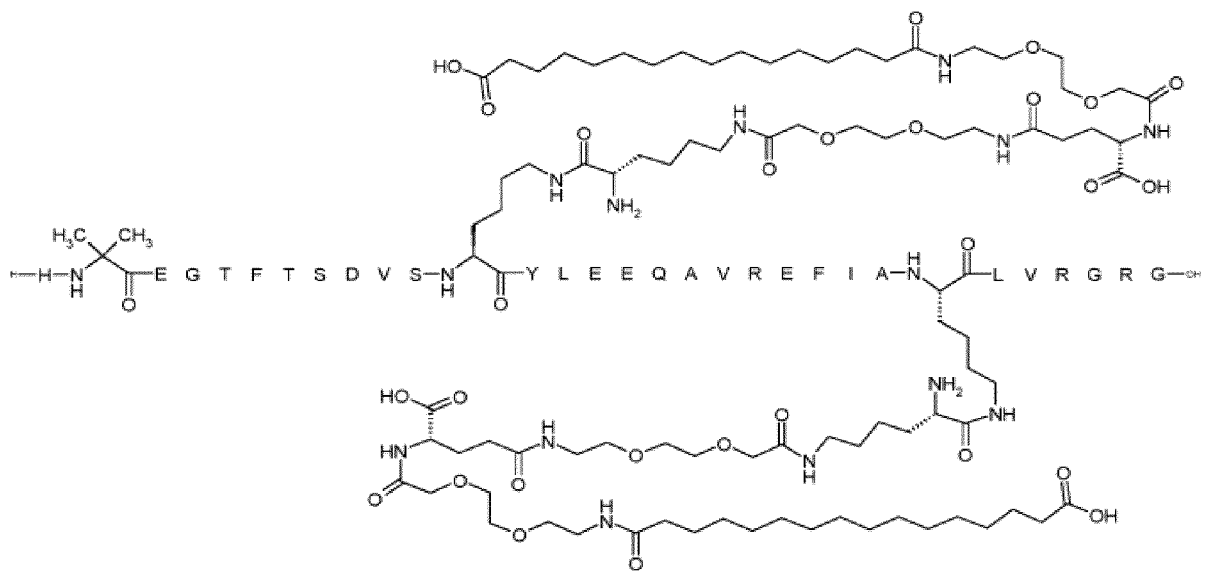

At column 189-190, claim number 7, chem. number 29, please replace with

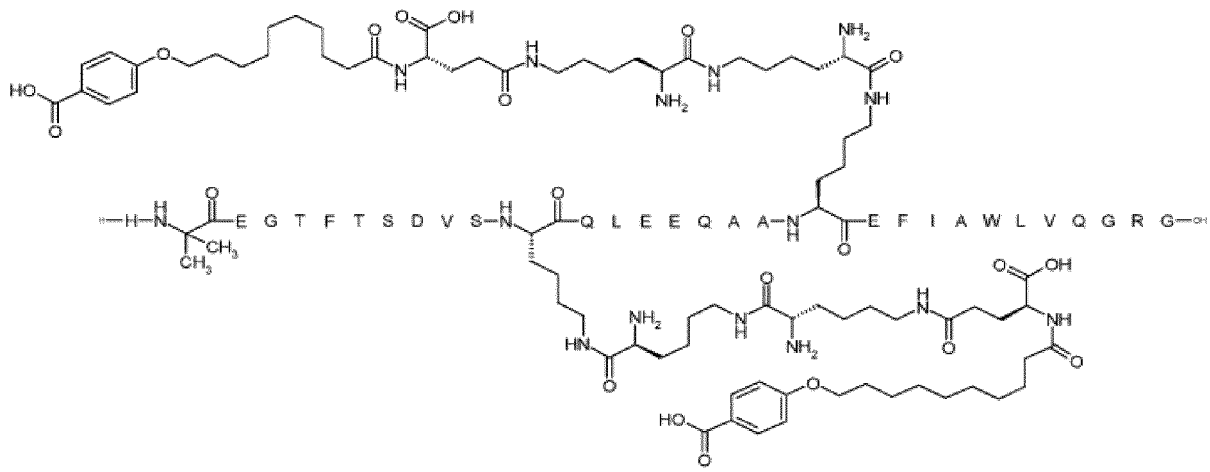

At column 191-192, claim number 7, chem. number 30, please replace with
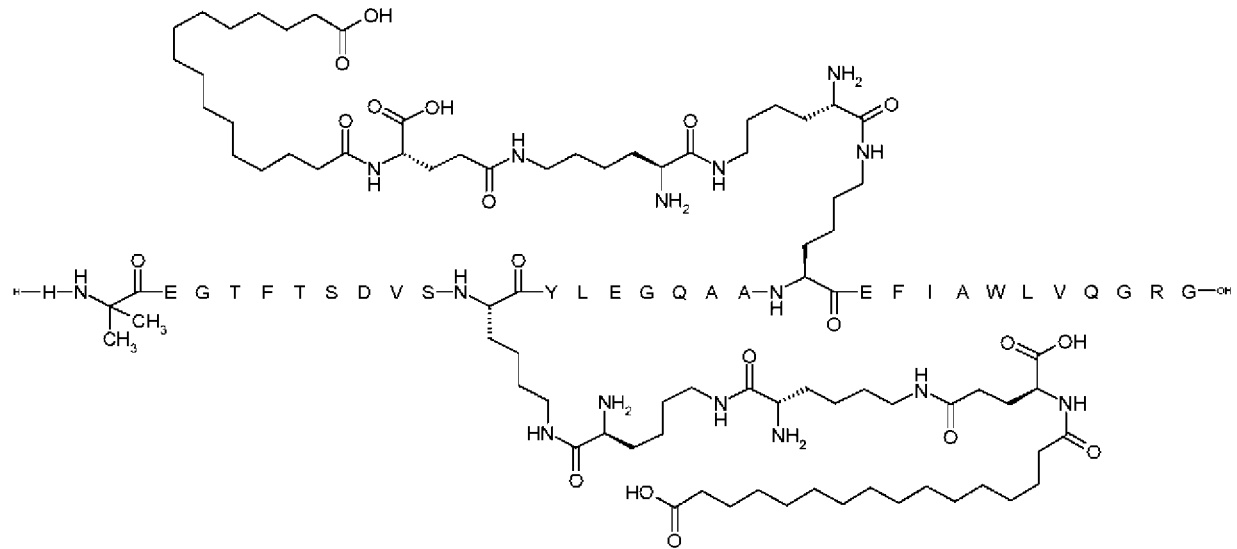
At column 191-192, claim number 7, chem. number 31, please replace with
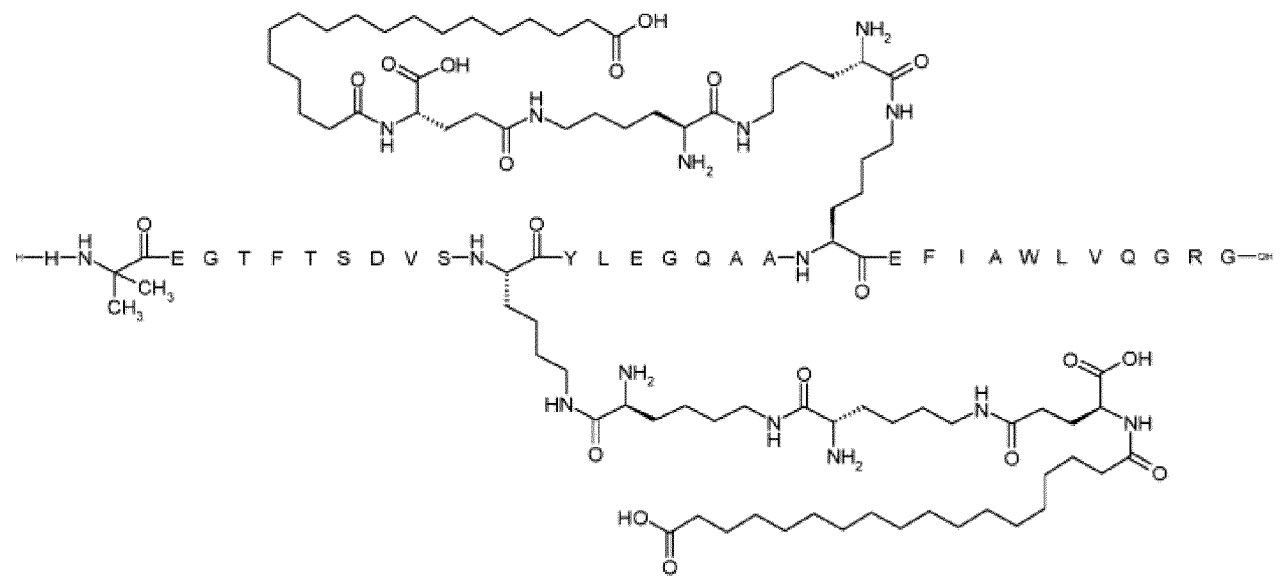
At column 193-194, claim number 7, chem. number 32, please replace with

CERTIFICATE OF CORRECTION (continued)
U.S. Pat. No. 9,006,178 B2

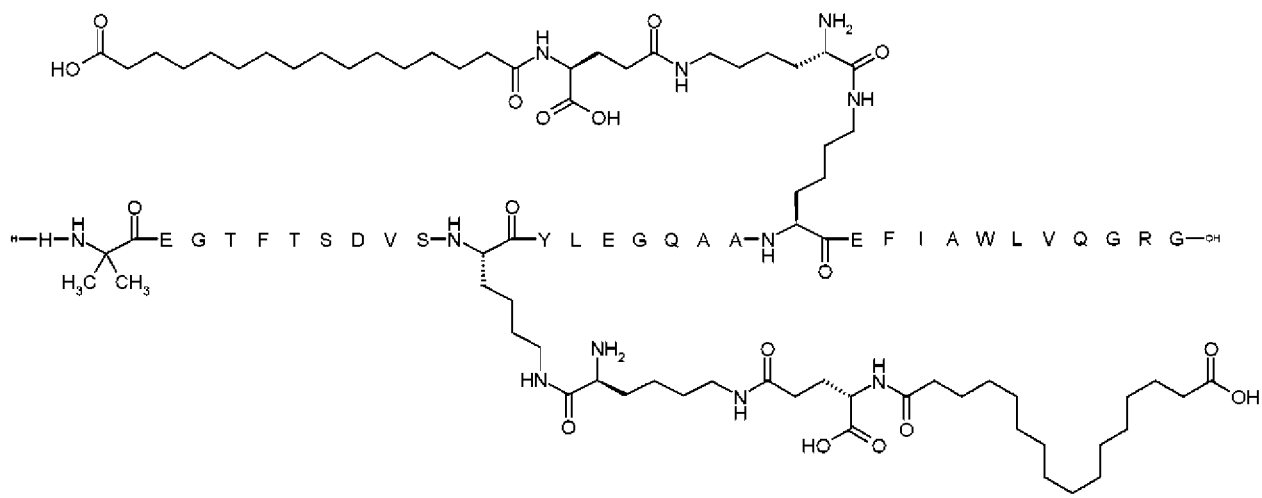

At column 193-194, claim number 7, chem. number 33, please replace with

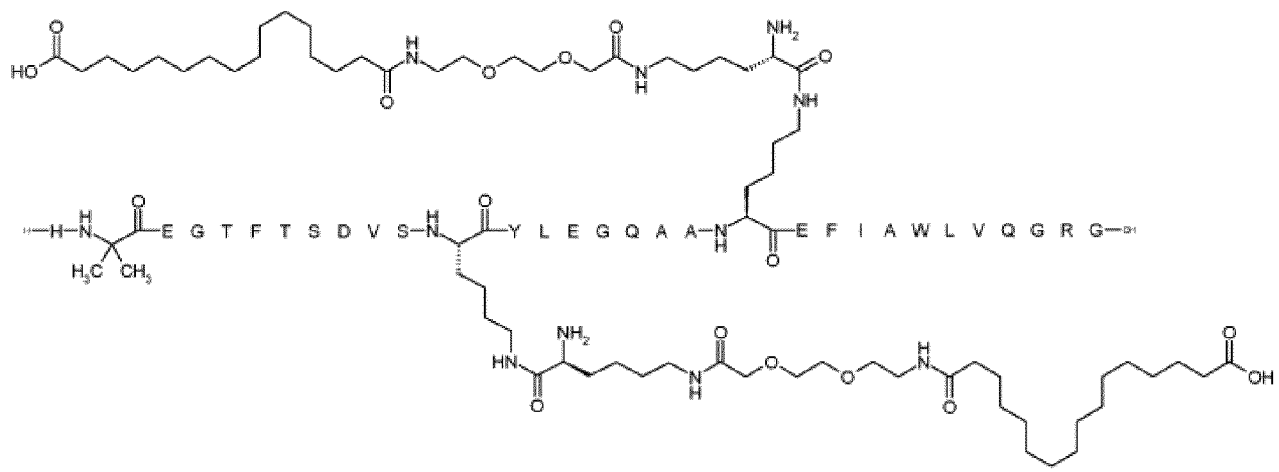

At column 195-196, claim number 7, chem. number 34, please replace with

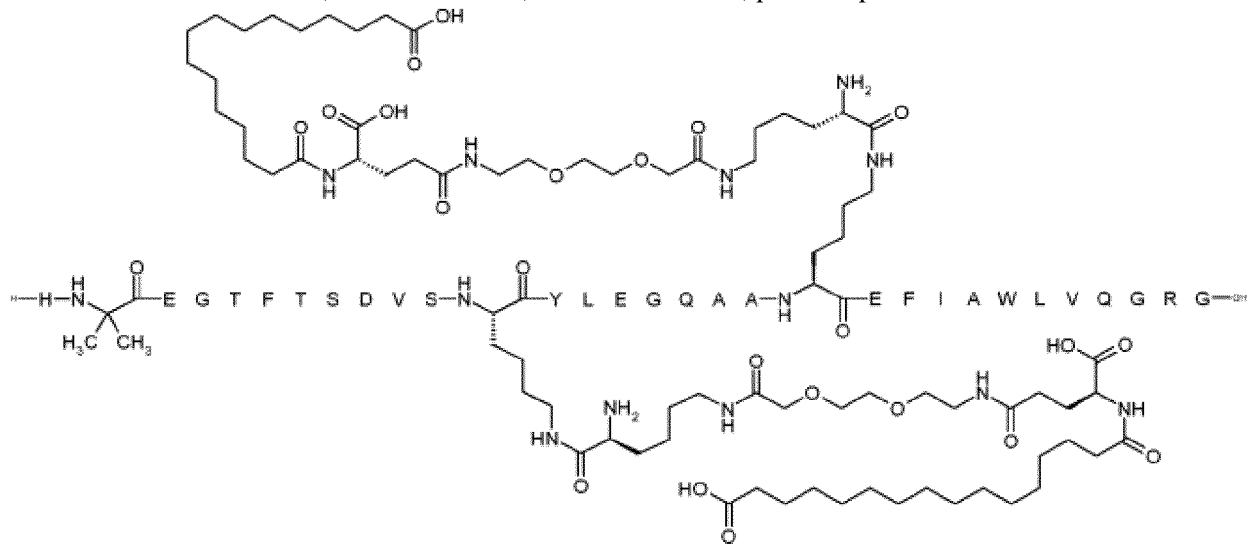

At column 195-196, claim number 7, chem. number 35, please replace with

CERTIFICATE OF CORRECTION (continued)
U.S. Pat. No. 9,006,178 B2

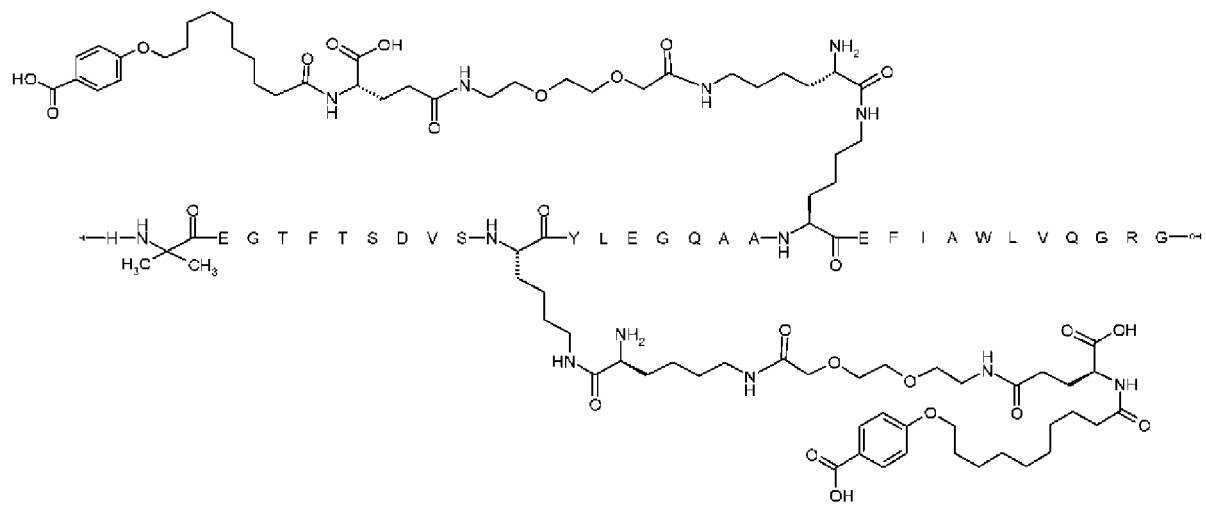

At column 197-198, claim number 7, chem. number 36, please replace with

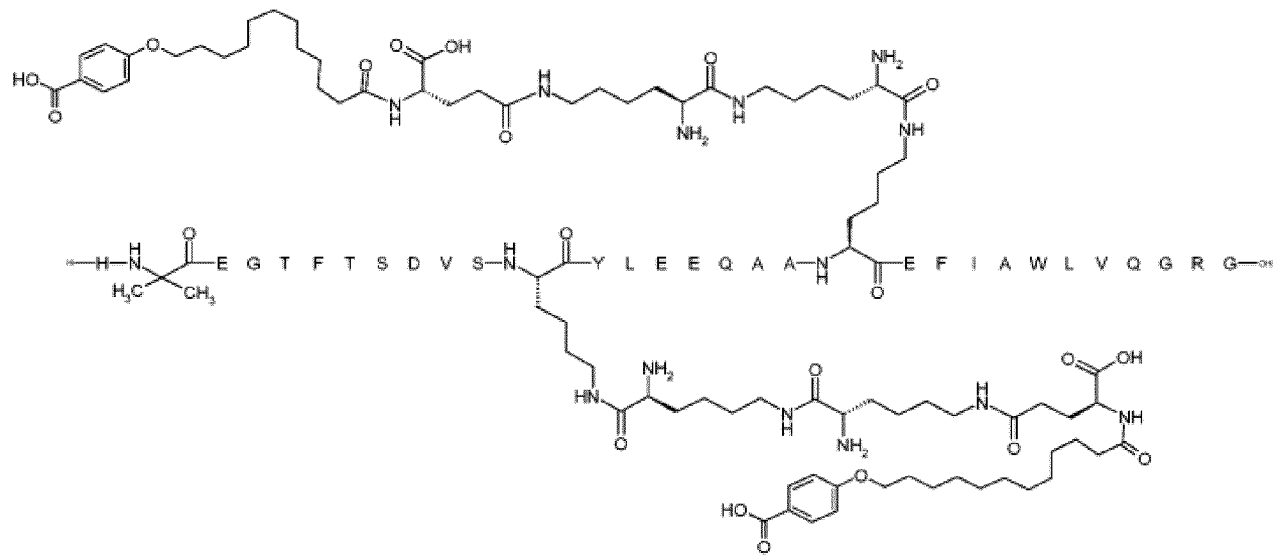

At column 199-200, claim number 7, chem. number 37, please replace with

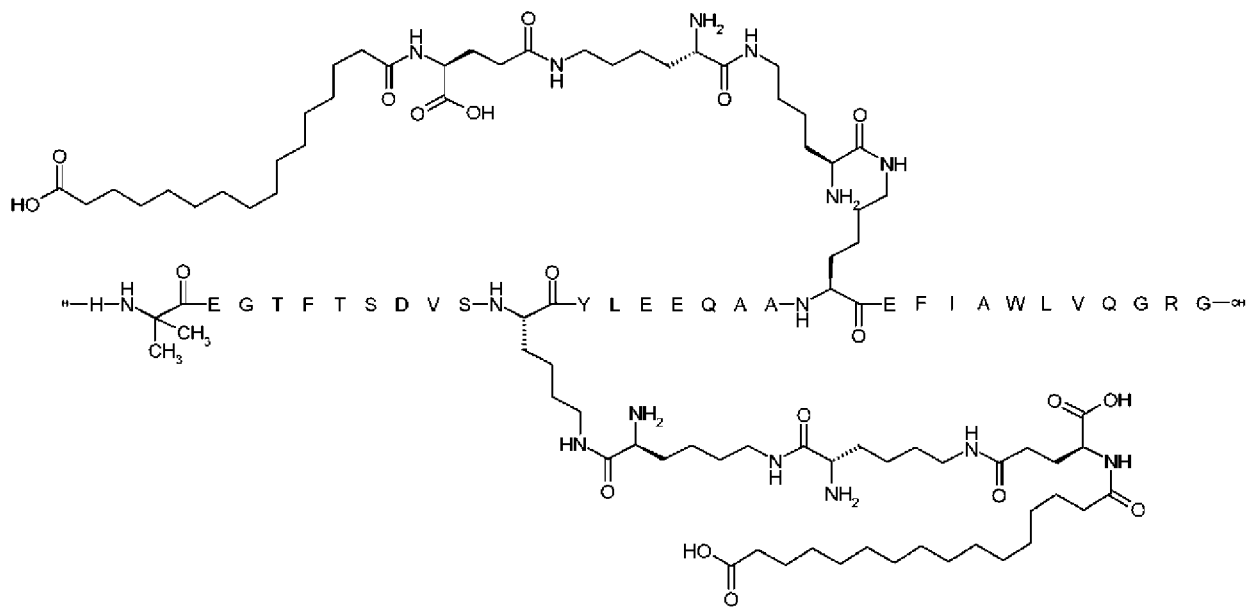
At column 205-206, claim number 7, chem. number 40, please replace with
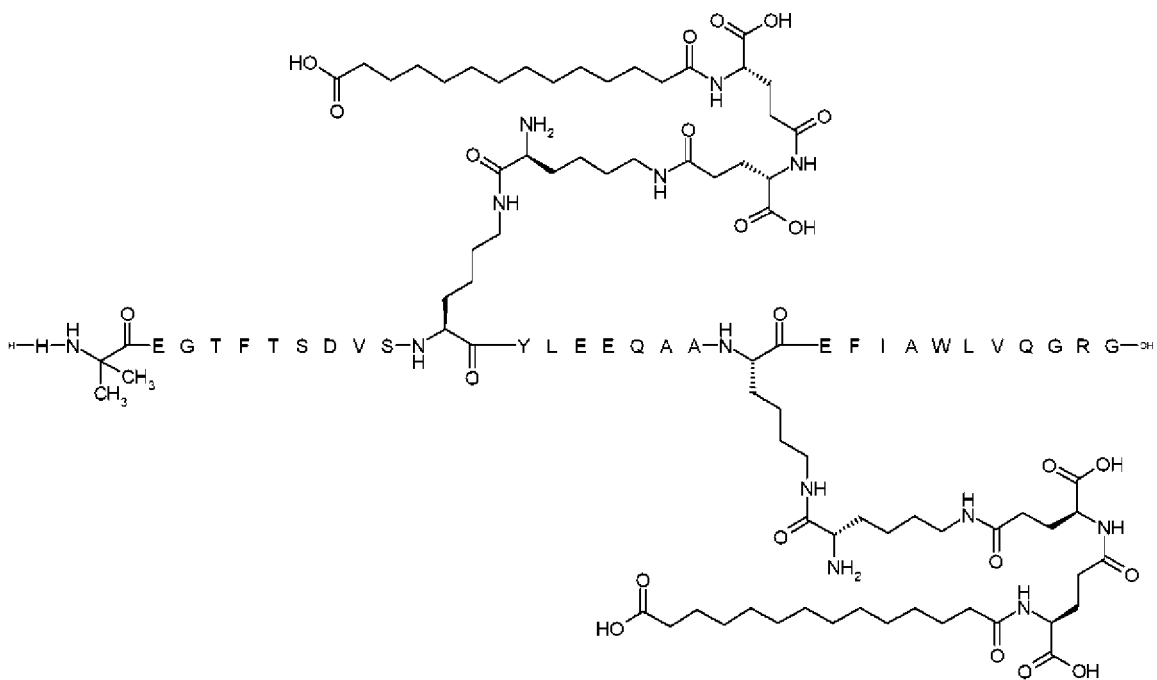
At column 221-222, claim number 7, chem. number 50, please replace with

CERTIFICATE OF CORRECTION (continued)
U.S. Pat. No. 9,006,178 B2

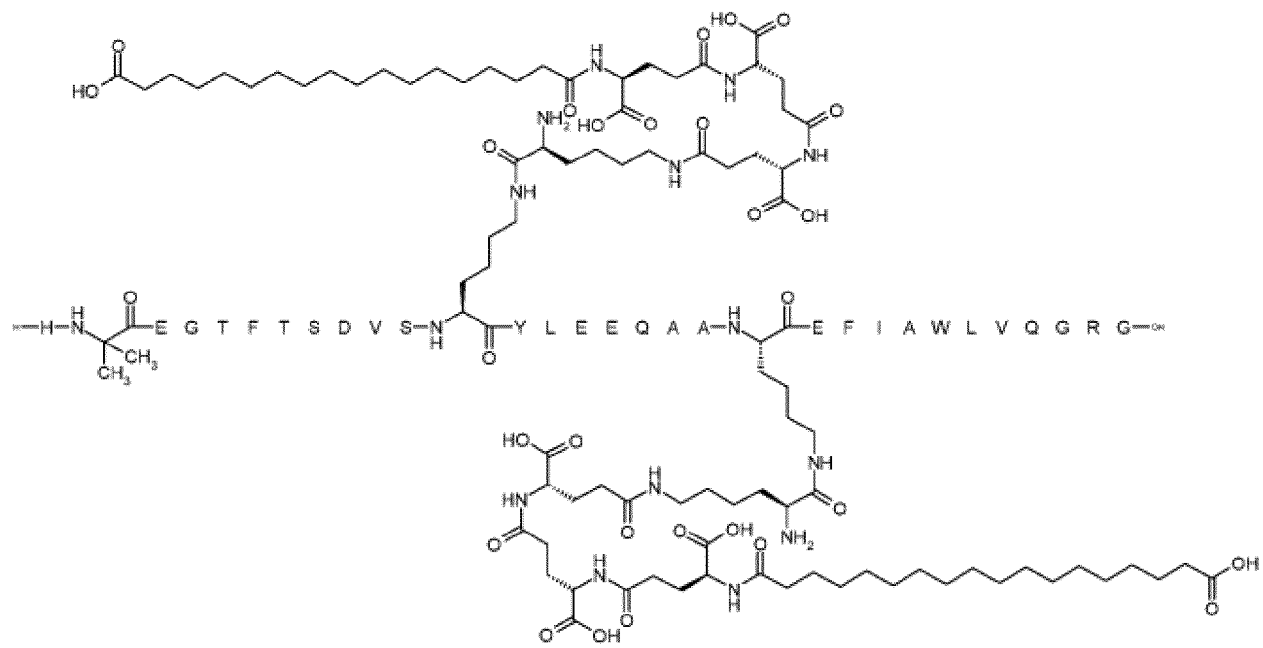

At column 221-222, claim number 7, chem. number 51, please replace with

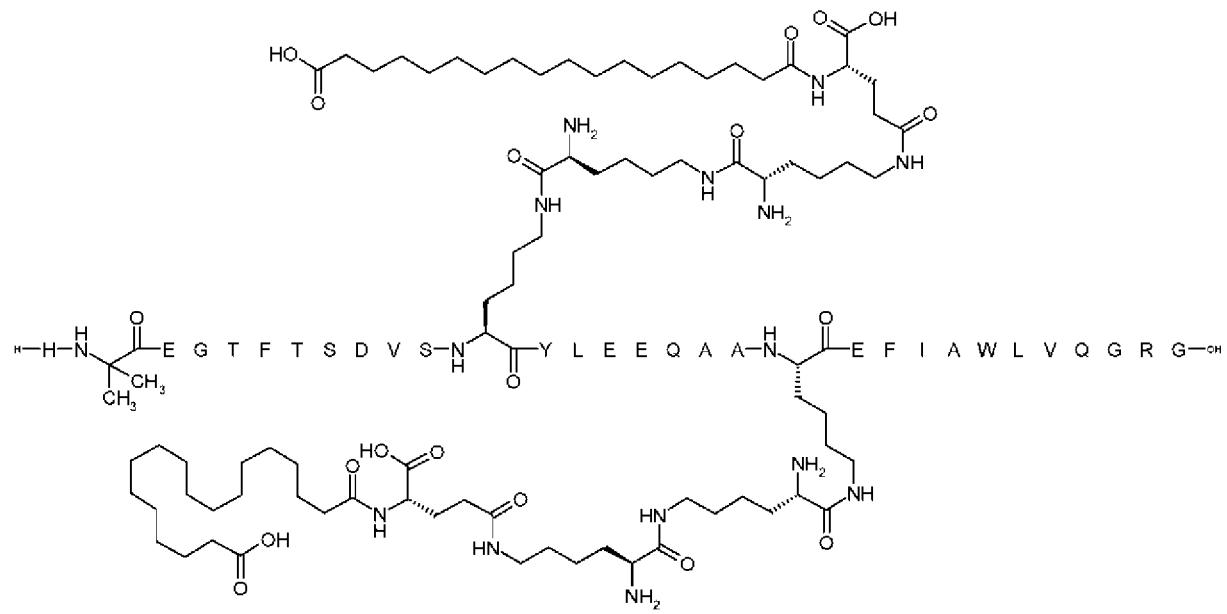

At column 223-224, claim number 7, chem. number 52, please replace with

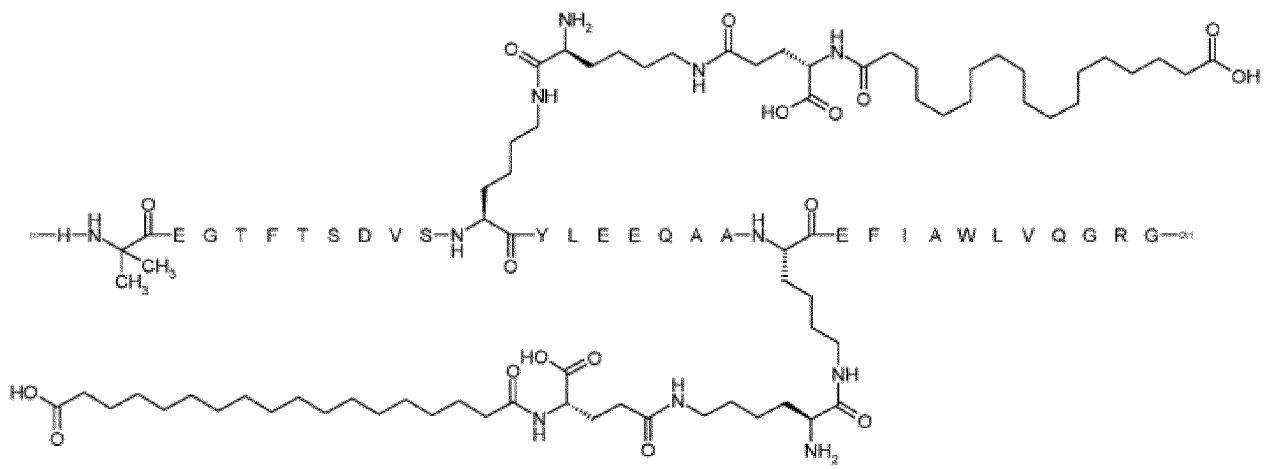
At column 223-224, claim number 7, chem. number 53, please replace with
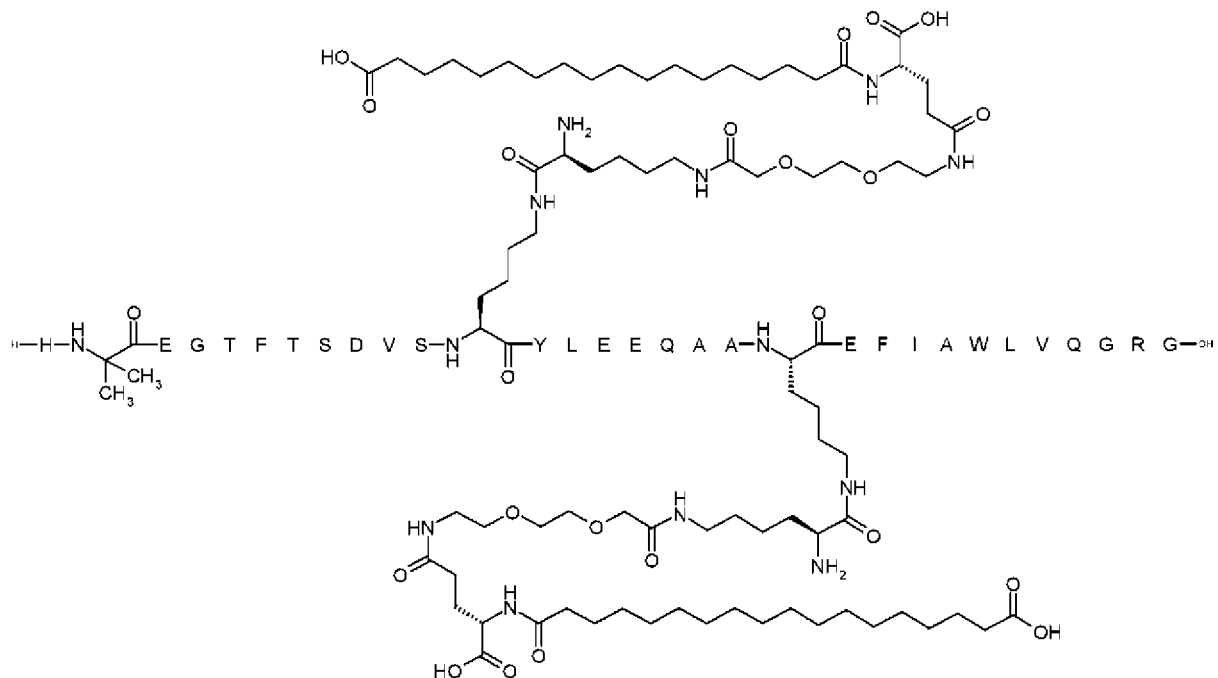
At column 225-226, claim number 7, chem. number 54, please replace with

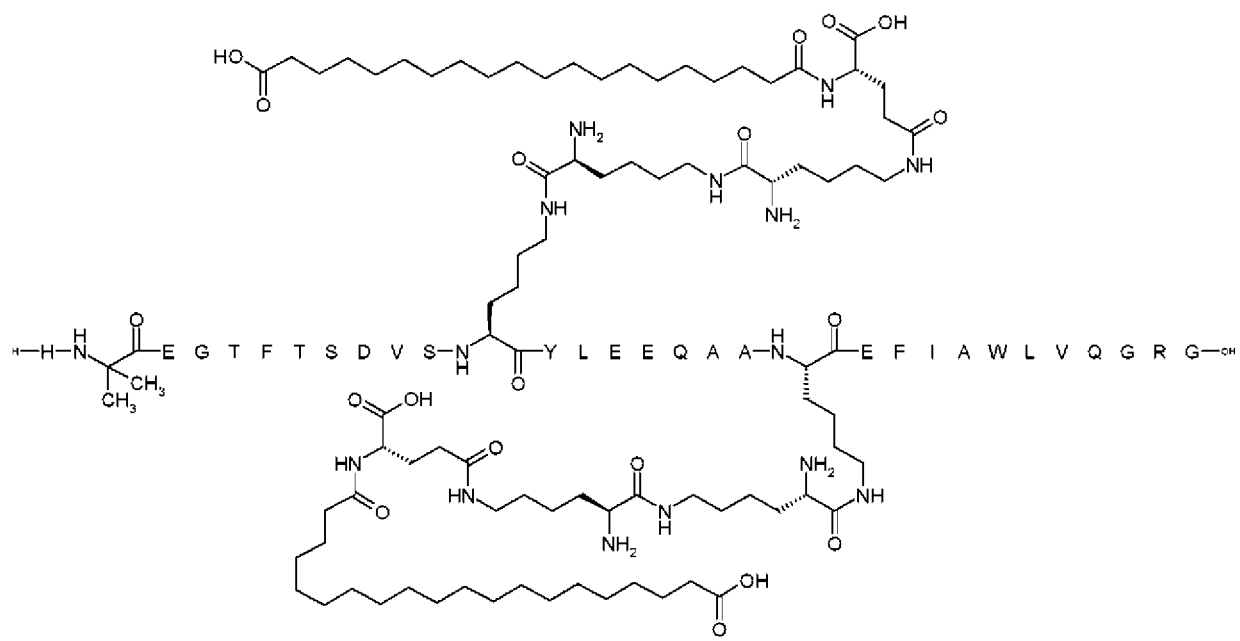
At column 227-228, claim number 7, chem. number 55, please replace with
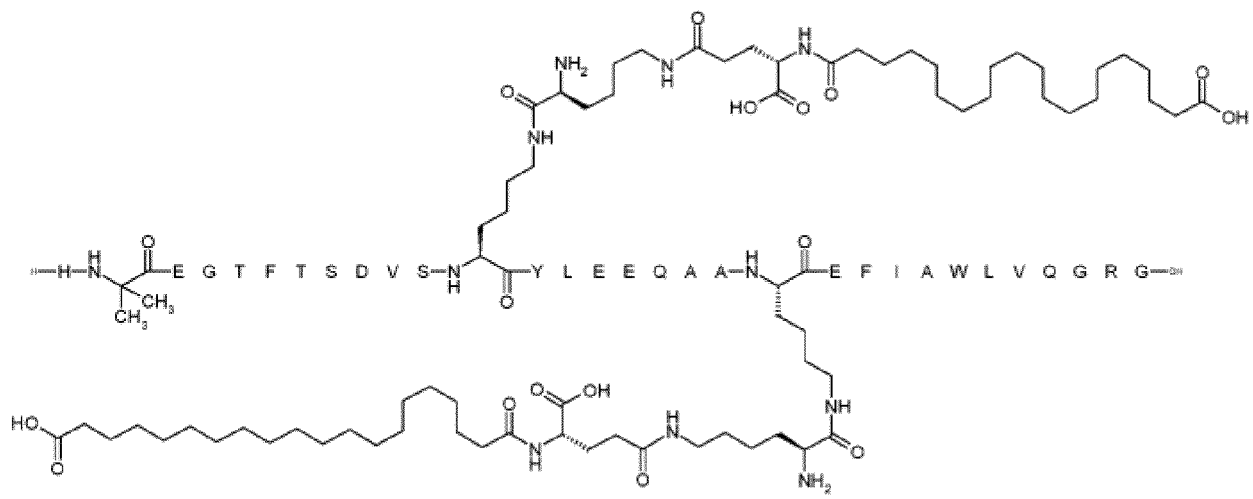
At column 227-228, claim number 7, chem. number 56, please replace with

CERTIFICATE OF CORRECTION (continued)
U.S. Pat. No. 9,006,178 B2

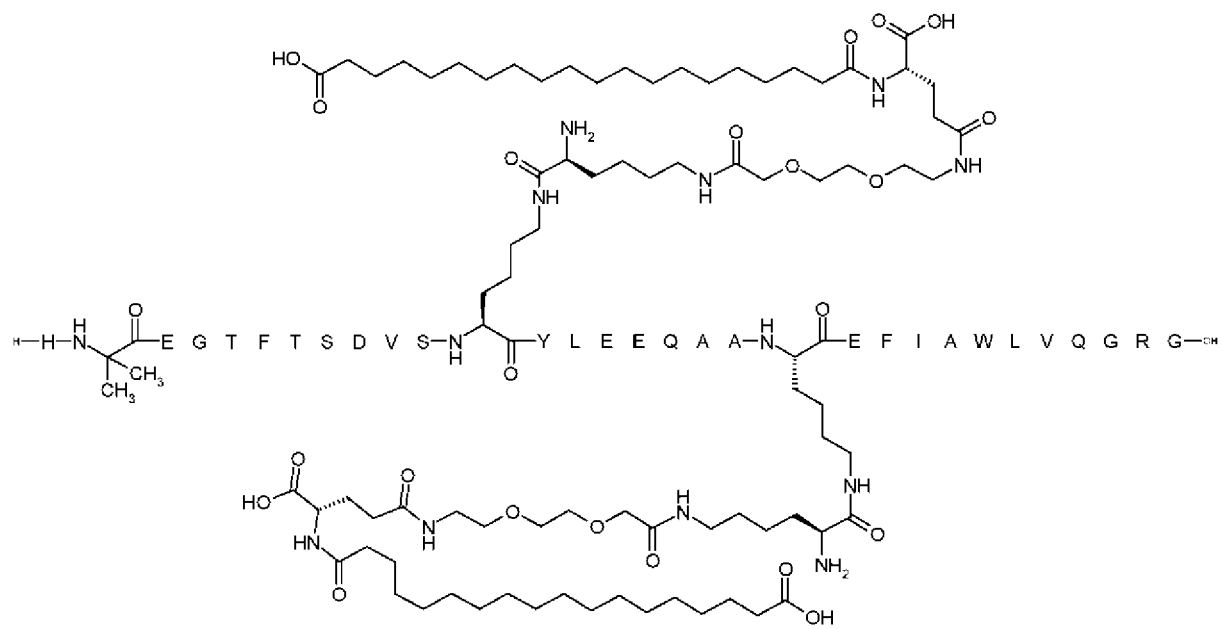

At column 229-230, claim number 7, chem. number 57, please replace with

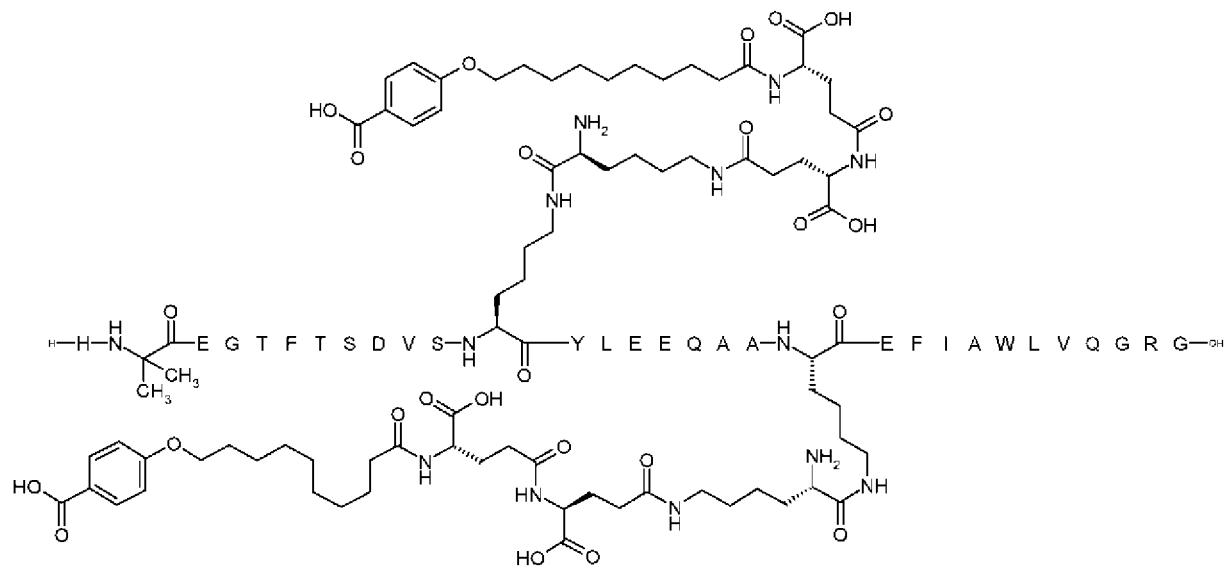

At column 231-232, claim number 7, chem. number 58, please replace with

CERTIFICATE OF CORRECTION (continued)
U.S. Pat. No. 9,006,178 B2

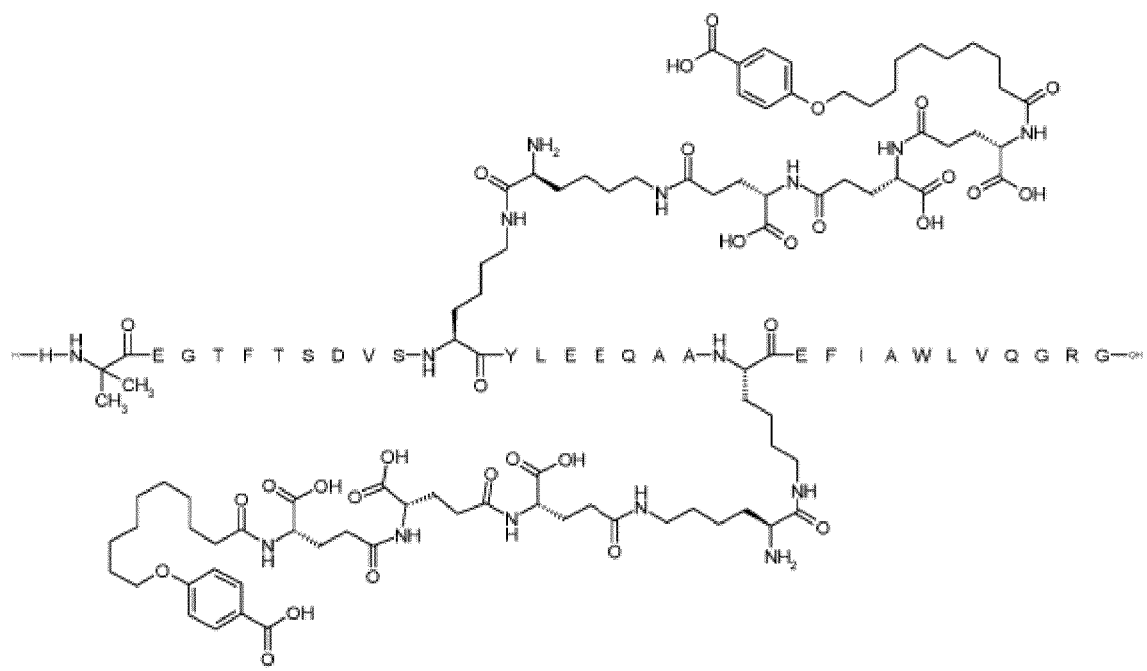

At column 233-234, claim number 7, chem. number 59, please replace with

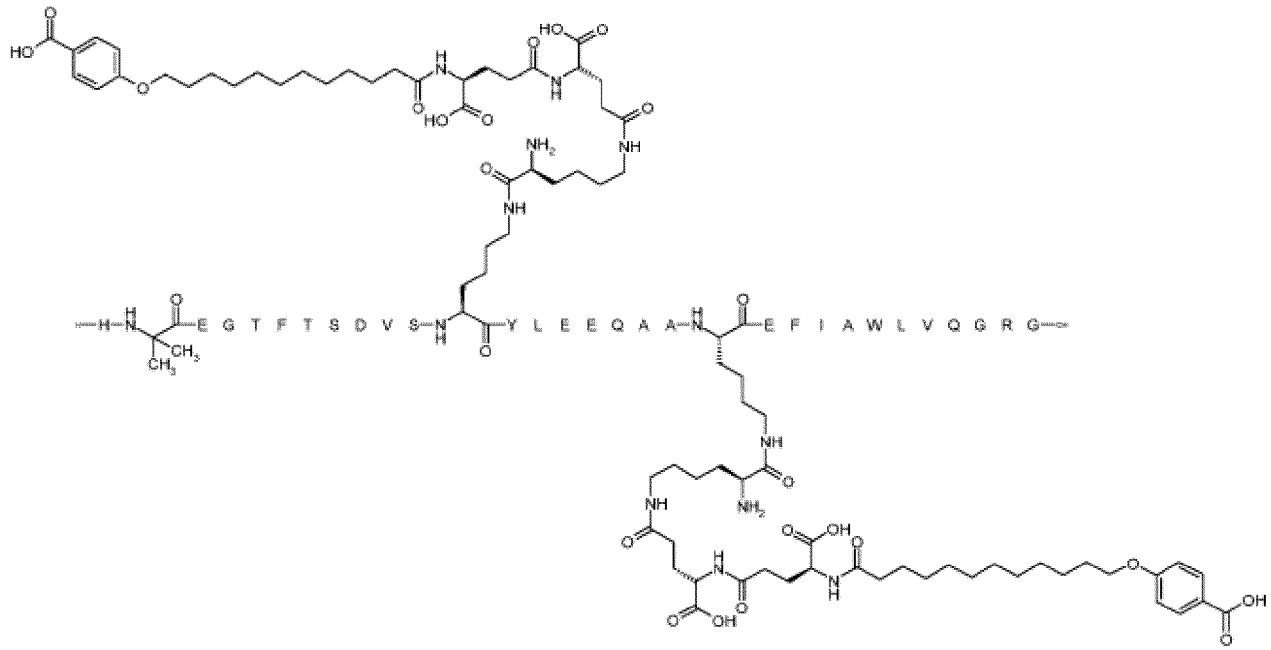

At column 233-234, claim number 7, chem. number 60, please replace with

CERTIFICATE OF CORRECTION (continued)
U.S. Pat. No. 9,006,178 B2

Page 14 of 21

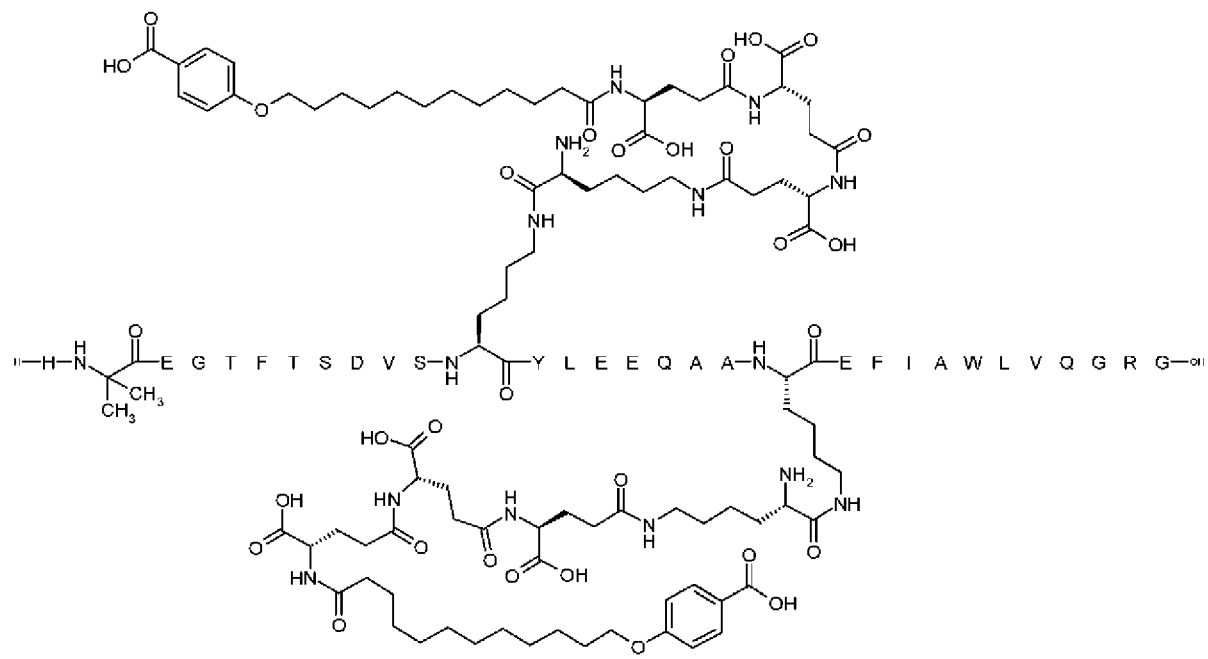

At column 235-236, claim number 7, chem. number 61, please replace with

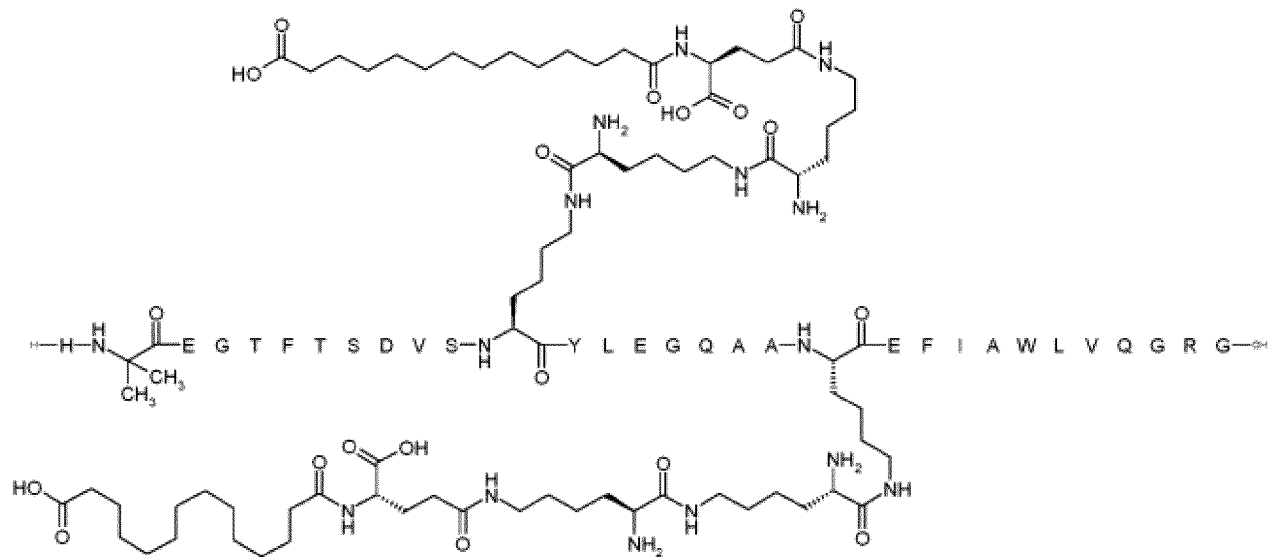

At column 237-238, claim number 7, chem. number 62, please replace with

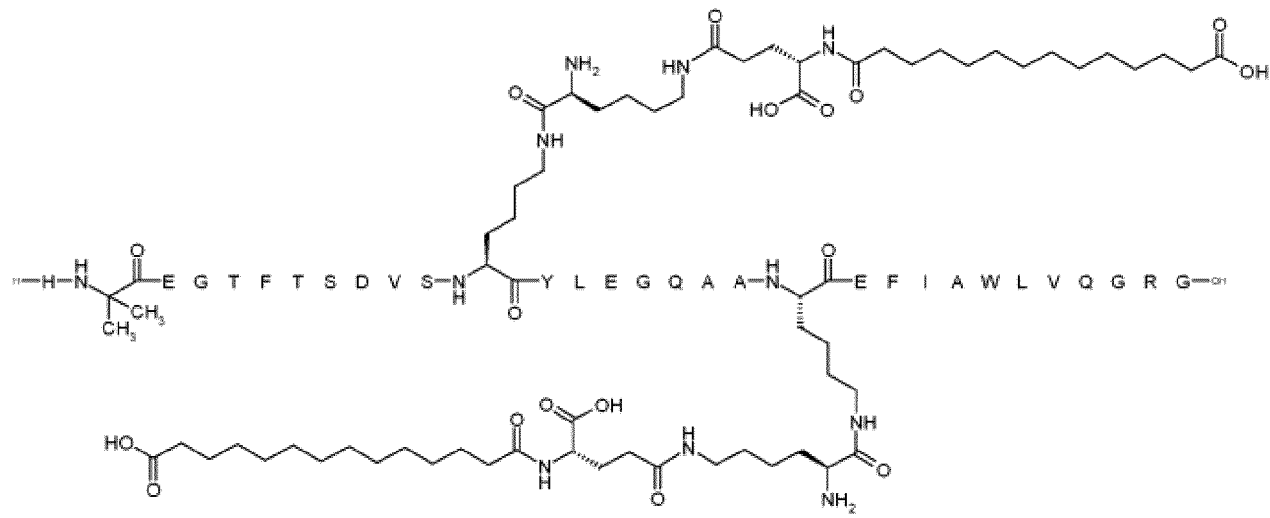
At column 241-242, claim number 7, chem. number 63, please replace with
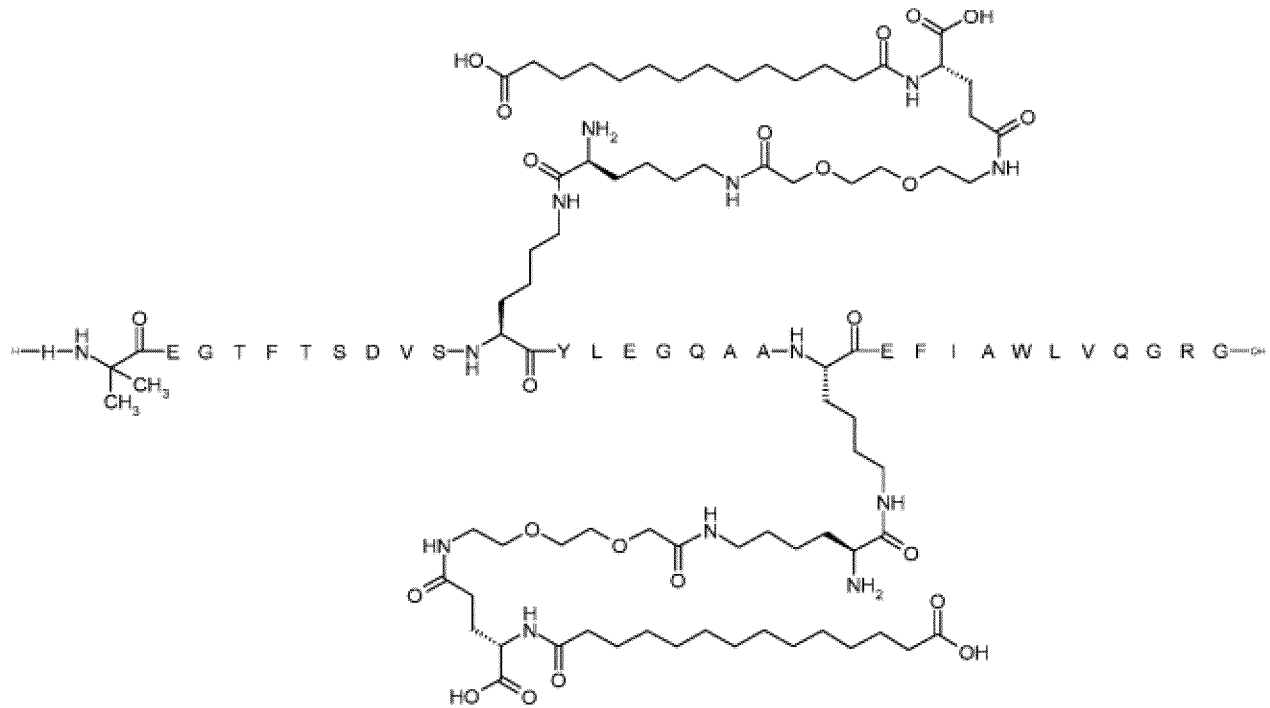
At column 241-242, claim number 7, chem. number 64, please replace with

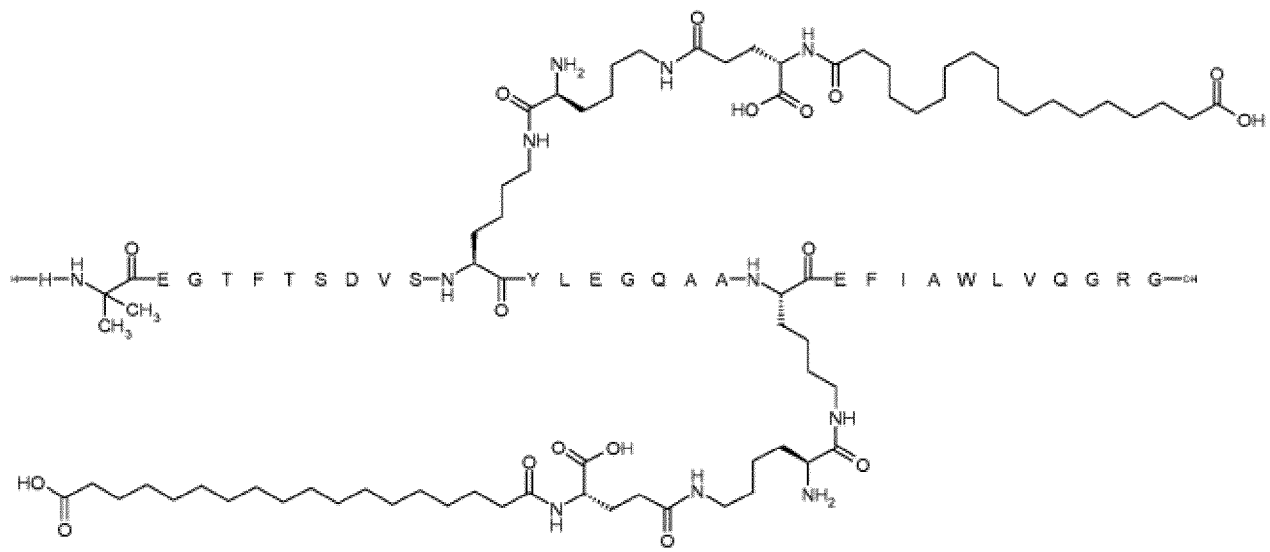
At column 243-244, claim number 7, chem. number 65, please replace with
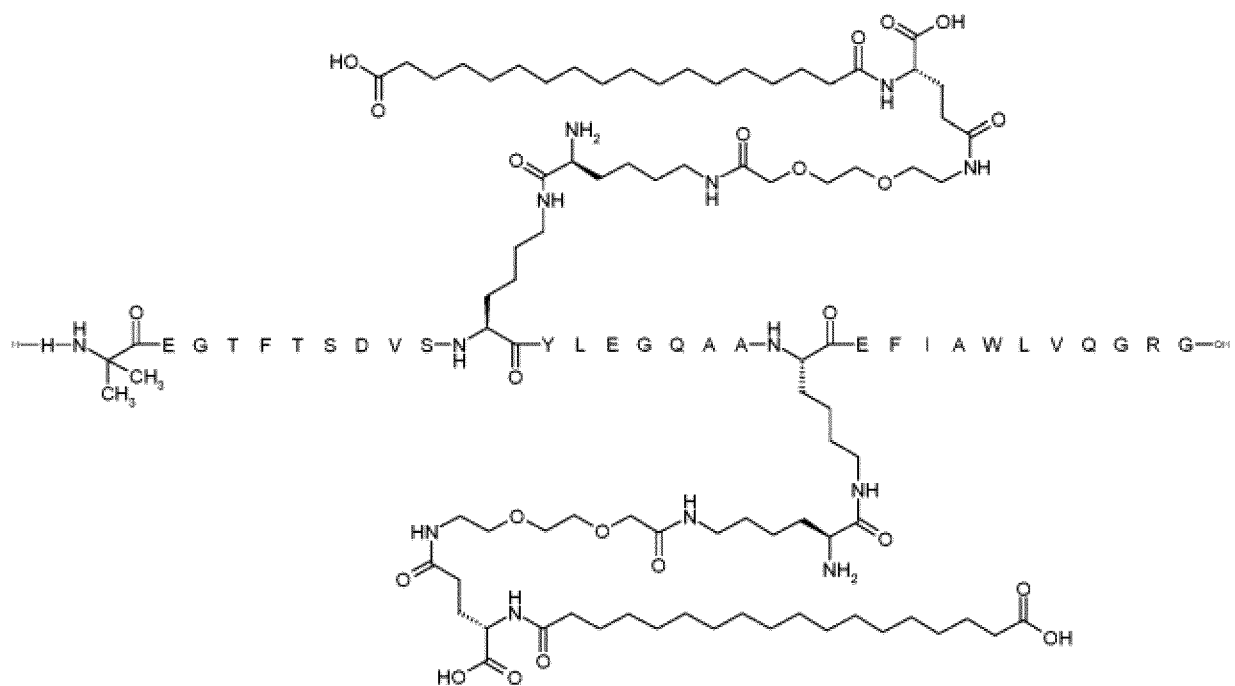
At column 245-246, claim number 7, chem. number 66, please replace with

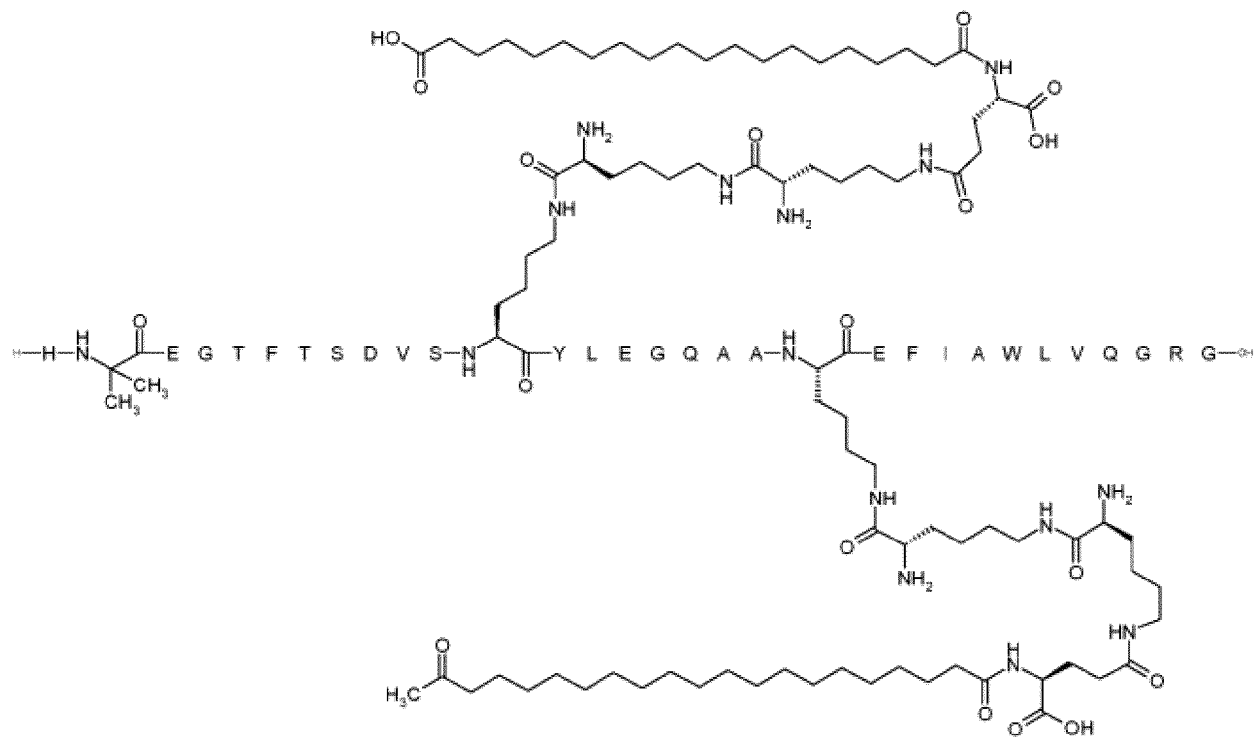
At column 249-250, claim number 7, chem. number 68, please replace with
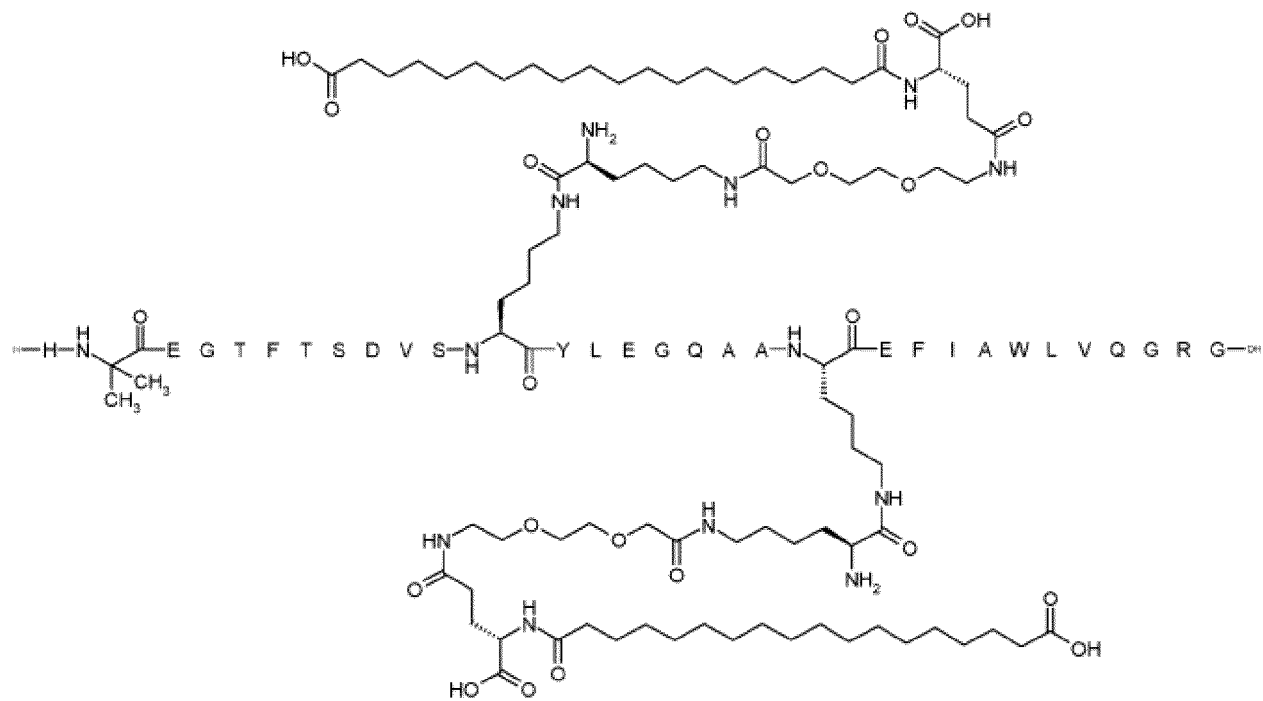
At column 249-250, claim number 7, chem. number 69, please replace with

CERTIFICATE OF CORRECTION (continued)
U.S. Pat. No. 9,006,178 B2

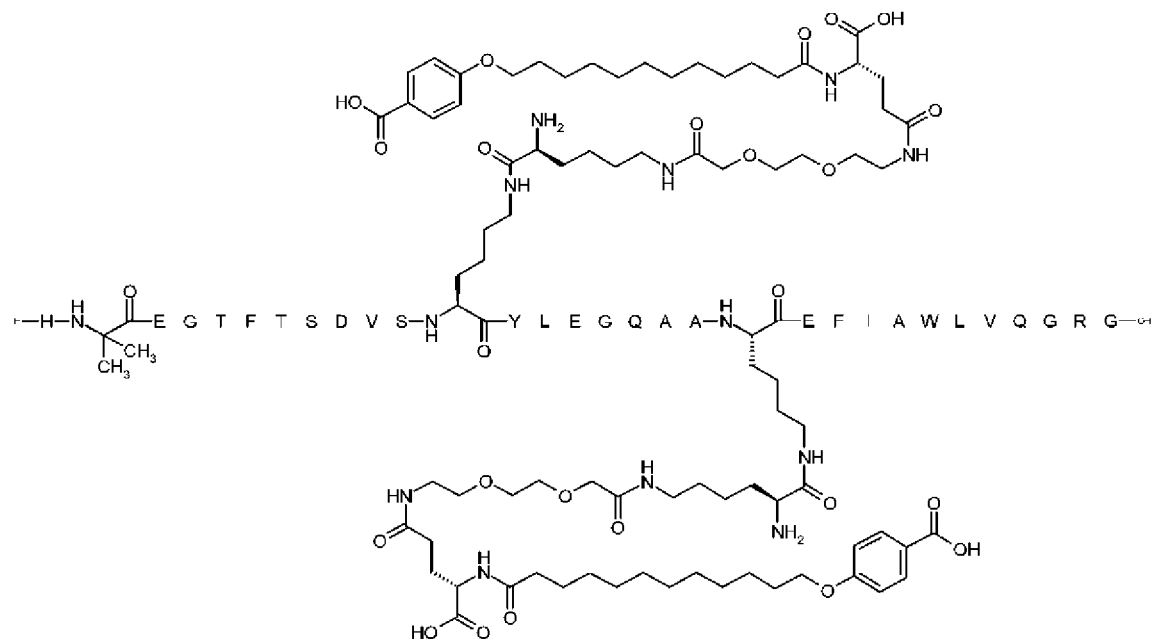

At column 251-252, claim number 7, chem. number 70, please replace with

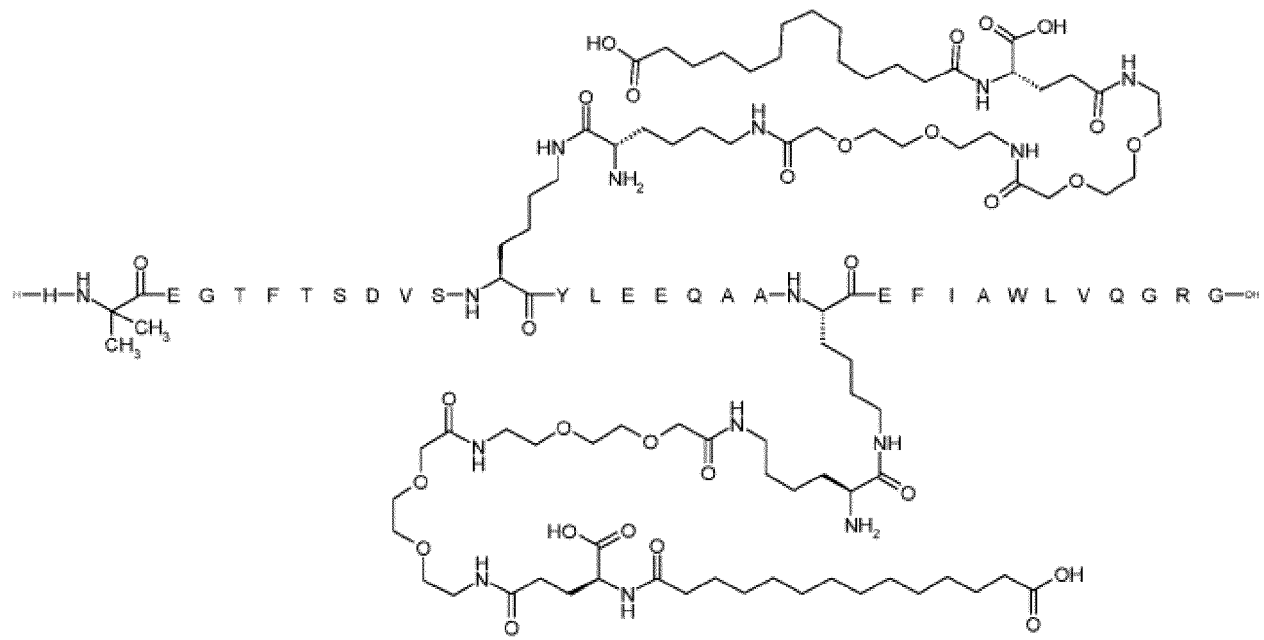

At column 253-254, claim number 7, chem. number 71, please replace with

CERTIFICATE OF CORRECTION (continued)
U.S. Pat. No. 9,006,178 B2

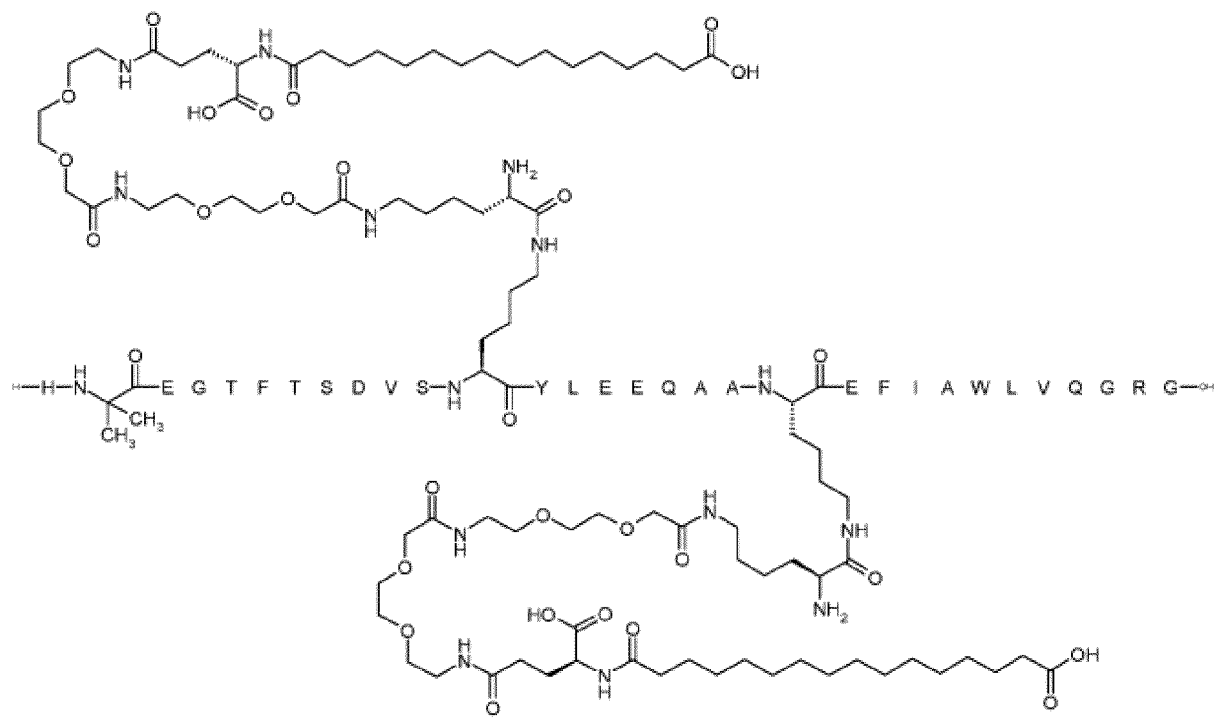

At column 253-254, claim number 7, chem. number 72, please replace with

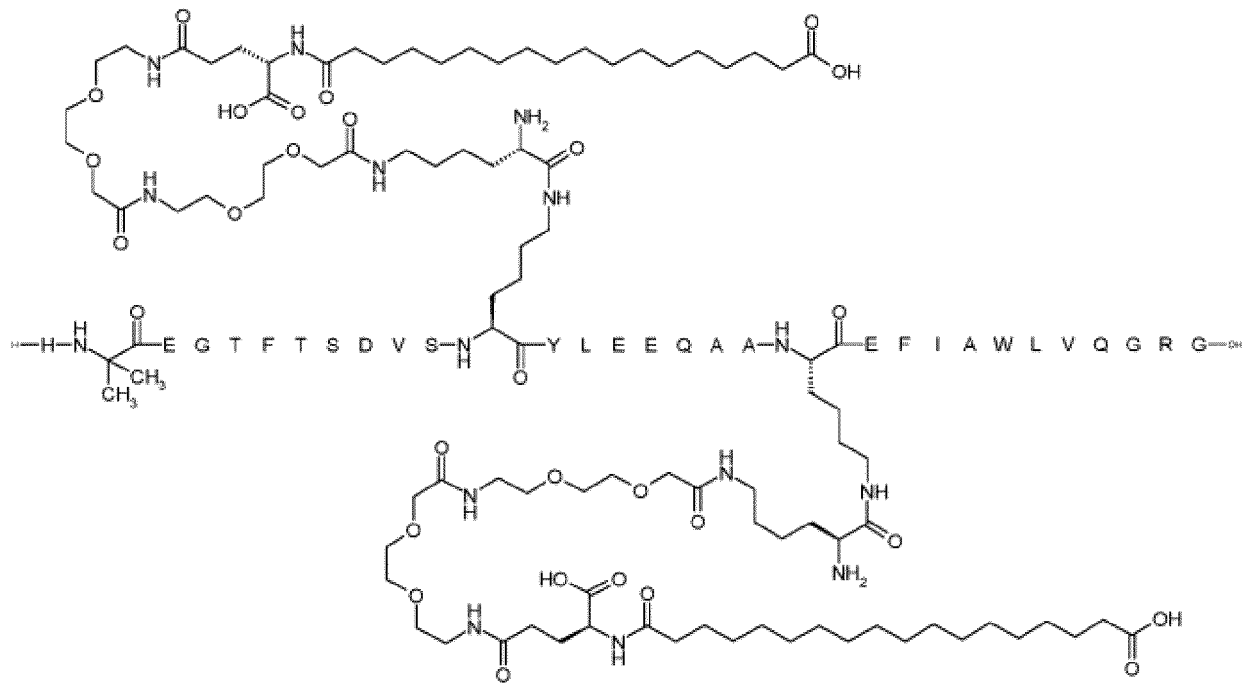

At column 255-256, claim number 7, chem. number 73, please replace with

CERTIFICATE OF CORRECTION (continued)
U.S. Pat. No. 9,006,178 B2

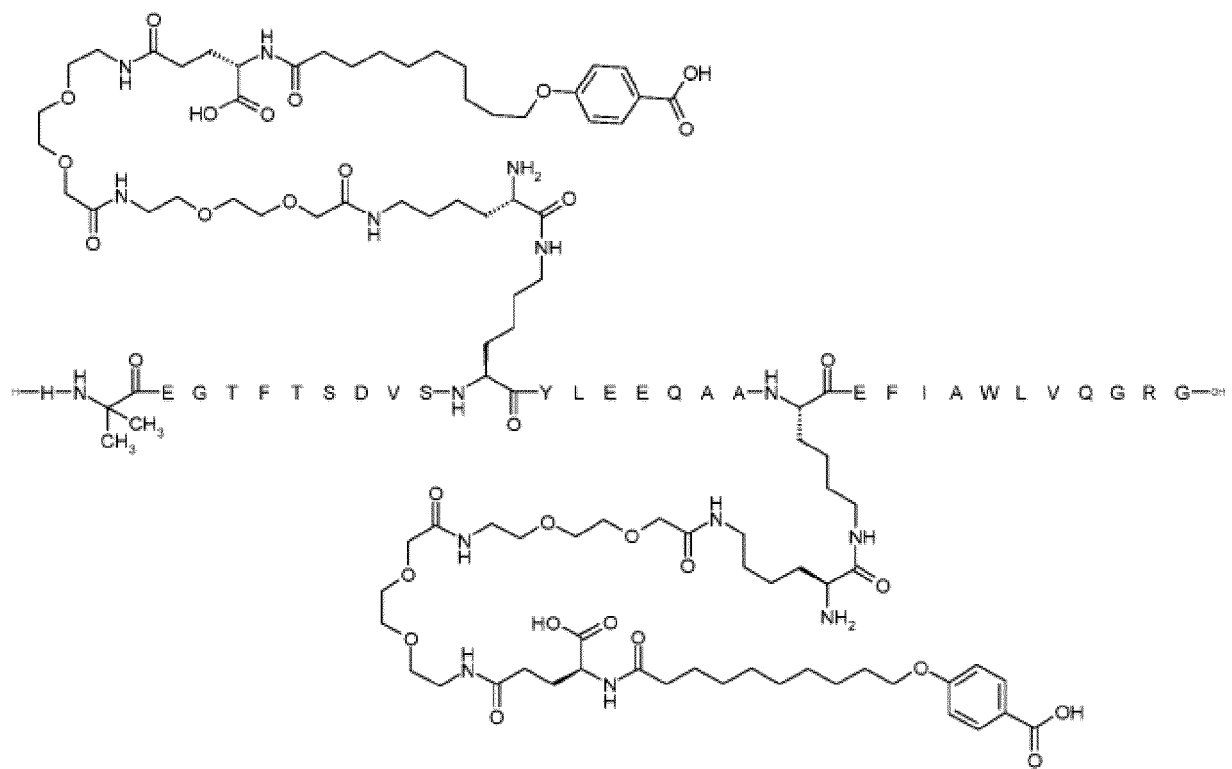

At column 257-258, claim number 7, chem. number 75, please replace with

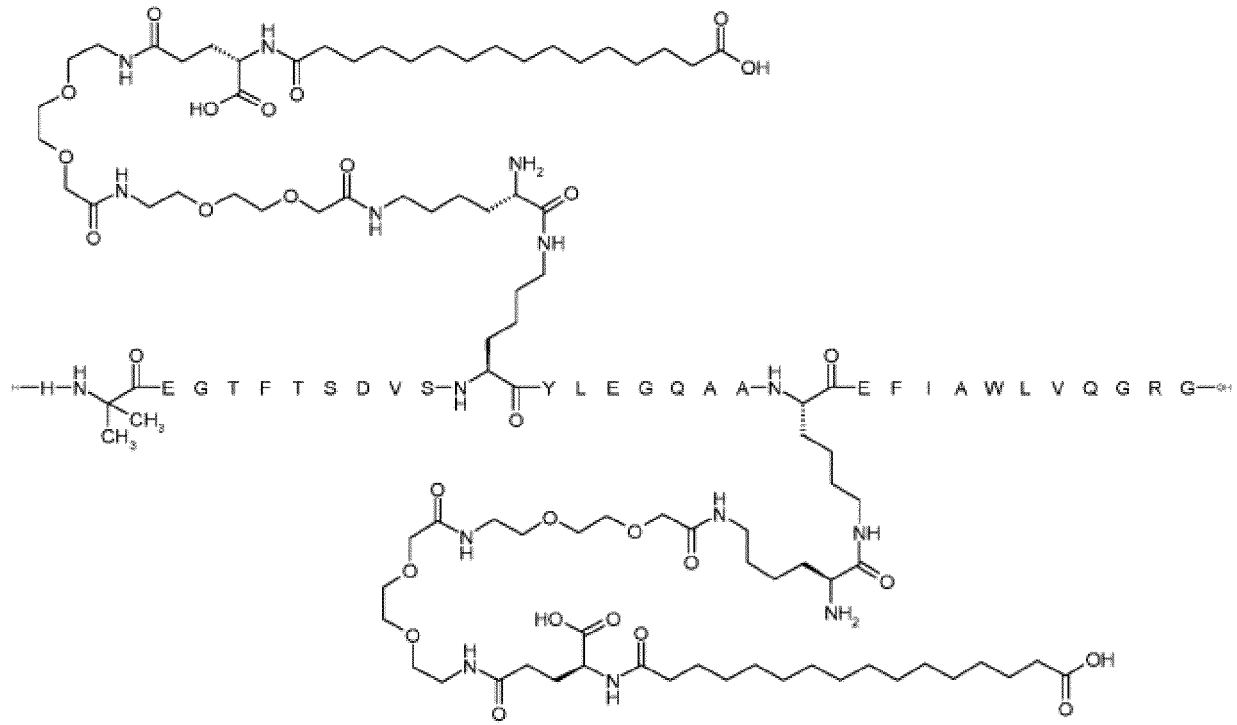

At column 259-260, claim number 7, chem. number 76, please replace with

SEQUENCE LISTING

```
<160> NUMBER OF SEQ ID NOS: 12

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

```
<210> SEQ ID NO 2
<211> LENGTH: 28
<212> TYPE: PRT
<213> ORGANISM: Artificial Sequence
<220> FEATURE:
<223> OTHER INFORMATION: Synthetic

<400> SEQUENCE: 2

His Ala Glu Gly Thr Phe Thr Ser Asp Val Ser Lys Tyr Leu Glu Glu
1               5                   10                  15

Gln Ala Ala Arg Lys Phe Ile Ala His Leu Val Gly
            20                  25

<210> SEQ ID NO 3
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=Aib
<220> FEATURE:
<221> NAME/KEY: MISC_FEATURE
<222> LOCATION: (12)..(12)
<223> OTHER INFORMATION: Xaa=Lys
<220> FEATURE:
<221> NAME/KEY: MISC_FEATURE
<222> LOCATION: (16)..(16)
<223> OTHER INFORMATION: Xaa=Glu
<220> FEATURE:
<221> NAME/KEY: MISC_FEATURE
<222> LOCATION: (19)..(19)
<223> OTHER INFORMATION: Xaa=Val
<220> FEATURE:
<221> NAME/KEY: MISC_FEATURE
<222> LOCATION: (20)..(20)
<223> OTHER INFORMATION: Xaa=Arg
<220> FEATURE:
<221> NAME/KEY: MISC_FEATURE
<222> LOCATION: (25)..(25)
<223> OTHER INFORMATION: Xaa=Lys
<220> FEATURE:
<221> NAME/KEY: MISC_FEATURE
<222> LOCATION: (28)..(28)
<223> OTHER INFORMATION: Xaa=Arg

<400> SEQUENCE: 3

His Xaa Glu Gly Thr Phe Thr Ser Asp Val Ser Xaa Tyr Leu Glu Xaa
1               5                   10                  15

Gln Ala Xaa Xaa Glu Phe Ile Ala Xaa Leu Val Xaa Gly Arg Gly
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = His or desamino-
      histidine(imidazopropionyl)
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
```

```
<222> LOCATION: (6)..(6)
<223> OTHER INFORMATION: Xaa = Phe
<220> FEATURE:
<221> NAME/KEY: MISC_FEATURE
<222> LOCATION: (10)..(10)
<223> OTHER INFORMATION: Xaa = Val
<220> FEATURE:
<221> NAME/KEY: MISC_FEATURE
<222> LOCATION: (13)..(13)
<223> OTHER INFORMATION: Xaa = Tyr
<220> FEATURE:
<221> NAME/KEY: MISC_FEATURE
<222> LOCATION: (14)..(14)
<223> OTHER INFORMATION: Xaa = Leu
<220> FEATURE:
<221> NAME/KEY: MISC_FEATURE
<222> LOCATION: (16)..(16)
<223> OTHER INFORMATION: Xaa = Gly or Glu
<220> FEATURE:
<221> NAME/KEY: MISC_FEATURE
<222> LOCATION: (17)..(17)
<223> OTHER INFORMATION: Xaa = Gln
<220> FEATURE:
<221> NAME/KEY: MISC_FEATURE
<222> LOCATION: (19)..(19)
<223> OTHER INFORMATION: Xaa = Ala or Val
<220> FEATURE:
<221> NAME/KEY: MISC_FEATURE
<222> LOCATION: (20)..(20)
<223> OTHER INFORMATION: Xaa = Lys
<220> FEATURE:
<221> NAME/KEY: MISC_FEATURE
<222> LOCATION: (21)..(21)
<223> OTHER INFORMATION: Xaa = Glu
<220> FEATURE:
<221> NAME/KEY: MISC_FEATURE
<222> LOCATION: (24)..(24)
<223> OTHER INFORMATION: Xaa = Ala
<220> FEATURE:
<221> NAME/KEY: MISC_FEATURE
<222> LOCATION: (25)..(25)
<223> OTHER INFORMATION: Xaa = Trp
<220> FEATURE:
<221> NAME/KEY: MISC_FEATURE
<222> LOCATION: (27)..(27)
<223> OTHER INFORMATION: Xaa = Val
<220> FEATURE:
<221> NAME/KEY: MISC_FEATURE
<222> LOCATION: (28)..(28)
<223> OTHER INFORMATION: Xaa = Gln
<220> FEATURE:
<221> NAME/KEY: MISC_FEATURE
<222> LOCATION: (29)..(29)
<223> OTHER INFORMATION: Xaa = Gly
<220> FEATURE:
<221> NAME/KEY: MISC_FEATURE
<222> LOCATION: (30)..(30)
<223> OTHER INFORMATION: Xaa = Arg
<220> FEATURE:
<221> NAME/KEY: MISC_FEATURE
<222> LOCATION: (31)..(31)
<223> OTHER INFORMATION: Xaa = Gly

<400> SEQUENCE: 4

Xaa Xaa Glu Gly Thr Xaa Thr Ser Asp Xaa Ser Lys Xaa Xaa Glu Xaa
1               5                   10                  15

Xaa Ala Xaa Xaa Xaa Phe Ile Xaa Xaa Leu Xaa Xaa Xaa Xaa Xaa
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: Xaa=Imp
<220> FEATURE:
<221> NAME/KEY: MISC_FEATURE
<222> LOCATION: (2)..(2)
<223> OTHER INFORMATION: Xaa=Aib
<220> FEATURE:
<221> NAME/KEY: MISC_FEATURE
<222> LOCATION: (12)..(12)
<223> OTHER INFORMATION: Xaa=Lys
<220> FEATURE:
<221> NAME/KEY: MISC_FEATURE
<222> LOCATION: (16)..(16)
<223> OTHER INFORMATION: Xaa=Glu
<220> FEATURE:
<221> NAME/KEY: MISC_FEATURE
<222> LOCATION: (28)..(28)
<223> OTHER INFORMATION: Xaa=Gln

<400> SEQUENCE: 5

Xaa Xaa Glu Gly Thr Phe Thr Ser Asp Val Ser Xaa Tyr Leu Glu Xaa
1               5                   10                  15

Gln Ala Ala Lys Glu Phe Ile Ala Trp Leu Val Xaa Gly Arg Gly
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa=Imp
<220> FEATURE:
<221> NAME/KEY: MISC_FEATURE
<222> LOCATION: (12)..(12)
<223> OTHER INFORMATION: Xaa=Lys
<220> FEATURE:
<221> NAME/KEY: MISC_FEATURE
<222> LOCATION: (16)..(16)
<223> OTHER INFORMATION: Xaa=Glu
<220> FEATURE:
<221> NAME/KEY: MISC_FEATURE
<222> LOCATION: (19)..(19)
<223> OTHER INFORMATION: Xaa=Val
<220> FEATURE:
<221> NAME/KEY: MISC_FEATURE
<222> LOCATION: (20)..(20)
<223> OTHER INFORMATION: Xaa=Arg
<220> FEATURE:
<221> NAME/KEY: MISC_FEATURE
<222> LOCATION: (25)..(25)
<223> OTHER INFORMATION: Xaa=Lys
<220> FEATURE:
<221> NAME/KEY: MISC_FEATURE
<222> LOCATION: (28)..(28)
<223> OTHER INFORMATION: Xaa=Arg

<400> SEQUENCE: 6

Xaa Ala Glu Gly Thr Phe Thr Ser Asp Val Ser Xaa Tyr Leu Glu Xaa
1               5                   10                  15

Gln Ala Xaa Xaa Glu Phe Ile Ala Xaa Leu Val Xaa Gly Arg Gly
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (2)..(2)
<223> OTHER INFORMATION: Xaa=Aib
<220> FEATURE:
<221> NAME/KEY: MISC_FEATURE
<222> LOCATION: (12)..(12)
<223> OTHER INFORMATION: Xaa=Lys
<220> FEATURE:
<221> NAME/KEY: MISC_FEATURE
<222> LOCATION: (13)..(13)
<223> OTHER INFORMATION: Xaa=Gln
<220> FEATURE:
<221> NAME/KEY: MISC_FEATURE
<222> LOCATION: (16)..(16)
<223> OTHER INFORMATION: Xaa=Glu
<220> FEATURE:
<221> NAME/KEY: MISC_FEATURE
<222> LOCATION: (28)..(28)
<223> OTHER INFORMATION: Xaa=Arg

<400> SEQUENCE: 7

His Xaa Glu Gly Thr Phe Thr Ser Asp Val Ser Xaa Xaa Leu Glu Xaa
1               5                   10                  15

Gln Ala Ala Lys Glu Phe Ile Ala Trp Leu Val Xaa Gly Arg Gly
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa=L-histidine, imidazopropionyl, a-hydroxy-
      histidine, D-histidine, desamino-histidine, 2-amino-histidine,
      b-hydroxy-histidine, homohistidine, Na-acetyl-histidine,
      Na-formyl-histidine, a-fluoromethyl-histidine,
<220> FEATURE:
<221> NAME/KEY: MISC_FEATURE
<222> LOCATION: (2)..(2)
<223> OTHER INFORMATION: Xaa=Ala, Gly, Val, Leu, Ile, Thr, Ser, Lys,
      Aib, (1-aminocyclopropyl) carboxylic acid, (1-aminocyclobutyl)
      carboxylic acid, (1-aminocyclopentyl) carboxylic acid,
      (1-aminocyclohexyl) carboxylic acid, (1-aminocycloheptyl)
<220> FEATURE:
<221> NAME/KEY: MISC_FEATURE
<222> LOCATION: (6)..(6)
<223> OTHER INFORMATION: Xaa=Phe or Leu
<220> FEATURE:
<221> NAME/KEY: MISC_FEATURE
<222> LOCATION: (10)..(10)
<223> OTHER INFORMATION: Xaa=Val or Leu
<220> FEATURE:
<221> NAME/KEY: MISC_FEATURE
<222> LOCATION: (13)..(13)
<223> OTHER INFORMATION: Xaa=Tyr or Gln
<220> FEATURE:
<221> NAME/KEY: MISC_FEATURE
<222> LOCATION: (14)..(14)
<223> OTHER INFORMATION: Xaa=Leu or Met
<220> FEATURE:
<221> NAME/KEY: MISC_FEATURE
<222> LOCATION: (16)..(16)
<223> OTHER INFORMATION: Xaa=Gly, Glu, Lys, or Aib
<220> FEATURE:
<221> NAME/KEY: MISC_FEATURE
<222> LOCATION: (17)..(17)
<223> OTHER INFORMATION: Xaa=Gln, Glu, or Arg
<220> FEATURE:
<221> NAME/KEY: MISC_FEATURE
<222> LOCATION: (19)..(19)
<223> OTHER INFORMATION: Xaa=Ala or Val
<220> FEATURE:
```

```
<221> NAME/KEY: MISC_FEATURE
<222> LOCATION: (20)..(20)
<223> OTHER INFORMATION: Xaa=Val, His, Lys or Arg
<220> FEATURE:
<221> NAME/KEY: MISC_FEATURE
<222> LOCATION: (21)..(21)
<223> OTHER INFORMATION: Xaa=Glu, Leu, or Lys
<220> FEATURE:
<221> NAME/KEY: MISC_FEATURE
<222> LOCATION: (24)..(24)
<223> OTHER INFORMATION: Xaa=Ala, Glu, Lys or Arg
<220> FEATURE:
<221> NAME/KEY: MISC_FEATURE
<222> LOCATION: (25)..(25)
<223> OTHER INFORMATION: Xaa=Trp, Lys or His
<220> FEATURE:
<221> NAME/KEY: MISC_FEATURE
<222> LOCATION: (27)..(27)
<223> OTHER INFORMATION: Xaa=Val or Lys
<220> FEATURE:
<221> NAME/KEY: MISC_FEATURE
<222> LOCATION: (28)..(28)
<223> OTHER INFORMATION: Xaa= Lys, Glu, Asn, Gly, Gln, Arg, His, or
      absent
<220> FEATURE:
<221> NAME/KEY: MISC_FEATURE
<222> LOCATION: (29)..(29)
<223> OTHER INFORMATION: Xaa= Gly, Aib, or absent
<220> FEATURE:
<221> NAME/KEY: MISC_FEATURE
<222> LOCATION: (30)..(30)
<223> OTHER INFORMATION: Xaa= Arg, Gly, Lys, or absent
<220> FEATURE:
<221> NAME/KEY: MISC_FEATURE
<222> LOCATION: (31)..(31)
<223> OTHER INFORMATION: Xaa= Gly, Ala, Glu, Pro, Lys, Arg, or absent
<220> FEATURE:
<221> NAME/KEY: MISC_FEATURE
<222> LOCATION: (32)..(32)
<223> OTHER INFORMATION: Xaa= Ser, Gly, Ala, Glu, Pro, Lys, Arg, or
      absent

<400> SEQUENCE: 8

Xaa Xaa Glu Gly Thr Xaa Thr Ser Asp Xaa Ser Lys Xaa Xaa Glu Xaa
1               5                   10                  15

Xaa Ala Xaa Xaa Xaa Phe Ile Xaa Xaa Leu Xaa Xaa Xaa Xaa Xaa Xaa
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=Aib
<220> FEATURE:
<221> NAME/KEY: MISC_FEATURE
<222> LOCATION: (12)..(12)
<223> OTHER INFORMATION: Xaa=Lys
<220> FEATURE:
<221> NAME/KEY: MISC_FEATURE
<222> LOCATION: (16)..(16)
<223> OTHER INFORMATION: Xaa=Glu
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: Xaa=Gln

<400> SEQUENCE: 9
```

```
His Xaa Glu Gly Thr Phe Thr Ser Asp Val Ser Xaa Tyr Leu Glu Gly
1               5                   10                  15

Gln Ala Ala Lys Glu Xaa Ile Ala Trp Leu Val Xaa Gly Arg Gly
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=Aib
<220> FEATURE:
<221> NAME/KEY: MISC_FEATURE
<222> LOCATION: (12)..(12)
<223> OTHER INFORMATION: Xaa=Lys
<220> FEATURE:
<221> NAME/KEY: MISC_FEATURE
<222> LOCATION: (13)..(13)
<223> OTHER INFORMATION: Xaa=Gln
<220> FEATURE:
<221> NAME/KEY: MISC_FEATURE
<222> LOCATION: (16)..(16)
<223> OTHER INFORMATION: Xaa=Glu
<220> FEATURE:
<221> NAME/KEY: MISC_FEATURE
<222> LOCATION: (28)..(28)
<223> OTHER INFORMATION: Xaa=Gln

<400> SEQUENCE: 10

His Xaa Glu Gly Thr Phe Thr Ser Asp Val Ser Xaa Xaa Leu Glu Xaa
1               5                   10                  15

Gln Ala Ala Lys Glu Phe Ile Ala Trp Leu Val Xaa Gly Arg Gly
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Xaa=Lys
<220> FEATURE:
<221> NAME/KEY: MISC_FEATURE
<222> LOCATION: (16)..(16)
<223> OTHER INFORMATION: Xaa=Glu
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: Xaa=Gln

<400> SEQUENCE: 11

His Ala Glu Gly Thr Phe Thr Ser Asp Val Ser Xaa Tyr Leu Glu Gly
1               5                   10                  15

Gln Ala Ala Lys Glu Xaa Ile Ala Trp Leu Val Xaa Gly Arg Gly
            20                  25                  30

<210> SEQ ID NO 12
<211> LENGTH: 31
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=Aib
<220> FEATURE:
<221> NAME/KEY: MISC_FEATURE
<222> LOCATION: (12)..(12)
<223> OTHER INFORMATION: Xaa=Lys
<220> FEATURE:
<221> NAME/KEY: MISC_FEATURE
<222> LOCATION: (28)..(28)
<223> OTHER INFORMATION: Xaa=Gln

<400> SEQUENCE: 12

His Xaa Glu Gly Thr Phe Thr Ser Asp Val Ser Xaa Tyr Leu Glu Gly
1               5                   10                  15

Gln Ala Ala Lys Glu Phe Ile Ala Trp Leu Val Xaa Gly Arg Gly
            20                  25                  30
```